US010633353B2

(12) United States Patent
Nose et al.

(10) Patent No.: US 10,633,353 B2
(45) Date of Patent: *Apr. 28, 2020

(54) POLYMERIZABLE COMPOUND, COMPOSITION, POLYMER, OPTICALLY ANISOTROPIC BODY, LIQUID CRYSTAL DISPLAY ELEMENT, AND ORGANIC EL DISPLAY

(71) Applicant: DIC Corporation, Tokyo (JP)

(72) Inventors: Sayaka Nose, Kita-adachi-gun (JP); Yuji Ohashi, Kita-adachi-gun (JP); Junichi Mamiya, Kita-adachi-gun (JP); Akihiro Koiso, Kita-adachi-gun (JP); Tatsufumi Yamazaki, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/532,224

(22) PCT Filed: Dec. 1, 2015

(86) PCT No.: PCT/JP2015/083728
§ 371 (c)(1),
(2) Date: Jun. 1, 2017

(87) PCT Pub. No.: WO2016/088749
PCT Pub. Date: Jun. 9, 2016

(65) Prior Publication Data
US 2017/0260150 A1 Sep. 14, 2017

(30) Foreign Application Priority Data

Dec. 4, 2014 (JP) .................... 2014-245866

(51) Int. Cl.
| | |
|---|---|
| *C09K 19/34* | (2006.01) |
| *C07D 277/82* | (2006.01) |
| *C07C 243/22* | (2006.01) |
| *C07D 209/40* | (2006.01) |
| *C07D 263/58* | (2006.01) |
| *C07D 277/50* | (2006.01) |
| *C08F 122/24* | (2006.01) |
| *H01L 51/00* | (2006.01) |
| *H01L 51/52* | (2006.01) |
| *C07D 277/84* | (2006.01) |

(52) U.S. Cl.
CPC .......... *C07D 277/82* (2013.01); *C07C 243/22* (2013.01); *C07D 209/40* (2013.01); *C07D 263/58* (2013.01); *C07D 277/50* (2013.01); *C07D 277/84* (2013.01); *C08F 122/24* (2013.01); *H01L 51/0036* (2013.01); *H01L 51/5293* (2013.01); *C07C 2601/14* (2017.05); *C07C 2603/18* (2017.05)

(58) Field of Classification Search
CPC ...................................................... C09K 19/00
See application file for complete search history.

(56) References Cited

U.S. PATENT DOCUMENTS

| | | | | |
|---|---|---|---|---|
| 5,445,854 A | * | 8/1995 | Newsham ............ | C07D 303/24 385/5 |
| 2007/0176145 A1 | | 8/2007 | Nishikawa et al. | |
| 2012/0224245 A1 | | 9/2012 | Adlem et al. | |
| 2014/0107247 A1 | | 4/2014 | Sakamoto et al. | |
| 2014/0142266 A1 | | 5/2014 | Sakamoto et al. | |
| 2014/0200320 A1 | | 7/2014 | Sakamoto et al. | |
| 2014/0309396 A1 | | 10/2014 | Sakamoto et al. | |
| 2015/0115199 A1 | | 4/2015 | Choi et al. | |
| 2015/0175564 A1 | * | 6/2015 | Sakamoto ............ | C07D 417/12 526/257 |
| 2015/0183902 A1 | * | 7/2015 | Sakamoto ............ | C07D 277/82 526/257 |
| 2015/0274647 A1 | | 10/2015 | Sakamoto et al. | |
| 2015/0274872 A1 | | 10/2015 | Sakamoto et al. | |
| 2015/0277007 A1 | * | 10/2015 | Matsuyama ......... | C07D 277/64 428/1.31 |
| 2015/0277010 A1 | | 10/2015 | Aimatsu et al. | |

(Continued)

FOREIGN PATENT DOCUMENTS

| | | | |
|---|---|---|---|
| JP | 2005-289980 A | 10/2005 | |
| JP | 2007-328053 A | 12/2007 | |

(Continued)

OTHER PUBLICATIONS

Scifinder CAS search Apr. 14, 2019 pp. 1-5.*
International Search Report dated Jan. 26, 2016, issued in counterpart International Application No. PCT/JP2015/083728 (3 pages).
Notification of Reasons for Refusal dated Jan. 31, 2017, issued in counterpart Japanese Patent Application No. 2016-562632, w/English translation (11 pages).
International Search Report dated Apr. 12, 2016, issued in counterpart to International Application No. PCT/JP2016/050322 (2 pages).
International Search Report and Written Opinion dated Feb. 16, 2016, issued in counterpart application No. PCT/JP2015/085342. (10 pages).

(Continued)

*Primary Examiner* — Chanceity N Robinson
(74) *Attorney, Agent, or Firm* — Westerman, Hattori, Daniels & Adrian, LLP

(57) ABSTRACT

It is an object of the present invention to provide a polymerizable compound having a good liquid crystal property, a good alignment property, sufficient solubility in solvents, high preservation stability in a solution state, and high optical stability; a composition including the polymerizable compound; a polymer produced by polymerizing the polymerizable compound, such as a resin produced using the polymerizable compound; an optically anisotropic body including the polymer; and a liquid crystal display element and an organic EL device that include the optically anisotropic body. As a result of conducting intensive studies in order to achieve the above object, the compound represented by General Formula (I) is developed.

13 Claims, No Drawings

(56) References Cited

U.S. PATENT DOCUMENTS

| | | | |
|---|---|---|---|
| 2015/0285979 A1* | 10/2015 | Aimatsu | C09K 19/02 349/194 |
| 2016/0002374 A1 | 1/2016 | Sakamoto et al. | |
| 2016/0200841 A1 | 7/2016 | Sakamoto | |
| 2016/0257659 A1 | 9/2016 | Sakamoto et al. | |
| 2017/0008833 A1 | 1/2017 | Sakamoto et al. | |
| 2018/0319755 A1* | 11/2018 | Teng | C07D 409/12 |

FOREIGN PATENT DOCUMENTS

| | | | | |
|---|---|---|---|---|
| JP | 2009-029795 A | 2/2009 | | |
| JP | 2009-062508 A | 3/2009 | | |
| JP | 2010-031223 A | 2/2010 | | |
| JP | 2010-100541 A | 5/2010 | | |
| JP | 2011-006361 A | 1/2011 | | |
| JP | 2011-207765 A | 10/2011 | | |
| JP | 2011-246381 A | 12/2011 | | |
| JP | 2012-077055 A | 4/2012 | | |
| JP | 2013-509458 A | 3/2013 | | |
| JP | 2015-200877 A | 11/2015 | | |
| WO | 2005/112540 A2 | 12/2005 | | |
| WO | 2012/141245 A1 | 10/2012 | | |
| WO | 2012/147904 A1 | 11/2012 | | |
| WO | 2012/176679 A1 | 12/2012 | | |
| WO | 2013/157888 A1 | 10/2013 | | |
| WO | 2013/180217 A1 | 12/2013 | | |
| WO | WO-2013180217 A1 * | 12/2013 | | C07D 277/82 |
| WO | 2014/010325 A1 | 1/2014 | | |
| WO | WO-2014010325 A1 * | 1/2014 | | C07D 417/12 |
| WO | 2014/061709 A1 | 4/2014 | | |
| WO | 2014/065176 A1 | 5/2014 | | |
| WO | 2014/065243 A1 | 5/2014 | | |
| WO | WO-2014069515 A1 * | 5/2014 | | C09K 19/02 |
| WO | 2014/126113 A1 | 8/2014 | | |
| WO | 2014/132978 A1 | 9/2014 | | |
| WO | 2015/025793 A1 | 2/2015 | | |
| WO | 2015/064698 A1 | 5/2015 | | |
| WO | 2015/122384 A1 | 8/2015 | | |
| WO | 2015/122385 A1 | 8/2015 | | |
| WO | 2016/056542 A1 | 4/2016 | | |
| WO | 2016/088749 A1 | 6/2016 | | |

OTHER PUBLICATIONS

Calvin, J. et al., "Rhodium-Catalyzed and Zinc(II)-Triftate-Promoted Asymmetric Hydrogenation of Tetrasubstituted Alpha, Beta-Unsaturated Ketones", Organic Letters, 2012, vol. 14, No. 4, pp. 1038-1041 (4 pages).

Szelinski, H. et al., "Porphyrins Linked to High Acceptor Strength Cyano Quinones as Models for the Photosynthetic Reaction Center", Tetrahedron, 1996, vol. 52, No. 25, pp. 8497-8516. (20 pages).

Kallitsis, J. et al., "Soluble Polymers with Laterally Attached Oligophenyl Units for Potential Use as Blue Luminescent Materials", Macromolecules, 1997, vol. 30, No. 10, pp. 2989-2996. (8 pages).

Benbow, J_ et al., "An Approach to Dibenzofuran Heterocycles. 1. Electron-Transfer Processes en Route to Dibenzofuran-1, 4-diones", J. Org. Chem., 1997, vol. 62, No. 26, pp. 9345-9347. (3 pages).

Yu, S. et al., "Self-Assembled Electroluminescent Polymers Derived from Terpyridine-Based Moieties", Advanced Materials, 2003, vol. 15, No. 19, pp. 1643-1647. (5 pages).

Benbow, J. et al., "Biaryl Formation Using the Suzuki Protocol: Considerations of Base, Halide, and Protecting Group" Tetrahedron Letters, 1996, vol. 37, No. 49, pp. 8829-8832. (4 pages).

Macdonald, D. et al., "Substituted 2,2-bisaryl-bicycloheptanes as novel and potent inhibitors of 5-lipxygenase activating protein", Bioorganic and Medicinal Chemistry Letters, 2008, vol. 18, pp. 2023-2027. (5 pages).

* cited by examiner

POLYMERIZABLE COMPOUND, COMPOSITION, POLYMER, OPTICALLY ANISOTROPIC BODY, LIQUID CRYSTAL DISPLAY ELEMENT, AND ORGANIC EL DISPLAY

TECHNICAL FIELD

The present invention relates to a polymerizable compound, a composition, a polymer, an optically anisotropic body, a liquid crystal display element, and an organic EL device.

BACKGROUND ART

Optically anisotropic bodies included in liquid crystal displays, such as a phase-retardation film or a polarizing plate, are produced by applying a solution containing a polymerizable liquid crystal compound to a rubbed base material or a base material including a photo-aligned film disposed thereon, drying the resulting coating film in order to remove the solvent, and causing polymerization using ultraviolet radiation or heat. In order to increase the viewing angles of liquid crystal displays, phase-retardation films are required to have an optical property such that the wavelength dispersion of birefringence ($\Delta n$) is small or reversed. Accordingly, polymerizable compounds having a reversed-dispersion property have been developed in order to achieve such a property (e.g., PTL 1). Note that, when the slope of a graph prepared by plotting the wavelength $\lambda$ of light incident to a phase-retardation film in the horizontal axis and the corresponding birefringence ($\Delta n$=refractive index $n_e$ measured using extraordinary light−refractive index $n_0$ measured using ordinary light) in the vertical axis is positive (rising to the right), it is commonly said that "the birefringence of the phase-retardation film has reversed-wavelength dispersion" or "the polymerizable compound constituting the phase-retardation film has a reversed-dispersion property".

One of the methods for converting a polymerizable compound constituting a phase-retardation film to be a polymerizable compound having a reversed-dispersion property is to introduce a portion (vertical unit) that has a large birefringence in a direction perpendicular to the longer axis of the molecule into the molecule. However, introducing the vertical unit into the molecule is likely to degrade the liquid crystal property and alignment property of the polymerizable compound. This requires a certain times of tests to be conducted in order to produce a polymerizable compound that does not degrade the alignment property.

When a polymerizable compound is applied to a base material, an adequate amount of polymerizable compound needs to be dissolved in a solvent that does not corrode the base material. However, the introduction of the vertical unit is likely to degrade the solubility of the polymerizable compound in the solvent. This results in failure to prepare a solution having a sufficiently high concentration. In addition, crystals may precipitate while the solution is stored.

The introduction of the vertical unit also changes the absorption spectrum of the polymerizable compound. Specifically, the absorption band shifts to longer-wavelength region in many cases. This is likely to degrade the optical stability of the compound and leads to, for example, yellowing of a phase-retardation film and cracking in a phase-retardation film.

CITATION LIST

Patent Literature

PTL 1: Japanese Unexamined Patent Application Publication (Translation of PCT Application) No. 2013-509458

SUMMARY OF INVENTION

Technical Problem

The present invention was made in light of the above-described facts. It is an object of the present invention to provide a polymerizable compound having a good liquid crystal property, a good alignment property, sufficient solubility in solvents, high preservation stability in a solution state, and high optical stability; a composition including the polymerizable compound; a resin, a resin additive, an oil, a filter, a bonding agent, an adhesive, a fat, an ink, a drug, a cosmetic, a detergent, a building material, a packaging material, a liquid crystal material, an organic EL material, an organic semiconductor material, an electronic material, an automotive component, an aircraft component, a machine component, an agricultural chemical, and a food that include the polymerizable compound and a product including any of the above items; a polymer produced by polymerizing the polymerizable compound; an optically anisotropic body including the polymer; and a liquid crystal display element and an organic EL device that include the optically anisotropic body.

Solution to Problem

The inventors of the present invention conducted extensive studies in order to address the above issues and, as a result, developed the compound represented by General Formula (I) below. Specifically, the present invention provides the compound represented by General Formula (1) below.

[Chem. 1]

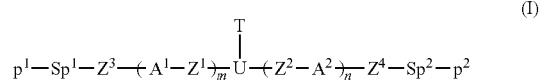

(wherein $P^1$ and $P^2$ represent a polymerizable functional group;

$Sp^1$ and $Sp^2$ represent a divalent spacer group or a single bond;

$A^1$ and $A^2$ each independently represent a divalent alicyclic or aromatic hydrocarbon group having 3 to 20 carbon atoms, the divalent alicyclic or aromatic hydrocarbon group may be optionally substituted with one or more substituents, and a carbon atom included in the alicyclic or aromatic hydrocarbon group may be replaced with a hetero atom;

$Z^1, Z^2, Z^3$, and $Z^4$ each independently represent a divalent linking group or a single bond;

U represents a trivalent aromatic group that may be optionally substituted with one or more substituents;

T represents a group selected from Formulae (T-1) and (T-2) below,

[Chem. 2]

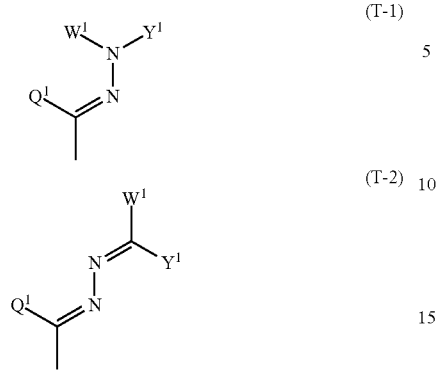

(where $Q^1$ represents a hydrogen atom or an alkyl group having 1 to 6 carbon atoms, and the alkyl group may be optionally substituted with one or more substituents;

$W^1$ represents an organic group having 2 to 30 carbon atoms, the organic group includes an aromatic hydrocarbon group, a carbon atom included in the aromatic hydrocarbon group may be replaced with a hetero atom, and the aromatic hydrocarbon group may be optionally substituted with one or more substituents;

$Y^1$ represents a hydrogen atom, an alkyl group having 1 to 20 carbon atoms, an alkenyl group having 2 to 20 carbon atoms, a cycloalkyl group having 3 to 12 carbon atoms, an organic group having 2 to 30 carbon atoms, the organic group including an aromatic hydrocarbon group (a carbon atom included in the aromatic hydrocarbon group may be replaced with a hetero atom), or —($Z^5$-$A^3$)q-$Z^6$—$Sp^3$-$P^3$, the alkyl group, the alkenyl group, and the cycloalkyl group may be optionally substituted with one or more substituents, one —CH$_2$— group included in the alkyl group or two or more —CH$_2$— groups that are included in the alkyl group and not adjacent to one another may be each independently replaced with —O—, —S—, —CO—, —COO—, —OCO—, —CO—S—, —S—CO—, —SO$_2$—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, $Z^5$ and $Z^6$ represent the same things as $Z^1$ to $Z^4$, $A^3$ represents the same thing as $A^1$ and $A^2$, $Sp^3$ represents the same thing as $Sp^1$ and $Sp^2$, $P^3$ represents the same thing as $P^1$ and $P^2$, and q represents an integer of 0 to 4; and the $W^1$ group and the $Y^1$ group may be bonded to each other to form a ring);

m and n each independently represent an integer of 0 to 4 (m+n is an integer of 1 or more); and, when a plurality of $A^1$ groups, $A^2$ groups, $A^3$ groups, $Z^1$ groups, $Z^2$ groups, and $Z^5$ groups are present, they may be identical to or different from one another). The present invention also provides a composition including the polymerizable compound; a resin, a resin additive, an oil, a filter, a bonding agent, an adhesive, a fat, an ink, a drug, a cosmetic, a detergent, a building material, a packaging material, a liquid crystal material, an organic EL material, an organic semiconductor material, an electronic material, an automotive component, an aircraft component, a machine component, an agricultural chemical, and a food that include the polymerizable compound and a product including any of the above items; a polymer produced by polymerizing the composition; and an optically anisotropic body, a liquid crystal display element, and an organic EL device that include the polymer.

Advantageous Effects of Invention

An optically anisotropic body having an excellent optical property may be produced by using the polymerizable compound according to the present invention. This enables a liquid crystal display element and an organic EL device that have an increased viewing angle to be produced.

DESCRIPTION OF EMBODIMENTS

The present invention is described below with reference to a preferable embodiment, which does not limit the present invention.

<<Polymerizable Compound>>

The polymerizable compound according to the present invention is the compound represented by General Formula (1) below.

The compound represented by General Formula (1) may have, but does not necessarily have, a liquid crystal property alone. In the case where the compound represented by General Formula (1) does not have a liquid crystal property alone, it is preferable to impart a liquid crystal property to the compound represented by General Formula (1) by adding another constituent having a liquid crystal property to the compound. It is more preferable that the compound represented by General Formula (1) have a liquid crystal property prior to polymerization. In other words, the compound represented by General Formula (1) is preferably a polymerizable liquid crystal compound.

<$P^1$ and $P^2$>

The polymerizable functional groups represented by $P^1$ and $P^2$ in General Formula (1) may be any polymerizable functional groups included in polymerizable liquid crystal compounds used in the related art.

The polymerizable functional groups $P^1$ and $P^2$ preferably each independently represent a group selected from Formulae (P-1) to (P-20) below.

[Chem. 3]

 (P-1)

 (P-2)

 (P-3)

 (P-4)

 (P-5)

 (P-6)

-continued

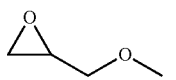
(P-7)

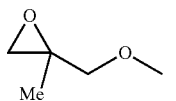
(P-8)

(P-9)

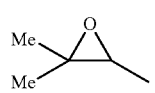
(P-10)

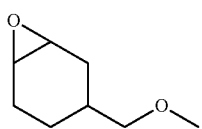
(P-11)

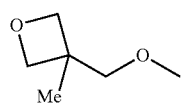
(P-12)

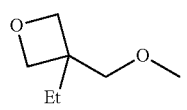
(P-13)

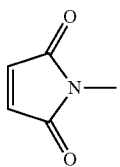
(P-14)

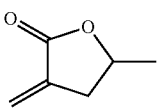
(P-15)

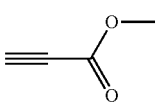
(P-16)

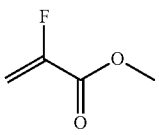
(P-17)

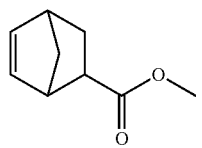
(P-18)

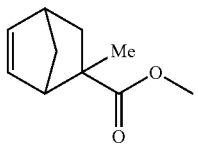
(P-19)

-continued (P-20)

The above polymerizable groups may be polymerized by radical polymerization, radical addition polymerization, cationic polymerization, and anionic polymerization. In particular, in the case where ultraviolet polymerization is employed as a polymerization method, Formulae (P-1), (P-2), (P-3), (P-4), (P-5), (P-7), (P-11), (P-13), (P-15), and (P-18) are preferable; Formulae (P-1), (P-2), (P-7), (P-11), and (P-13) are more preferable; Formulae (P-1), (P-2), and (P-3) are further preferable; and Formulae (P-1) and (P-2) are particularly preferable.

<$Sp^1$ and $Sp^2$>

In General Formula (1), $Sp^1$ and $Sp^2$ represent a divalent spacer group or a single bond. The spacer group is a divalent linking group capable of connecting the polymerizable functional group $P^1$ to $Z^3$ or the polymerizable functional group $P^2$ to $Z^4$ and is preferably a linking group that does not impair the liquid crystal property of the polymerizable compound represented by General Formula (1).

Examples of suitable divalent spacer groups represented by $Sp^1$ and $Sp^2$ include linear alkylene groups having 1 to 20 carbon atoms. In the alkylene group, one $CH_2$ group or two or more $CH_2$ groups that are not adjacent to one another may be each independently replaced with —O—, —S—, —NH—, —N(CH$_3$)—, —CO—, —COO—, —OCO—, —OCOO—, —SCO—, —COS—, —CH=CH—, or —C≡C— such that two oxygen atoms, two sulfur atoms, or an oxygen atom and a sulfur atom are not directly bonded to each other. The $P^1$—$Sp^1$ bond, the $Sp^1$-$Z^3$ bond, the $Z^4$—$Sp^2$ bond, and the $Sp^2$-$P^2$ bond are not —O—O— bonds. The number of carbon atoms included in the alkylene group is preferably 2 to 10, is more preferably 3 to 8, and is further preferably 3 to 6 in order to enhance the liquid crystal property of the polymerizable compound.

It is also suitable that $Sp^1$ and/or $Sp^2$ represent a single bond. A polymer produced by polymerizing a composition including a compound represented by General Formula (1) according to the present invention in which the $Sp^1$ and/or $Sp^2$ group is a single bond has enhanced optical stability. Thus, in the case where high optical stability is required, it is preferable that at least one of the $Sp^1$ and $Sp^2$ groups be a single bond, and it is more preferable that both of $Sp^1$ and $Sp^2$ represent a single bond.

<$A^1$ and $A^2$>

In General Formula (1), $A^1$ and $A^2$ each independently represent a divalent alicyclic or aromatic hydrocarbon group having 3 to 20 carbon atoms which may be optionally substituted with one or more substituents. A carbon atom included in the alicyclic or aromatic hydrocarbon group may be replaced with a hetero atom. More specifically, a carbon atom included in the alicyclic or aromatic hydrocarbon group may be replaced with an oxygen atom, a sulfur atom, or a nitrogen atom. The aromatic hydrocarbon group may be an aromatic heterocyclic group or have a condensed-ring structure or a structure formed by the condensation of an alicyclic hydrocarbon group with an aromatic hydrocarbon group. In the case where plural $A^1$ groups and/or plural $A^2$ groups are present, they may be identical to or different from one another.

Examples of the alicyclic or aromatic hydrocarbon group include a 1,4-phenylene group, a 1,4-cyclohexylene group, a 1,4-cyclohexenyl group, a tetrahydropyran-2,5-diyl group, a 1,3-dioxane-2,5-diyl group, a tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a 1,2,3,4-tetrahydronaphthalene-2,6-diyl group, a naphthalene-2,6-diyl group, a phenanthrene-2,7-diyl group, a 9,10-dihydrophenanthrene-2,7-diyl group, a 1,2,3,4,4a,9,10a-octahydrophenanthrene-2,7-diyl group, and a fluorene-2,7-diyl group. The above alicyclic or aromatic hydrocarbon groups may be optionally substituted with one or more substituents L.

The substituent L is a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. A hydrogen atom included in the alkyl group may be replaced with a fluorine atom. The substituent L may also be a group represented by $P^L$—($Sp^L$-$X^L$)$_{kL}$— where $P^L$ represents a polymerizable group and $Sp^L$ represents a spacer group or a single bond. Examples of the spacer group include those described above as examples of the divalent spacer group. In the case where plural $Sp^L$ groups are present, they may be identical to or different from one another. $X^L$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond. In the case where plural $X^L$ groups are present, they may be identical to or different from one another ($P^L$—($Sp^L$-$X^L$)$_{kL}$— does not include a —O—O— bond). In the above formula, kL represents an integer of 0 to 10. In the case where plural L substituents are present in the compound, the respective kL values may be identical to or different from one another. In consideration of the liquid crystal property of the polymerizable compound and ease of synthesis, L preferably represents a fluorine atom, a chlorine atom, a pentafluorosulfanyl group, a nitro group, a methylamino group, a dimethylamino group, a diethylamino group, a diisopropylamino group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with a group selected from —O—, —S—, —CO—, —COO—, —OCO—, —O—CO—O—, —CH=CH—, —CF=CF—, and —C≡C—; more preferably represents a fluorine atom, a chlorine atom, or a linear or branched alkyl group having 1 to 12 carbon atoms in which a hydrogen atom may be replaced with a fluorine atom and one —$CH_2$— group or two or more —$CH_2$— groups that are not adjacent to one another may be each independently replaced with a group selected from —O—, —COO—, and —OCO—; further preferably represents a fluorine atom, a chlorine atom, or a linear or branched alkyl or alkoxy group having 1 to 12 carbon atoms in which a hydrogen atom may be replaced with a fluorine atom; and particularly preferably represents a fluorine atom, a chlorine atom, or a linear alkyl or alkoxy group having 1 to 8 carbon atoms.

In General Formula (1), $A^1$ and $A^2$ preferably each independently represent a 1,4-phenylene group, a naphthalene-2,6-diyl group, or a 1,4-cyclohexylene group that may be optionally substituted with one or more substituents L and more preferably each independently represent a 1,4-phenylene group or a 1,4-cyclohexylene group. When $A^1$ and $A^2$ in General Formula (1) represent a group selected from the above preferable groups, the liquid crystal property of the polymerizable compound according to the embodiment may be enhanced and, as a result, the alignment property of a polymer produced using the polymerizable compound may be readily enhanced.

It is also preferable that all of the $A^1$ groups and/or all of the $A^2$ groups in General Formula (1) be divalent alicyclic hydrocarbon groups that may optionally include a substituent (e.g., when plural $A^1$ groups are present, it is preferable that all of the $A^1$ groups be divalent alicyclic hydrocarbon groups). Specifically, the divalent alicyclic hydrocarbon groups are preferably selected from a 1,4-cyclohexylene group, a 1,4-cyclohexenyl group, a tetrahydropyran-2,5-diyl group, and a 1,3-dioxane-2,5-diyl group. It is more preferable that all of the $A^1$ groups and all of the $A^2$ groups in General Formula (1) be selected from a 1,4-cyclohexylene group, a 1,4-cyclohexenyl group, a tetrahydropyran-2,5-diyl group, and a 1,3-dioxane-2,5-diyl group. When all of the $A^1$ groups and all of the $A^2$ groups are selected from the above groups, the solubility of the polymerizable compound according to the embodiment may be enhanced and the reversed-dispersion property of a polymer produced using the polymerizable compound may be enhanced readily. Using a 1,4-cyclohexylene group is preferable because it markedly enhances the solubility of the polymerizable compound according to the embodiment and makes it easy to enhance the reversed-dispersion property of a polymer produced using the polymerizable compound. From the above viewpoint, in the case where plural $A^1$ groups and plural AZ groups are present, that is, for example, m and n described below represent 2, it is more preferable that both of the two $A^1$ groups be 1,4-cyclohexylene groups and/or both of the two AZ groups be 1,4-cyclohexylene groups.

<$Z^1$, $Z^2$, $Z^3$, and $Z^4$>

In General Formula (1), $Z^1$, $Z^2$, $Z^3$, and $Z^4$ each independently represent a divalent linking group or a single bond. In the case where plural $Z^1$ groups and/or plural $Z^2$ groups are present, they may be identical to or different from one another.

It is preferable that $Z^1$, $Z^2$, $Z^3$, and $Z^4$ each independently represent an acyclic aliphatic group having 1 to 20 carbon atoms which may be optionally substituted with one or more substituents (in the acyclic aliphatic group, one —$CH_2$— group or two or more —$CH_2$— groups that are not adjacent to one another may be each independently replaced with —O—, —S—, —COO—, —OCO—, —CO—S—, —S—CO—, —$OCF_2$—, —$CF_2O$—, —$SCF_2$—, —$CF_2S$—, —CF=CF—, —O—COO—, —$NR^3$—CO—, —CO—$NR^3$—, —$NR^3$—COO—, —OCO—$NR^3$—, or —OCO—

COO—, where $R^3$ represents a hydrogen atom or an alkyl group having 1 to 6 carbon atoms), —C≡C—, —N═N—, —C═N—, —N═C—, —C═N—N═C—, —CH═CH—COO—, —OCO—CH═C—, —OCO—COO—, or a single bond. Examples of the acyclic aliphatic group having 1 to 20 carbon atoms include an alkylene group having 1 to 20 carbon atoms and an alkenylene group having 2 to 20 carbon atoms. In the case where the acyclic aliphatic group having 1 to 20 carbon atoms is an alkylene group having 1 carbon atom, $Z^1$, $Z^2$, $Z^3$, or $Z^4$ represents —CH$_2$— when not substituted with a substituent and, when the alkylene group is substituted with, for example, —O—, $Z^1$, $Z^2$, $Z^3$, or $Z^4$ represents —O—. More specifically, in consideration of the liquid crystal property of the polymerizable compound, availability of raw materials, and ease of synthesis, when plural $Z^1$ groups and plural $Z^2$ groups are present, they may be identical to or different from one another. $Z^1$ and $Z^2$ preferably each independently represent —OCH$_2$—, —CH$_2$O—, —COO—, —OCO—, —CF$_2$O—, —OCF$_2$—, —CH$_2$CH$_2$—, —CF$_2$CF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —CH═CH—, —CF═CF—, —C≡C—, or a single bond; more preferably each independently represent —OCH$_2$—, —CH$_2$O—, —COO—, —OCO—, —CF$_2$O—, —OCF$_2$—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —CH═CH—, —C≡C—, or a single bond; further preferably each independently represent —OCH$_2$—, —CH$_2$O—, —COO—, —OCO—, —CF$_2$O—, —OCF$_2$—, or a single bond; further more preferably each independently represent —OCH$_2$—, —CH$_2$O—, —COO—, —OCO—, or a single bond; and particularly preferably each independently represent —OCH$_2$—, —CH$_2$O—, —COO—, or —OCO—.

In consideration of the availability of raw materials and ease of synthesis, more specifically, it is preferable that $Z^3$ and $Z^4$ each independently represent —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, or a single bond; it is more preferable that $Z^3$ and $Z^4$ each independently represent —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond and, when plural $Z^3$ groups and plural $Z^4$ groups are present, they may be identical to or different from one another; and it is particularly preferable that $Z^3$ and $Z^4$ each independently represent —O—, —COO—, —OCO—, or a single bond and, when plural $Z^3$ groups and plural $Z^4$ groups are present, they may be identical to or different from one another.

<<$Z^1$ and $Z^2$ Directly Connected to U>>

In General Formula (1), $Z^1$, $Z^2$, $Z^3$, and $Z^4$ represent a group selected from the above divalent linking group and a single bond. It is preferable that one or both of $Z^1$ and $Z^2$ that are directly connected to U each independently represent a linking group selected from —CH$_2$—, an acyclic aliphatic group having 2 to 20 carbon atoms which may be optionally substituted with one or more substituents (in the acyclic aliphatic group, one —CH$_2$— group or two or more —CH$_2$— groups that are not adjacent to one another may be each independently replaced with —O—, —S—, —COO—, —OCO—, —CO—S—, —S—CO—, —OCF$_2$—, —CF$_2$O—, —SCF$_2$—, —CF$_2$S—, —CF═CF—, —O—COO—, —NR$^3$—CO—, —CO—NR$^3$—, —NR$^3$—COO—, —OCO—NR$^3$—, or —OCO—COO—, but the acyclic aliphatic group includes at least one —CH$_2$— group, where $R^3$ represents a hydrogen atom or an alkyl group having 1 to 6 carbon atoms), —C≡C—, —N═N—, —C═N—, —N═C—, —C═N—N═C—, —CH═CH—COO—, —OCO—CH═C—, and —OCO—COO—. More specifically, it is preferable that one or both of $Z^1$ and $Z^2$ that are directly connected to U each independently represent —OCH$_2$—, —CH$_2$O—, —CH$_2$CH$_2$—, —CH═CH—COO—, —OCO—CH═CH—, —COO—CH$_2$CH$_2$—, —OCO—CH$_2$CH$_2$—, —CH$_2$CH$_2$—COO—, —CH$_2$CH$_2$—OCO—, —C≡C—, or a single bond. It is more preferable that one or both of $Z^1$ and $Z^2$ that are directly connected to U each independently represent —OCH$_2$—, —CH$_2$O—, —COO—CH$_2$CH$_2$—, or —CH$_2$CH$_2$—OCO—.

When one or both of $Z^1$ and $Z^2$ that are directly connected to U are the above preferable linking groups, the alignment property of a polymer produced using the polymerizable compound according to the embodiment may be readily enhanced without impairing the liquid crystal property of the polymerizable compound. It is considered that introducing the above linking group to a portion of the molecule which is adjacent to the portion (vertical unit) bulky in a direction perpendicular to the longer axis of the molecule results in the enhancement of the alignment property of a polymer produced using the polymerizable compound. In the case where both of m and n described below are integers of 2 or more, plural $Z^1$ and $Z^2$ groups other than the $Z^1$ and $Z^2$ groups directly connected to U may be any group selected from the above divalent linking group and a single bond, while one or both of $Z^1$ and $Z^2$ that are directly connected to U include the above specific linking group.

<<$Z^3$ and $Z^4$>>

In General Formula (1), $Z^3$ and $Z^4$ represent a group selected from the above divalent linking group and a single bond.

It is preferable that one or both of $Z^3$ and $Z^4$ each independently represent a linking group selected from —OCO—CH═CH—*, —OCO—CH$_2$CH$_2$—*, —COO—CH$_2$CH$_2$—*, —O—CH═CH—*, and —O—CH$_2$CH$_2$—* (the above groups are capable of bonding to $A^1$ or $A^2$ on the side denoted by *) in order to enhance the solubility of the compound in solvents. While the above groups bond to $A^1$ or $A^2$ on the side denoted by *, they bond to the U-ring when m=0 or n=0.

In the case where one or both of $Z^3$ and $Z^4$ represent the specific linking group described above, it is preferable that $Sp^1$ and/or $Sp^2$ do not represent a single bond but a spacer group. It is more preferable that one or both of $Z^3$ and $Z^4$ each independently represent a linking group selected from —OCO—CH═CH—, —OCO—CH$_2$CH$_2$—, —CH═CH—COO—, and —CH$_2$CH$_2$—COO—.

<m and n>

In General Formula (1), m and n each independently represent an integer of 0 to 4, and m+n is an integer of 1 or more.

In the case where primary importance is placed on the solubility of the polymerizable compound according to the embodiment in solvents and the preservation stability of the polymerizable compound, it is preferable that one of m and n be zero.

In the case where primary importance is placed on the liquid crystal property and alignment property of the polymerizable compound, it is preferable that one or both of m and n represent an integer of 2 to 4, it is more preferable that both of m and n represent an integer of 2 to 4, and it is further preferable that both of m and n represent 2. In the case where one or both of m and n represent an integer of 2 to 4, it is preferable that the two or more $A^2$ groups and/or the two or more $A^2$ groups be each independently a divalent aromatic hydrocarbon group that may be optionally substituted with one or more substituents and $Z^1$ that connects the two or more $A^1$ groups to one another and/or $Z^2$ that connects the two or more $A^2$ groups to one another be not a single bond. Specifically, for example, when m=2, that is, when the joint section is represented by -$A^{12}$-$Z^{12}$-$A^{11}$-$Z^{11}$—U—, it is preferable that $A^{12}$ and $A^{11}$ represent a divalent aromatic hydrocarbon group that may be optionally substituted with one or more substituents and $Z^{12}$ represent a linking group other than a single bond.

In the case where primary importance is placed on the liquid crystal property of the polymerizable compound, a high liquid-crystal-phase temperature, and the preservation stability of the compound dissolved in a solvent, it is preferable that one or both of m and n represent 1 or 2 and it is particularly preferable that m+n be 3. More specifically, the compound represented by General Formula (1-k) below is preferable,

[Chem. 4]

(1-k)

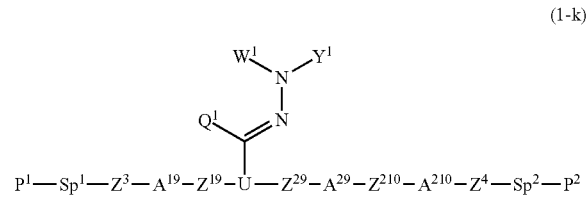

$P^1$—$Sp^1$—$Z^3$—$A^{19}$–$Z^{19}$–U—$Z^{29}$–$A^{29}$–$Z^{210}$–$A^{210}$–$Z^4$—$Sp^2$—$P^2$ (In General Formula (1-k), $P^1$, $P^2$, $Sp^1$, $Sp^2$, $Z^3$, $Z^4$, U, $Q^1$, $W^1$, and $Y^1$ represent the same things as in General Formula (1); $A^{19}$, $A^{29}$, and $A^{210}$ each independently represent a 1,4-cyclohexylene group or a 1,4-phenylene group, and the 1,4-phenylene group may be optionally substituted with one or more substituents $L^{11}$; $L^{11}$ represents a fluorine atom, a chlorine atom, or a linear or branched alkyl group having 1 to 20 carbon atoms in which one —$CH_2$— group or two or more —$CH_2$— groups that are not adjacent to one another may be each independently replaced with —O—, —CO—, —COO—, or —OCO—, and a hydrogen atom included in the alkyl group may be replaced with a fluorine atom; in the case where the compound includes plural $L^{11}$ substituents, the $L^{11}$ substituents may be identical to or different from one another; and $Z^{19}$, $Z^{29}$, and $Z^{210}$ each independently represent —$OCH_2$—, —$CH_2O$—, —COO—, —OCO—, —$CF_2O$—, —$OCF_2$—, —$CH_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —CH=CH—, —CF=CF—, —C≡C—, or a single bond). In the compound represented by Formula (1-k) above, in consideration of ease of synthesis, it is more preferable that $Z^{29}$ represent —$OCH_2$—, —$CH_2O$—, —$CF_2O$—, —$OCF_2$—, —$CH_2CH_2$—, —$CF_2CF_2$—, —COO—$CH_2CH_2$—, —$CH_2CH_2$—OCO—, —CH=CH—, —CF=CF—, —C≡C—, or a single bond and it is particularly preferable that $Z^{29}$ represent a single bond. It is more preferable that $A^{19}$ and $A^{210}$ represent a 1,4-phenylene group that may be optionally substituted with one or more substituents $L^{11}$.

<U>

In General Formula (1), the U-ring is a trivalent aromatic group that may have a substituent. The aromatic group is preferably a group selected from Formulae (U-1) to (U-6) below and is more preferably a group selected from Formulae (U-1) and (U-2) below.

[Chem. 5]

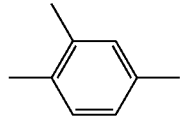
(U-1)

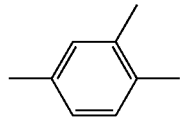
(U-2)

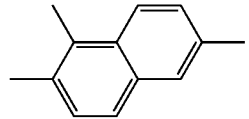
(U-3)

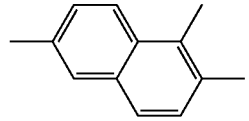
(U-4)

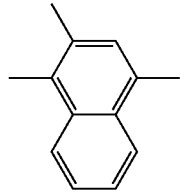
(U-5)

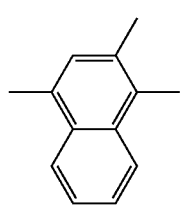
(U-6)

One or more hydrogen atoms bonded to each of the above rings may be replaced with F, Cl, $CF_3$, $OCF_3$, a cyano group, a nitro group, an amino group, a methylamino group, a dimethylamino group, an alkyl group having 1 to 8 carbon atoms, an alkoxy group having 1 to 8 carbon atoms, an alkanoyl group having 1 to 8 carbon atoms, an alkanoyloxy group having 1 to 8 carbon atoms, an alkenyl group having 2 to 8 carbon atoms, an alkenyloxy group having 2 to 8 carbon atoms, an alkenoyl group having 2 to 8 carbon atoms, or an alkenoyloxy group having 2 to 8 carbon atoms.

<$Q^1$>

In General Formula (1), $Q^1$ represents a hydrogen atom or an alkyl group having 1 to 6 carbon atoms. The alkyl group may be optionally substituted with one or more substituents. One or more hydrogen atoms bonded to the alkyl group may be replaced with F, Cl, $CF_3$, $OCF_3$, a cyano group, or an aromatic hydrocarbon group having 3 to 20 carbon atoms. $Q^1$ preferably represents a hydrogen atom or an alkyl group having 1 to 6 carbon atoms which may be substituted with one or more F atoms and more preferably represents a hydrogen atom.

<$W^1$>

$W^1$ represents an organic group having 2 to 30 carbon atoms which includes at least one aromatic ring selected from the group consisting of aromatic hydrocarbon rings and aromatic heterocyclic rings. The aromatic ring is preferably a group selected from Formulae (W-1) to (W-20) below.

[Chem. 6]

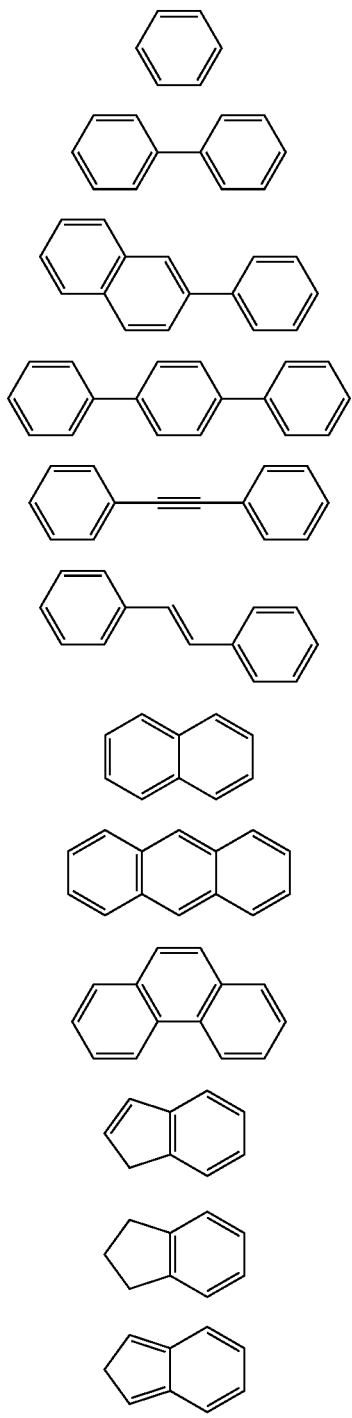

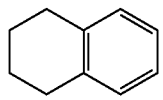

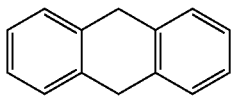

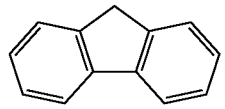

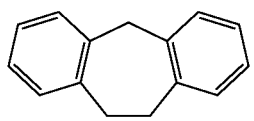

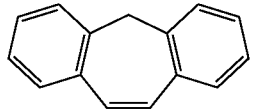

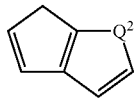

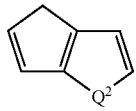

The above groups may have a bond at any position. $Q^2$ represents —O—, —S—, —NR$^4$— (where R$^4$ represents a hydrogen atom or an alkyl group having 1 to 8 carbon atoms), or —CO—. The —CH= groups included in the above groups may be each independently replaced with —N=. The —CH$_2$— groups included in the above groups may be each independently replaced with —O—, —S—, —NR$^5$— (where R$^5$ represents a hydrogen atom or an alkyl group having 1 to 8 carbon atoms), —SO—, —SO$_2$—, or —CO— (excluding the case where two oxygen atoms are directly bonded to each other). One or more hydrogen atoms bonded to each of the above rings may be replaced with a substituent L$^W$. The substituent L$^W$ is a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms. The alkyl group may be linear or branched. A hydrogen atom included in the alkyl group may be replaced with a fluorine atom. One —CH$_2$— group included in the alkyl group or two or more —CH$_2$— groups that are included in the alkyl group and not adjacent to one another may be each independently replaced with a group selected from —O—, —S—, —CO—, —COO—, —OCO—, —CO—S—, —S—CO—, —O—

CO—O—, —CO—NH—, —NH—CO—, —CH=CH—COO—, —CH=CH—OCO—, —COO—CH=CH—, —OCO—CH=CH—, —CH=CH—, —CF=CF—, and —C≡C—. Examples of the alkyl group and an alkyl group included in the alkoxy group include a methyl group, an ethyl group, a propyl group, an isopropyl group, a butyl group, an isobutyl group, a sec-butyl group, a tert-butyl group, a pentyl group, and a hexyl group. The number of carbon atoms included in the alkyl group is preferably 1 to 4, is more preferably 1 or 2, and is further preferably 1.

The group represented by Formula (W-1) is preferably a group selected from Formulae (W-1-1) to (W-1-8) below which may be optionally substituted with one or more substituents $L^W$.

[Chem. 7]

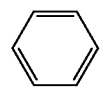 (W-1-1)

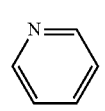 (W-1-2)

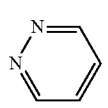 (W-1-3)

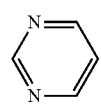 (W-1-4)

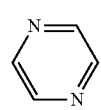 (W-1-5)

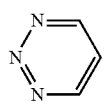 (W-1-6)

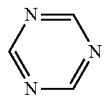 (W-1-7)

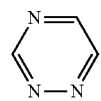 (W-1-8)

The above groups may have a bond at any position.

The group represented by Formula (W-7) is preferably a group selected from Formulae (W-7-1) to (W-7-7) below which may be optionally substituted with one or more substituents $L^W$.

[Chem. 8]

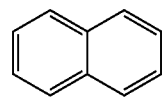 (W-7-1)

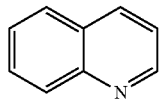 (W-7-2)

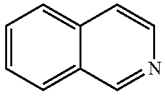 (W-7-3)

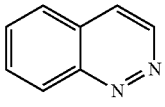 (W-7-4)

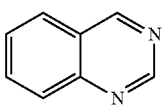 (W-7-5)

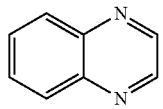 (W-7-6)

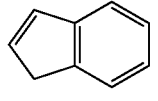 (W-7-7)

The above groups may have a bond at any position.

The group represented by Formula (W-10) is preferably a group selected from Formulae (W-10-1) to (W-10-8) below which may be optionally substituted with one or more substituents $L^W$,

[Chem. 9]

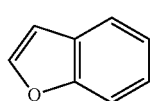 (W-10-1)

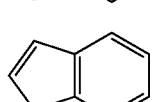 (W-10-2)

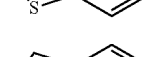 (W-10-3)

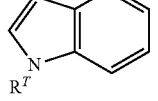 (W-10-4)

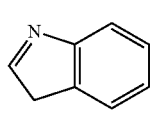 (W-10-5)

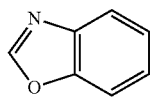 (W-10-6)

(W-10-7)
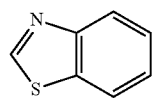

(W-10-8)
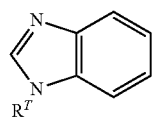

(in Formulae (W-10-1) to (W-10-8), $R^T$ represents a hydrogen atom or an alkyl group having 1 to 6 carbon atoms, and the above groups may have a bond at any position).

The group represented by Formula (W-11) is preferably a group selected from Formulae (W-11-1) to (W-11-12) below which may be optionally substituted with one or more substituents $L^W$,

[Chem. 10]

(W-11-1)
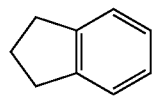

(W-11-2)
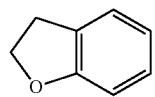

(W-11-3)
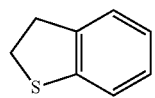

(W-11-4)
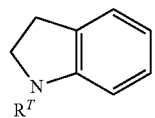

(W-11-5)
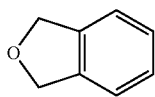

(W-11-6)
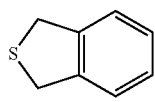

(W-11-7)
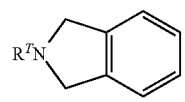

(W-11-8)
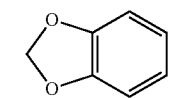

(W-11-9)
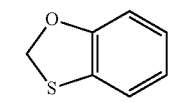

(W-11-10)
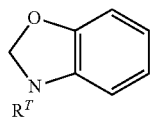

(W-11-11)
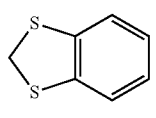

(W-11-12)
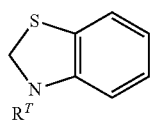

(in Formulae (W-11-1) to (W-11-12), $R^T$ represents a hydrogen atom or an alkyl group having 1 to 6 carbon atoms, and the above groups may have a bond at any position).

The group represented by Formula (W-13) is preferably a group selected from Formulae (W-13-1) to (W-13-19) below which may be optionally substituted with one or more substituents $L^W$,

[Chem. 11]

(W-13-1)
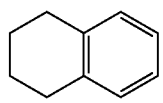

(W-13-2)
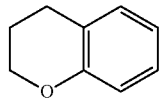

(W-13-3)
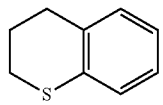

(W-13-4)
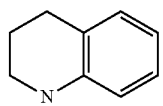

(W-13-5)
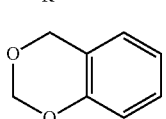

(W-13-6)
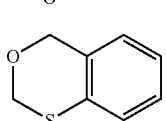

(W-13-7)
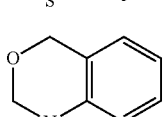

(W-13-8)
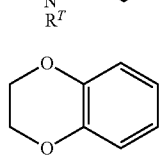

-continued (W-13-9) 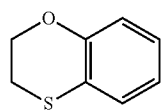

(W-13-10) 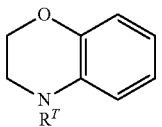

(W-13-11) 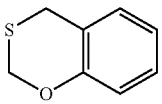

(W-13-12) 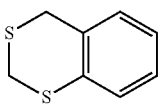

(W-13-13) 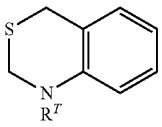

(W-13-14) 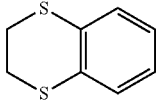

(W-13-15) 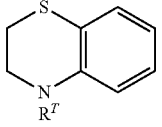

(W-13-16) 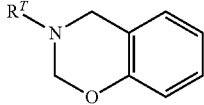

(W-13-17) 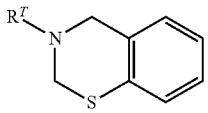

(W-13-18) 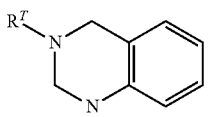

(W-13-19) 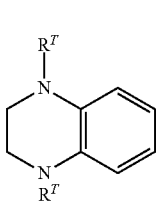

(in Formulae (W-13-1) to (W-13-19), $R^T$ represents a hydrogen atom or an alkyl group having 1 to 6 carbon atoms, and the above groups may have a bond at any position).

The group represented by Formula (W-14) is preferably a group selected from Formulae (W-14-1) to (W-14-10) below which may be optionally substituted with one or more substituents $L^W$,

[Chem. 12]

(W-14-1) 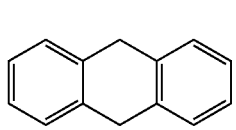

(W-14-2) 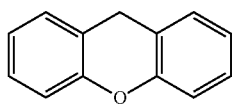

(W-14-3) 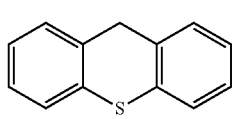

(W-14-4) 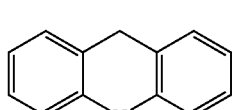

(W-14-5) 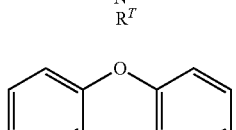

(W-14-6) 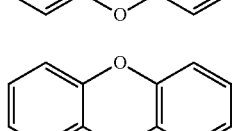

(W-14-7) 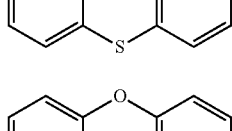

(W-14-8) 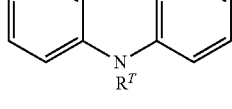

(W-14-9) 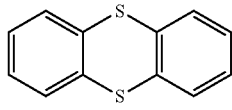

(W-14-10) 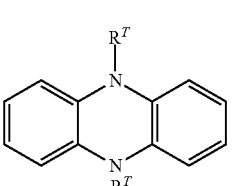

(in Formulae (W-14-1) to (W-14-10), $R^T$ represents a hydrogen atom or an alkyl group having 1 to 6 carbon atoms, and the above groups may have a bond at any position).

The group represented by Formula (W-15) is preferably a group selected from Formulae (W-15-1) to (W-15-4) below which may be optionally substituted with one or more substituents $L^W$,

[Chem. 13]

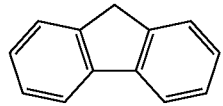
(W-15-1)

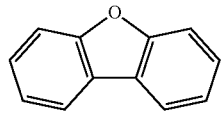
(W-15-2)

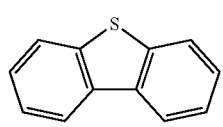
(W-15-3)

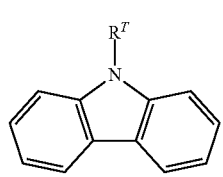
(W-15-4)

(in Formulae (W-15-1) to (W-15-4), $R^T$ represents a hydrogen atom or an alkyl group having 1 to 6 carbon atoms, and the above groups may have a bond at any position).

The group represented by Formula (W-16) is preferably a group selected from Formulae (W-16-1) to (W-16-16) below which may be optionally substituted with one or more substituents $L^W$,

[Chem. 14]

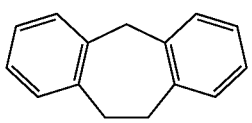
(W-16-1)

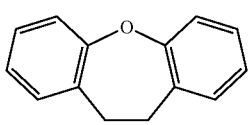
(W-16-2)

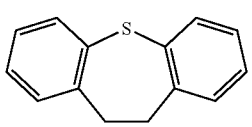
(W-16-3)

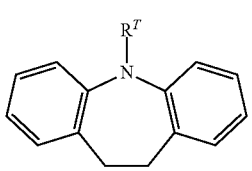
(W-16-4)

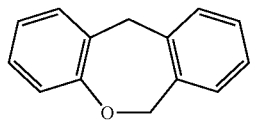
(W-16-5)

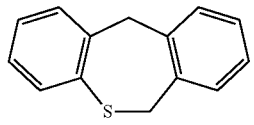
(W-16-6)

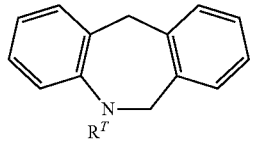
(W-16-7)

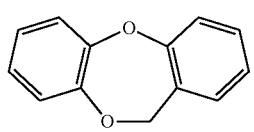
(W-16-8)

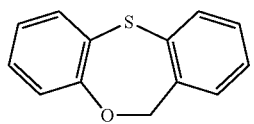
(W-16-9)

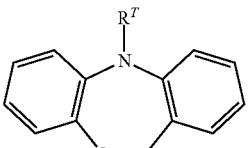
(W-16-10)

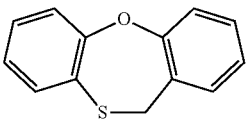
(W-16-11)

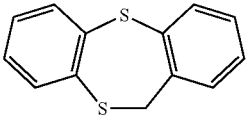
(W-16-12)

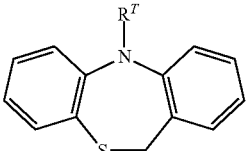
(W-16-13)

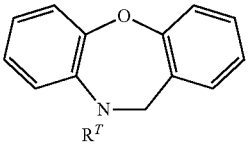
(W-16-14)

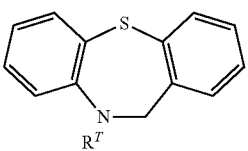
(W-16-15)

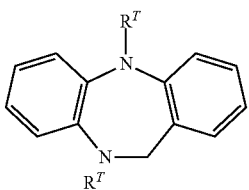
(W-16-16)

(in Formulae (W-16-1) to (W-16-16), $R^T$ represents a hydrogen atom or an alkyl group having 1 to 6 carbon atoms, and the above groups may have a bond at any position).

The group represented by Formula (W-17) is preferably a group selected from Formulae (W-17-1) to (W-17-4) below which may be optionally substituted with one or more substituents $L^W$,

[Chem. 15]

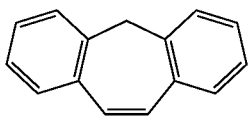
(W-17-1)

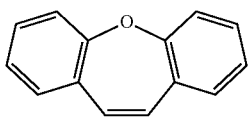
(W-17-2)

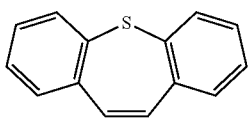
(W-17-3)

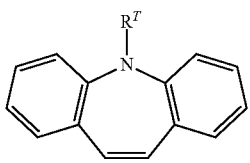
(W-17-4)

(in Formulae (W-17-1) to (W-17-4), $R^T$ represents a hydrogen atom or an alkyl group having 1 to 6 carbon atoms, and the above groups may have a bond at any position).

The group represented by Formula (W-18) is preferably a group selected from Formulae (W-18-1) to (W-18-6) below which may be optionally substituted with one or more substituents $L^W$,

[Chem. 16]

(W-18-1)

(W-18-2)

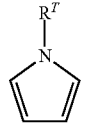
(W-18-3)

(W-18-4)

(W-18-5)

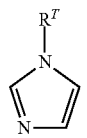
(W-18-6)

(in Formulae (W-18-1) to (W-18-6), $R^T$ represents a hydrogen atom or an alkyl group having 1 to 6 carbon atoms, and the above groups may have a bond at any position).

The group represented by Formula (W-19) is preferably a group selected from Formulae (W-19-1) to (W-19-6) below which may be optionally substituted with one or more substituents $L^W$,

[Chem. 17]

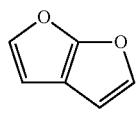
(W-19-1)

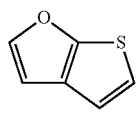
(W-19-2)

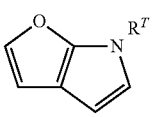
(W-19-3)

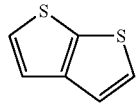
(W-19-4)

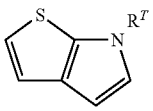
(W-19-5)

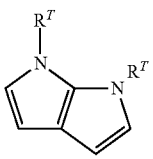
(W-19-6)

(in Formulae (W-19-1) to (W-19-6), $R^T$ represents a hydrogen atom or an alkyl group having 1 to 6 carbon atoms, and the above groups may have a bond at any position).

The group represented by Formula (W-20) is preferably a group selected from Formulae (W-20-1) to (W-20-9) below which may be optionally substituted with one or more substituents $L^W$,

[Chem. 18]

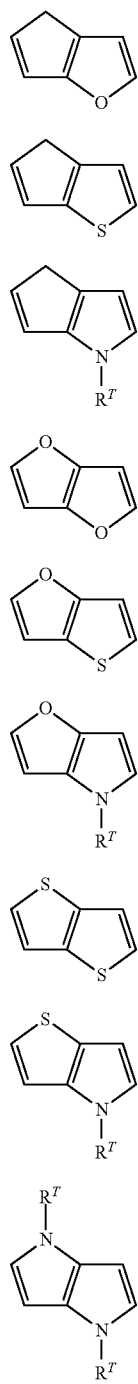

(in Formulae (W-20-1) to (W-20-9), $R^T$ represents a hydrogen atom or an alkyl group having 1 to 6 carbon atoms, and the above groups may have a bond at any position).

The aromatic group included in $W^1$ is more preferably a group selected from Formulae (W-1-1), (W-7-1), (W-7-2), (W-7-7), (W-8), (W-10-6), (W-10-7), (W-10-8), (W-11-8), (W-11-9), (W-11-10), (W-11-11), and (W-11-12) which may be optionally substituted with one or more substituents $L^W$ and is particularly preferably a group selected from Formulae (W-1-1), (W-7-1), (W-7-2), (W-7-7), (W-10-6), (W-10-7), and (W-10-8) which may be optionally substituted with one or more substituents $L^W$. It is particularly preferable that $W^1$ represent a group selected from Formulae (W-a-1) to (W-a-6) below,

[Chem. 19]

(W-a-1)

(W-a-2)

(W-a-3)

(W-a-4)

(W-a-5)

(W-a-6)

(in Formulae (W-a-1) to (W-a-6), r represents an integer of 0 to 5, s represents an integer of 0 to 4, and t represents an integer of 0 to 3).

<$Y^1$>

$Y^1$ represents a hydrogen atom, an alkyl group having 1 to 20 carbon atoms, an alkenyl group having 2 to 20 carbon atoms, a cycloalkyl group having 3 to 12 carbon atoms, an organic group having 2 to 30 carbon atoms which includes an aromatic hydrocarbon group (a carbon atom included in the aromatic hydrocarbon group may be replaced with a hetero atom), or —$(Z^5$-$A^3)$ q-$Z^6$—$Sp^3$-$P^3$. The alkyl group, the alkenyl group, and the cycloalkyl group may be optionally substituted with one or more substituents. One —$CH_2$— group included in the alkyl group or two or more —$CH_2$— groups that are included in the alkyl group and not adjacent to one another may be each independently replaced with —O—, —S—, —CO—, —COO—, —OCO—, —CO—

—S—, —S—CO—, —SO$_2$—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. $Z^5$ and $Z^6$ represent the same things as $Z^1$ to $Z^4$, $A^3$ represents the same thing as $A^1$ and $A^2$, $Sp^3$ represents the same thing as $Sp^1$ and $Sp^2$, $P^3$ represents the same thing as $P^1$ and $P^2$, and q represents an integer of 0 to 4. The $Y^1$ group may be bonded to the $W^1$ group described above.

In the case where primary importance is placed on the reversed-dispersion property and liquid crystal property of the polymerizable compound, $Y^1$ preferably represents a hydrogen atom.

In the case where primary importance is placed on the resistance of the compound to degradation which may occur when the compound is dissolved in an organic solvent and then stored over a prolonged period of time, the resistance of the compound to degradation which may occur when the compound is added to a composition and then stored over a prolonged period of time, and the consistency in the phase retardation of a film produced using the compound, $Y^1$ preferably represents a linear or branched alkyl group having 1 to 20 carbon atoms in which a hydrogen atom may be replaced with a fluorine atom and one —CH$_2$— group or two or more —CH$_2$— groups that are not adjacent to one another may be each independently replaced with —O—, —CO—, —COO—, or —OCO— or a group represented by —($Z^5$-$A^3$)q-$Z^6$—$Sp^3$-$P^3$. Among the above groups, $Y^1$ more preferably represents a linear alkyl group having 1 to 12 carbon atoms in which one —CH$_2$— group or two or more —CH$_2$— groups that are not adjacent to one another may be each independently replaced with —O— or a group represented by —($Z^5$-$A^3$)q-$Z^6$—$Sp^3$-$P^3$. The preferable structures of $Z^5$ and $Z^6$, $A^3$, and $P^3$ are the same as Z to $Z^4$, $A^1$ and $A^2$, and $P^1$ and $P^2$, respectively. In order to reduce the cure shrinkage of a film prepared using the compound, $Sp^3$ preferably represents a spacer group and more preferably represents an alkylene group having 1 to 20 carbon atoms in which one —CH$_2$— group or two or more —CH$_2$— groups that are not adjacent to one another may be each independently replaced with —O—, —COO—, —OCO—, —OCO—O—, —CO—NH—, —NH—CO—, —CH=CH—, or —C≡C—. In consideration of ease of synthesis, $Sp^3$ further preferably represents an alkylene group having 1 to 20 carbon atoms in which one —CH$_2$— group or two or more —CH$_2$— groups that are not adjacent to one another may be each independently replaced with —O—, and q preferably represents an integer of 0 to 4, more preferably represents an integer of 0 to 2, further preferably represents 0 or 1, and particularly preferably represents 0. More specifically, in consideration of ease of synthesis, $Y^1$ more preferably represents a linear or branched alkyl group having 1 to 20 carbon atoms in which one —CH$_2$— group or two or more —CH$_2$— groups that are not adjacent to one another may be each independently replaced with —O— or a group represented by —$Z^{61}$—$Sp^{31}$-$P^{31}$ (where $P^{31}$ represents a group selected from Formulae (P-1) to (P-20); $Sp^{31}$ represents a linear alkylene group having 1 to 20 carbon atoms in which one —CH$_2$— group or two or more —CH$_2$— groups that are not adjacent to one another may be each independently replaced with —O—, —COO—, —OCO—, or —OCO—O—; and $Z^{61}$ represents —O—, —S—, —CO—, —COO—, —OCO—, —O—CO—O—, —CO—NH—, —NH—CO—, —CF$_2$O—, —OCF$_2$—, or a single bond). $Y^1$ further preferably represents a linear alkyl group having 1 to 12 carbon atoms in which one —CH$_2$— group or two or more —CH$_2$— groups that are not adjacent to one another may be each independently replaced with —O— or a group represented by -$Sp^{311}$-$P^{311}$ (where $P^{311}$ represents a group selected from Formulae (P-1) and (P-2); and $Sp^{311}$ represents a linear alkylene group having 1 to 10 carbon atoms in which one —CH$_2$— group or two or more —CH$_2$— groups that are not adjacent to one another may be each independently replaced with —O—).

In the case where primary importance is placed on the balance among the reversed-dispersion property, small anisotropy of refractive index, and liquid crystal property of the polymerizable compound, a compound selected from General Formulae (1-f-i) and (1-f-ii) below is preferable.

[Chem. 20]

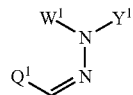

(1-f-i)

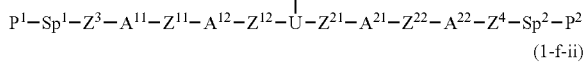

(1-f-ii)

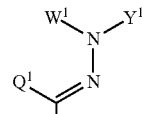

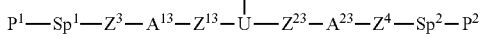

(in General Formulae (1-f-i) and (1-f-ii), $P^1$, $P^2$, $Sp^1$, $Sp^2$, $Z^3$, $Z^4$, U, $Q^1$, $W^1$, and $Y^1$ represent the same things as in General Formula (1); $A^{11}$, $A^{12}$, $A^{21}$, $A^{22}$, $A^{13}$, and $A^{23}$ represent a 1,4-cyclohexylene group; $Z^{11}$ and $Z^{22}$ each independently represent —OCH$_2$—, —CH$_2$O—, —COO—, —OCO—, or a single bond; and $Z^{12}$, $Z^{21}$, $Z^{13}$, and $Z^{23}$ each independently represent —OCH$_2$—, —CH$_2$O—, —COO—, or —OCO—).

In the case where primary importance is placed on the balance among reversed-dispersion property, large anisotropy of refractive index, and good liquid crystal property of a composition prepared using the compound, a compound selected from General Formulae (1-c-i) and (1-c-ii) is preferable,

[Chem. 21]

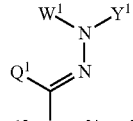

(1-c-i)

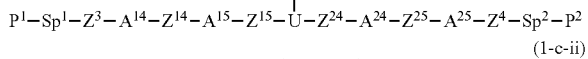

(1-c-ii)

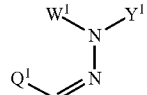

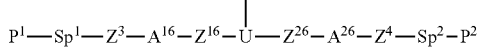

(in General Formulae (1-c-i) and (1-c-ii), $P^1$, $P^2$, $Sp^1$, $Sp^2$, $Z^3$, $Z^4$, U, $Q^1$, $W^1$, and $Y^1$ represent the same things as in General Formula (1); $A^{14}$, $A^{25}$, $A^{16}$, and $A^{26}$ each independently represent a 1,4-phenylene group which may be optionally substituted with one or more substituents $L^{11}$; $L^{11}$ represents a fluorine atom, a chlorine atom, or a linear or branched alkyl group having 1 to 20 carbon atoms in which one —CH$_2$— group or two or more —CH$_2$— groups that are not adjacent to one another may be each independently replaced with —O—, —CO—, —COO—, or —OCO—, and a hydrogen atom included in the alkyl group may be replaced with a fluorine atom; in the case where plural $L^{11}$ substituents are present in the compound, they may be identical to or different from one another; $A^{15}$ and $A^{24}$ represent a 1,4-cyclohexylene group; $Z^{14}$ and $Z^{25}$ each independently represent —$OCH_2$—, —$CH_2O$—, —COO—, —OCO—, or a single bond; $Z^{15}$, $Z^{24}$, $Z^{16}$, and $Z^{26}$ each independently represent —$OCH_2$—, —$CH_2O$—, —COO—$CH_2CH_2$—, —$CH_2CH_2$—OCO—, —COO—, or —OCO—; and at least one of $Z^{15}$ and $Z^{24}$ and at least one of $Z^{16}$ and $Z^{26}$ represent a group selected from —$OCH_2$—, —$CH_2O$—, —COO—$CH_2CH_2$—, and —$CH_2CH_2$—OCO—). The compound represented by General Formula (1-cm) below is more preferable,

[Chem. 22]

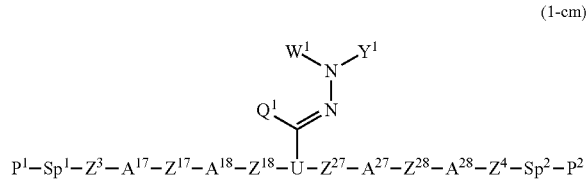

$$P^1-Sp^1-Z^3-A^{17}-Z^{17}-A^{18}-Z^{18}-U-Z^{27}-A^{27}-Z^{28}-A^{28}-Z^4-Sp^2-P^2$$

(1-cm)

(in General Formula (1-cm), $P^1$, $P^2$, $Sp^1$, $Sp^2$, $Z^3$, $Z^4$, U, $Q^1$, $W^1$, and $Y^1$ represent the same things as in General Formula (1); $A^{17}$ and $A^{28}$ each independently represent a 1,4-phenylene group which may be optionally substituted with one or more substituents $L^{11}$; $L^{11}$ represents a fluorine atom, a chlorine atom, or a linear or branched alkyl group having 1 to 20 carbon atoms in which one —$CH_2$— group or two or more —$CH_2$— groups that are not adjacent to one another may be each independently replaced with —O—, —CO—, —COO—, or —OCO—, and a hydrogen atom included in the alkyl group may be replaced with a fluorine atom; in the case where plural $L^{11}$ substituents are present in the compound, they may be identical to or different from one another; $A^{18}$ and $A^{27}$ represent a 1,4-cyclohexylene group; $Z^{17}$ and $Z^{28}$ each independently represent —$OCH_2$—, —$CH_2O$—, —COO—, —OCO—, or a single bond; and $Z^{18}$ and $Z^{21}$ each independently represent —$OCH_2$— or —$CH_2O$—).

In the case where primary importance is placed on the balance among reversed-dispersion property, large anisotropy of refractive index, and good liquid crystal property of a composition that includes the compound, the resistance of the compound to degradation which may occur when the compound is dissolved in an organic solvent and then stored over a prolonged period of time, the resistance of the compound to degradation which may occur when the compound is added to a composition and then stored over a prolonged period of time, and the consistency in the phase retardation of a film produced using the compound, the compound represented by General Formula (1-cmn) below is preferable,

[Chem. 23]

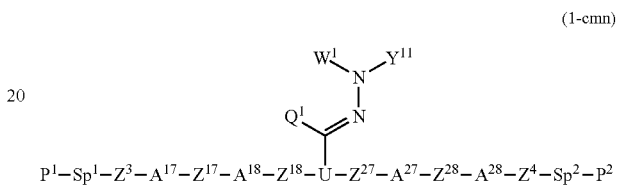

$$P^1-Sp^1-Z^3-A^{17}-Z^{17}-A^{18}-Z^{18}-U-Z^{27}-A^{27}-Z^{28}-A^{28}-Z^4-Sp^2-P^2$$

(1-cmn)

(in General Formula (1-cmn), $P^1$, $P^2$, $Sp^1$, $Sp^2$, $Z^3$, $Z^4$, U, $Q^1$, and $W^1$ represent the same things as in General Formula (1); $A^{17}$, $A^{28}$, $A^{18}$, $A^{27}$, $Z^{17}$, $Z^{28}$, $Z^{19}$, and $Z^{27}$ represent the same things as in General Formula (1-cm); and $Y^{11}$ represents a group selected from a linear or branched alkyl group having 1 to 20 carbon atoms in which one —$CH_2$— group or two or more —$CH_2$— groups that are not adjacent to one another may be each independently replaced with —O— and a group represented by -$Sp^{312}$-$P^{312}$ (where $P^{312}$ represents a group selected from Formulae (P-1) to (P-20); and $Sp^{312}$ represents a linear alkylene group having 1 to 20 carbon atoms in which one —$CH_2$— group or two or more —$CH_2$— groups that are not adjacent to one another may be each independently replaced with —O—, —COO—, —OCO—, or —OCO—O—)).

Specifically, the compound represented by General Formula (1) is preferably selected from the compounds represented by Formulae (1-1) to (1-172) below.

[Chem. 24]

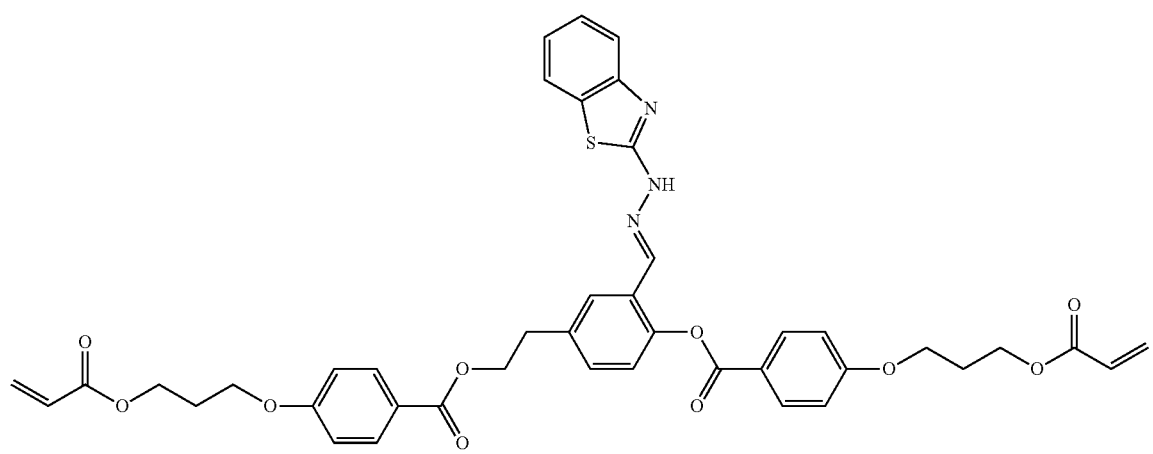

(1-1)

-continued
(1-2)
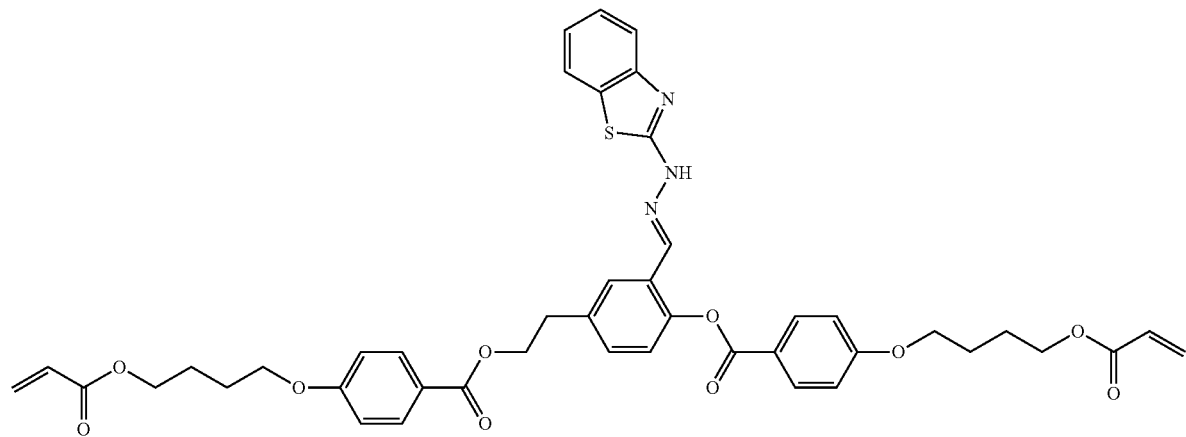
(1-3)
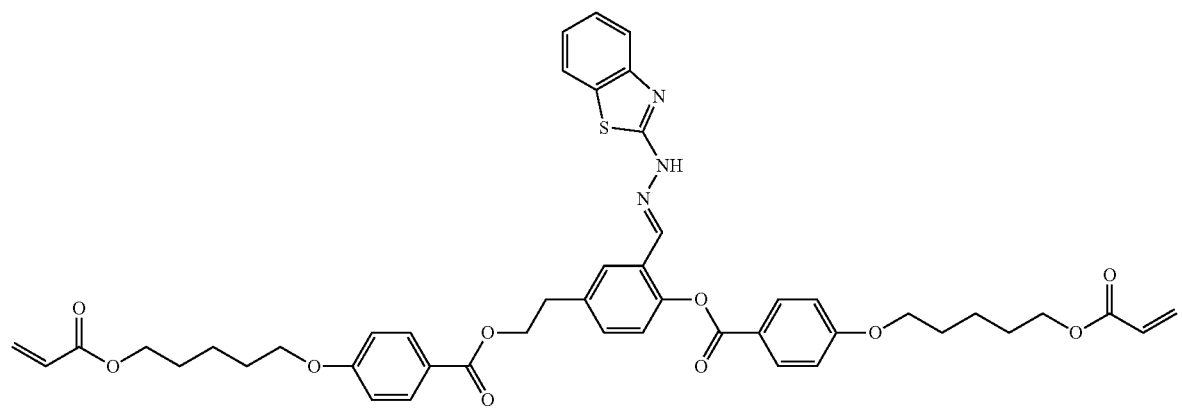
(1-4)
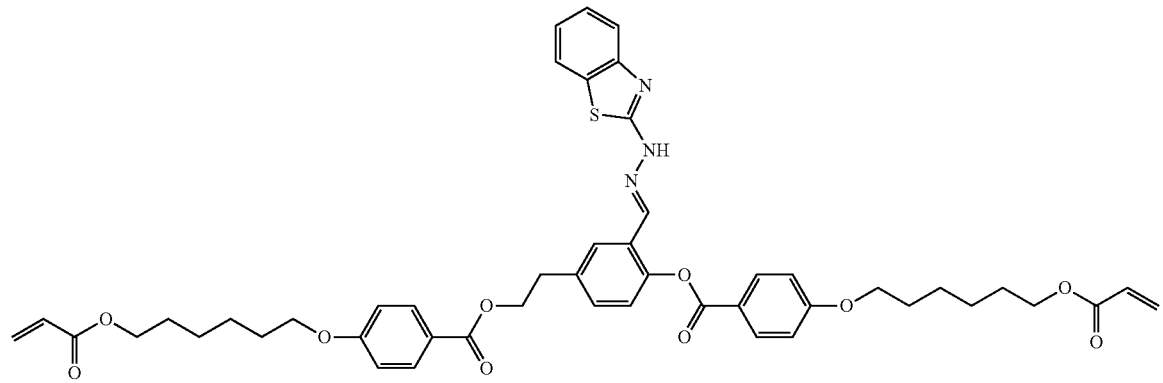

[Chem. 25]
(1-5)
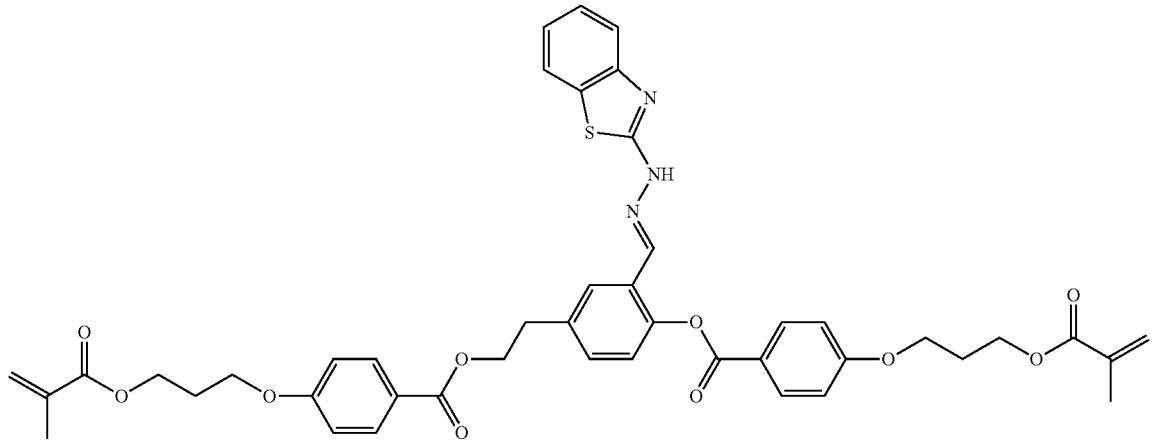
(1-6)
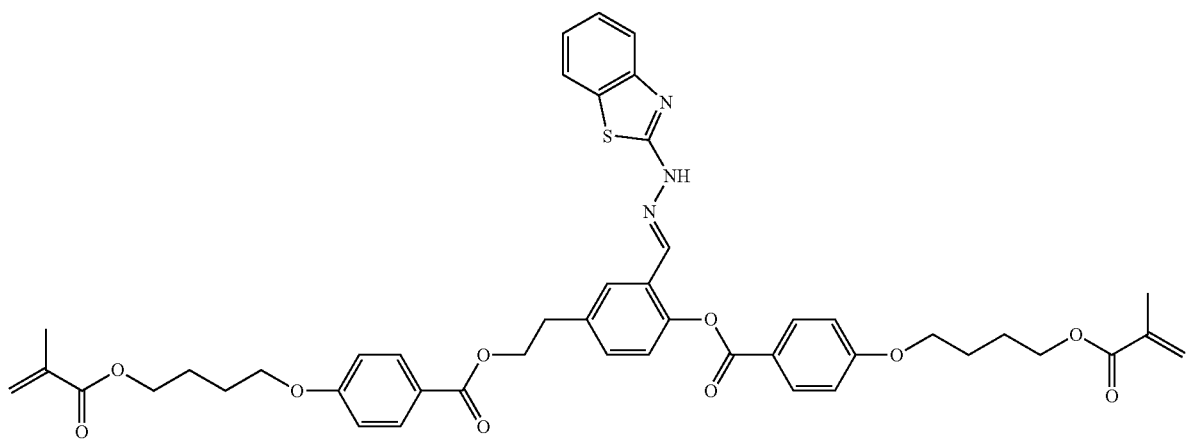
(1-7)
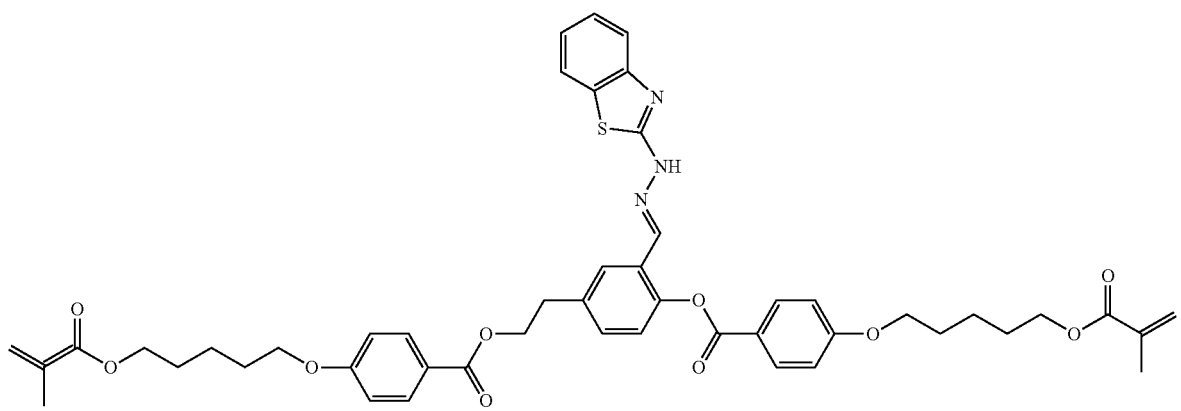

(1-8)
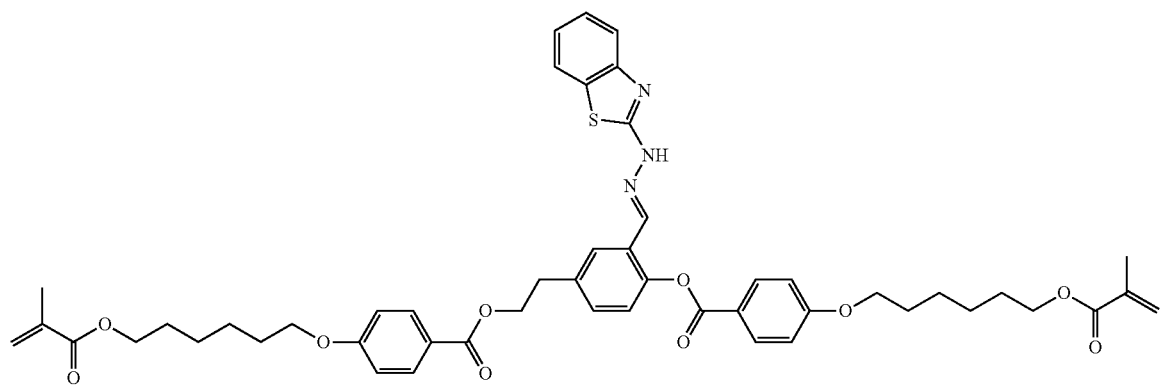
[Chem. 26]
(1-9)
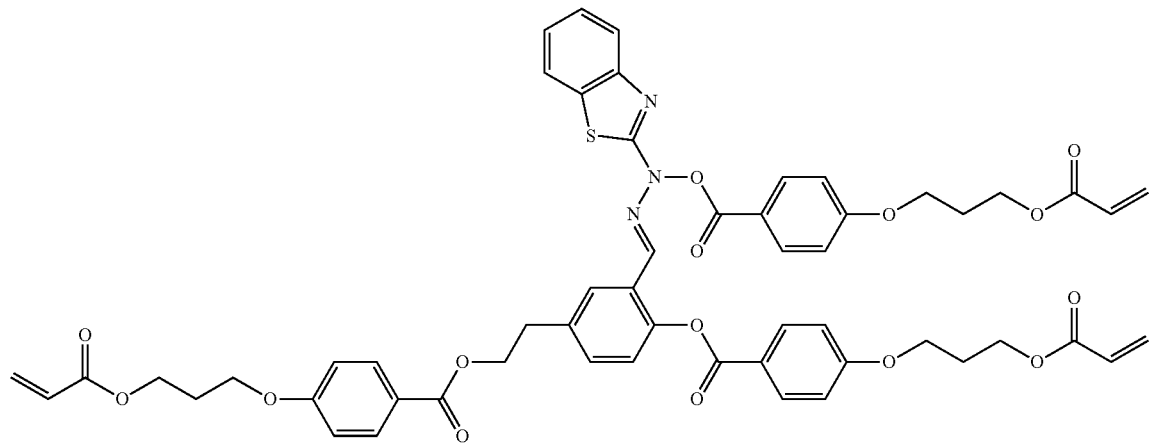
(1-10)
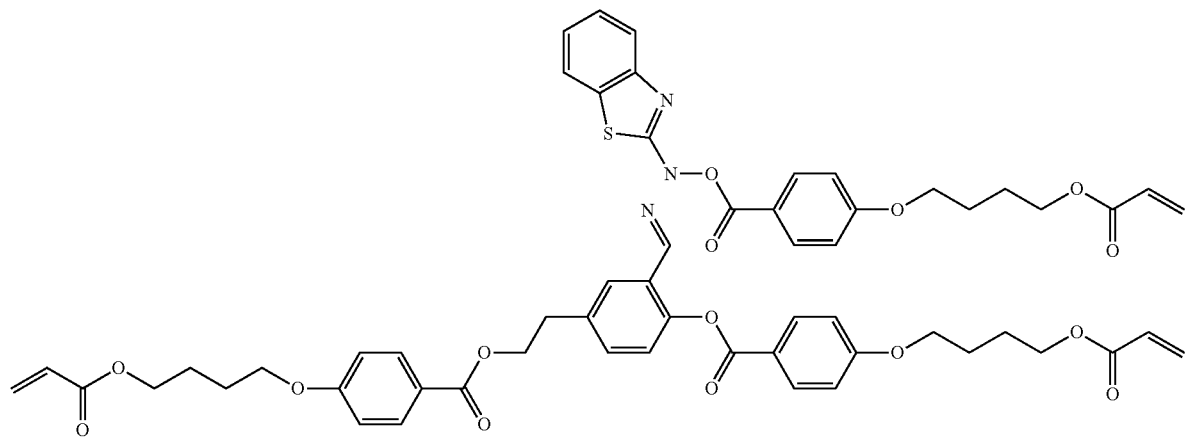

(1-11)
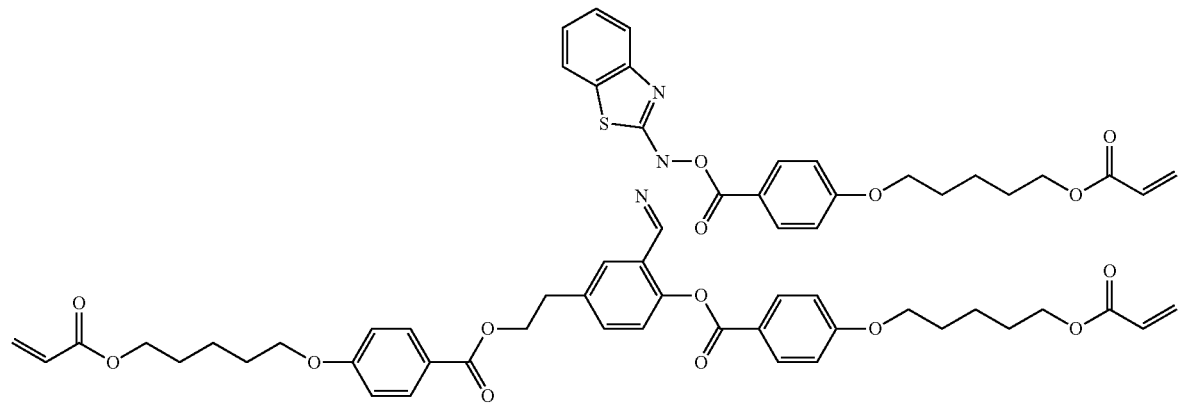
(1-12)
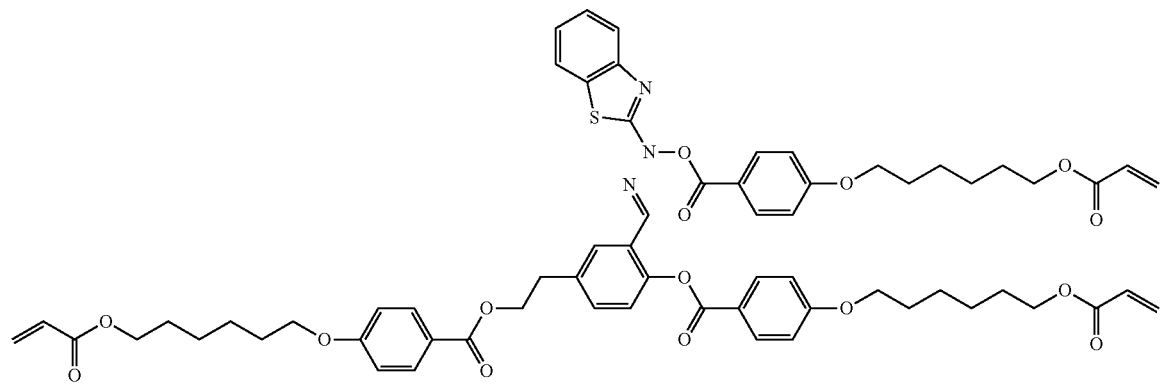
[Chem. 27]
(1-13)
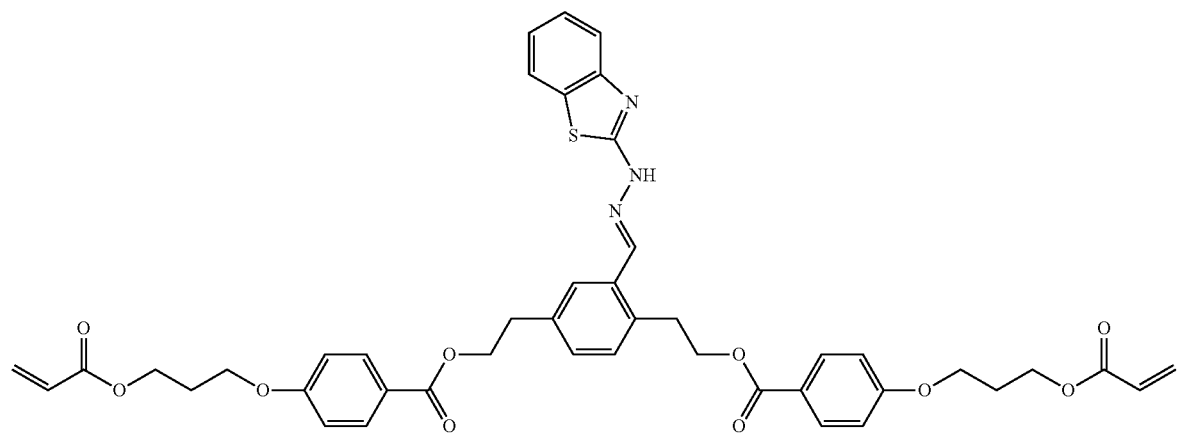

-continued
(1-14)
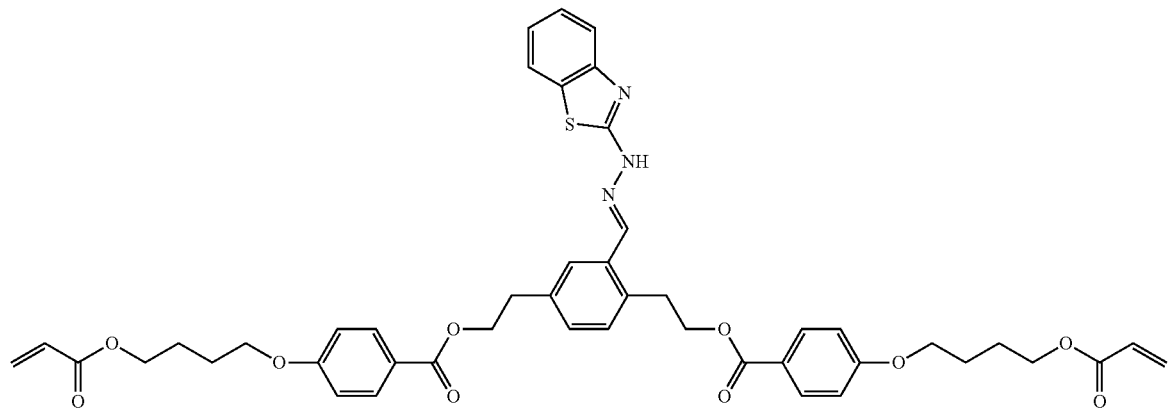
(1-15)
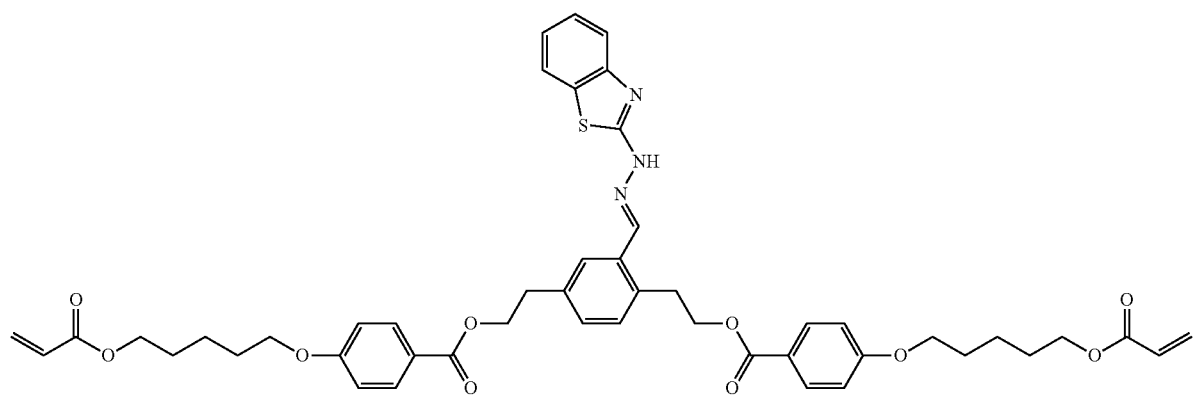
(1-16)
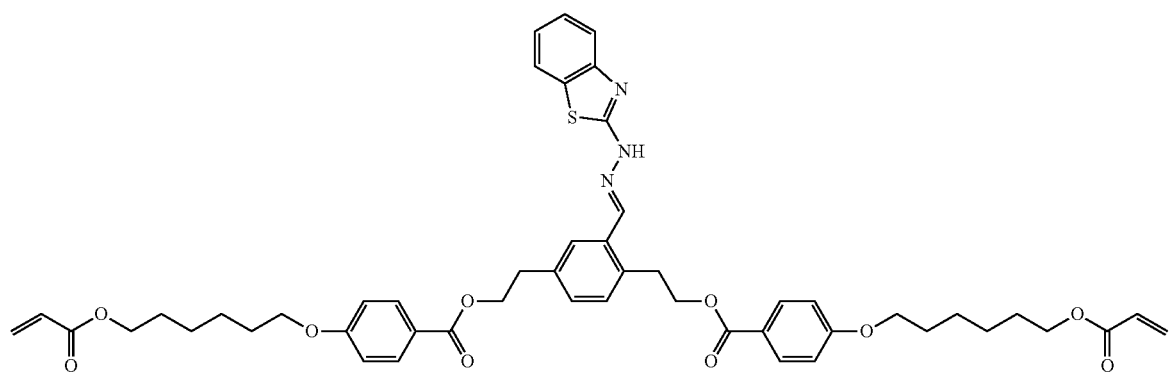
[Chem. 28]
(1-17)
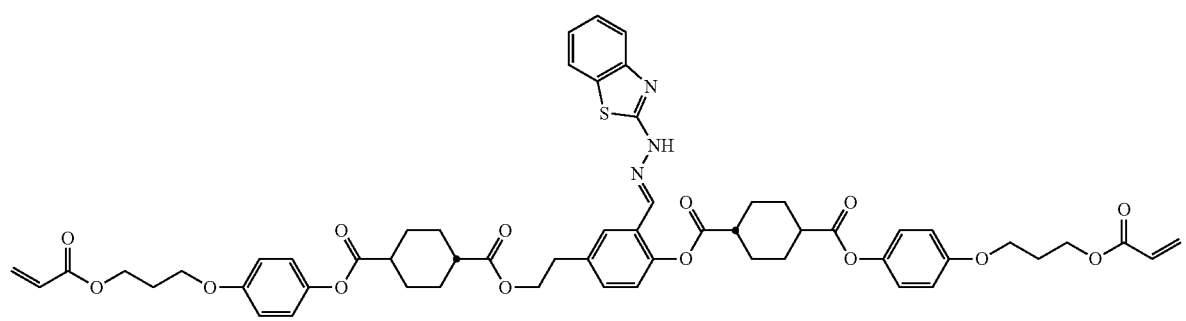

(1-18)
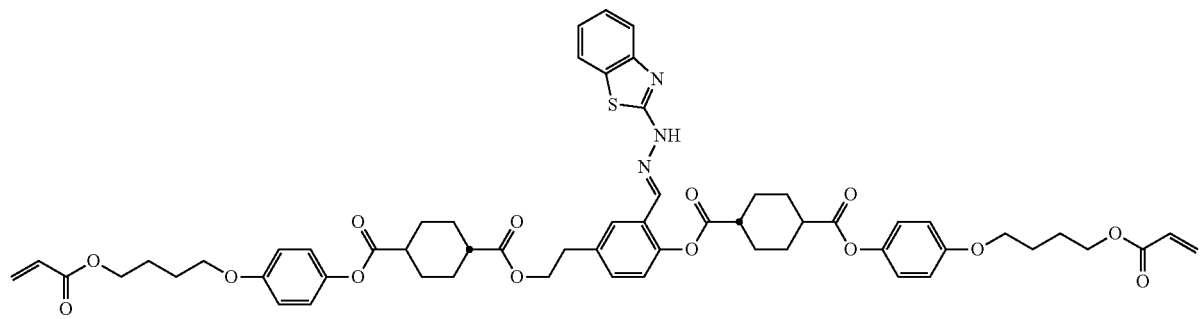
(1-19)
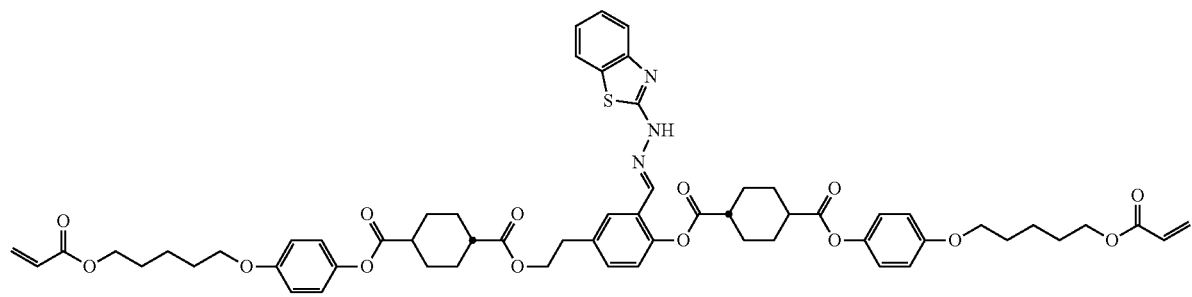
(1-20)
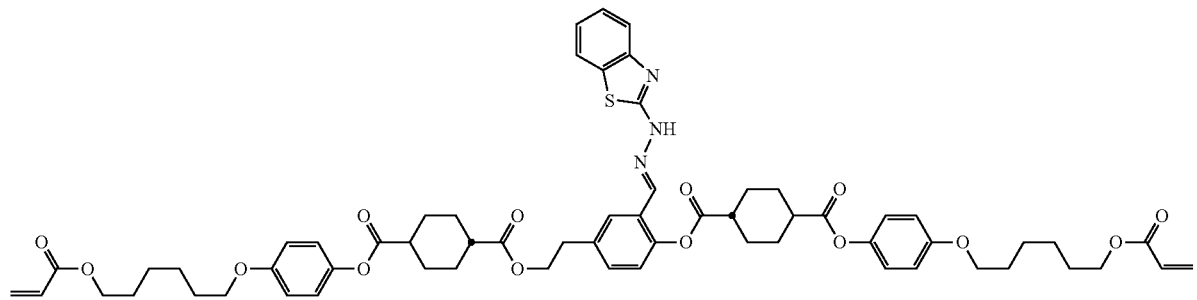
[Chem. 29]
(1-21)
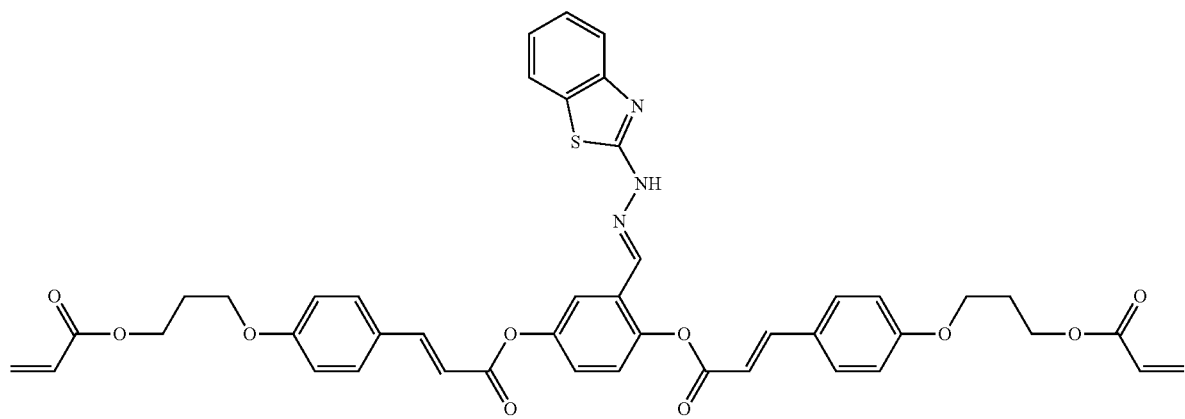

(1-22)
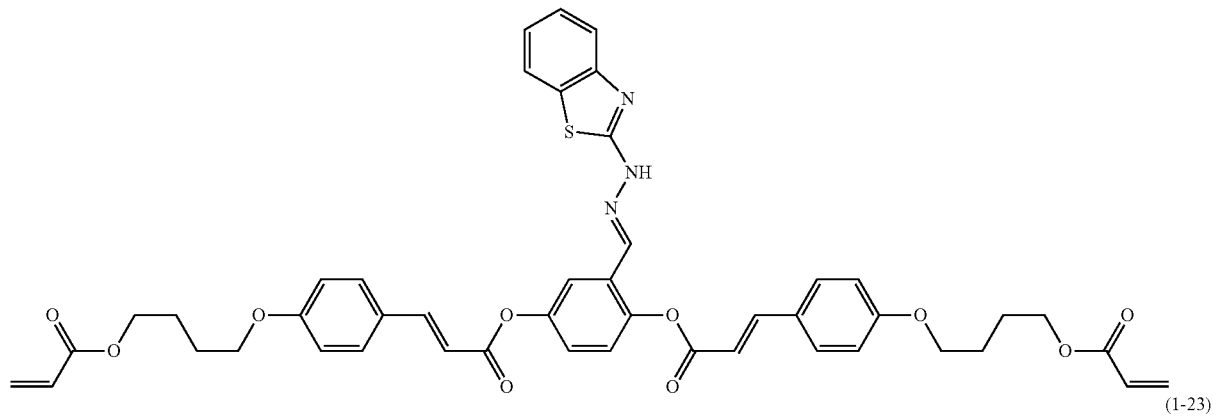
(1-23)
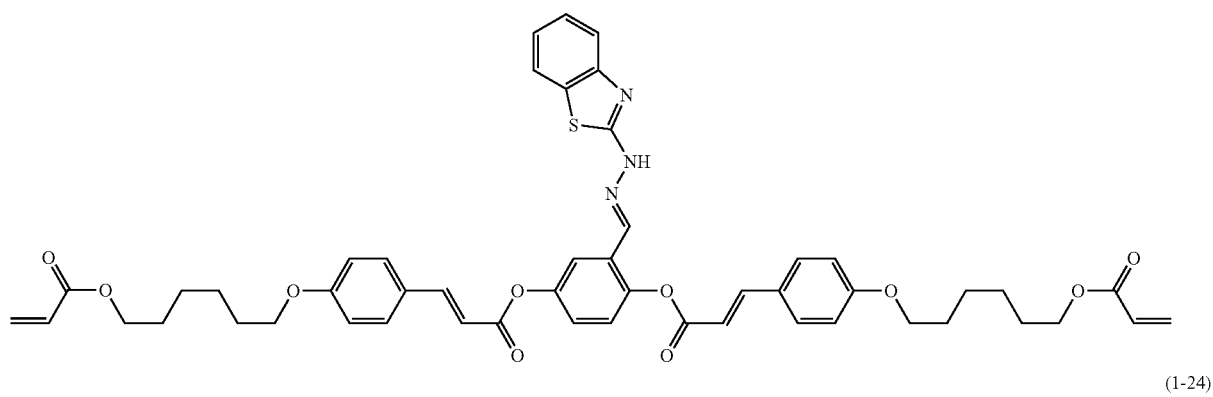
(1-24)
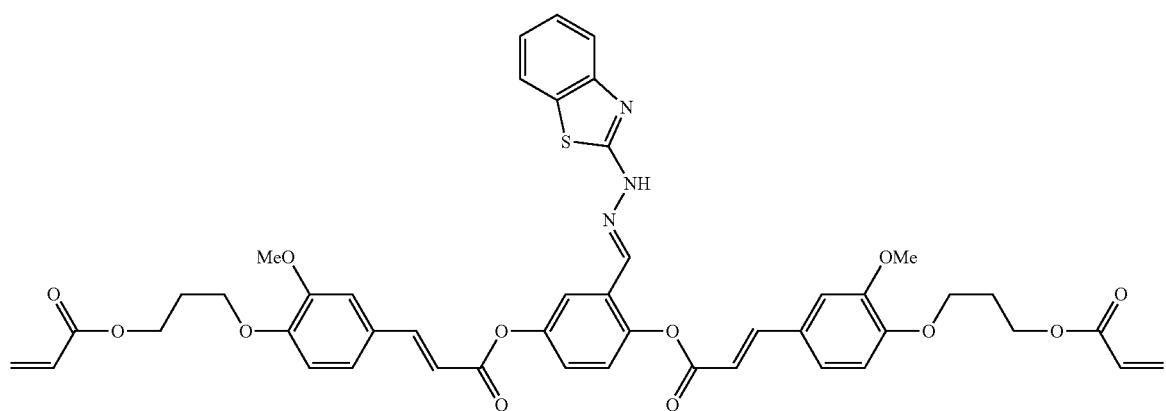
[Chem. 30]
(1-25)
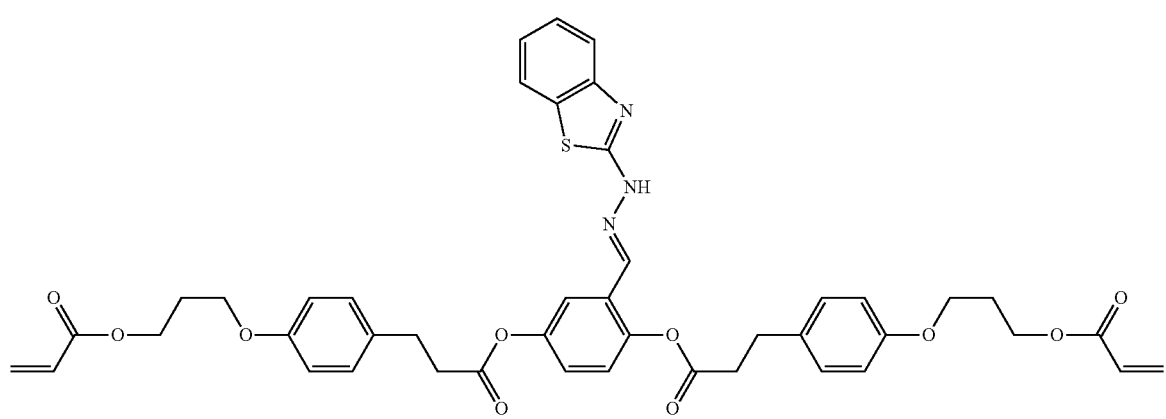

-continued
(1-26)
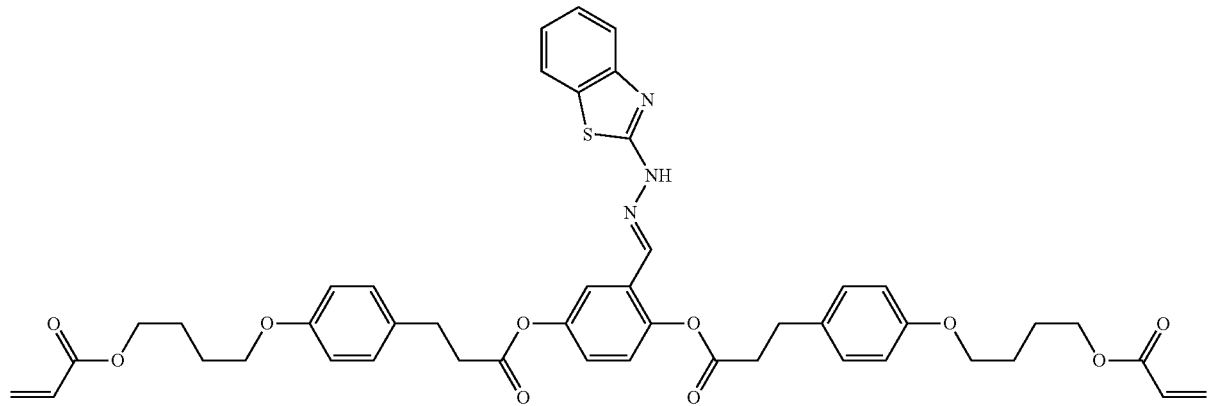
(1-27)
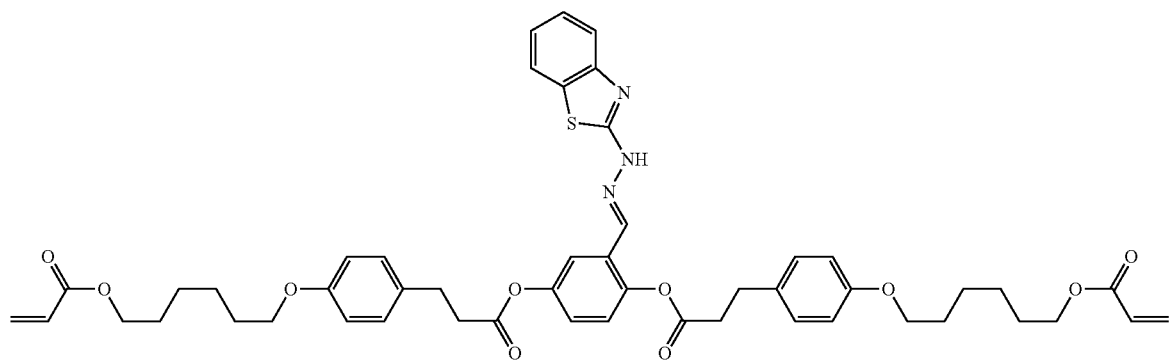
(1-28)
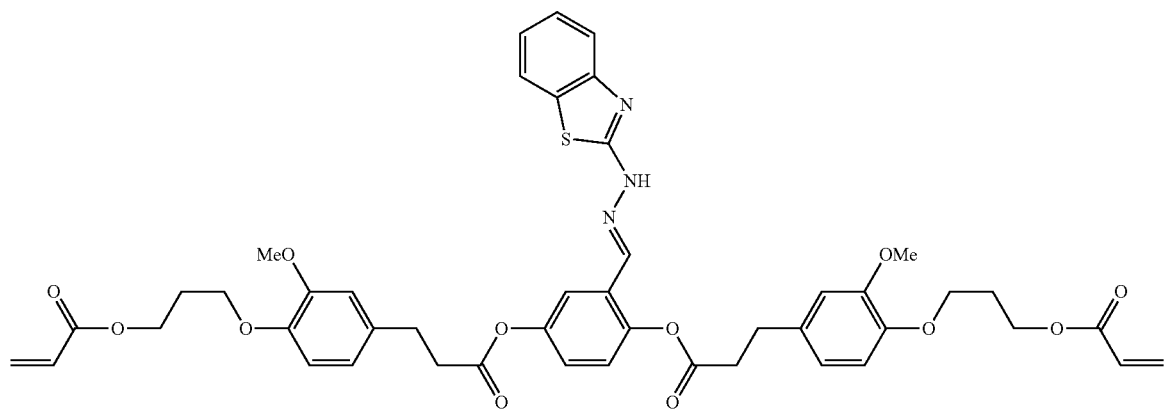

-continued
(1-29)
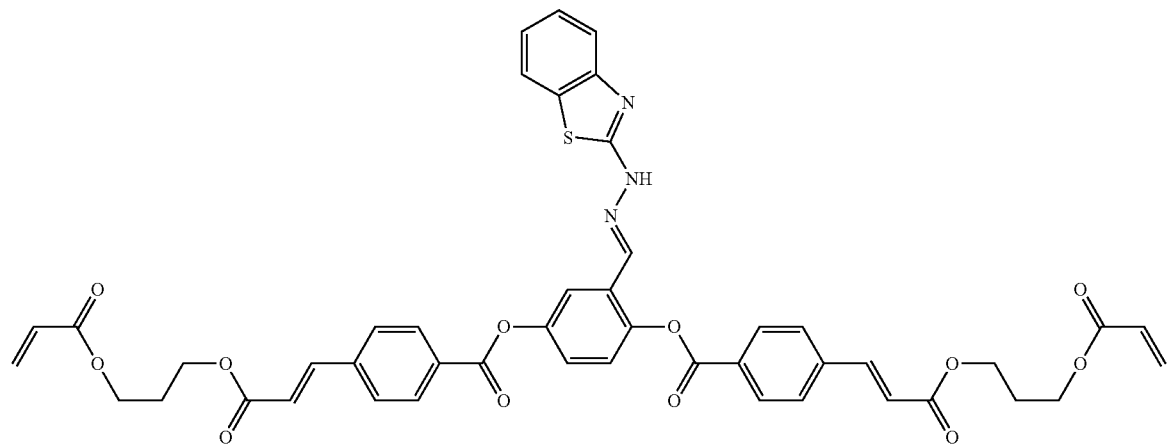
(1-30)
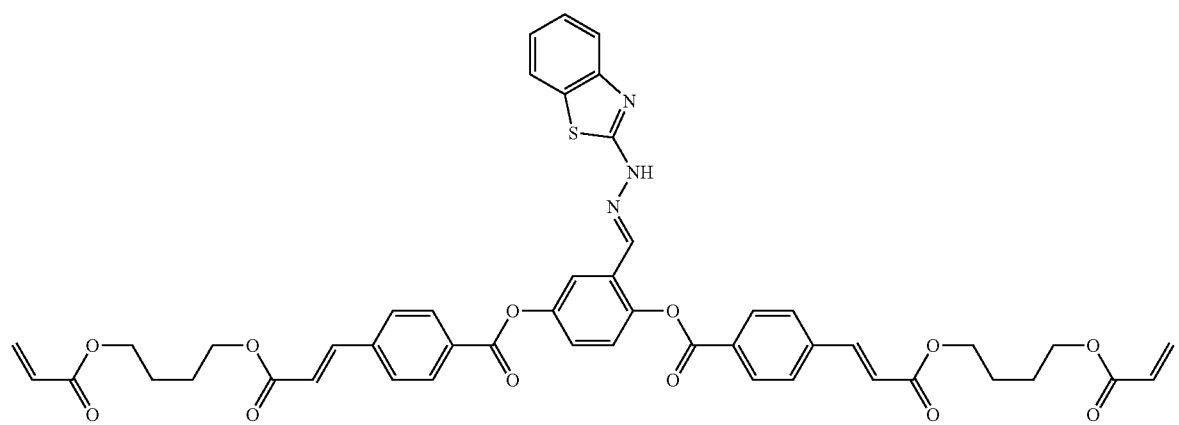
(1-31)
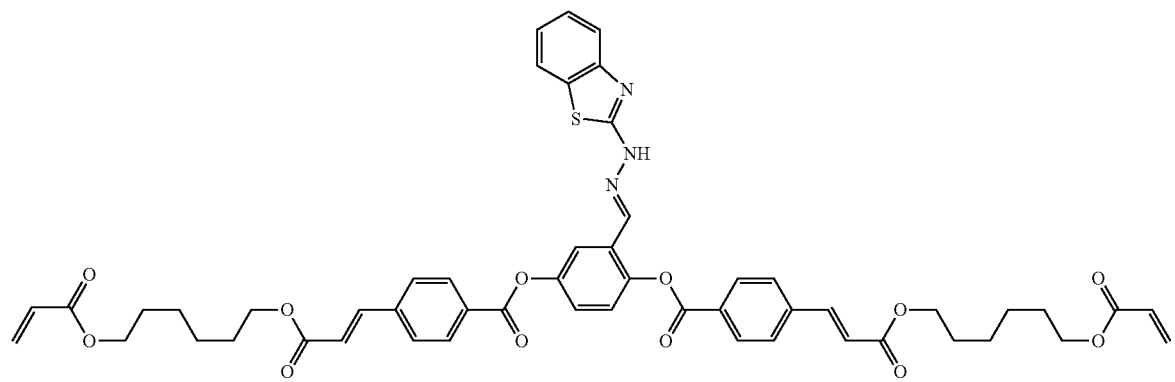

-continued
(1-32)
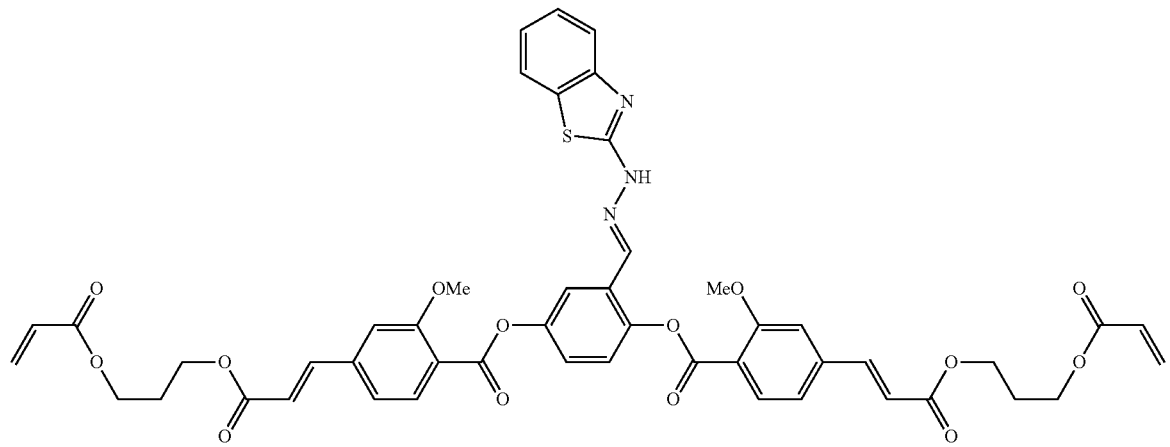
[Chem. 32]
(1-33)
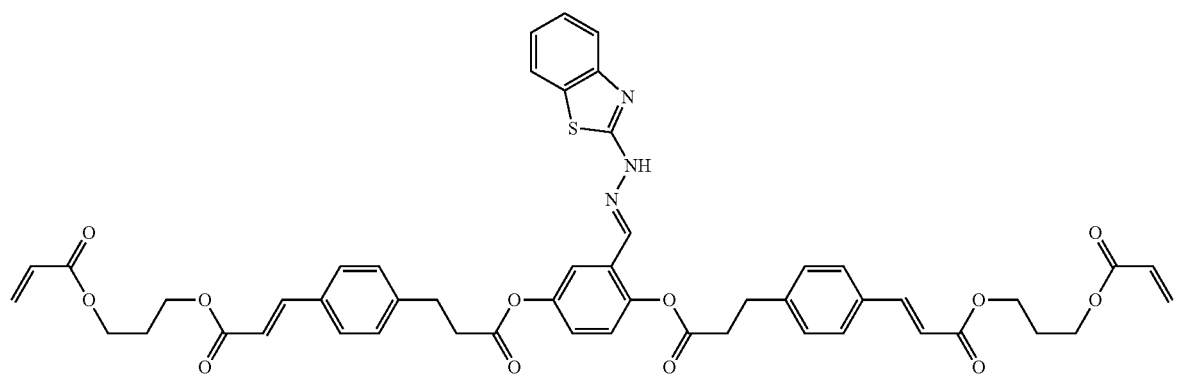
(1-34)
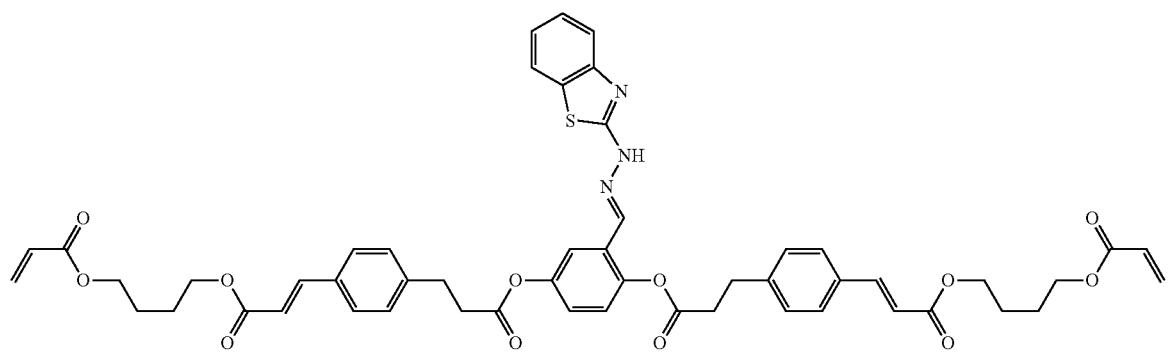
(1-35)
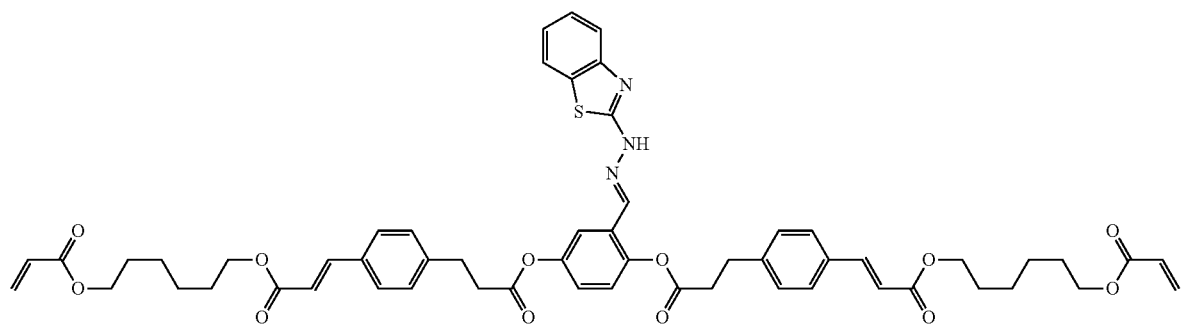

[Chem. 33]
(1-36)
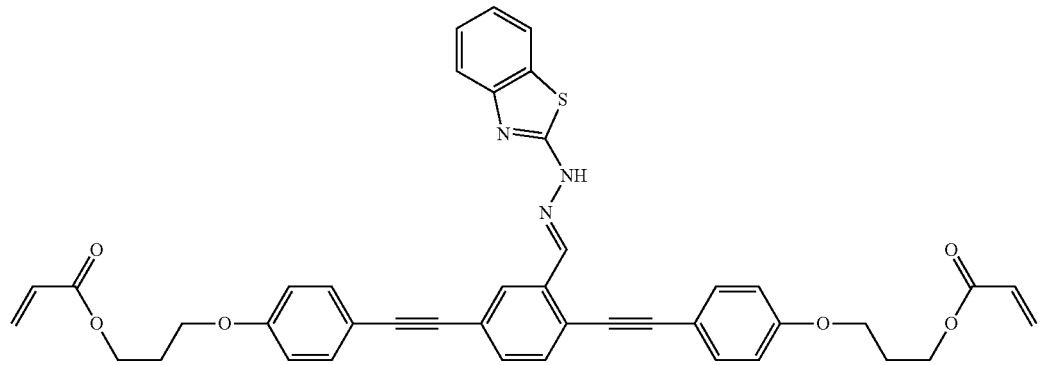
(1-37)
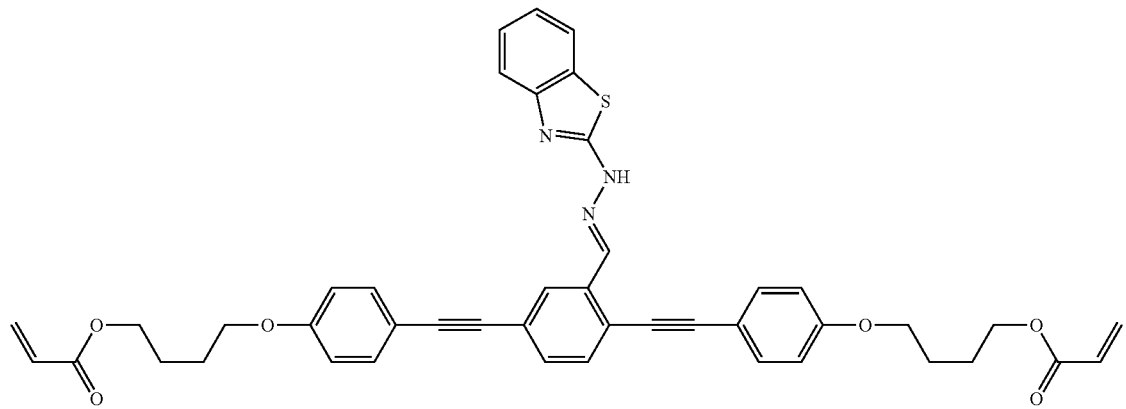
(1-38)
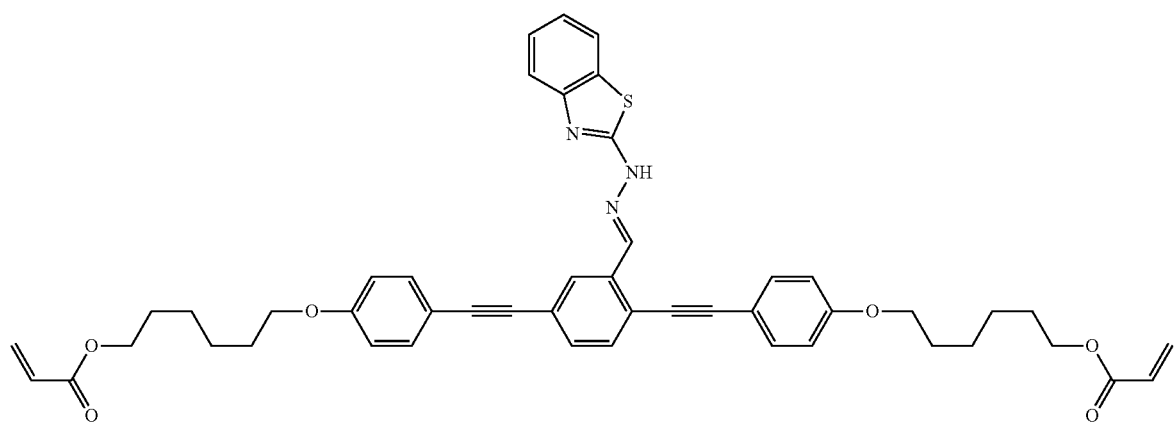

[Chem. 34]
(1-39)
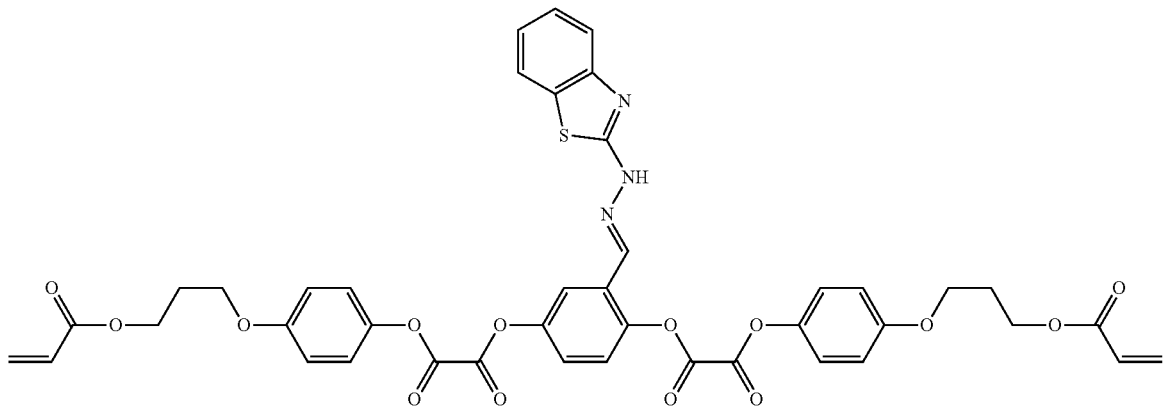
(1-40)
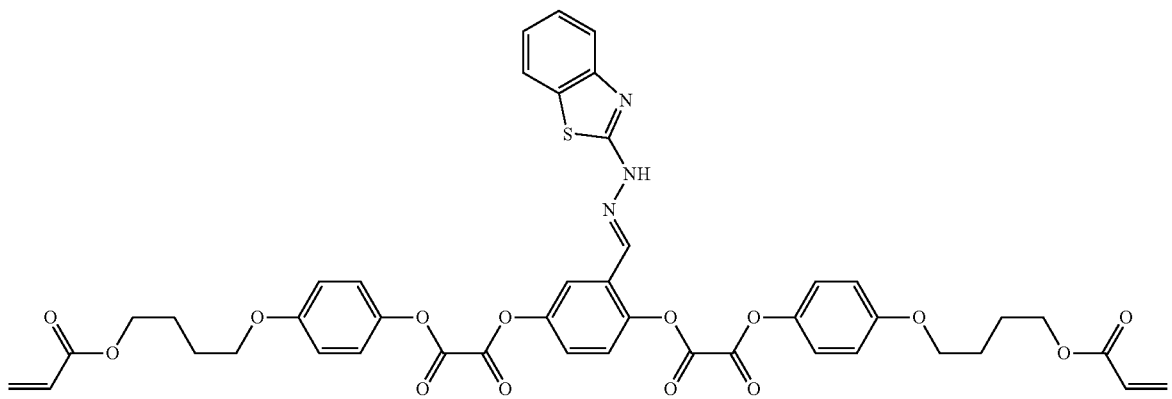
(1-41)
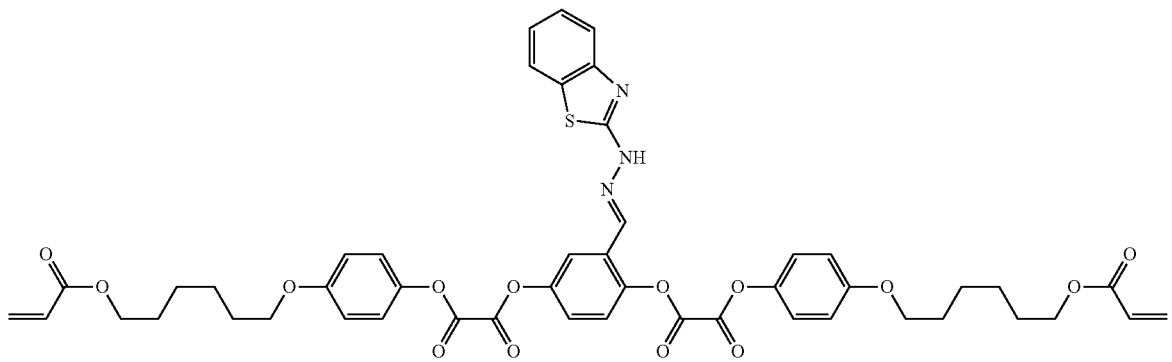

(1-42)
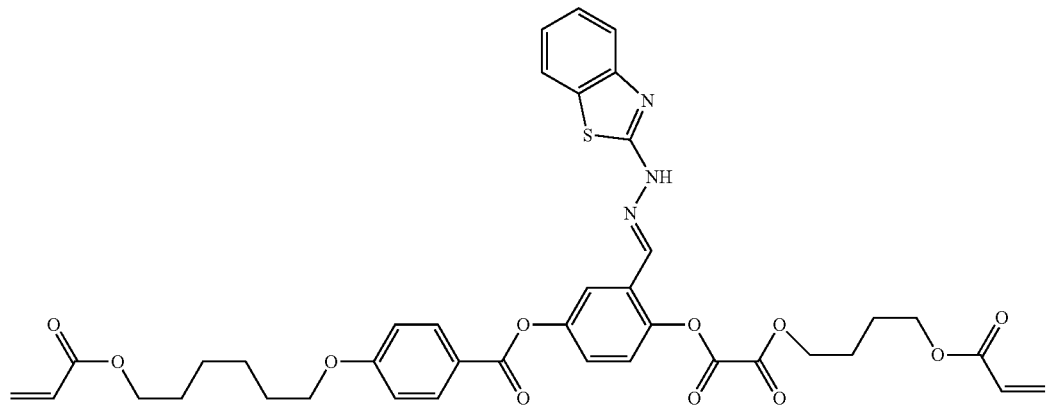
[Chem. 35]
(1-43)
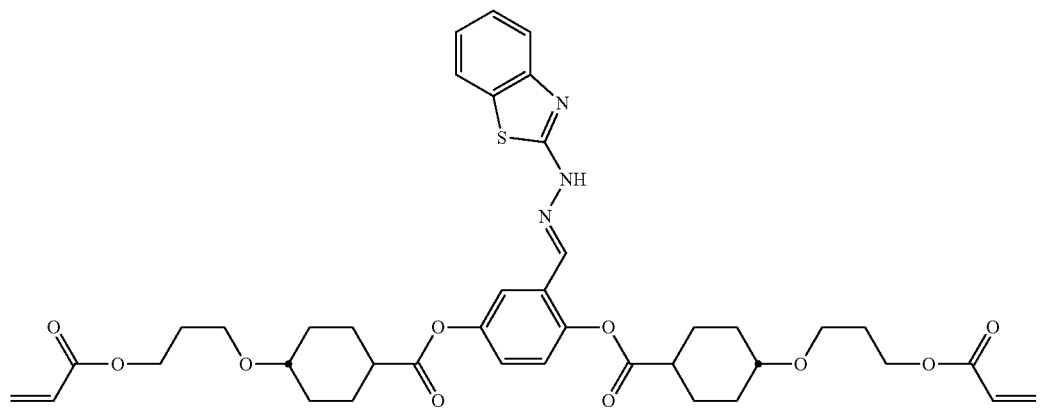
(1-44)
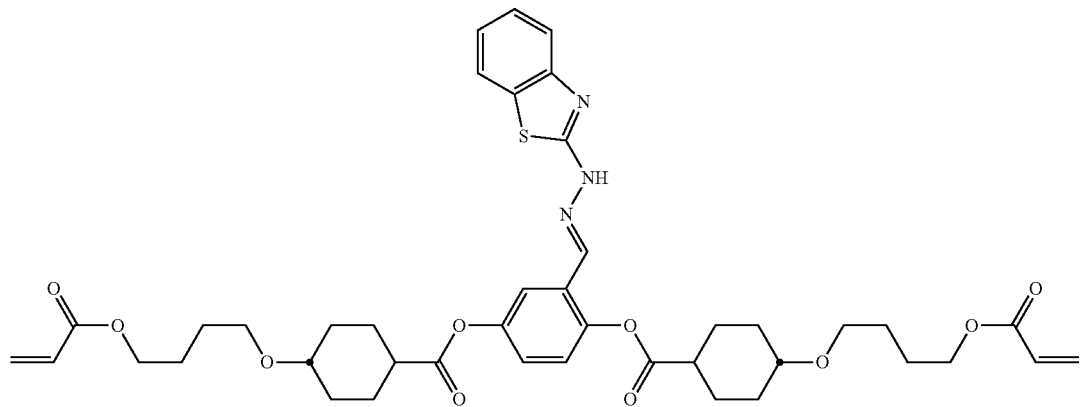

(1-45)
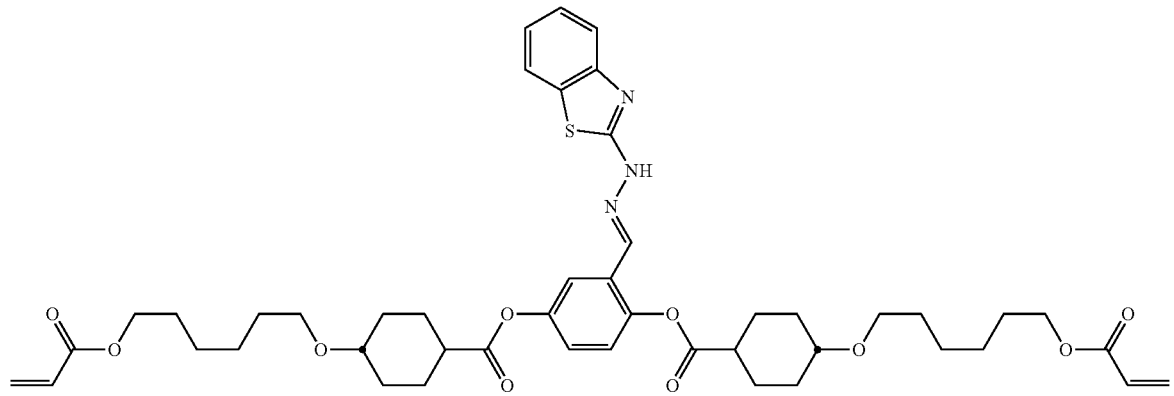
(1-46)
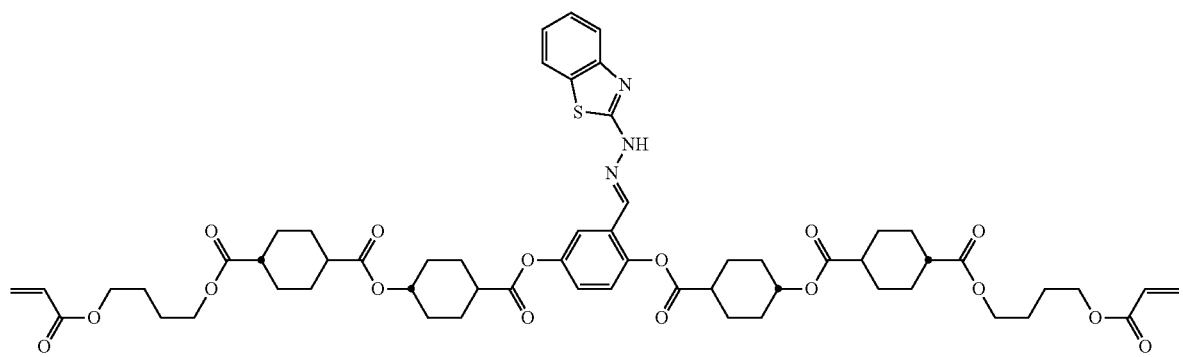
[Chem. 36]
(1-47)
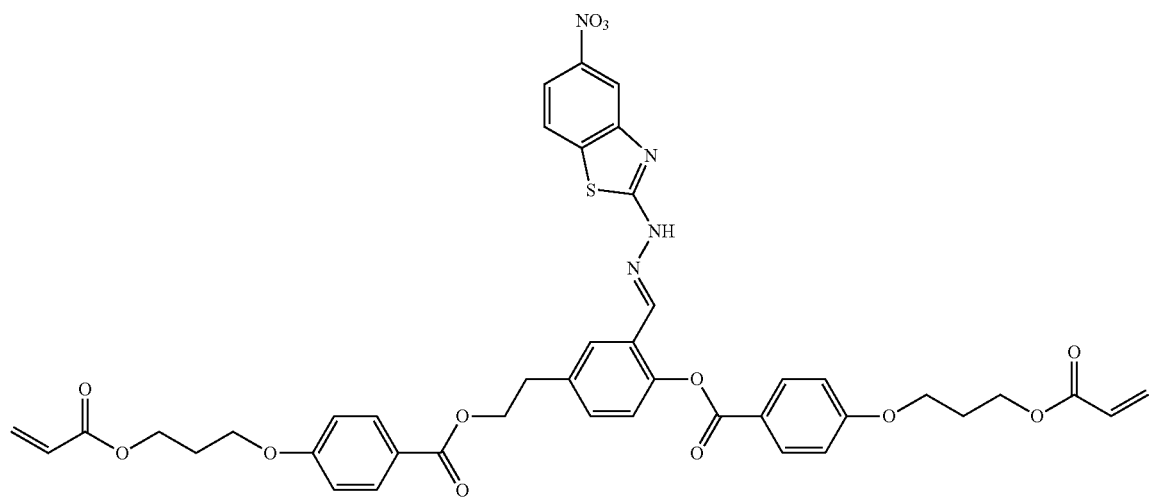

-continued
(1-48)
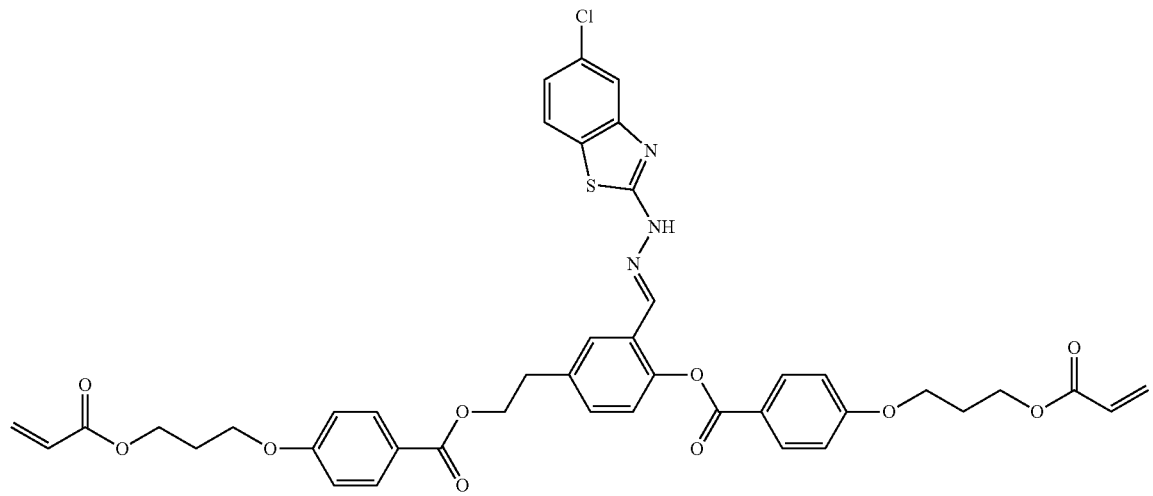
(1-49)
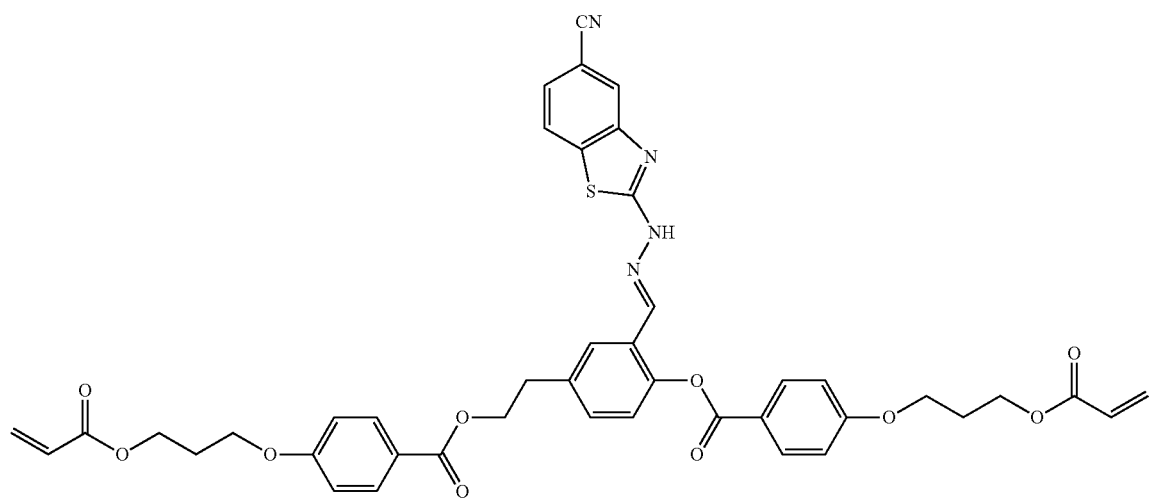
(1-50)
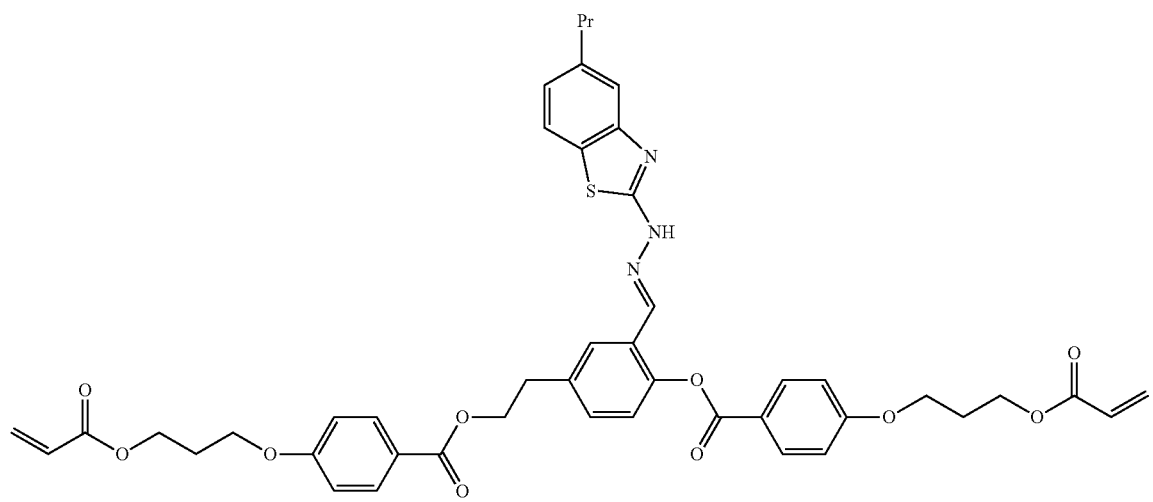

-continued
(1-51)
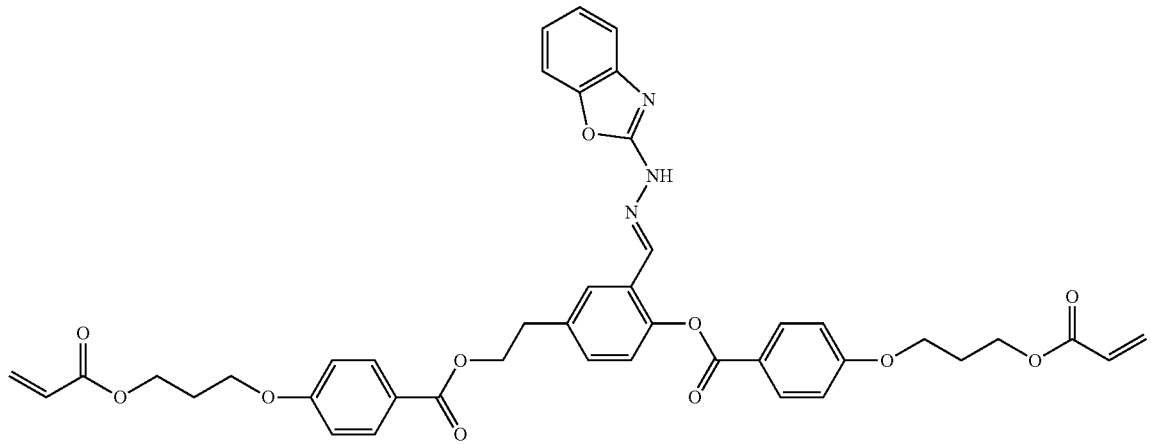
(1-52)
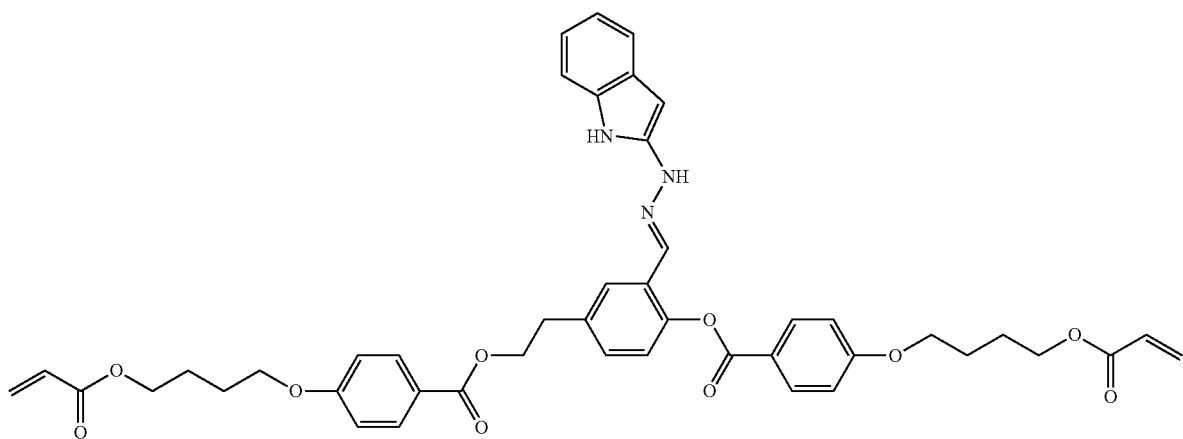
(1-53)
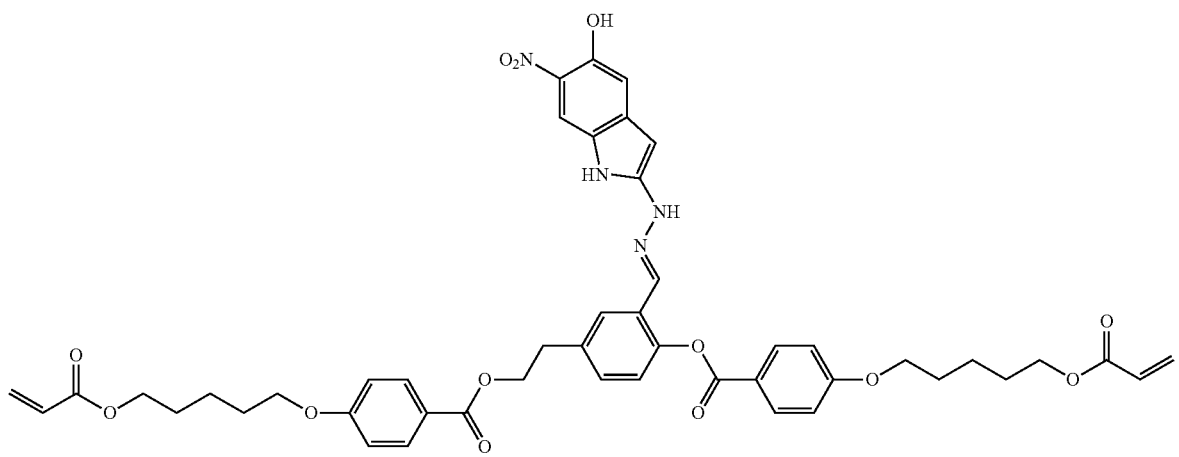

-continued
(1-54)
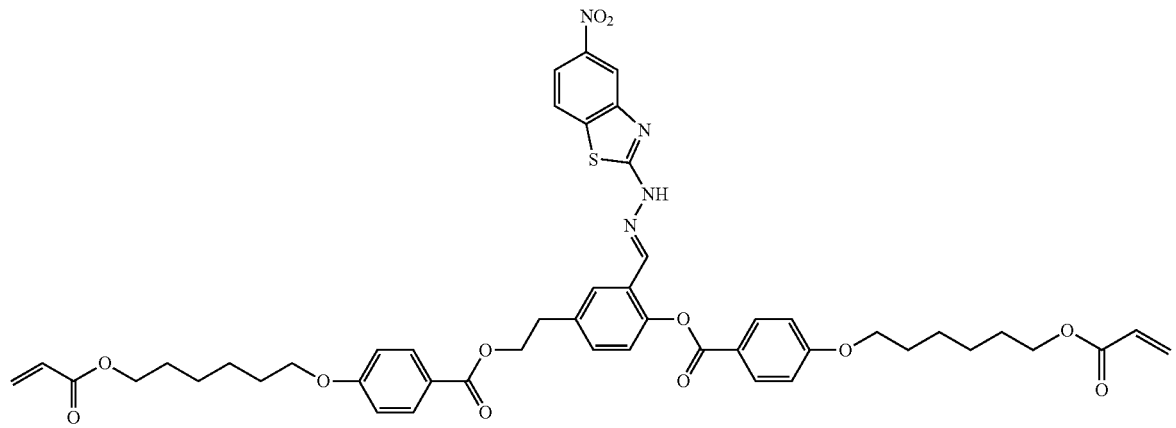
[Chem. 38]
(1-55)
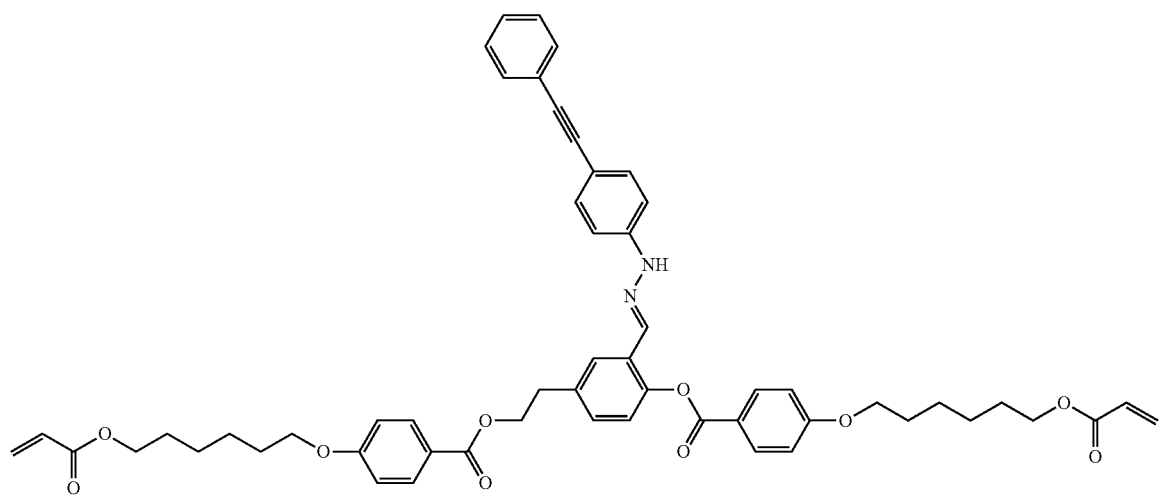
(1-56)
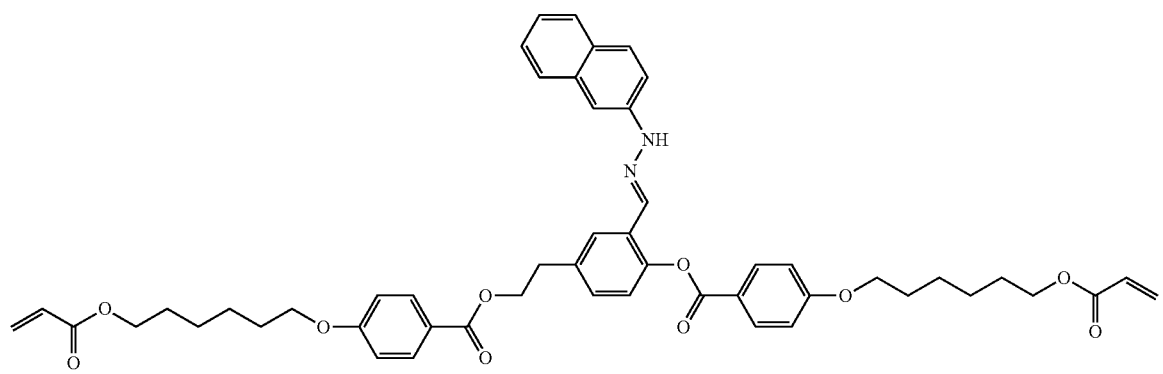

(1-57)
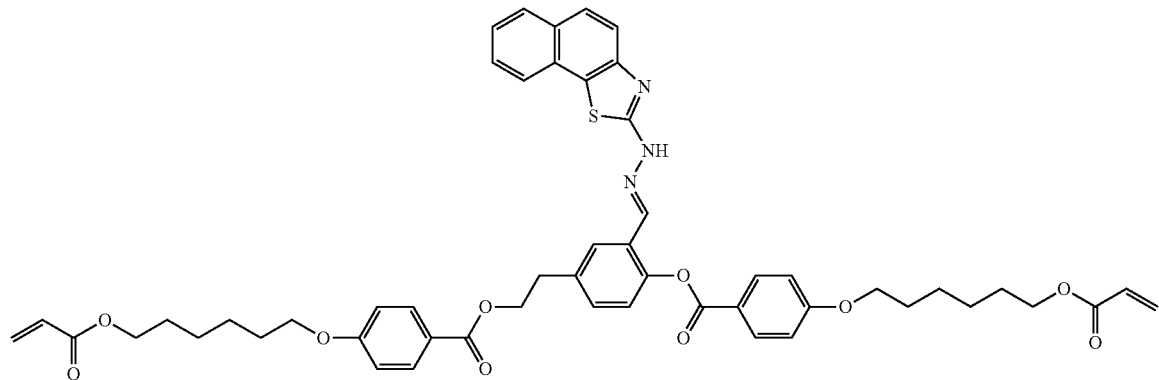
(1-58)
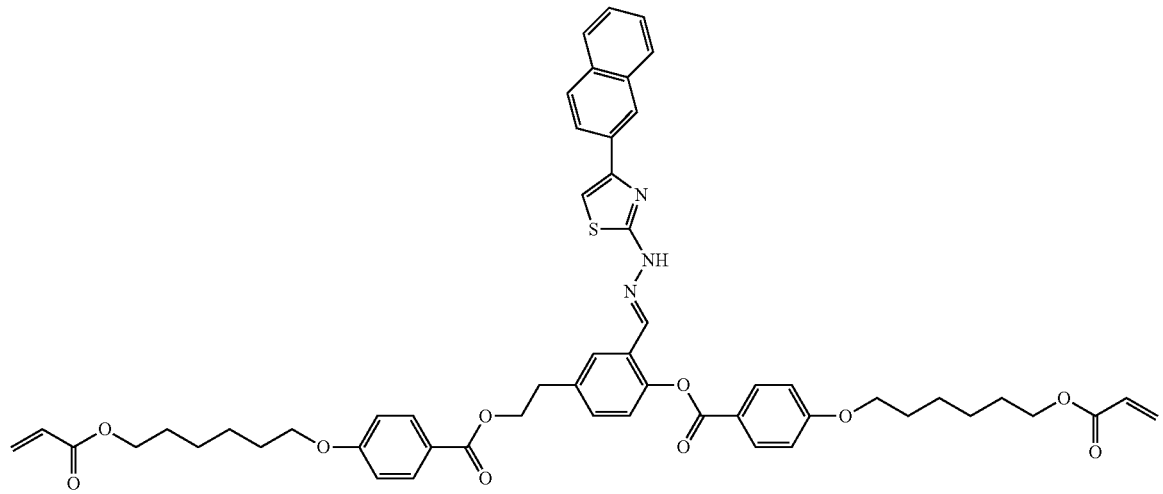
[Chem. 39]
(1-59)
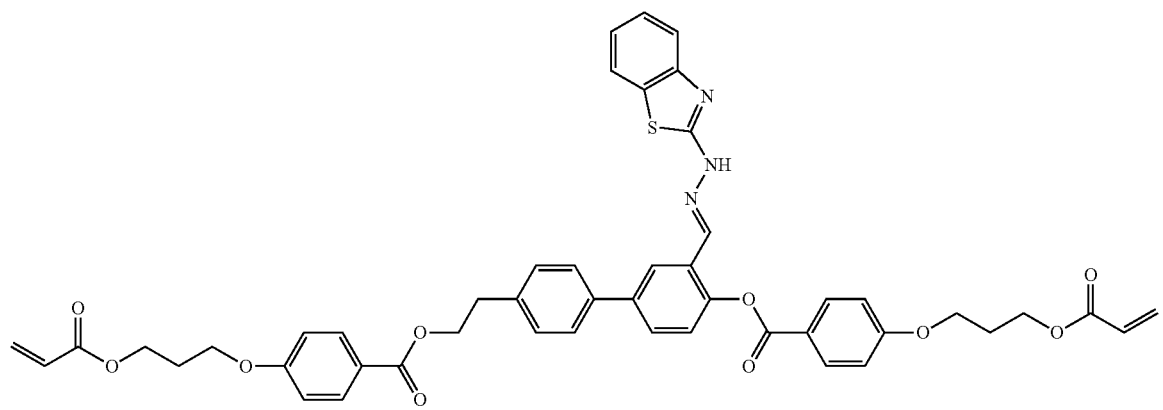

(1-60)
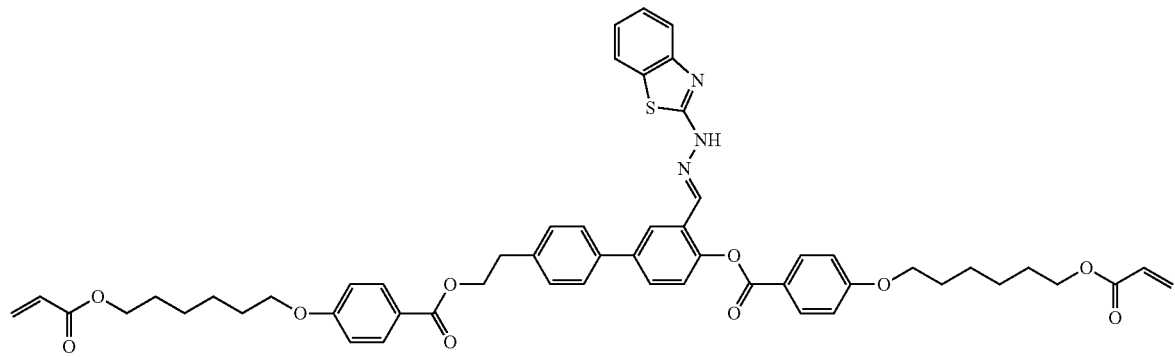
(1-61)
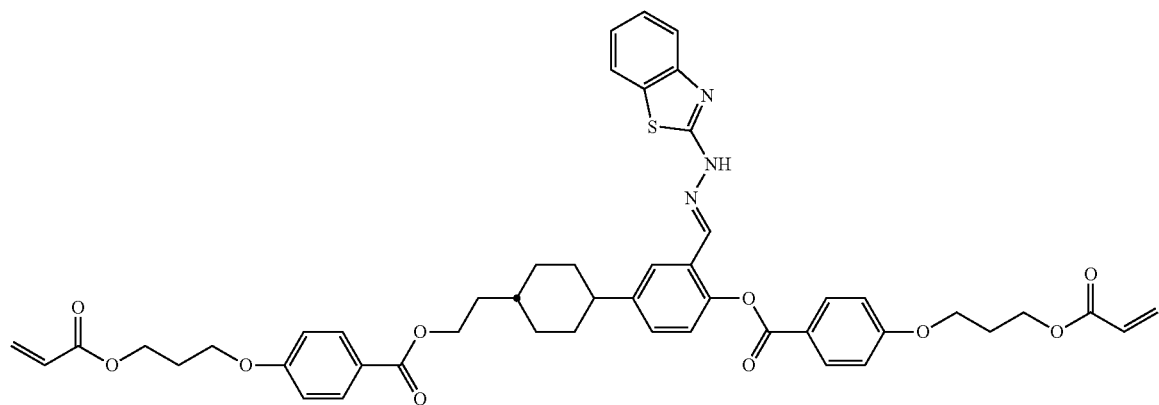
(1-62)
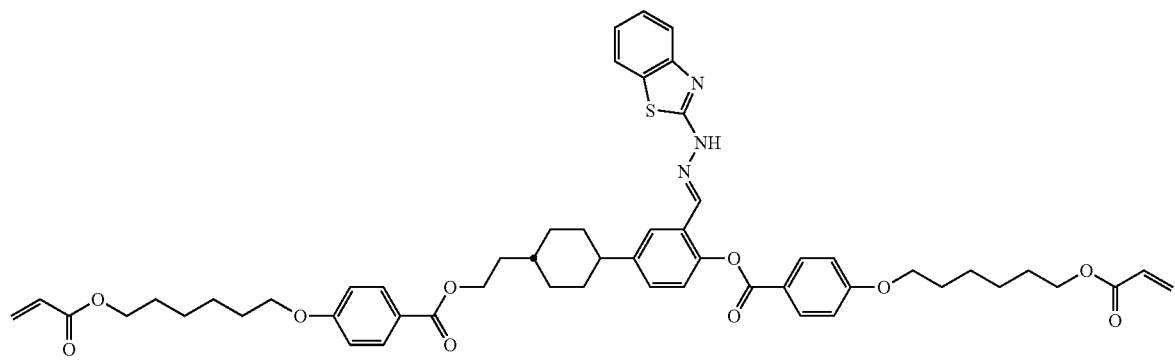
[Chem. 40]
(1-63)
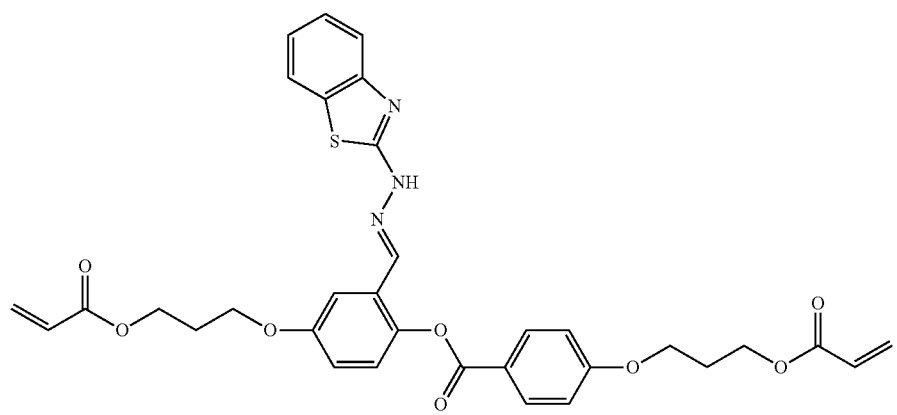

(1-64)
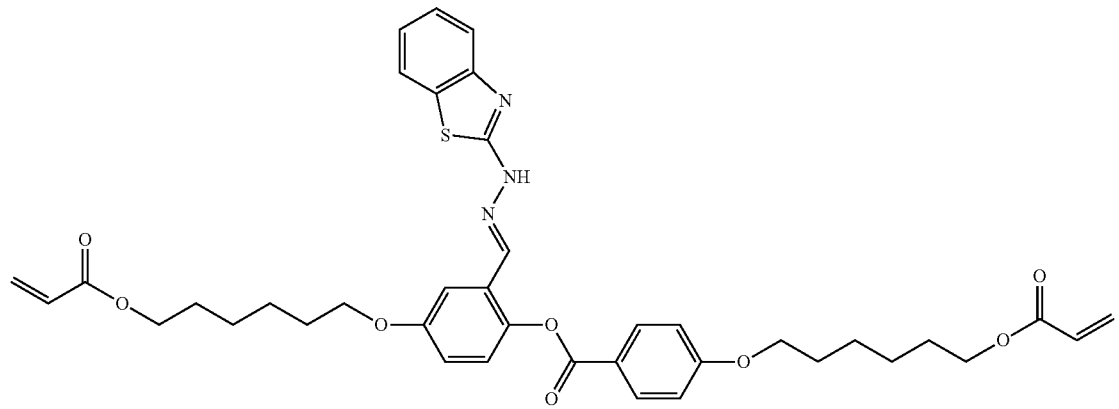
(1-65)
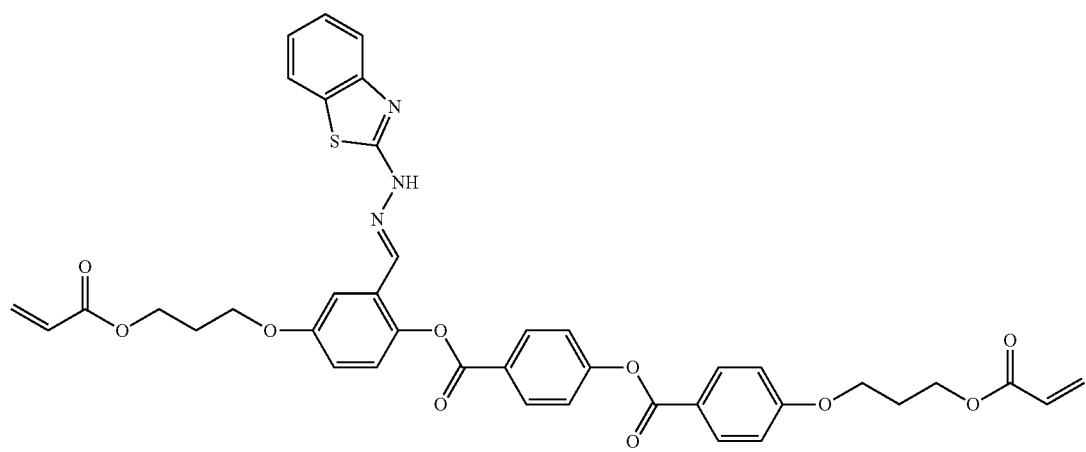
(1-66)
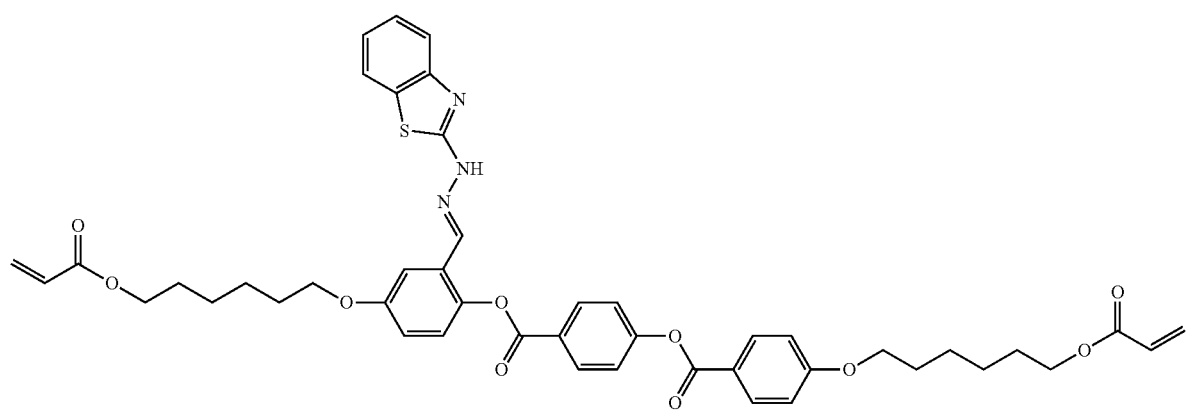

[Chem. 41]
(1-67)
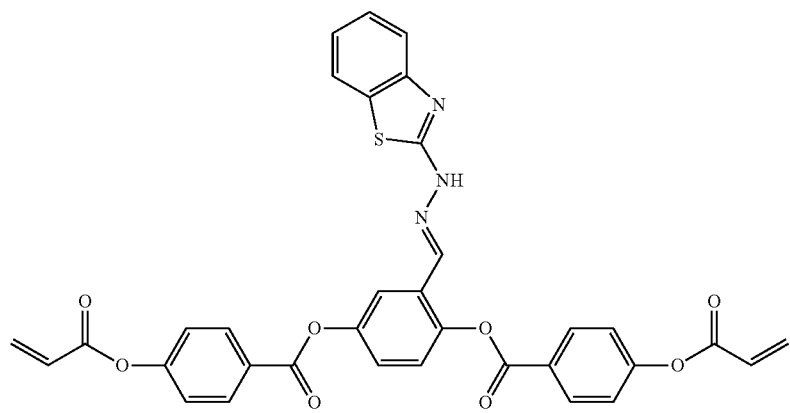
(1-68)
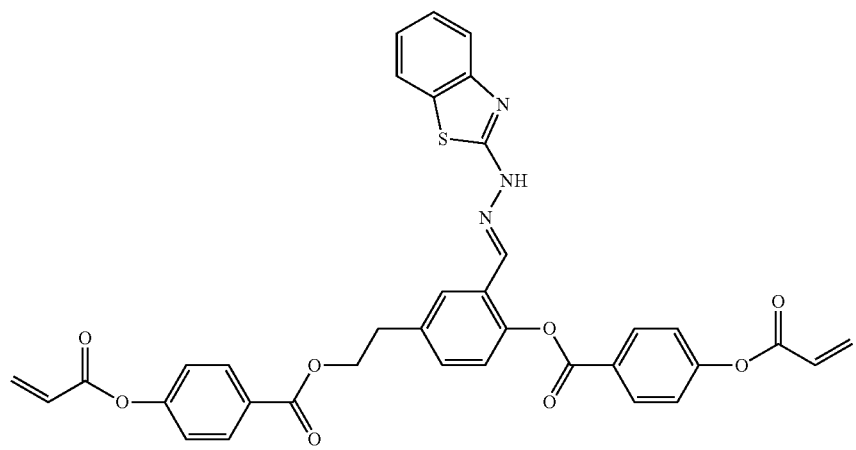
(1-69)
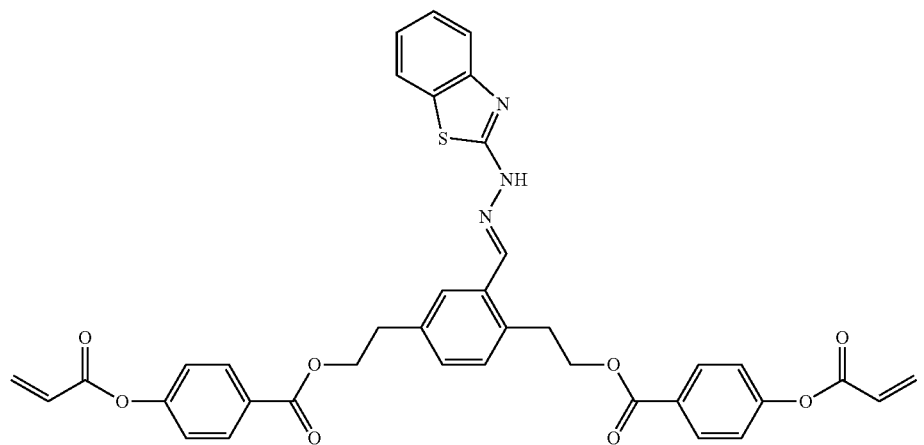

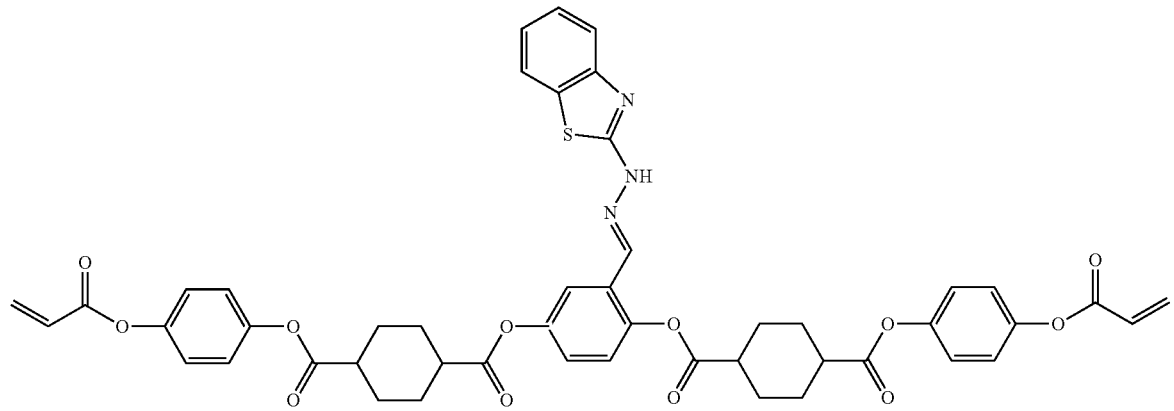
(1-70)
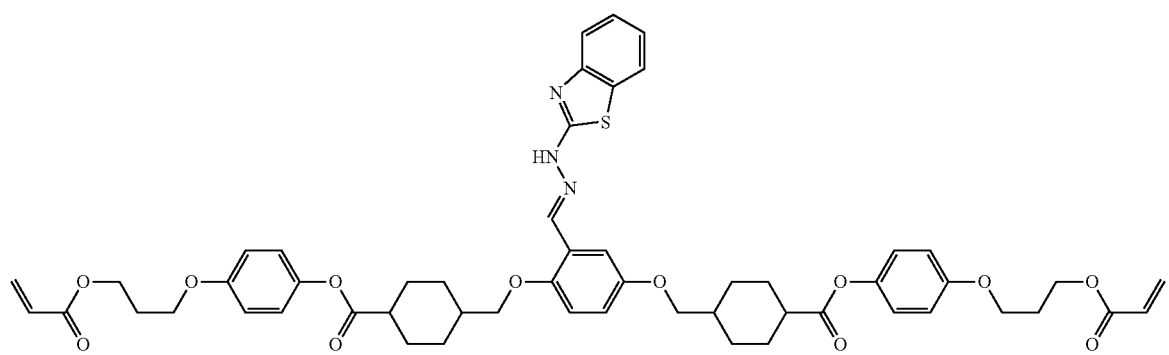
[Chem. 42]
(1-71)
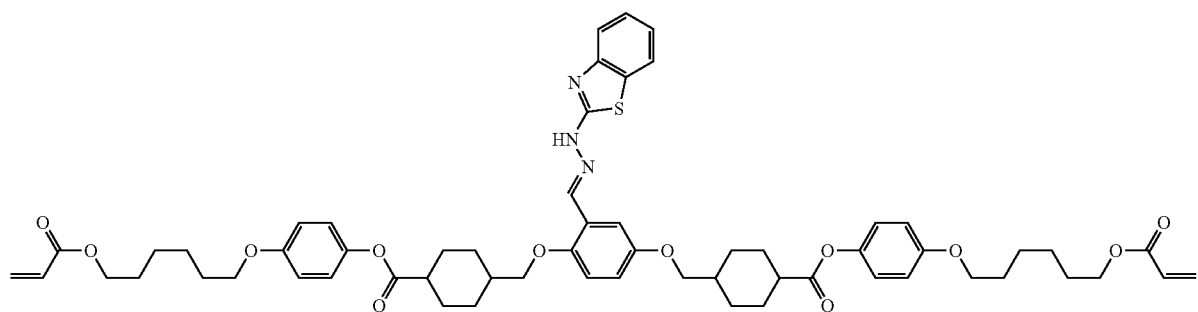
(1-72)
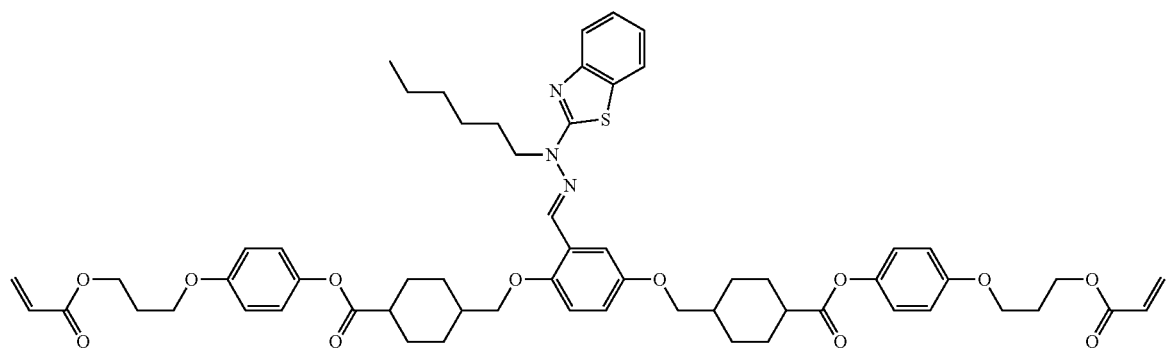
(1-73)

(1-74)
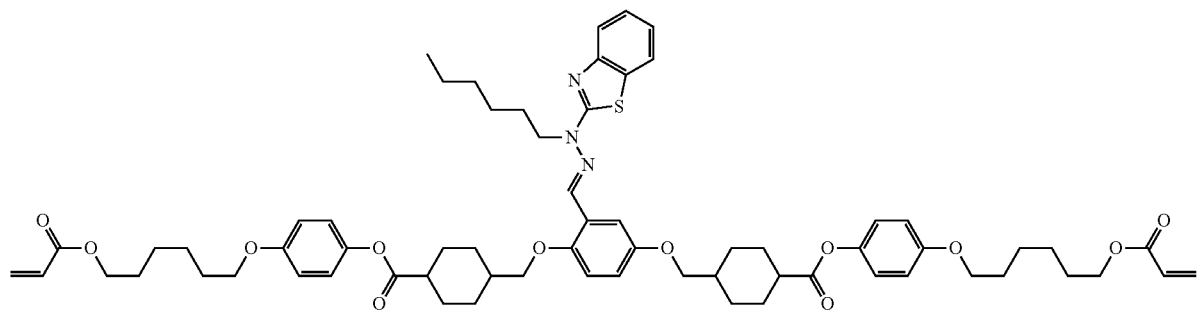
(1-75)
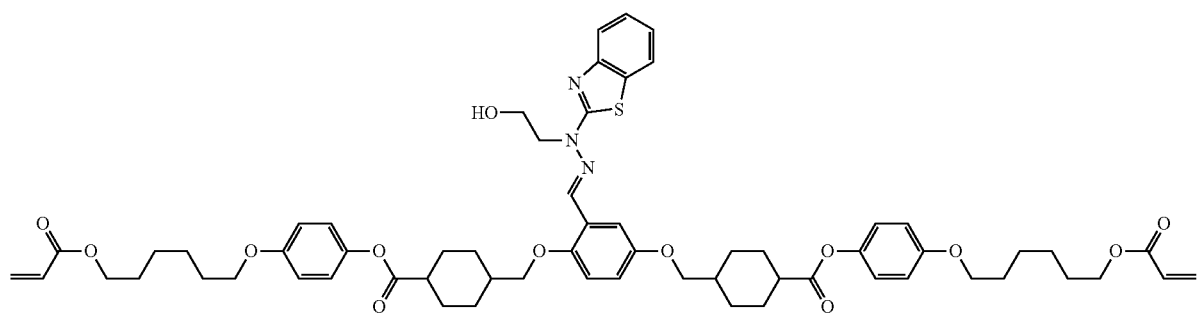
[Chem. 43]
(1-76)
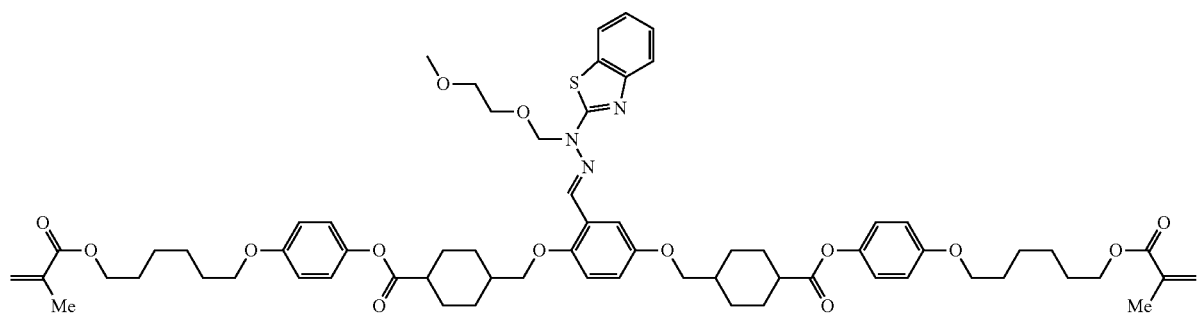
(1-77)
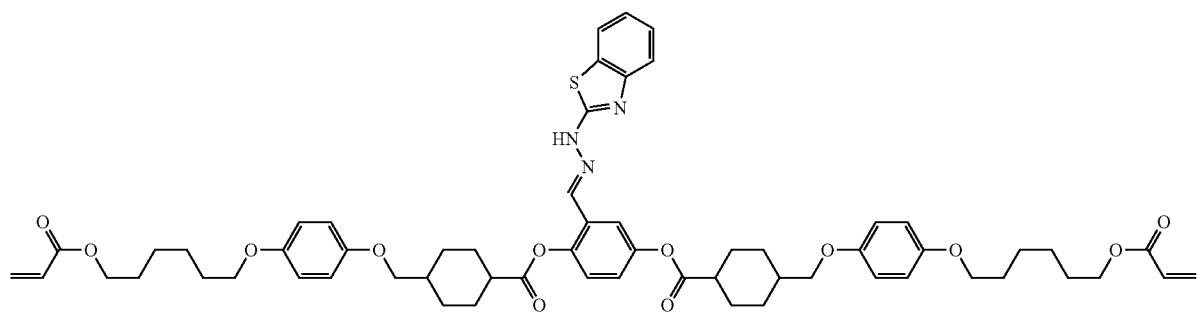

(1-78)
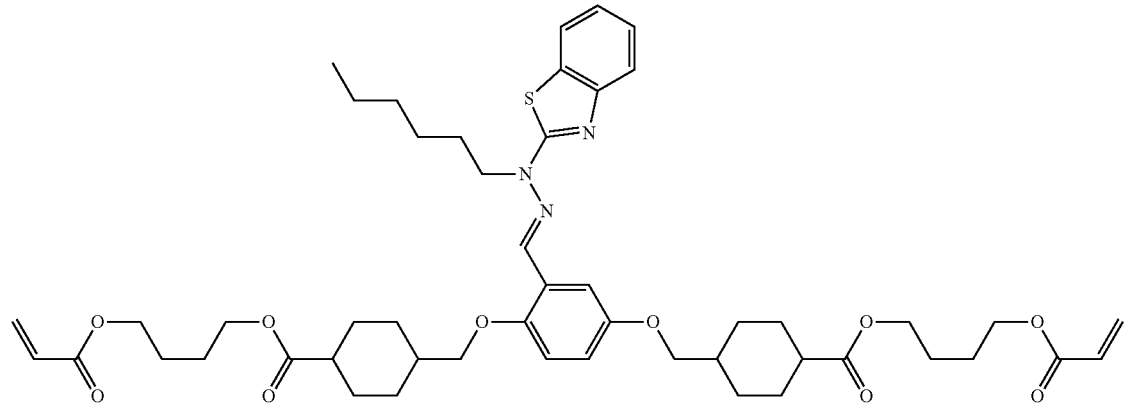
(1-79)
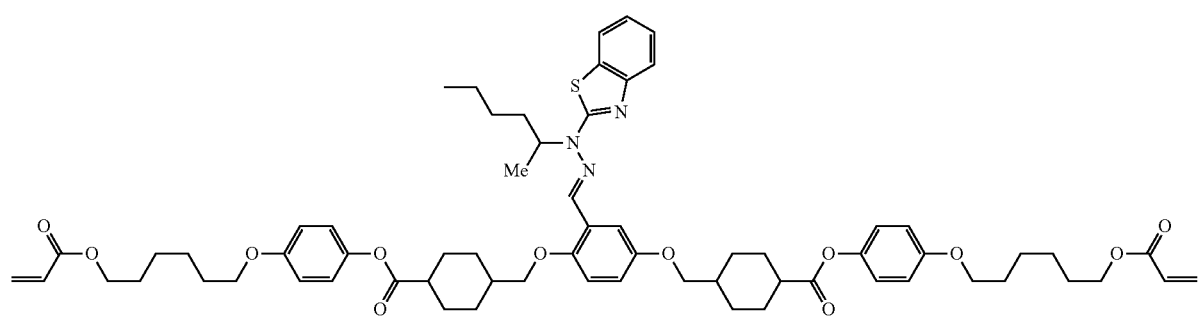
(1-80)
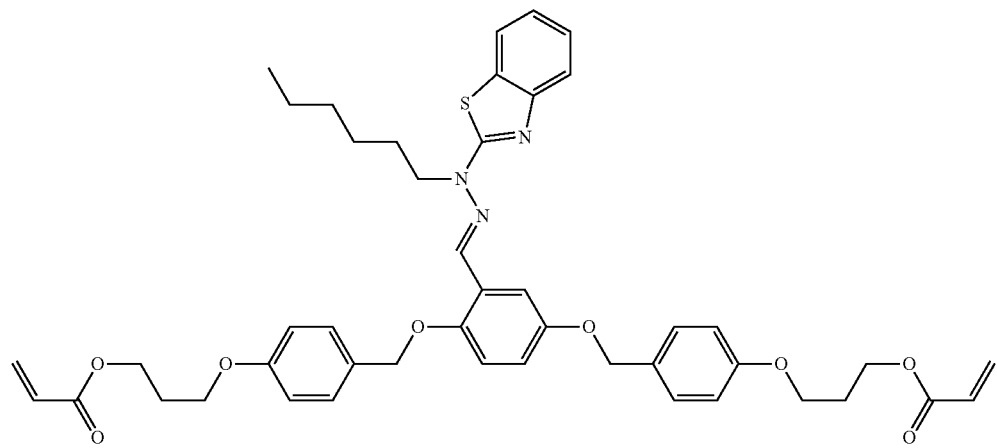
[Chem. 44]
(1-81)
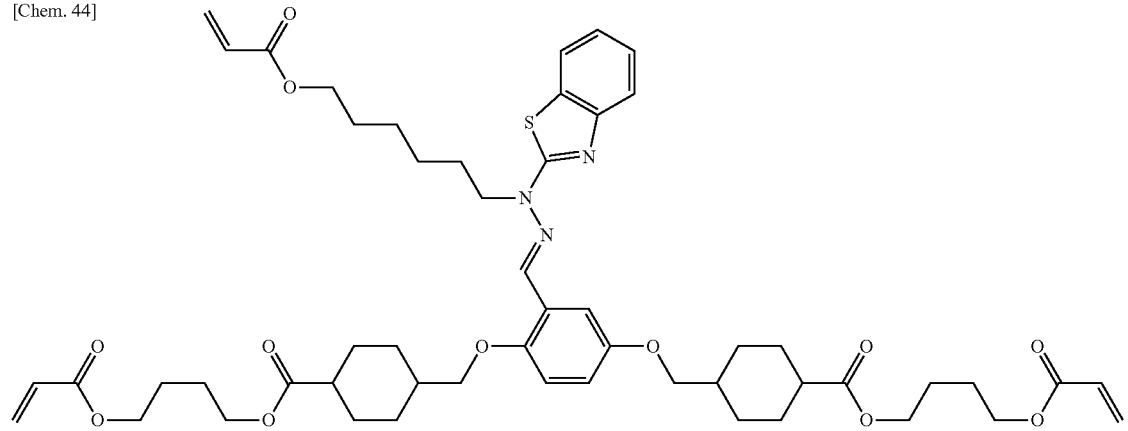

(1-82)
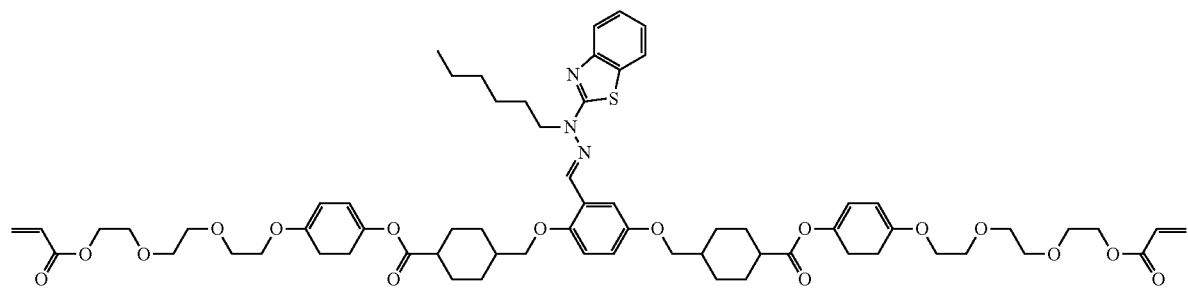
(1-83)
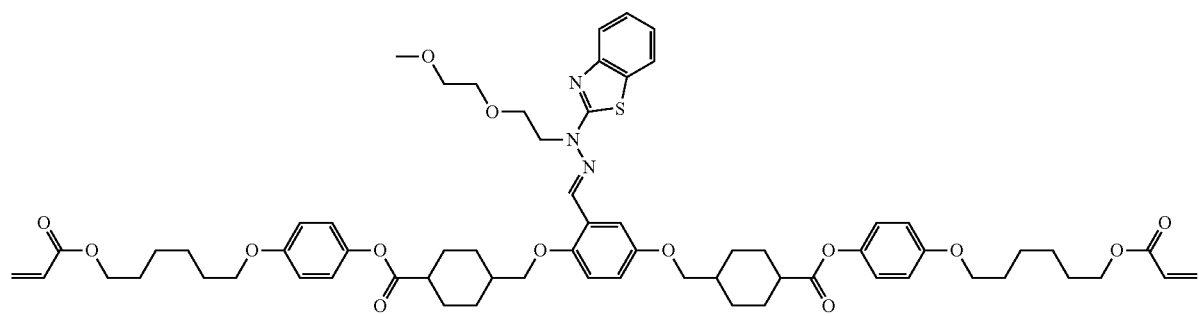
(1-84)
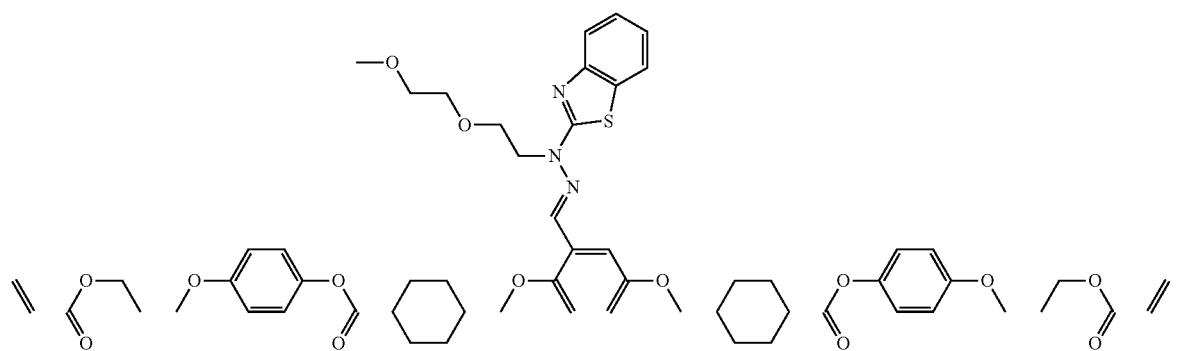
(1-85)
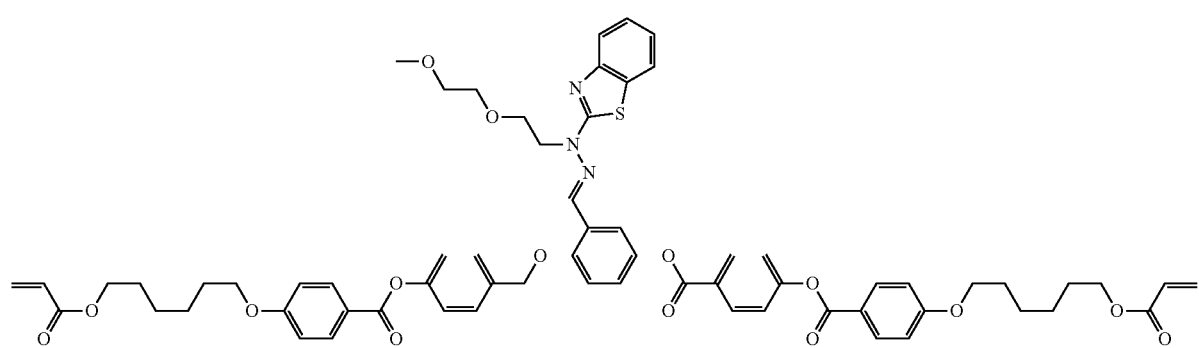

[Chem. 45]
(1-86)
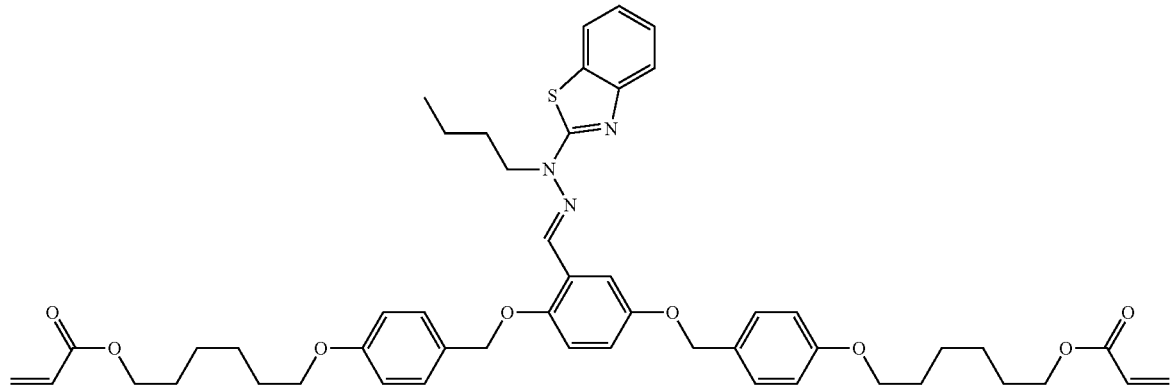
(1-87)
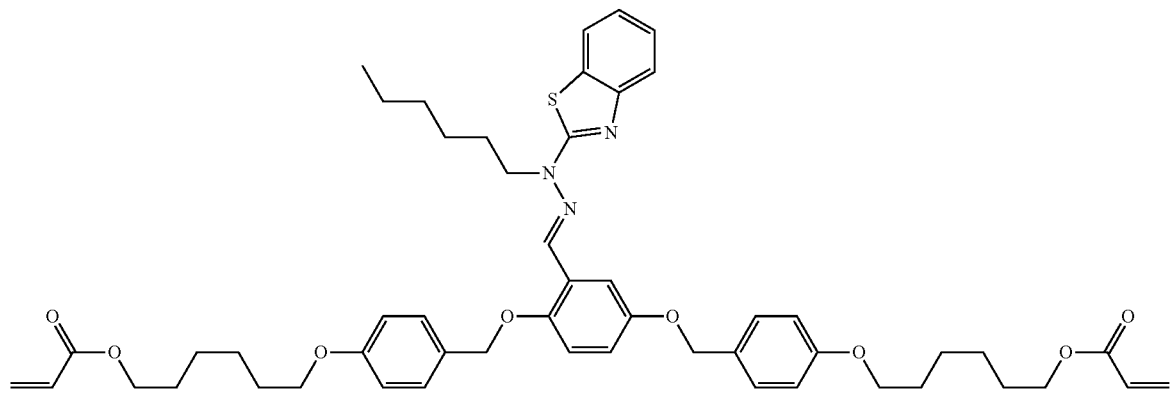
(1-88)
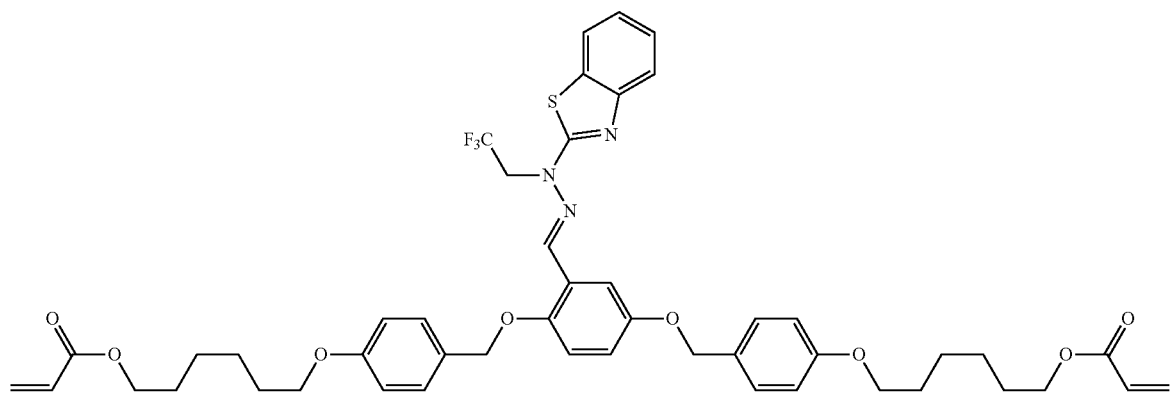

(1-89)
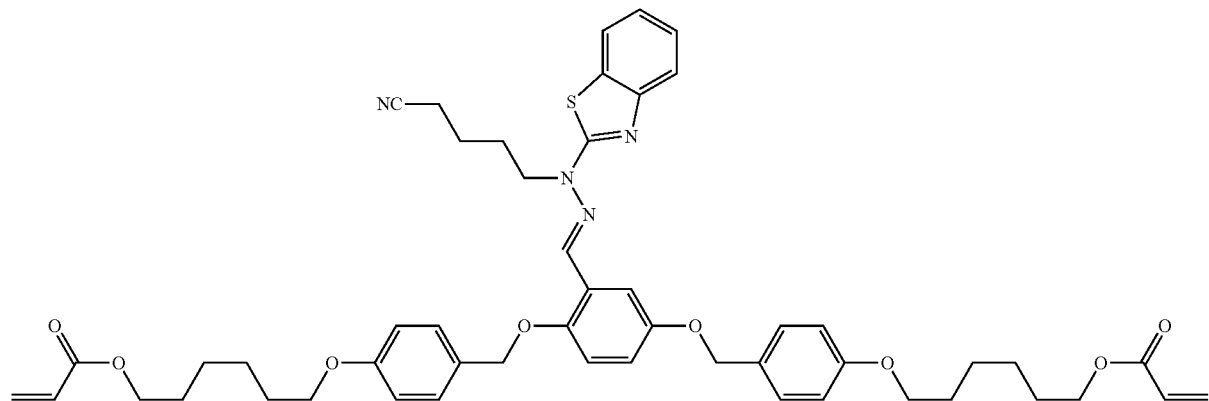
(1-90)
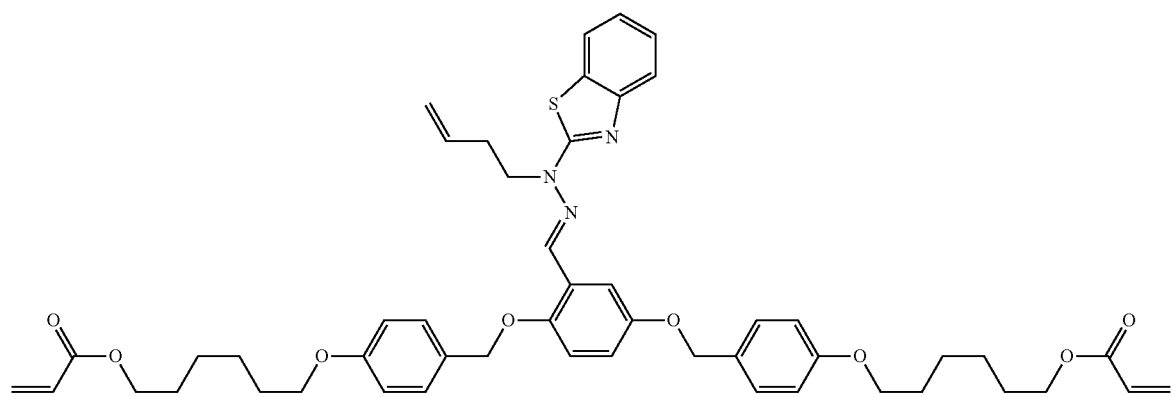
[Chem. 46]
(1-91)
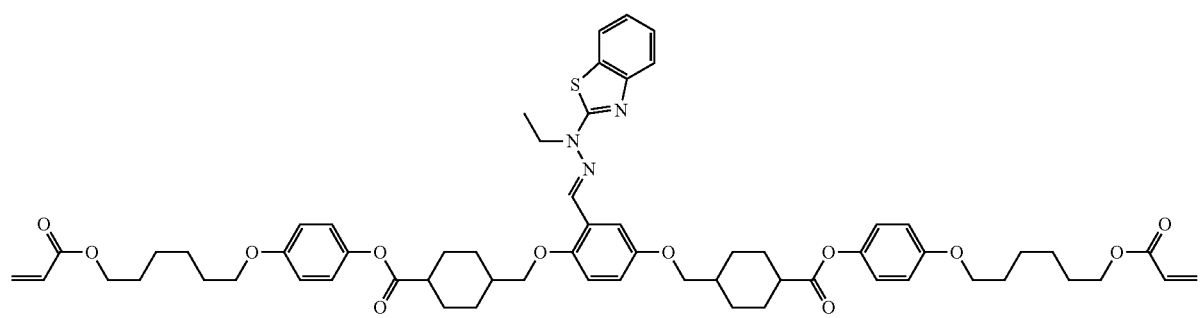
(1-92)
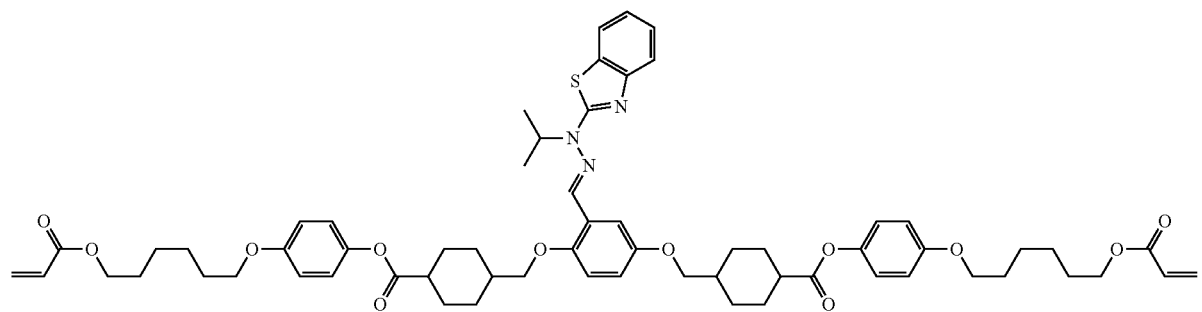

(1-93)
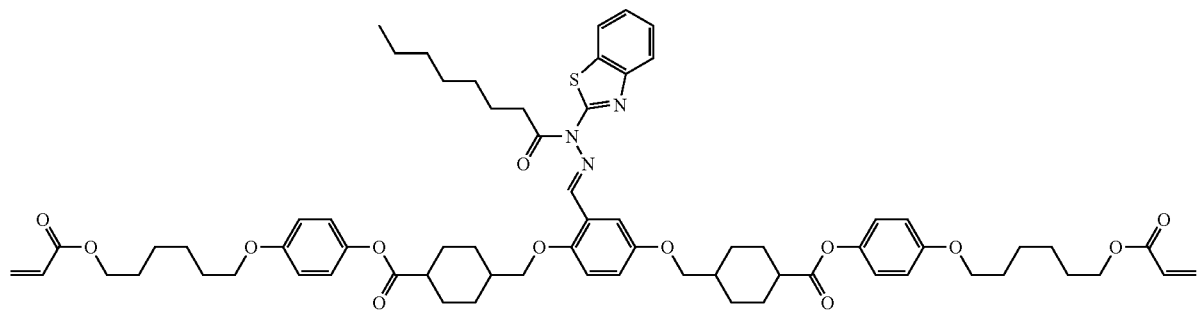
(1-94)
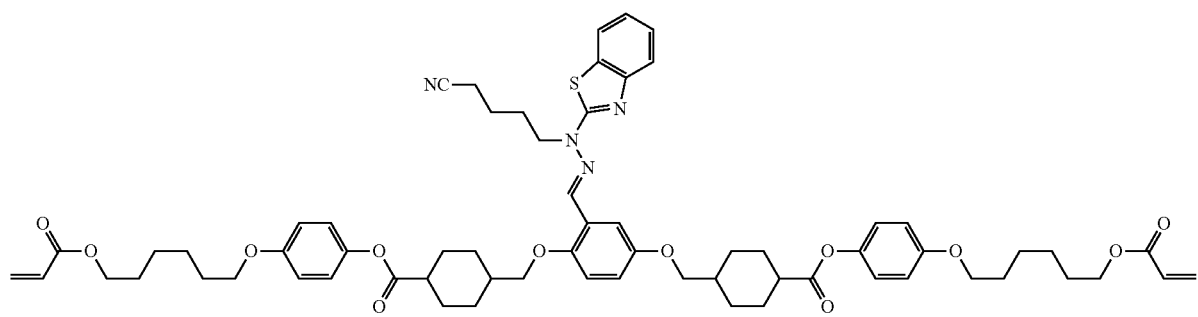
(1-95)
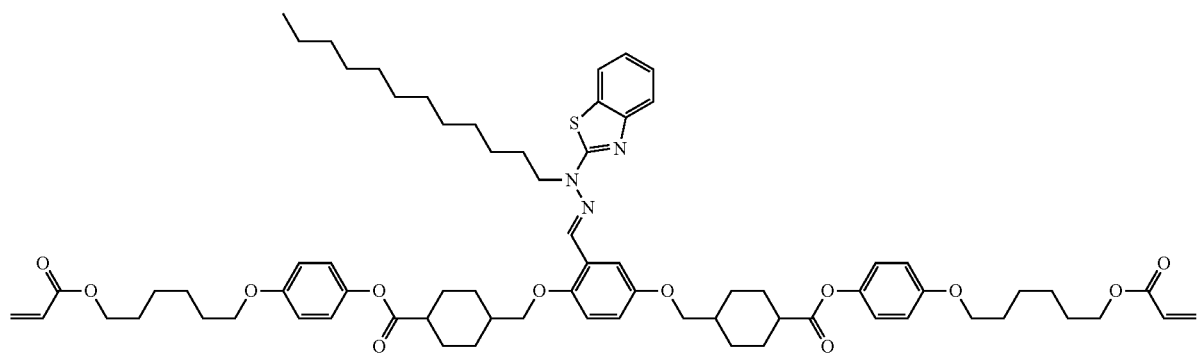
[Chem. 47]
(1-96)
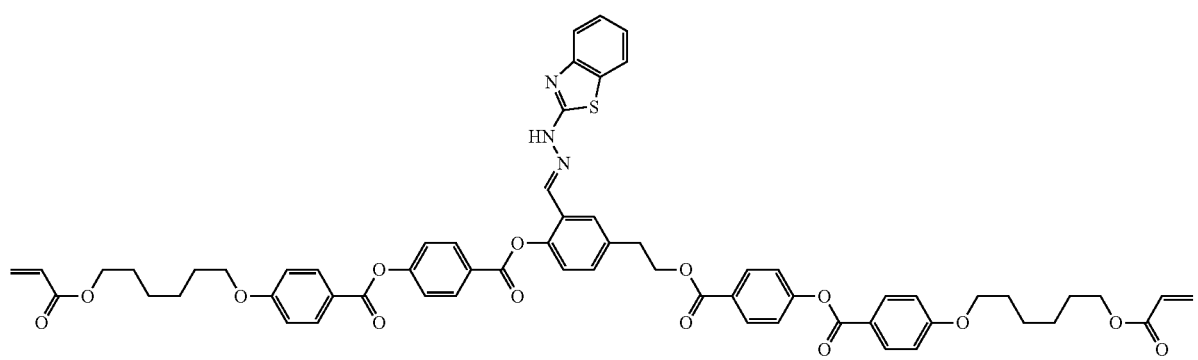

(1-97)
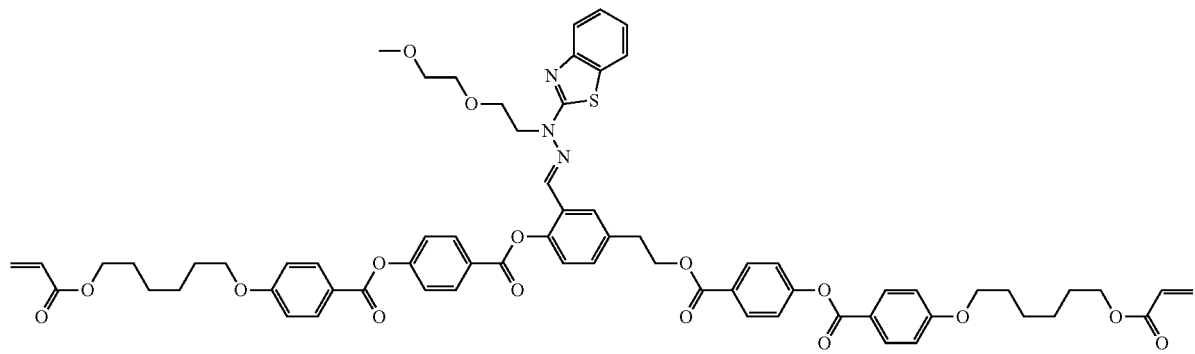
(1-98)
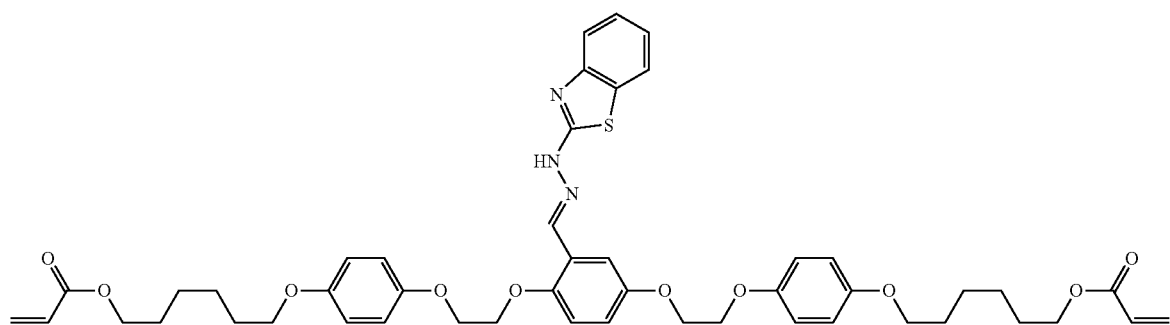
(1-99)
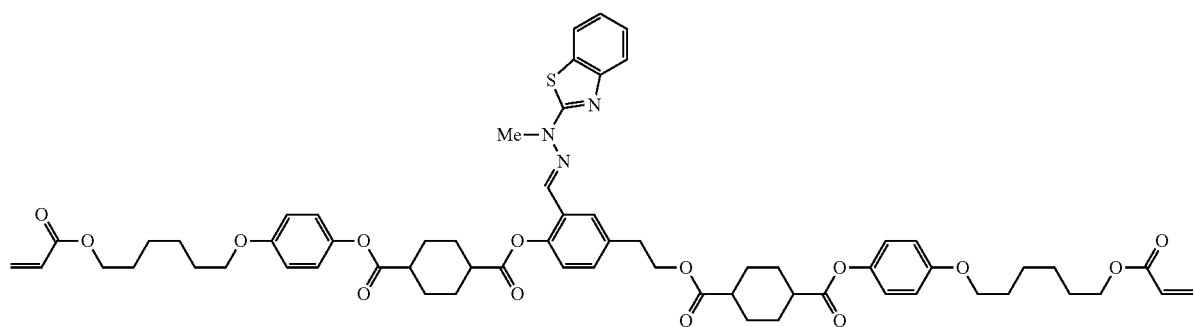
(1-100)
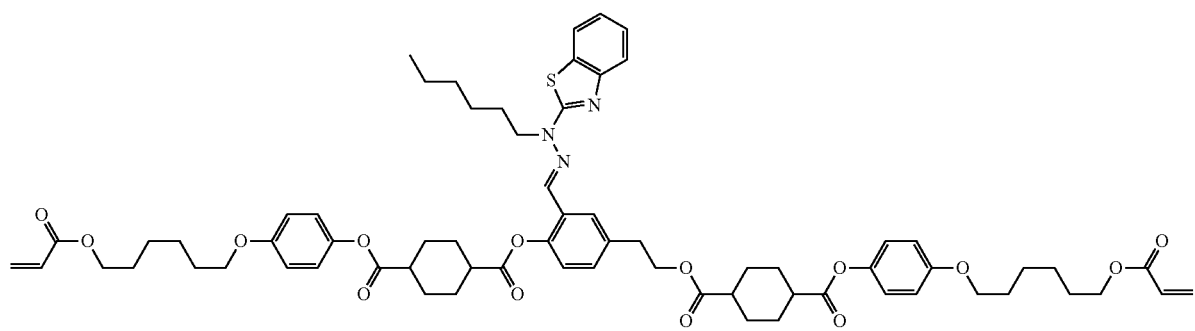

[Chem. 48]
(1-101)
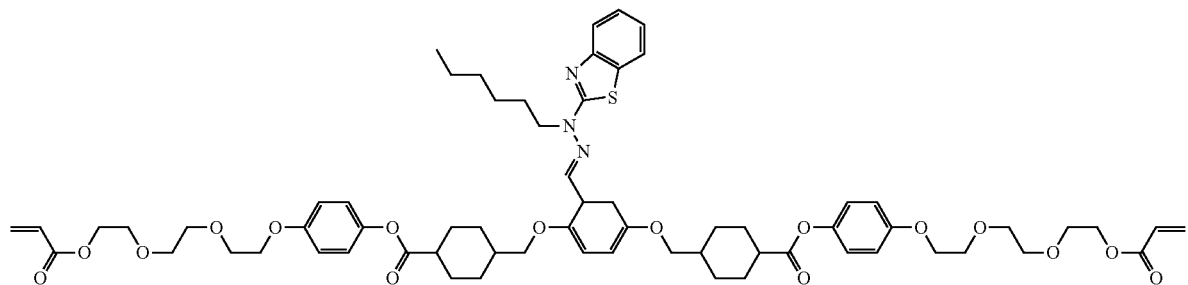
(1-102)
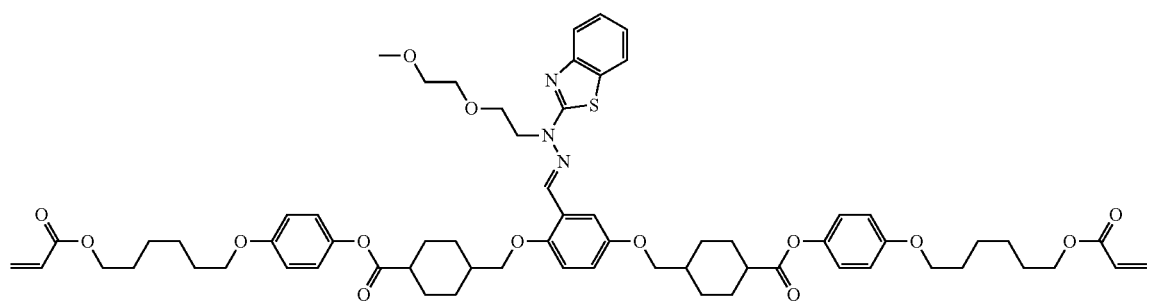
(1-103)
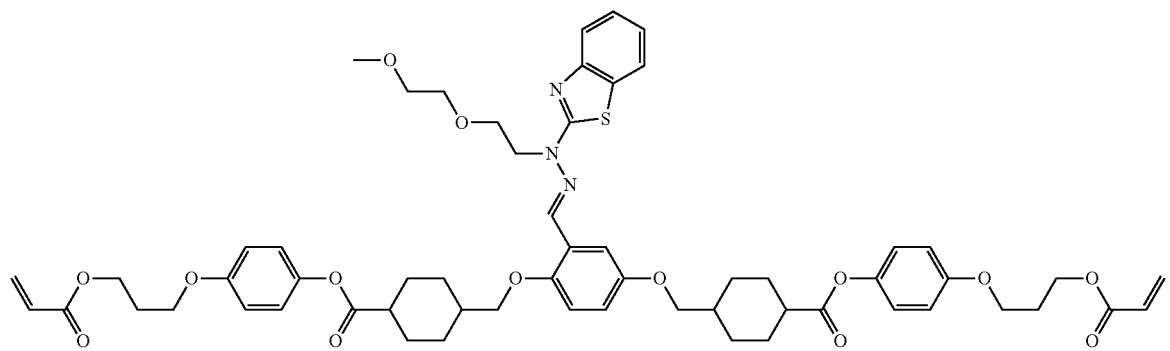
(1-104)
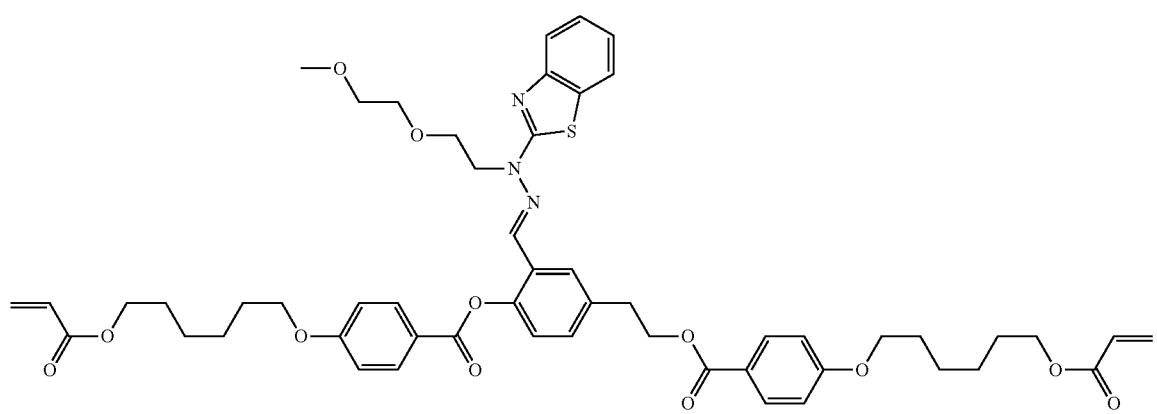

-continued
(1-105)
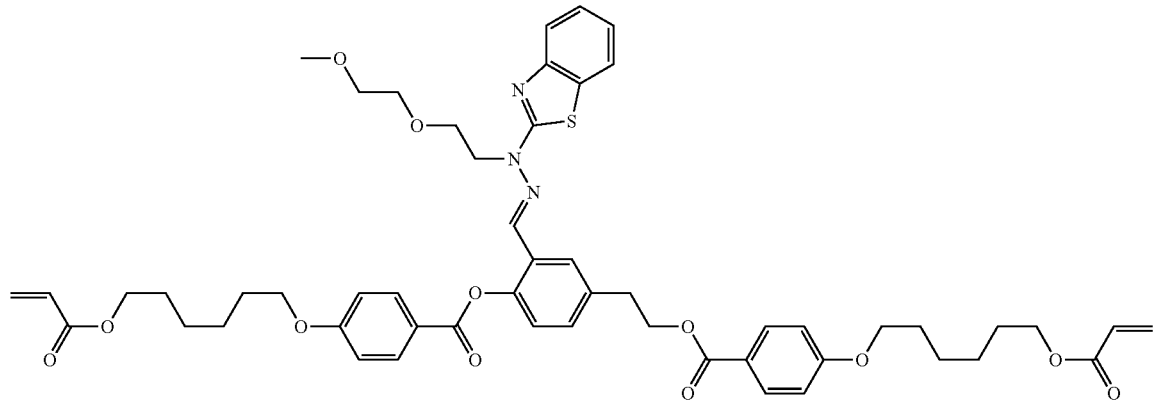
[Chem. 49]
(1-106)
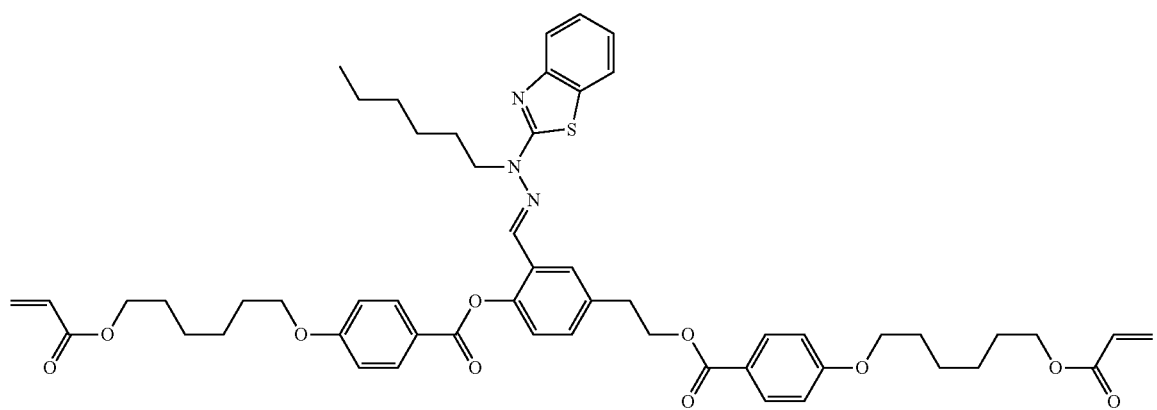
(1-107)
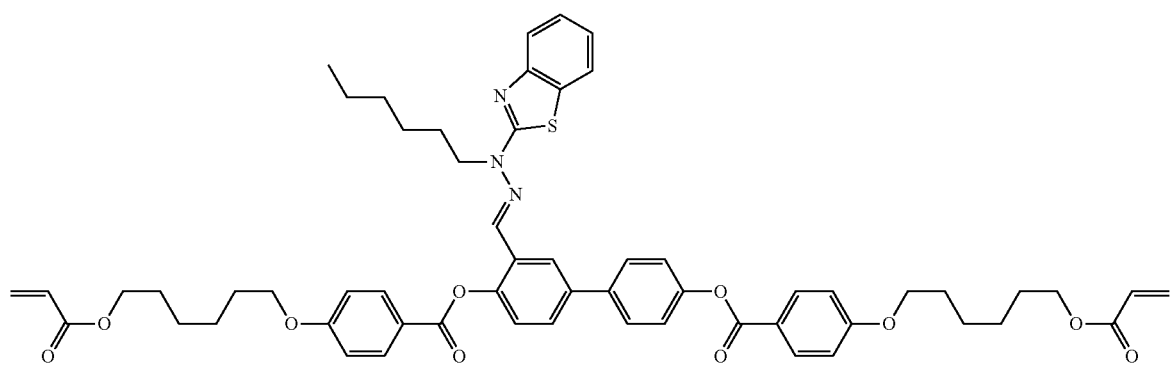
(1-108)
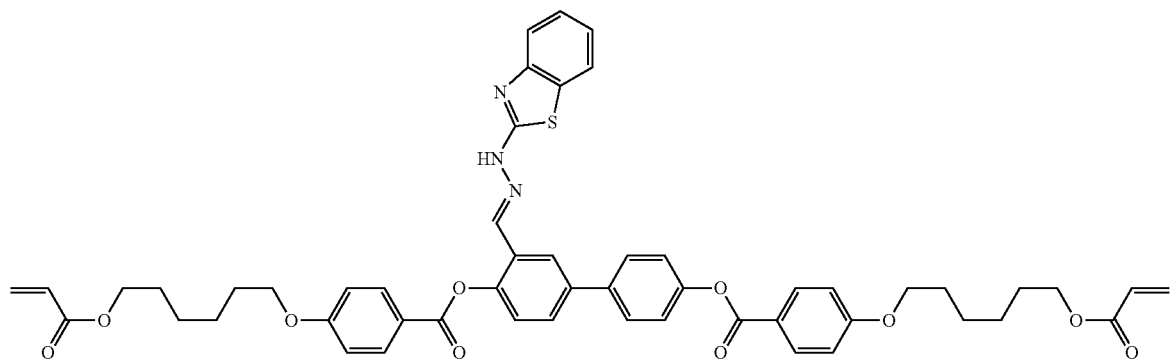

(1-109)
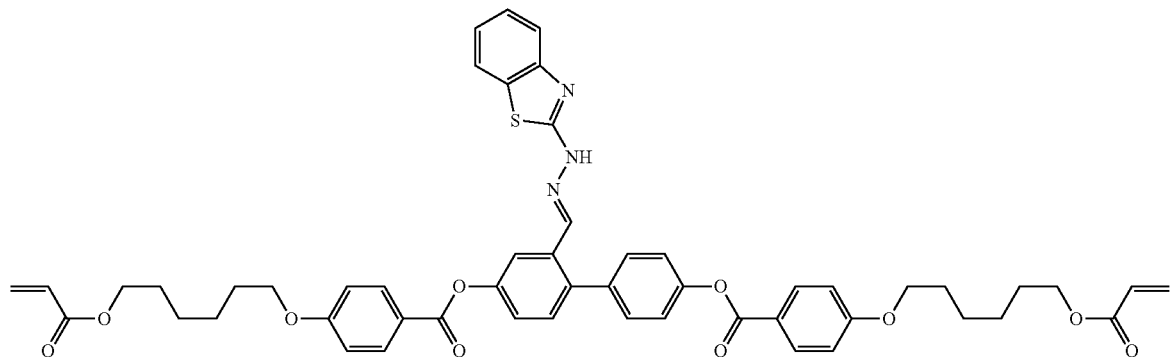
(1-110)
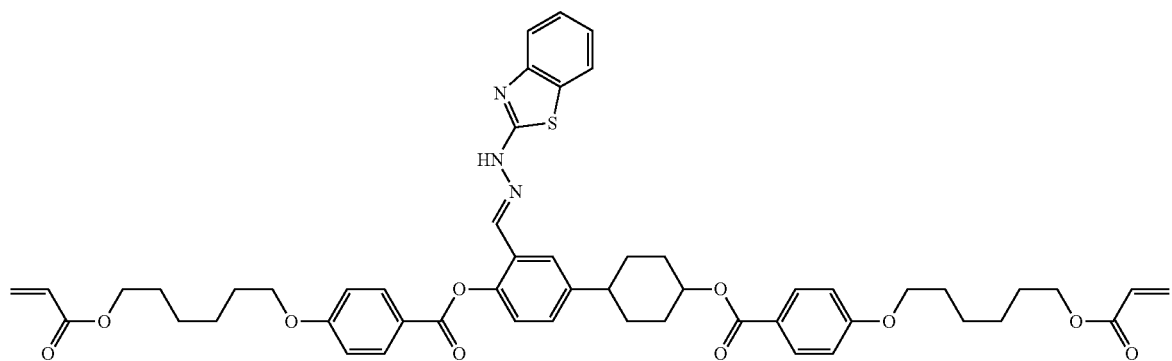
[Chem. 50]
(1-111)
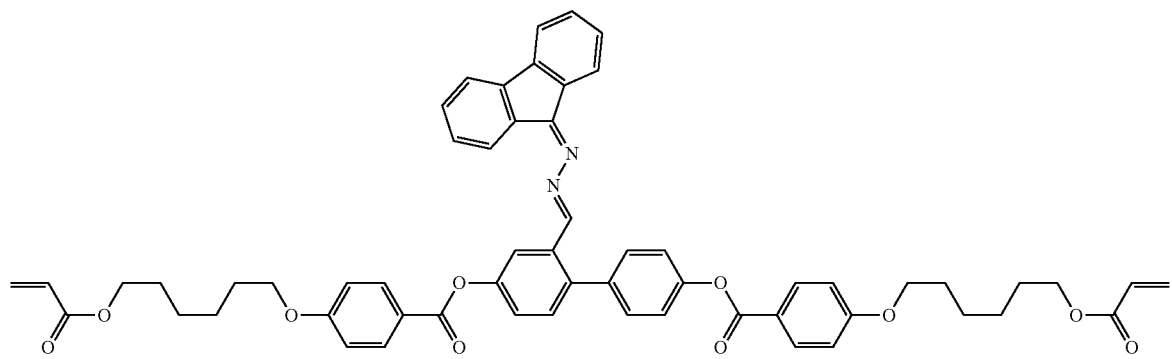
(1-112)
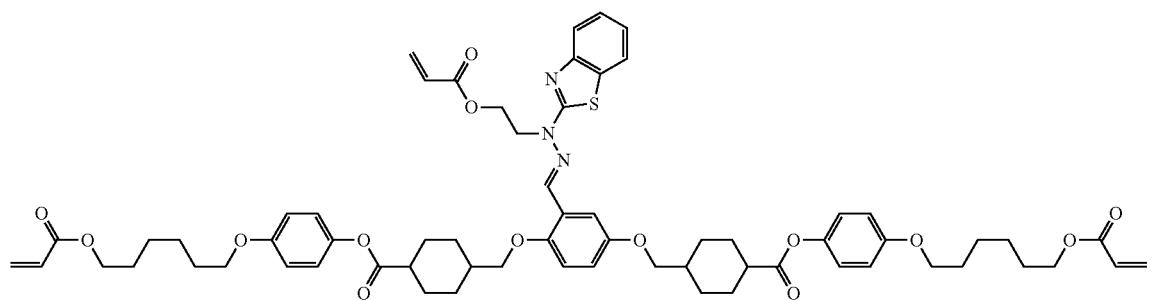

(1-113)
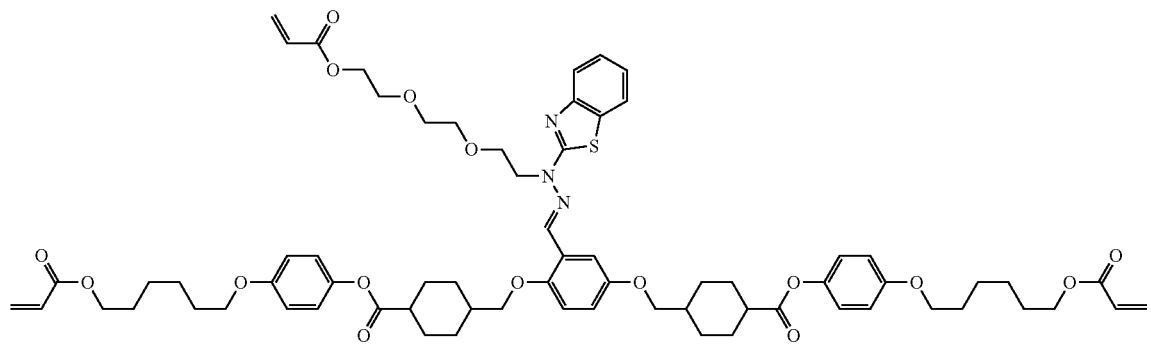
(1-114)
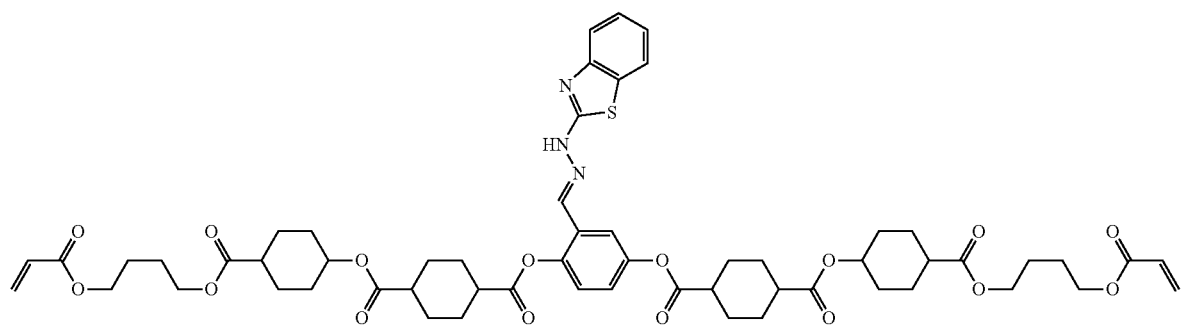
(1-115)
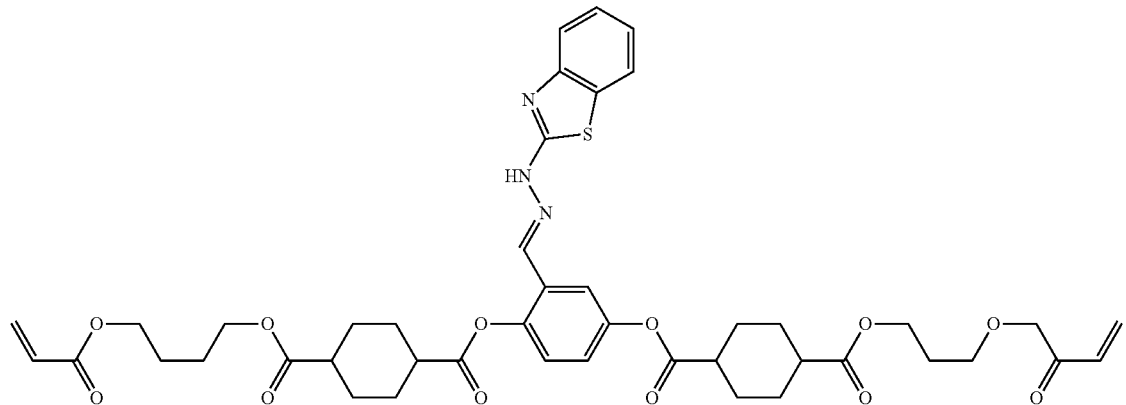
[Chem. 51]
(1-116)
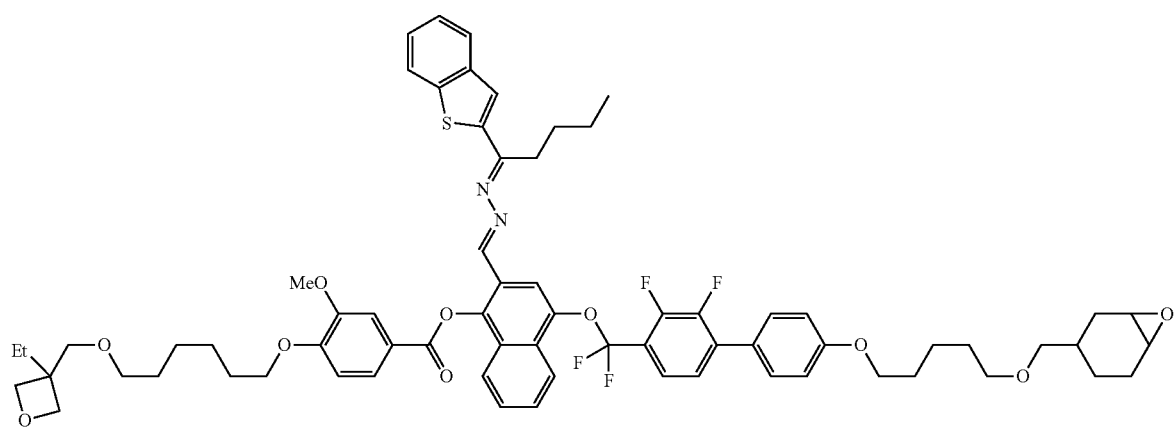

-continued
(1-117)
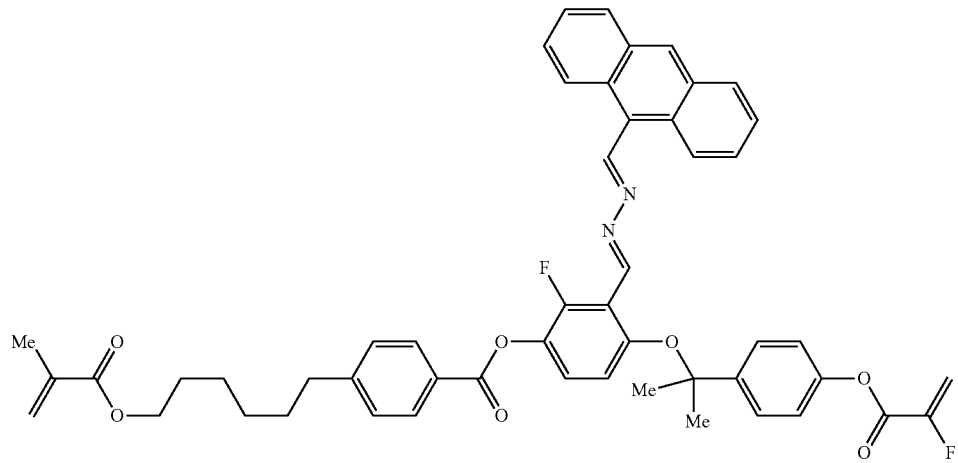
(1-118)
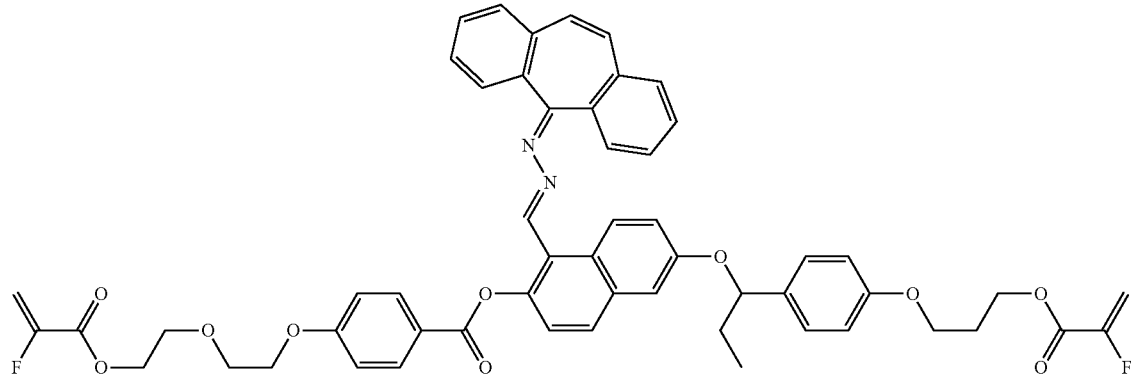
(1-119)
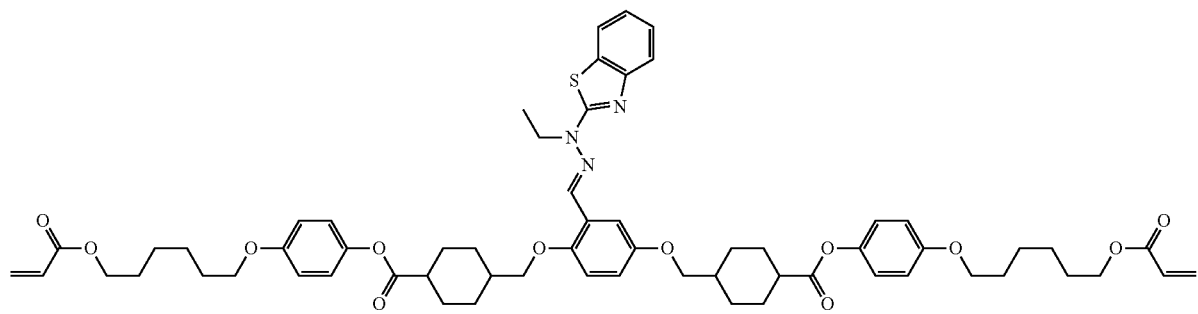
(1-120)
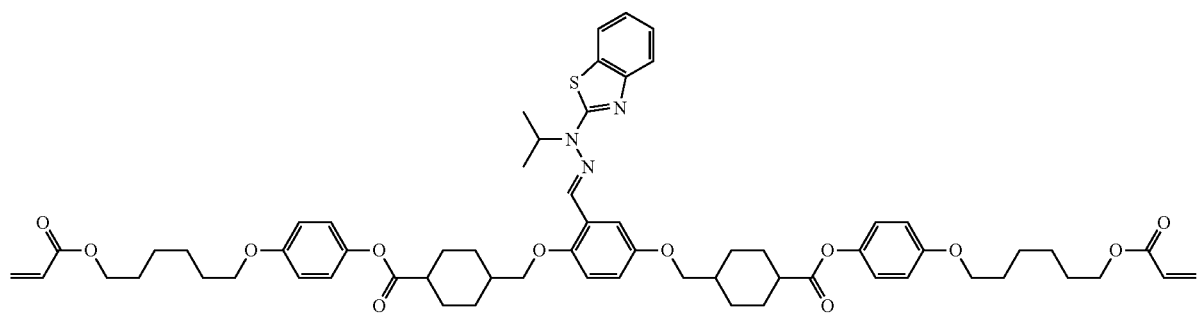

[Chem. 52]
(1-121)
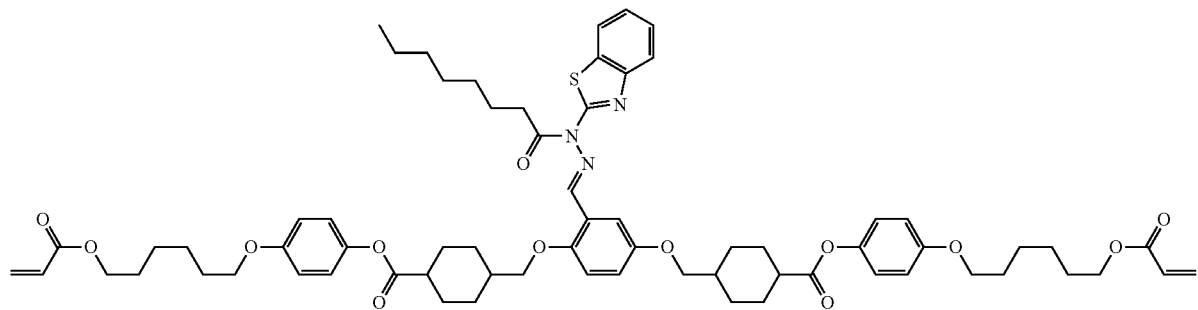
(1-122)
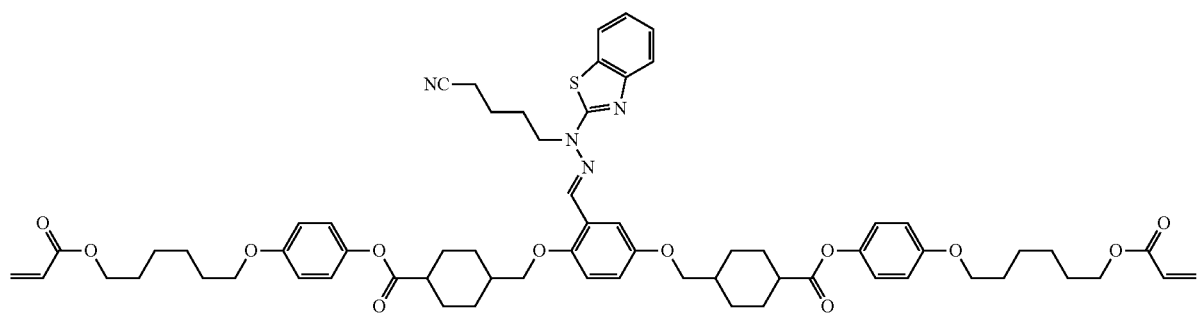
(1-123)
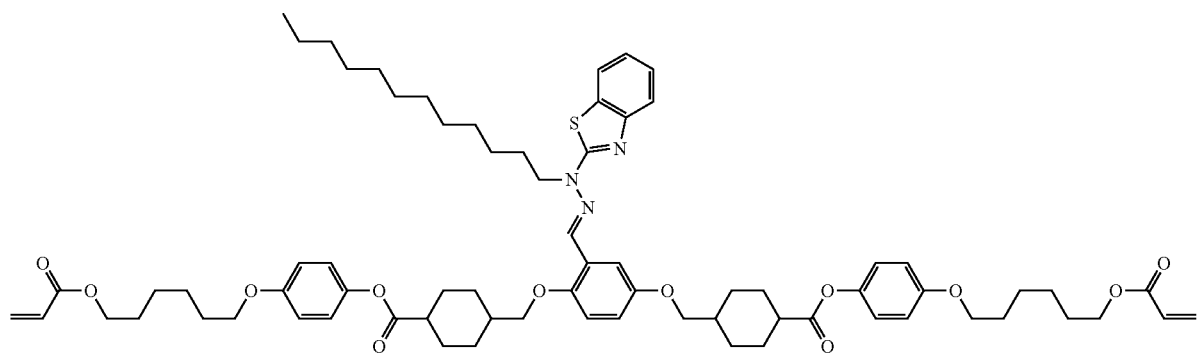
(1-124)
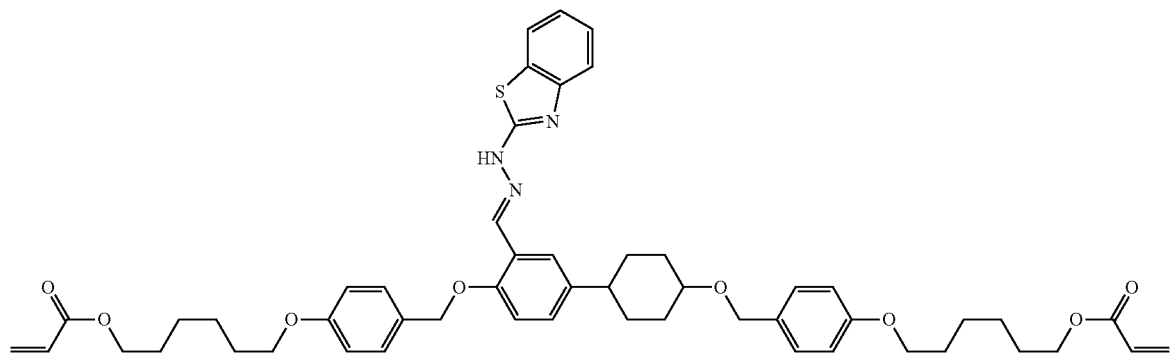

(1-125)
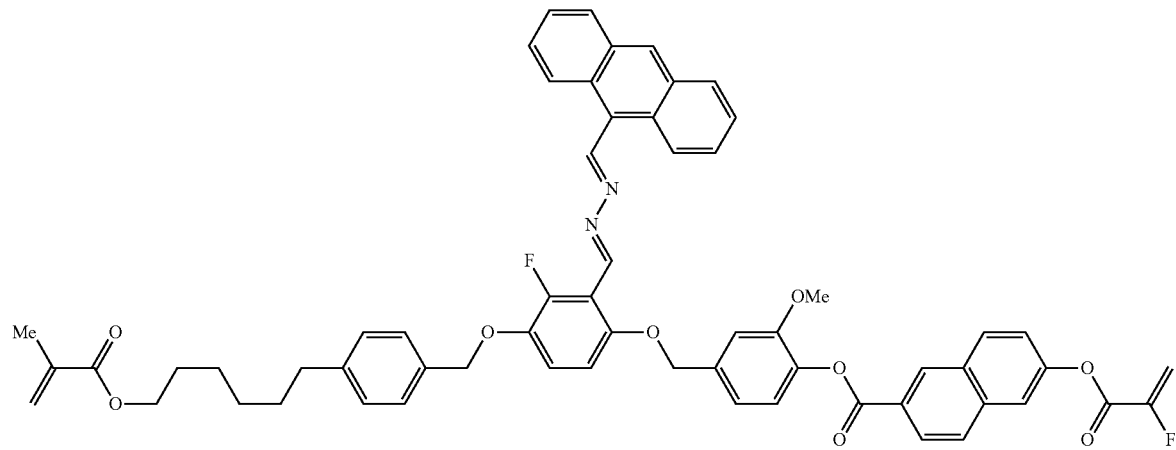
[Chem. 53]
(1-126)
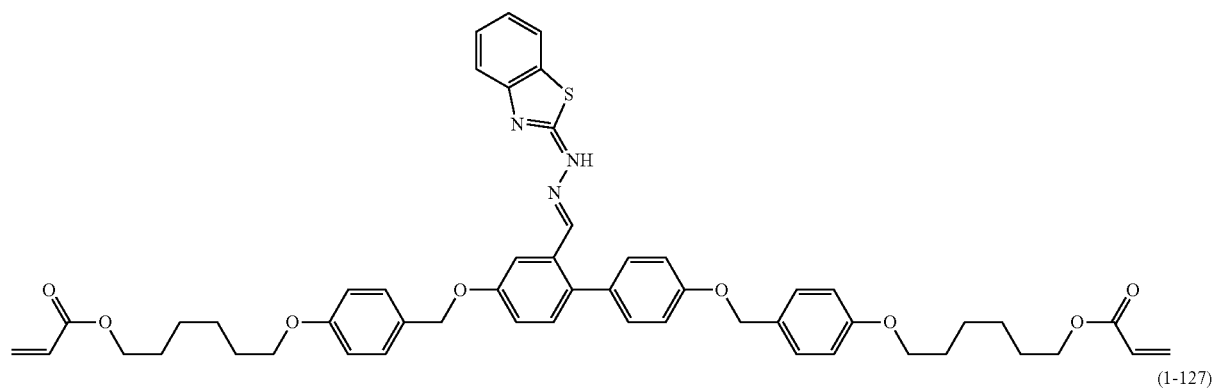
(1-127)
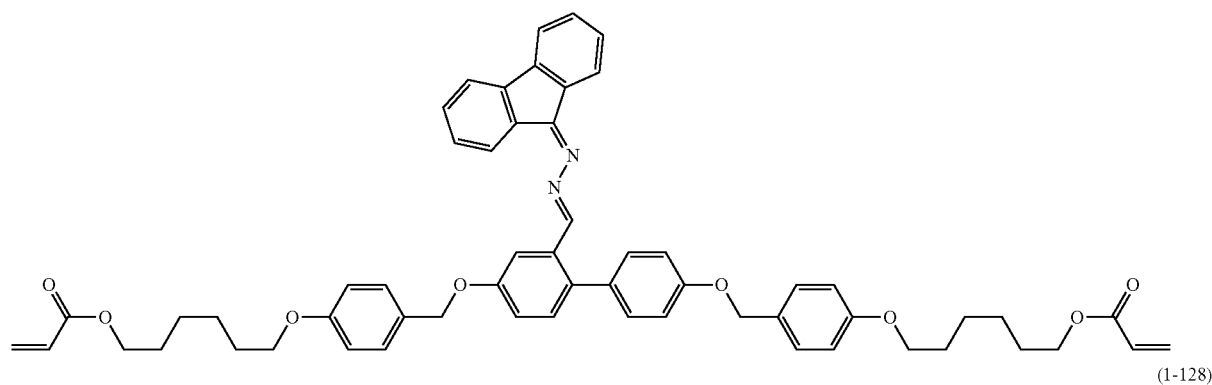
(1-128)
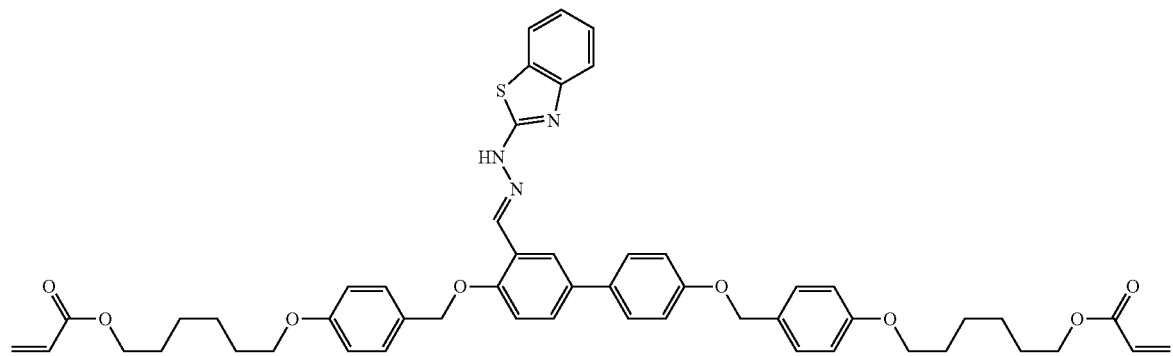

-continued
(1-129)
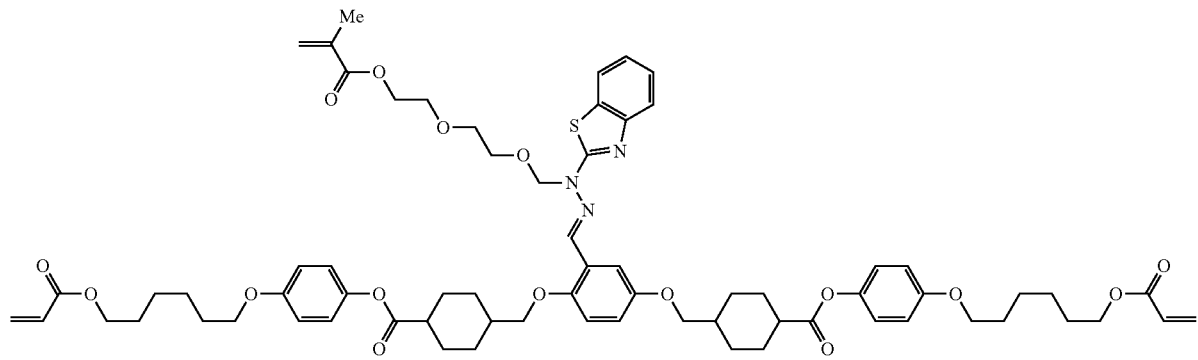
(1-130)
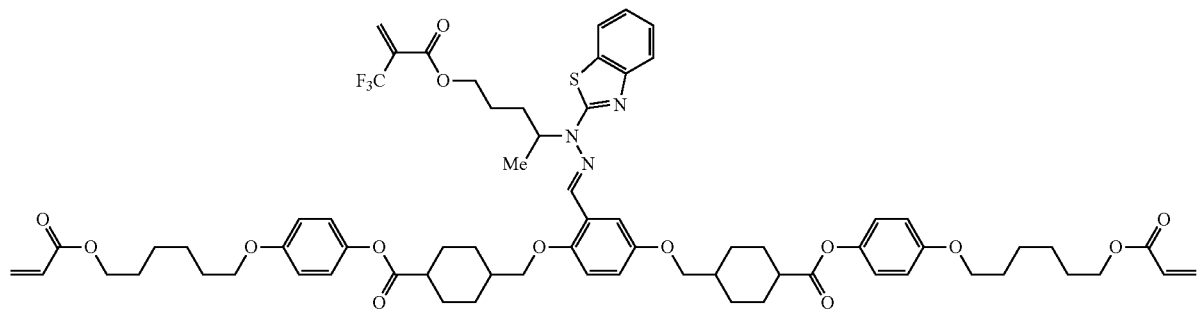
[Chem. 54]
(1-131)
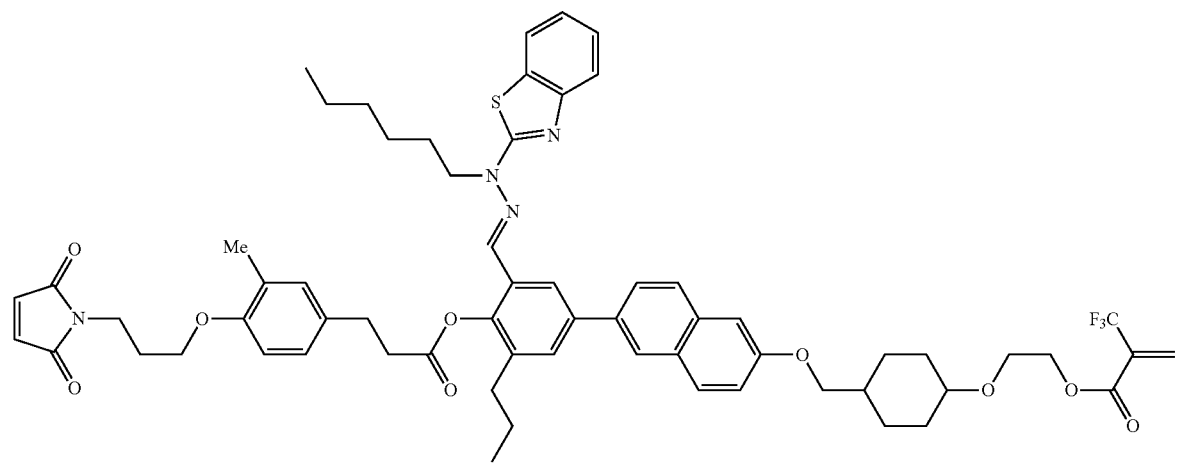

(1-132)
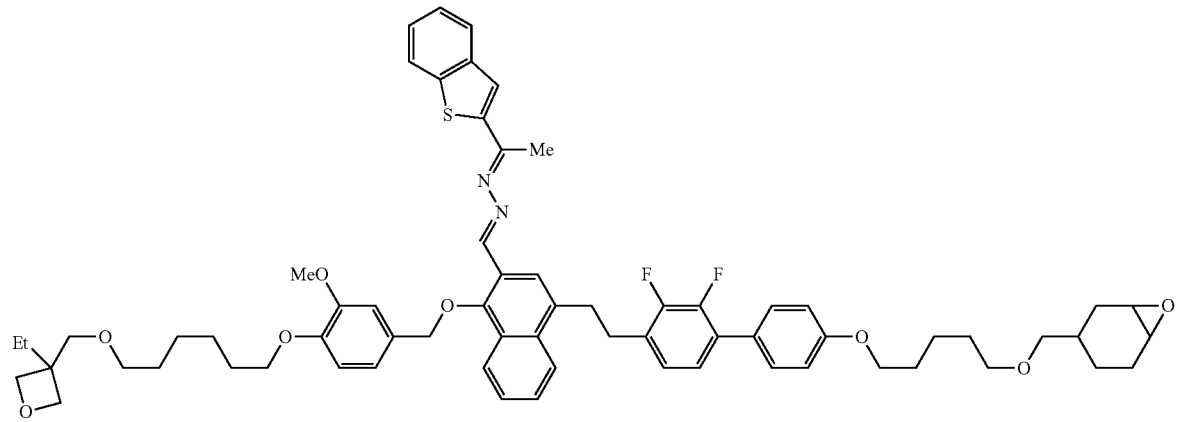
(1-133)
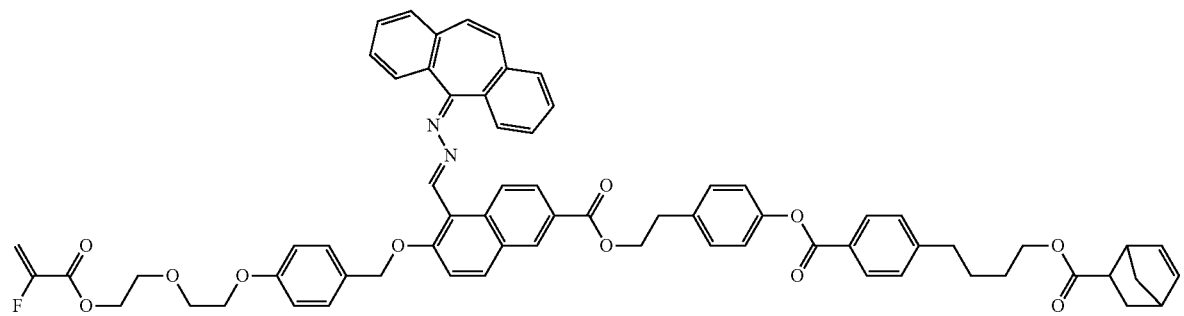
(1-134)
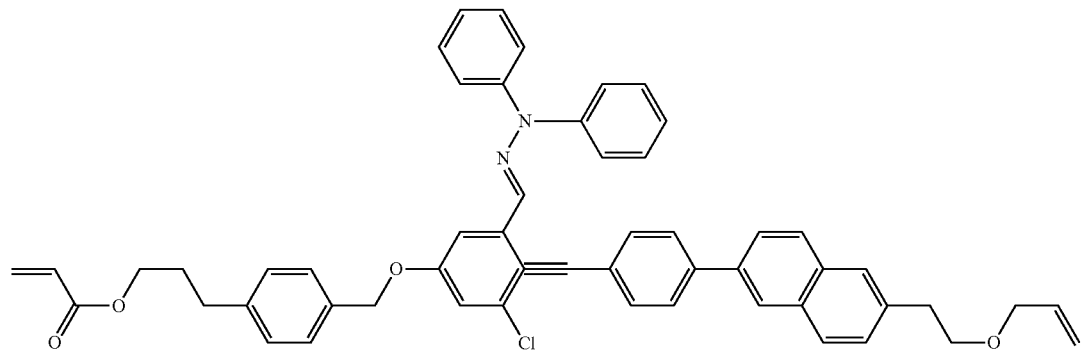
(1-135)
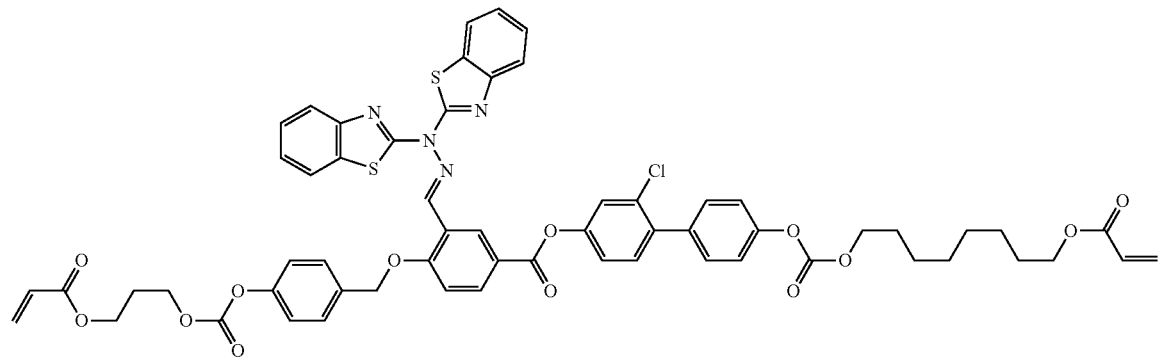

[Chem. 55]
(1-136)
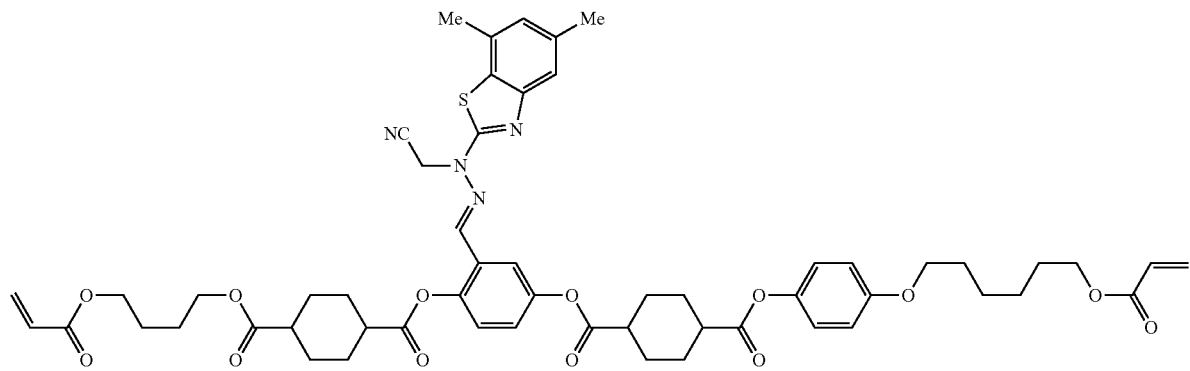
(1-137)
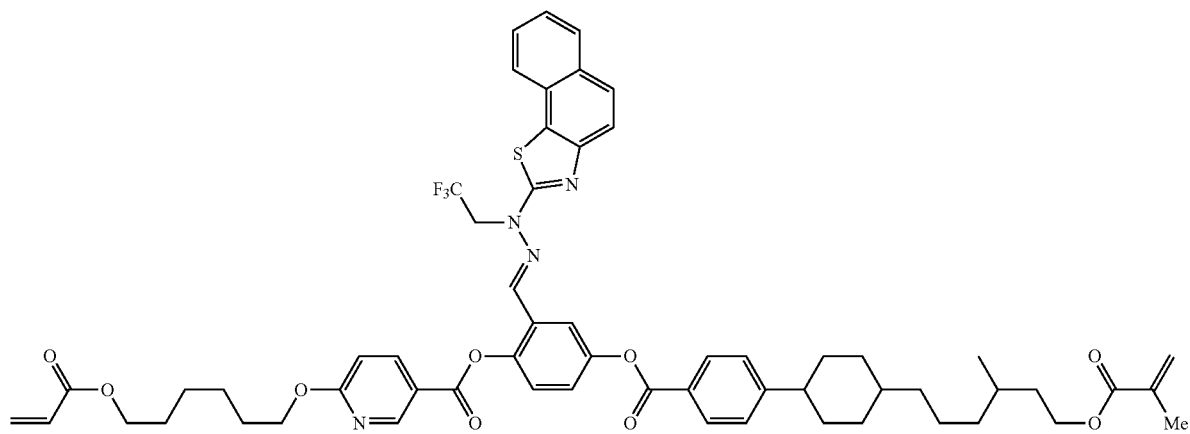
(1-138)
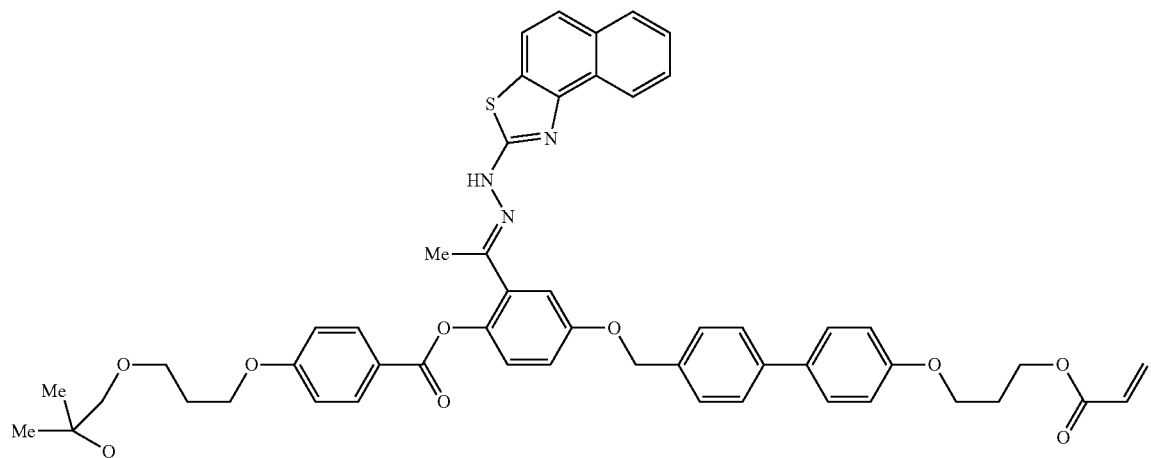

(1-139)
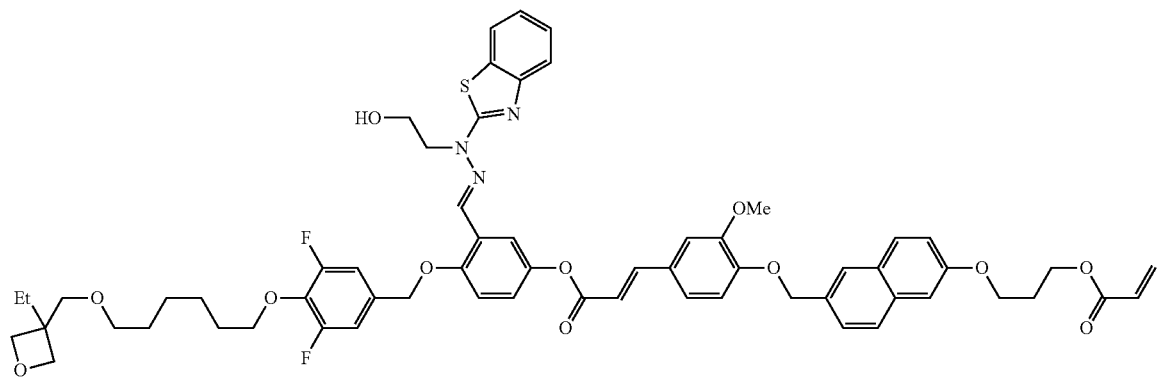
(1-140)
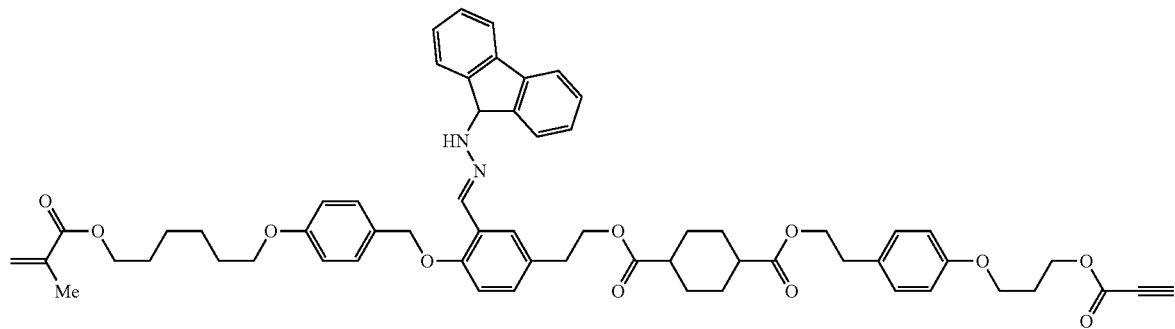
[Chem. 56]
(1-141)
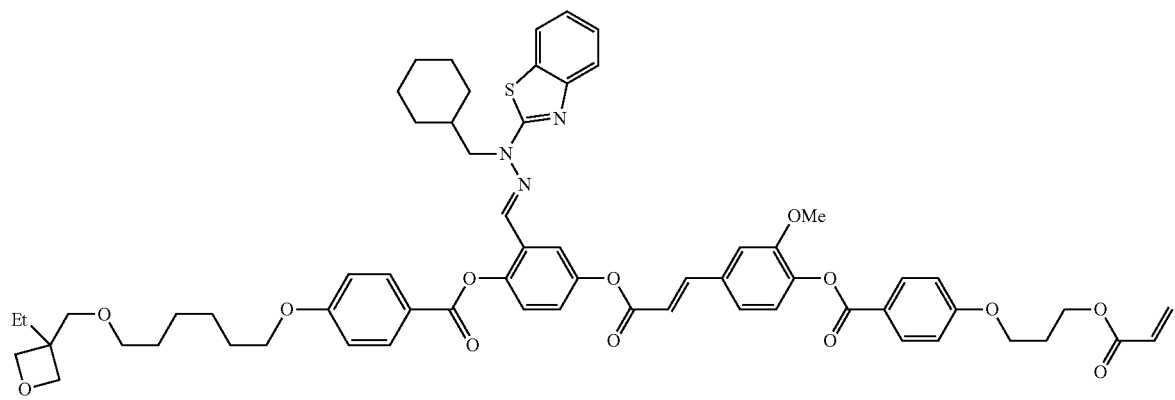

(1-142)
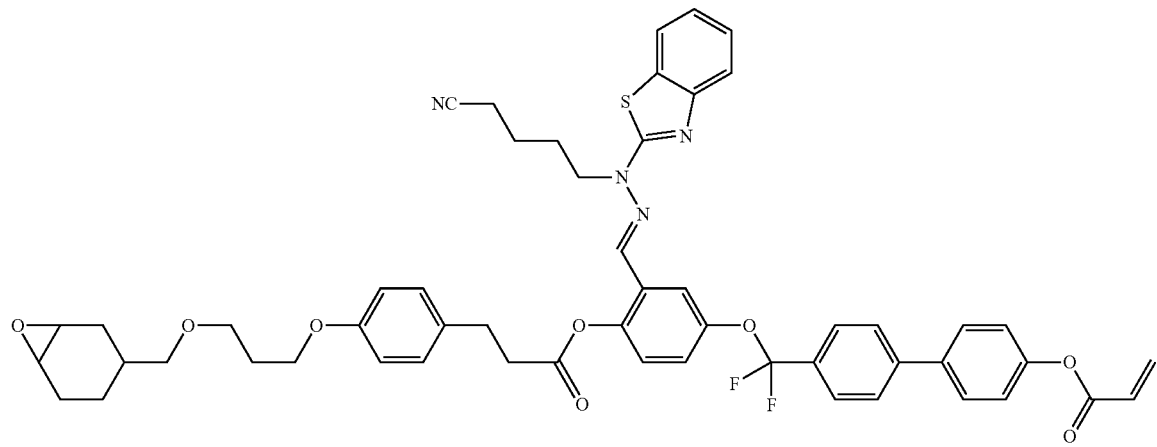
(1-143)
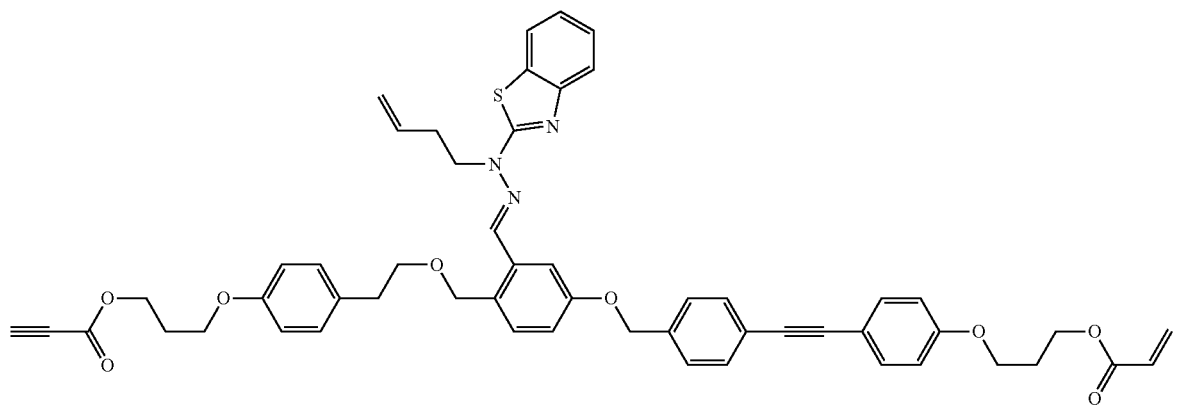
(1-144)
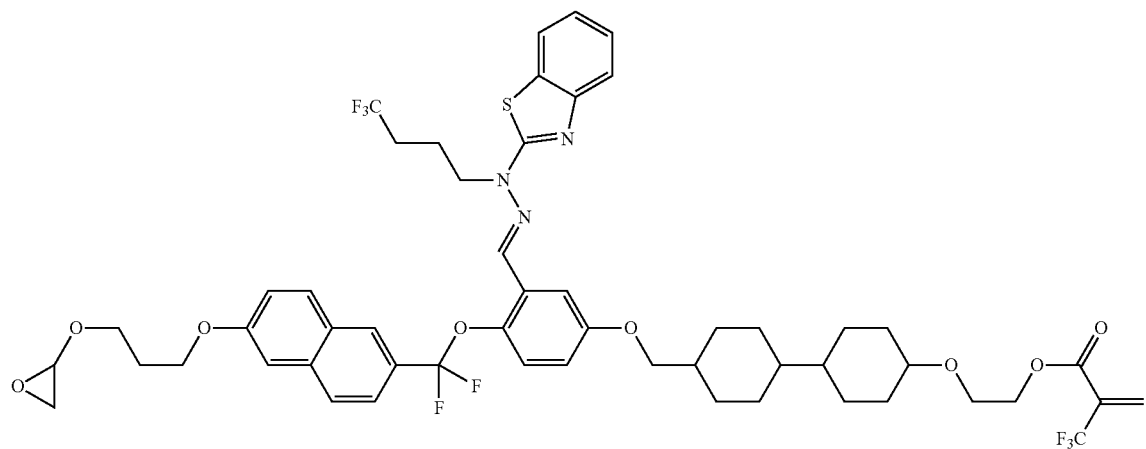

(1-145)
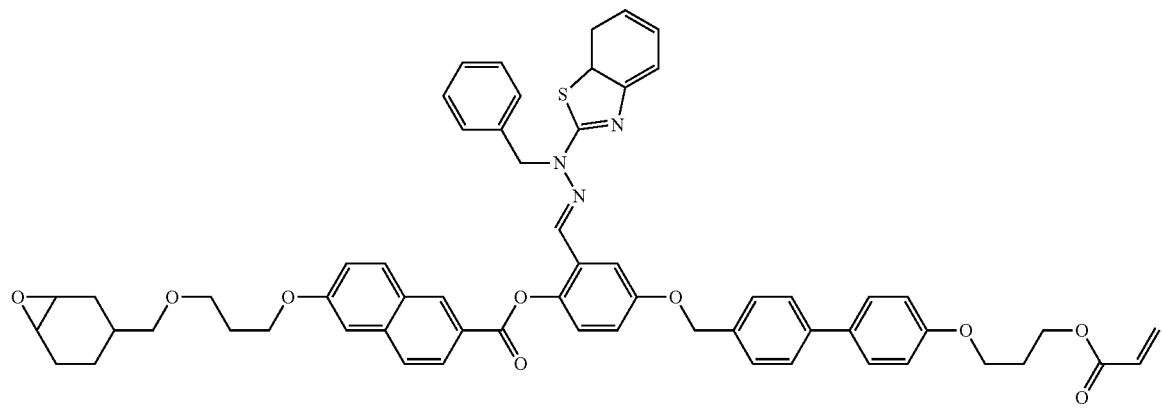
[Chem. 57]
(1-146)
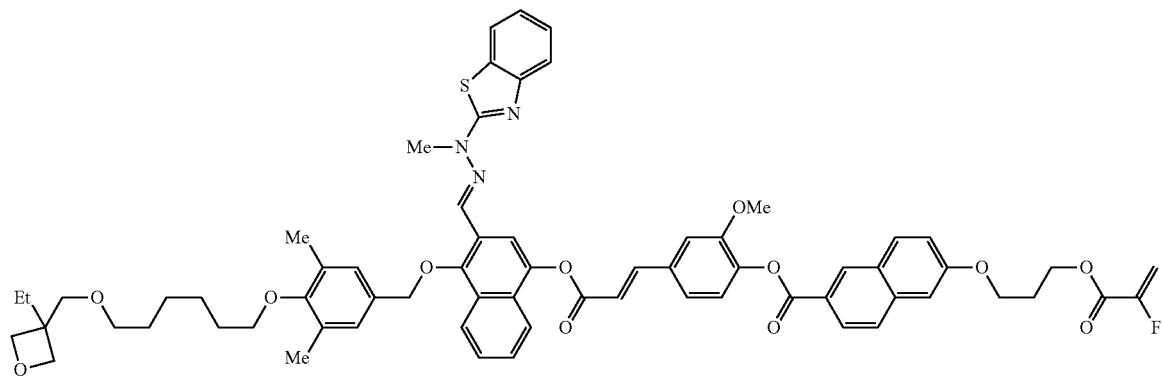
(1-147)
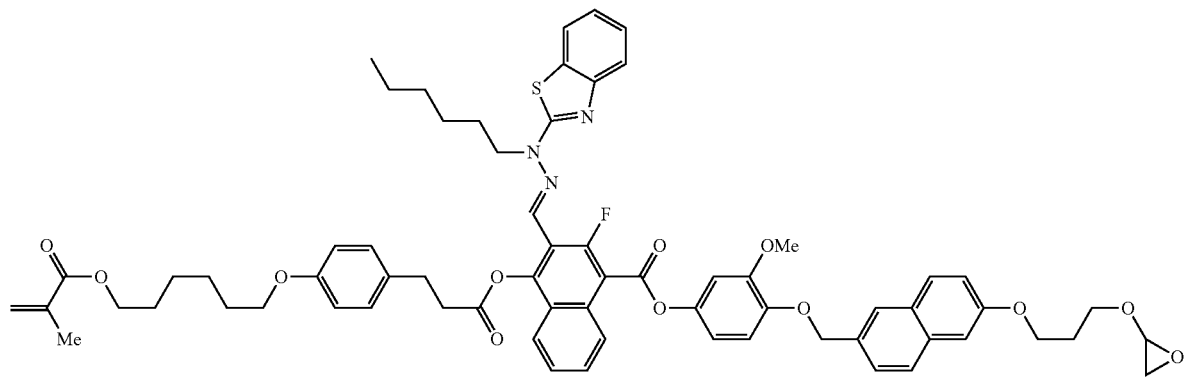

(1-148)
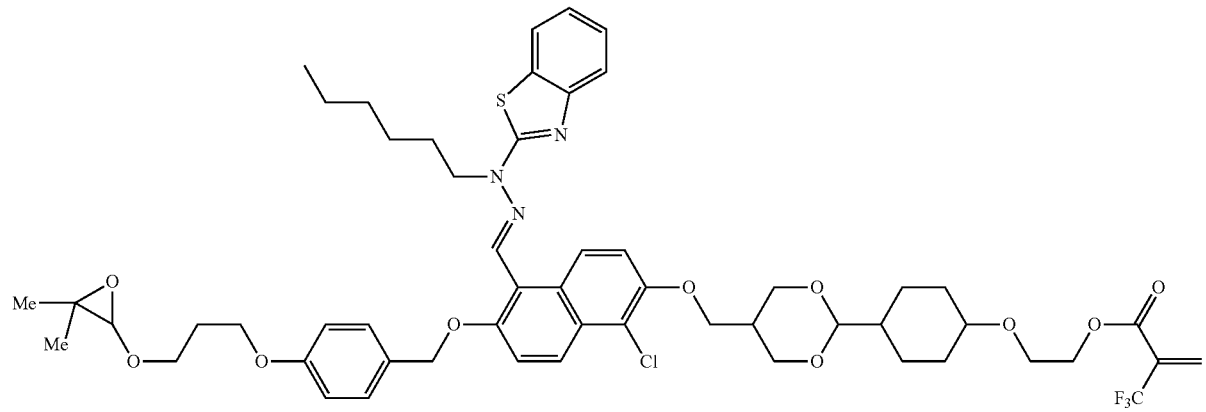
(1-149)
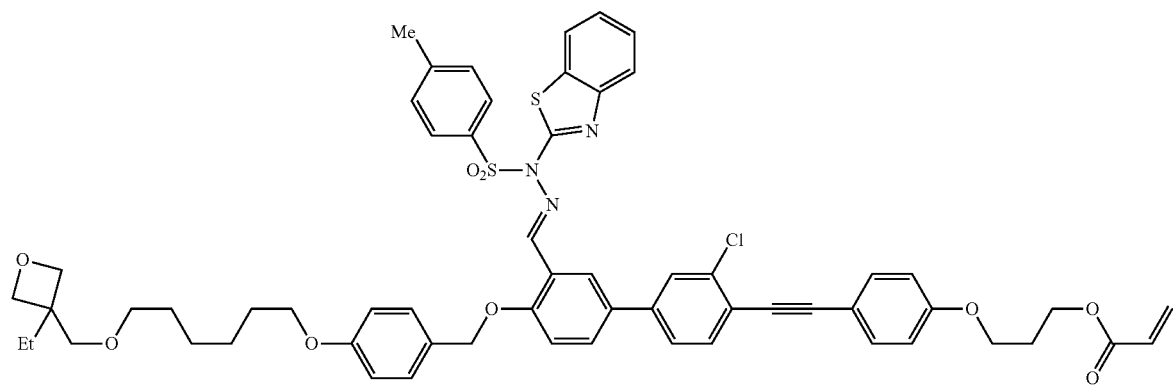
(1-150)
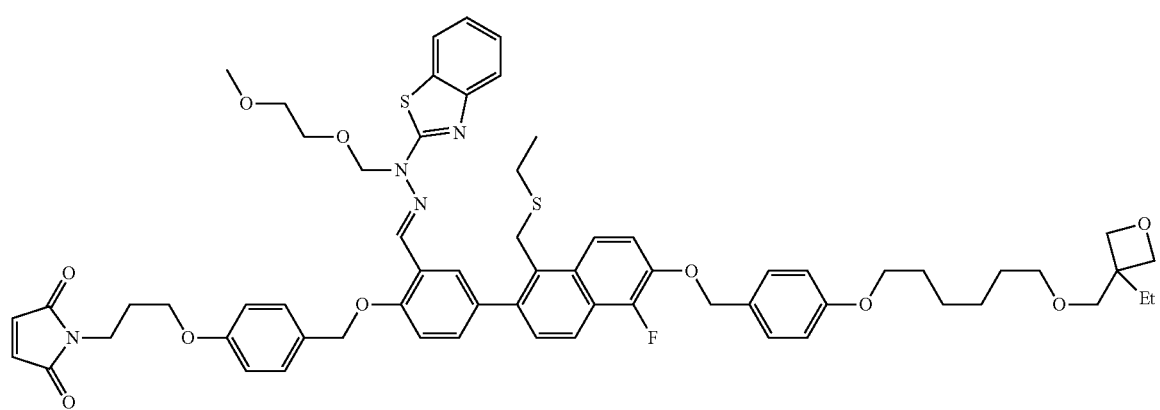

-continued
(1-151)
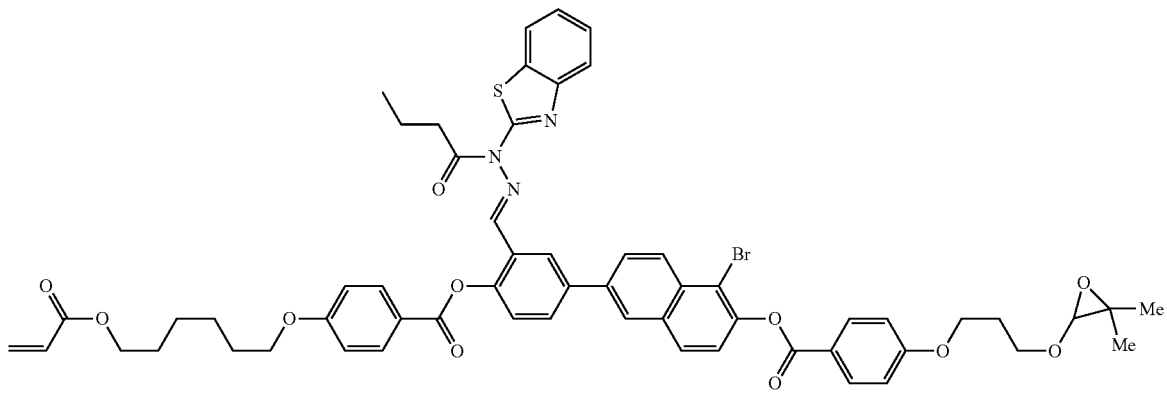
(1-152)
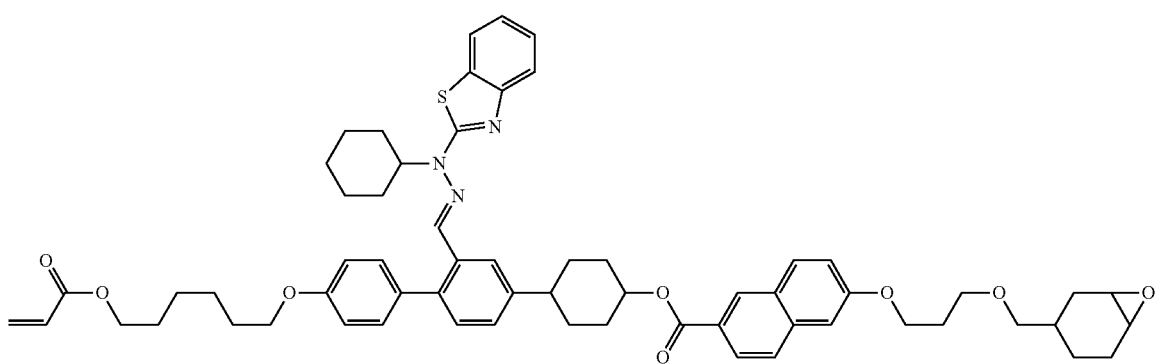
(1-153)
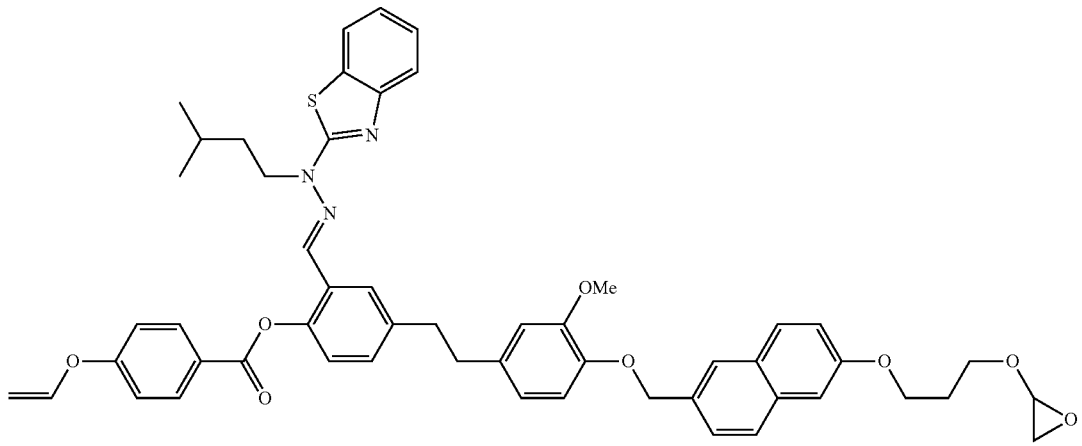
(1-154)
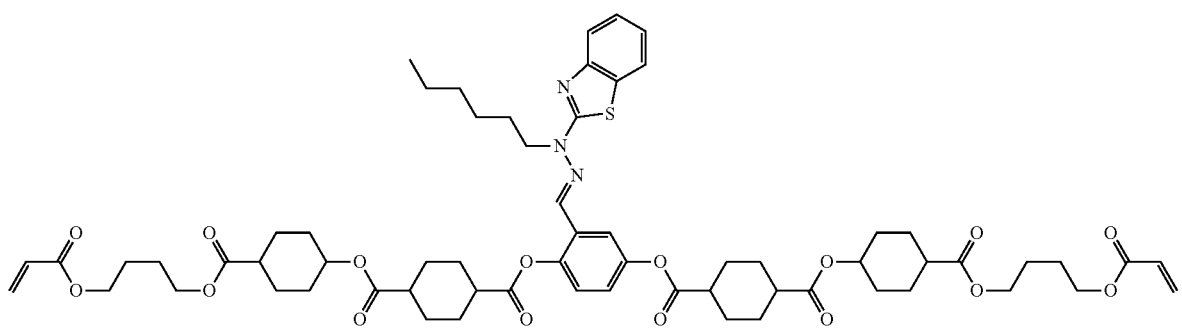

(1-155)
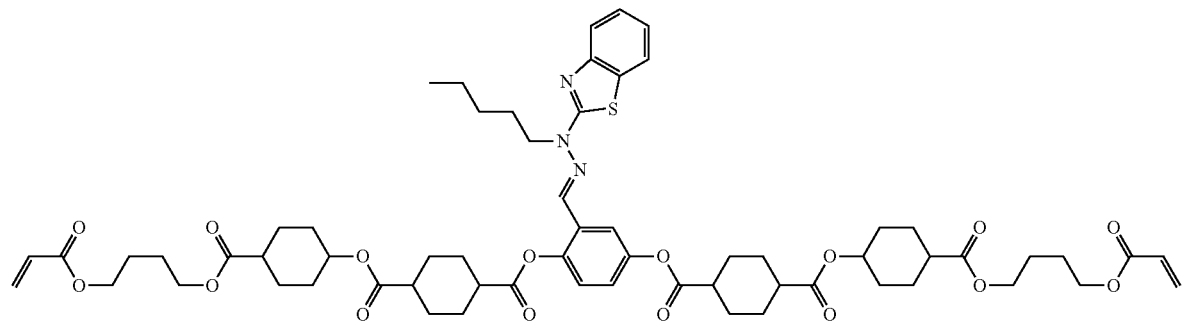
[Chem. 59]
(1-156)
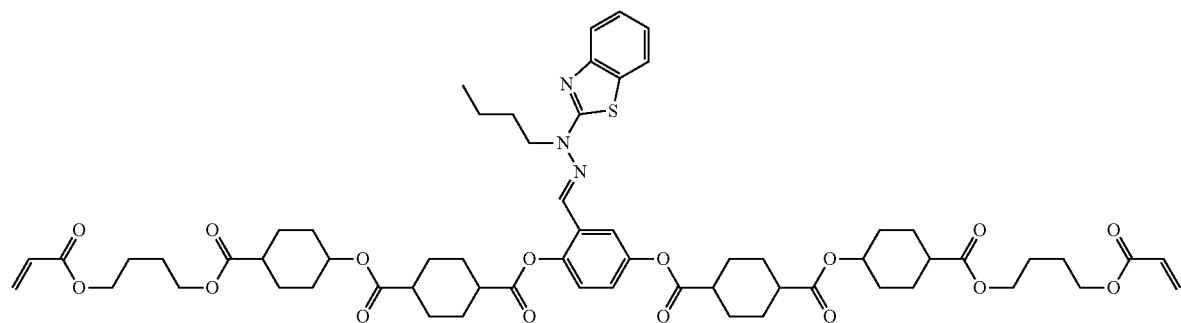
(1-157)
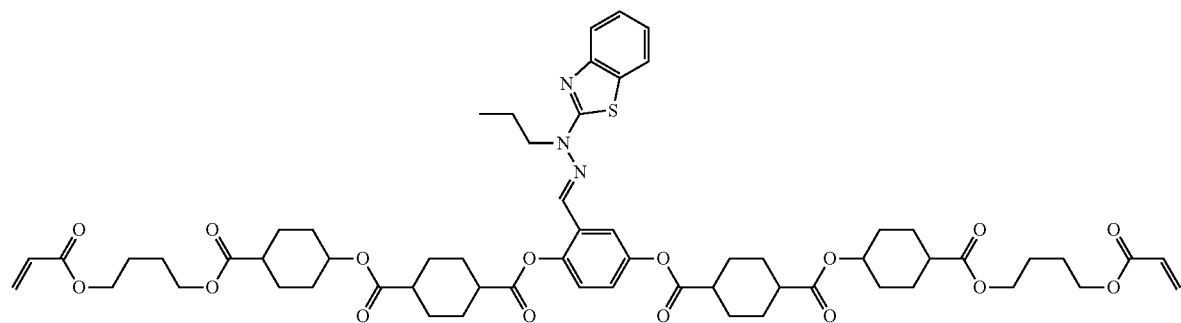
(1-158)
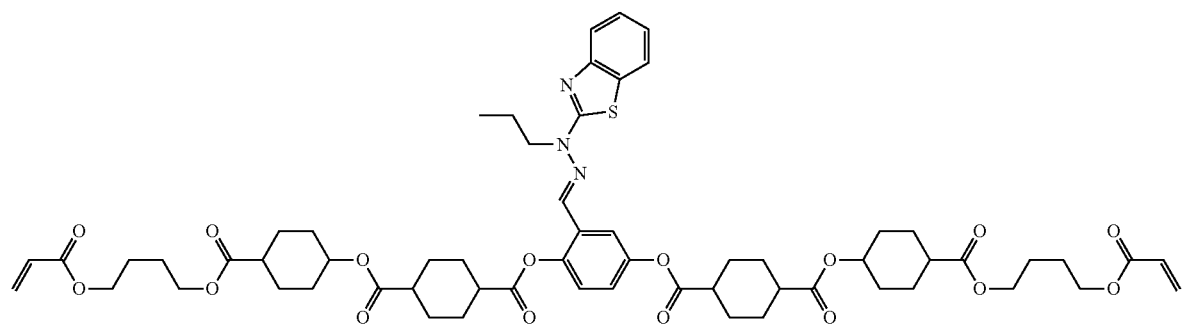

(1-159)
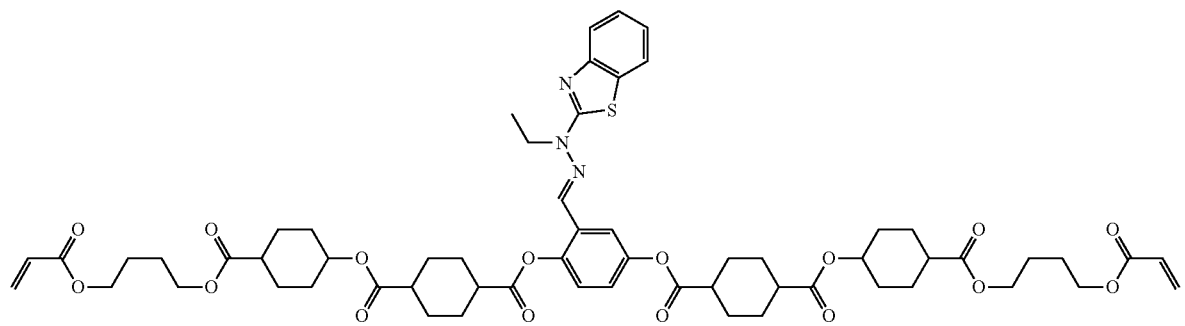
(1-160)
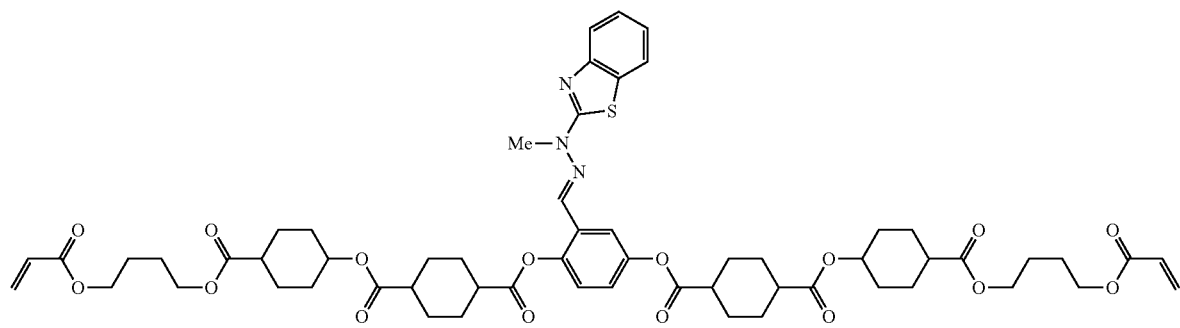
[Chem. 60]
(1-161)
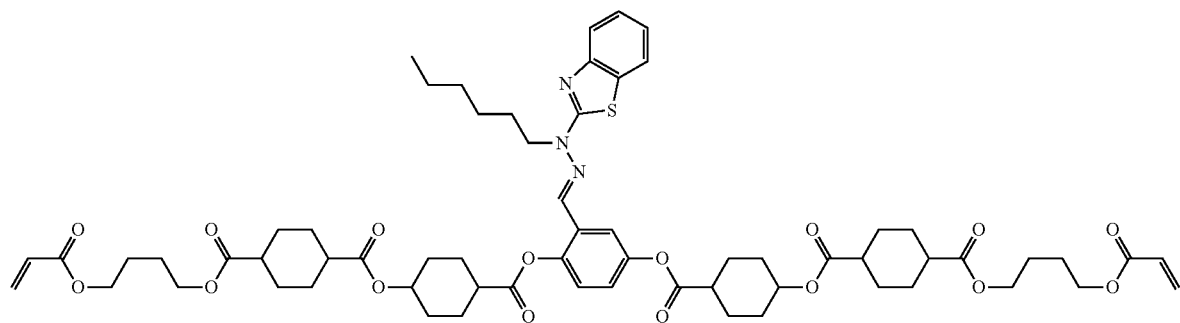
(1-162)
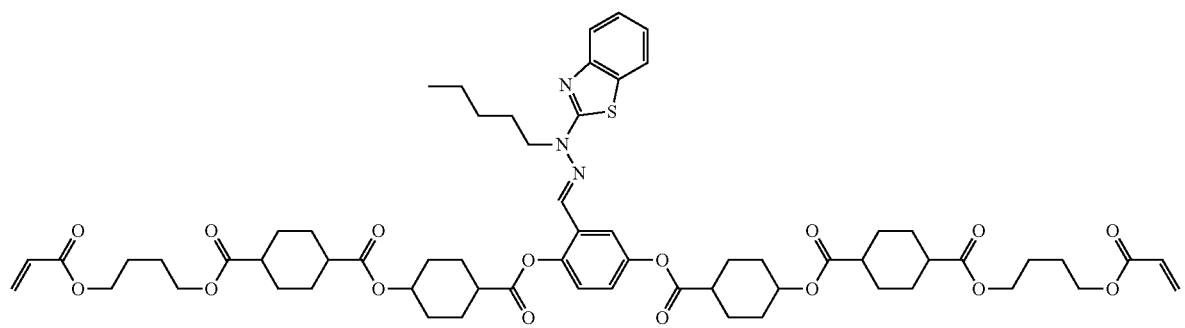

(1-163)
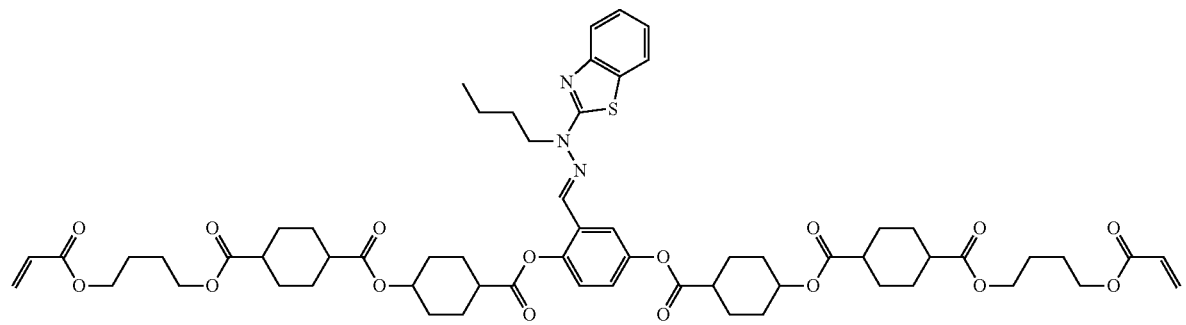
(1-164)
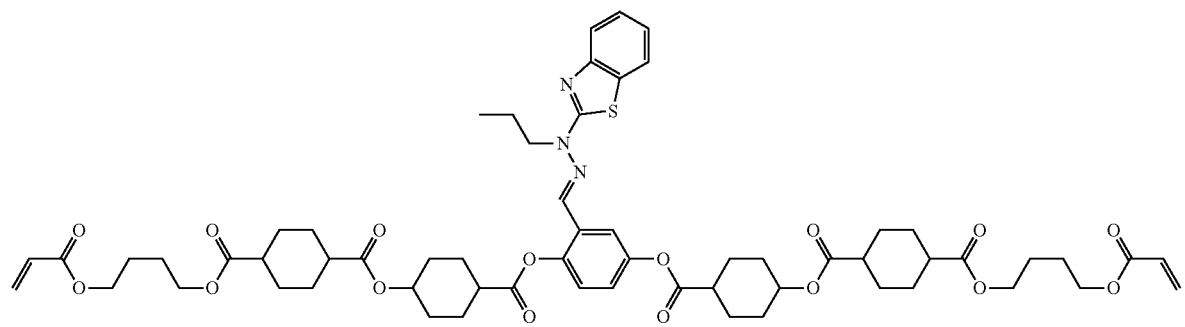
(1-165)
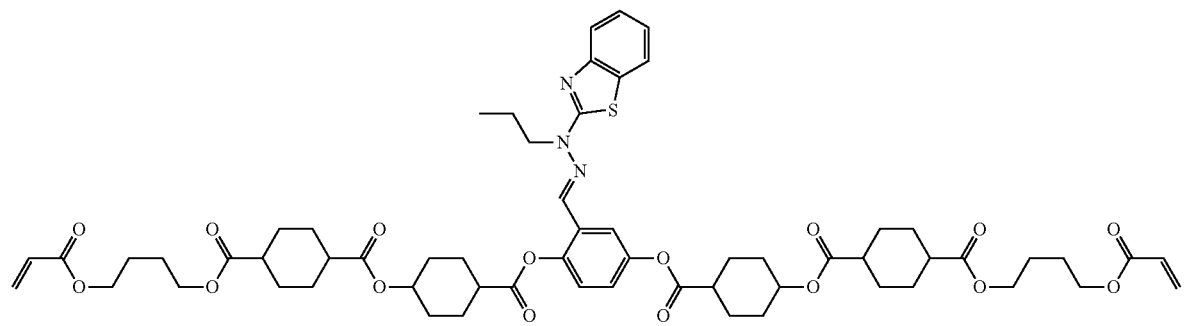
[Chem. 61]
(1-166)
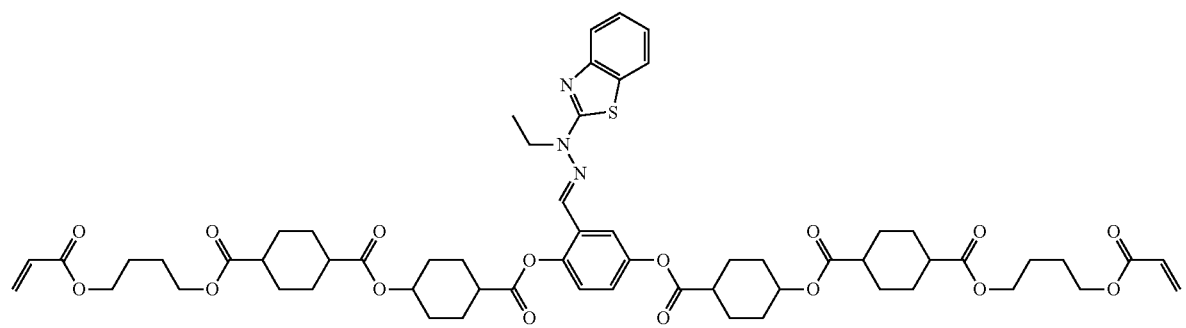

(1-167)
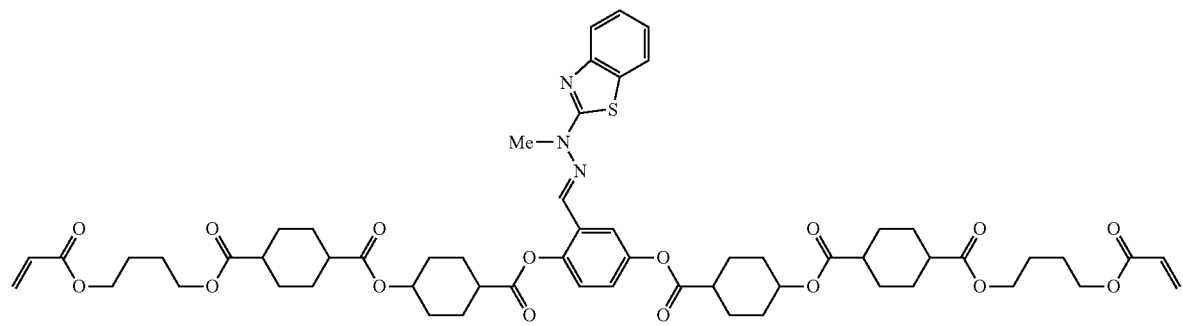
(1-168)
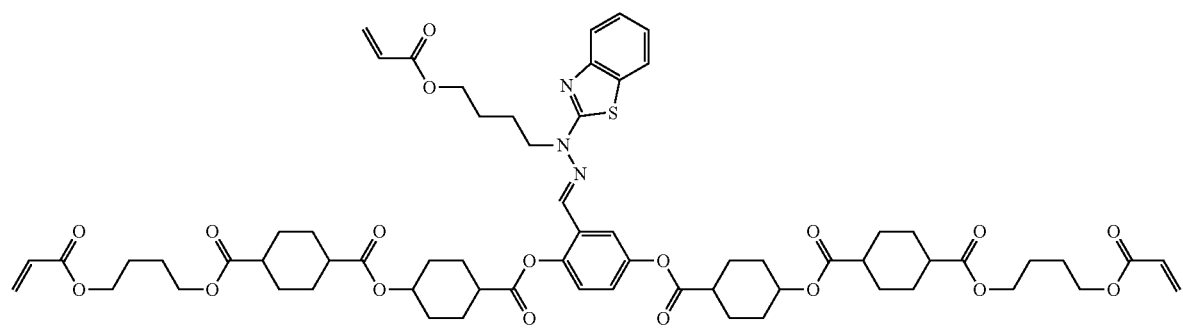
(1-169)
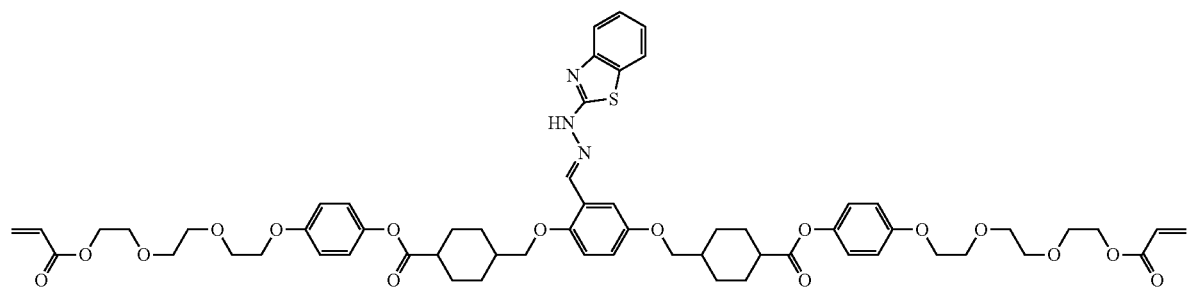
(1-170)
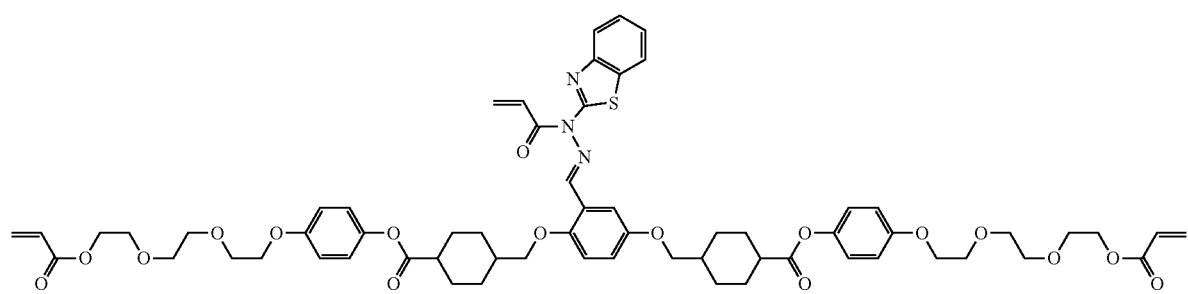

[Chem. 62]

(1-171)

(1-172)

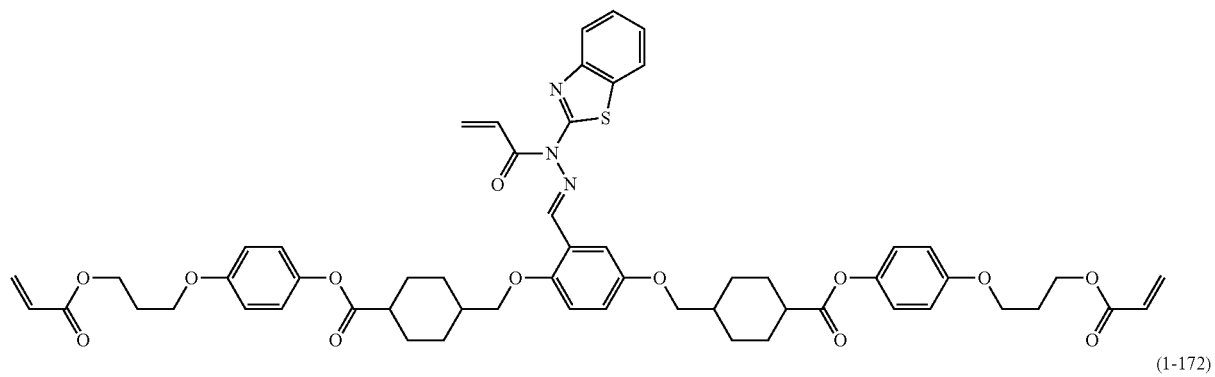

The compound according to the present invention can be produced by the following method.

(Production Method 1) Production of the Compound Represented by Formula (S-9) Below

[Chem. 63]

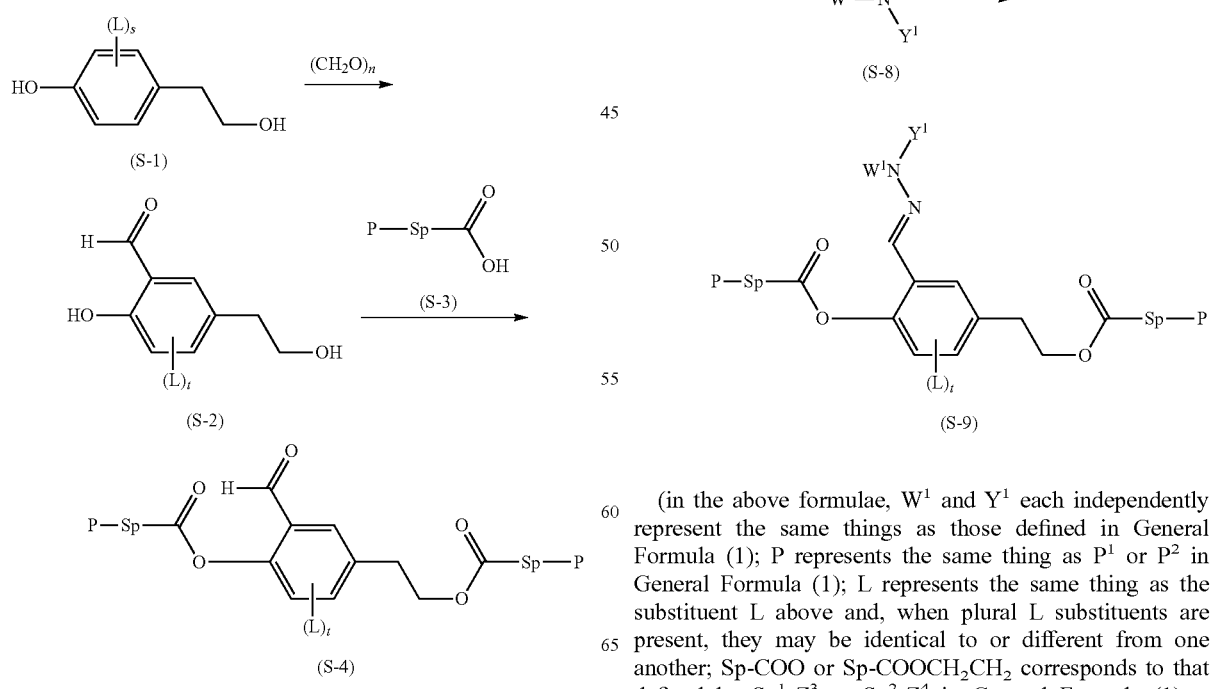

(in the above formulae, $W^1$ and $Y^1$ each independently represent the same things as those defined in General Formula (1); P represents the same thing as $P^1$ or $P^2$ in General Formula (1); L represents the same thing as the substituent L above and, when plural L substituents are present, they may be identical to or different from one another; Sp-COO or Sp-COOCH$_2$CH$_2$ corresponds to that defined by $Sp^1$-$Z^3$ or $Sp^2$-$Z^4$ in General Formula (1); s represents an integer of 0 to 4; t represents an integer of 0 to 3, and "halogen" represents a halogen atom or a halogen equivalent)

Formylation of the compound represented by Formula (S-1) gives the compound represented by Formula (S-2). An example of the reaction is conducted by a method in which the compound represented by Formula (S-1) is reacted with para-formaldehyde in the presence of magnesium chloride and a base. An example of the base is triethylamine.

The compound represented by Formula (S-2) is reacted with the compound represented by Formula (S-3) to produce the compound represented by Formula (S-4). The above reaction may be conducted under conditions in which, for example, a condensing agent is used or in which the compound represented by Formula (S-3) is formed into an acid chloride, a mixed acid anhydride, or a carboxylic acid anhydride, which is subsequently reacted with the compound represented by General Formula (S-2) in the presence of a base. In the case where a condensing agent is used, examples of the condensing agent include N,N'-dicyclohexylcarbodiimide, N,N'-diisopropylcarbodiimide, and 1-ethyl-3-(3-dimethylaminopropyl)carbodiimide hydrochloride. Examples of the base include triethylamine and diisopropylethylamine.

The compound represented by Formula (S-5) is reacted with, for example, hydrazine monohydrate to produce the compound represented by Formula (S-6).

The compound represented by Formula (S-6) is reacted with the compound represented by Formula (S-7) in the presence of a base to produce the compound represented by Formula (S-8). Examples of the base include potassium carbonate and cesium carbonate.

The compound represented by Formula (S-8) is reacted with the compound represented by Formula (S-4) in the presence of an acid catalyst to produce the compound represented by Formula (S-9). Examples of the acid include p-toluenesulfonic acid, pyridinium p-toluenesulfonate, and 10-camphorsulfonic acid.

(Production Method 2) Production of the Compound Represented by Formula (S-15) Below

[Chem. 64]

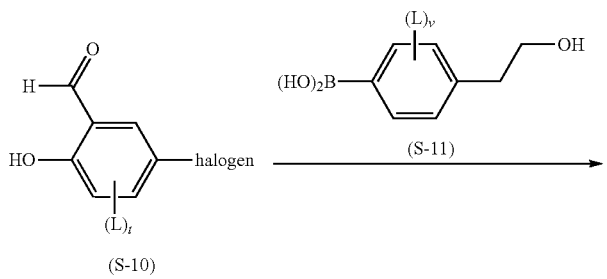

(S-10)

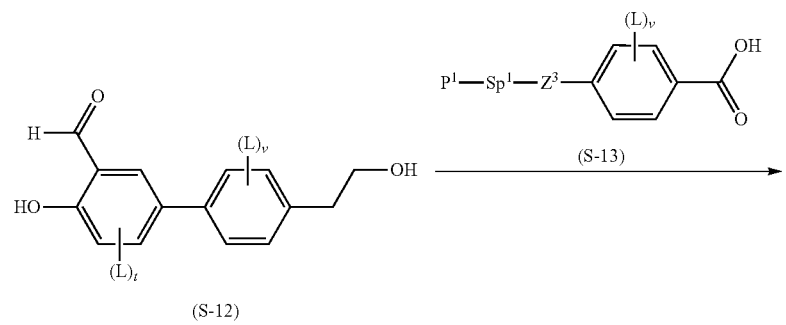

(S-12)

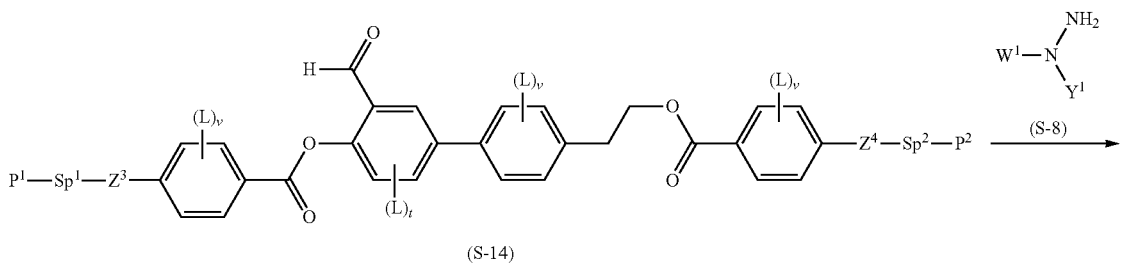

(S-14)

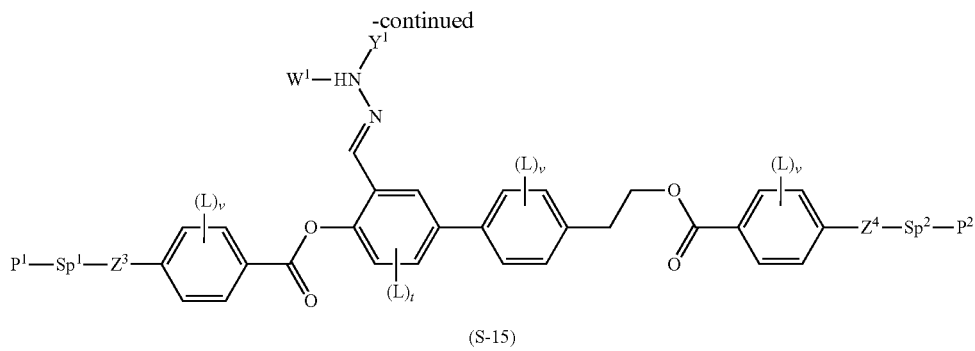

(S-15)

(in the above formulae, $P^1$, $P^2$, $Sp^1$, $Sp^2$, $Z^3$, $Z^4$, $W^1$, and $Y^1$ each independently represent the same things as those defined in General Formula (1); L represents the same things as the substituent L defined above and, in the case where plural L substituents are present, they may be identical to or different from one another; v represents an integer of 0 to 4; t represents an integer of 0 to 3; and "halogen" represents a halogen atom or a halogen equivalent)

The compound represented by Formula (S-10) is reacted with the compound represented by Formula (S-11) to produce the compound represented by Formula (S-12). The above reaction may be conducted, for example, by a method in which cross-coupling is performed in the presence of a metal catalyst and a base. Examples of the metal catalyst include [1,1'-bis(diphenylphosphino)ferrocene]palladium (II) dichloride, palladium acetate(II), and tetrakis(triphenylphosphine)palladium(0). An example of the base is triethylamine. The above reaction may be conducted under the conditions based on, for example, the methods described in the following literature: Metal-Catalyzed Cross-Coupling Reactions (Armin de Meijere and Francois Diedrich, Wiley-VCH), Palladium Reagents and Catalysts: New Perspectives for the 21st Century (Jiro Tsuji, Wiley & Sons, Ltd.), Cross-Coupling Reactions: A Practical Guide (Topics in Current Chemistry) (S. L. Buchwald, K. Fugami, T. Hiyama, M. Kosugi, M. Miura, N. Miyaura, A. R. Muci, M. Nomura, E. Shirakawa, and K. Tamao, Springer).

The compound represented by Formula (S-12) is reacted with the compound represented by Formula (S-13) as in Production Method 1 to produce the compound represented by Formula (S-14).

The compound represented by Formula (S-14) is reacted with the compound represented by Formula (S-8) as in Production Method 1 to produce the compound represented by Formula (S-15).

(Production Method 3) Production of the Compound Represented by Formula (S-23) Below

[Chem. 65]

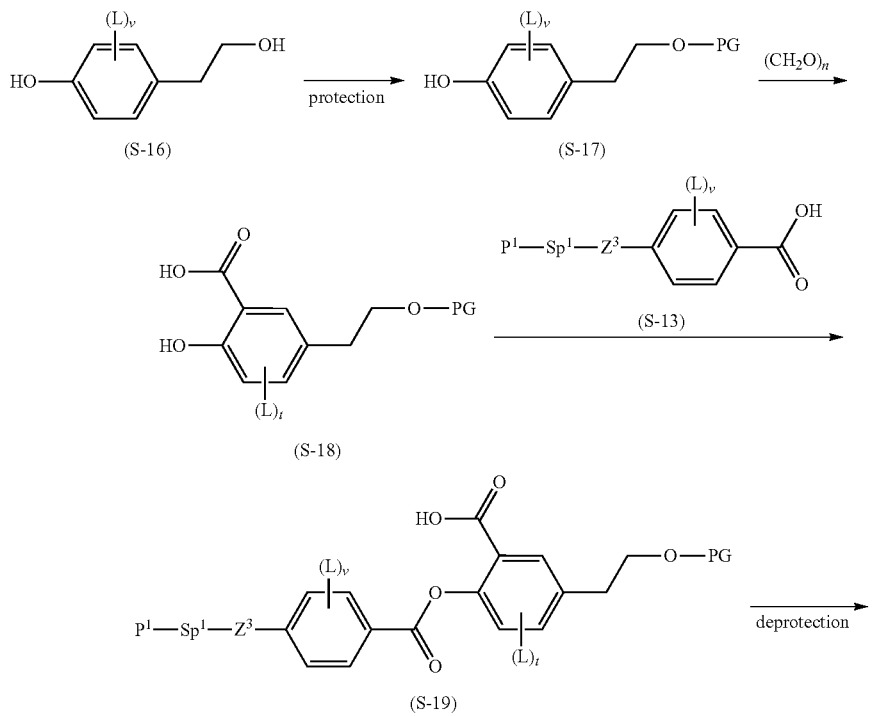

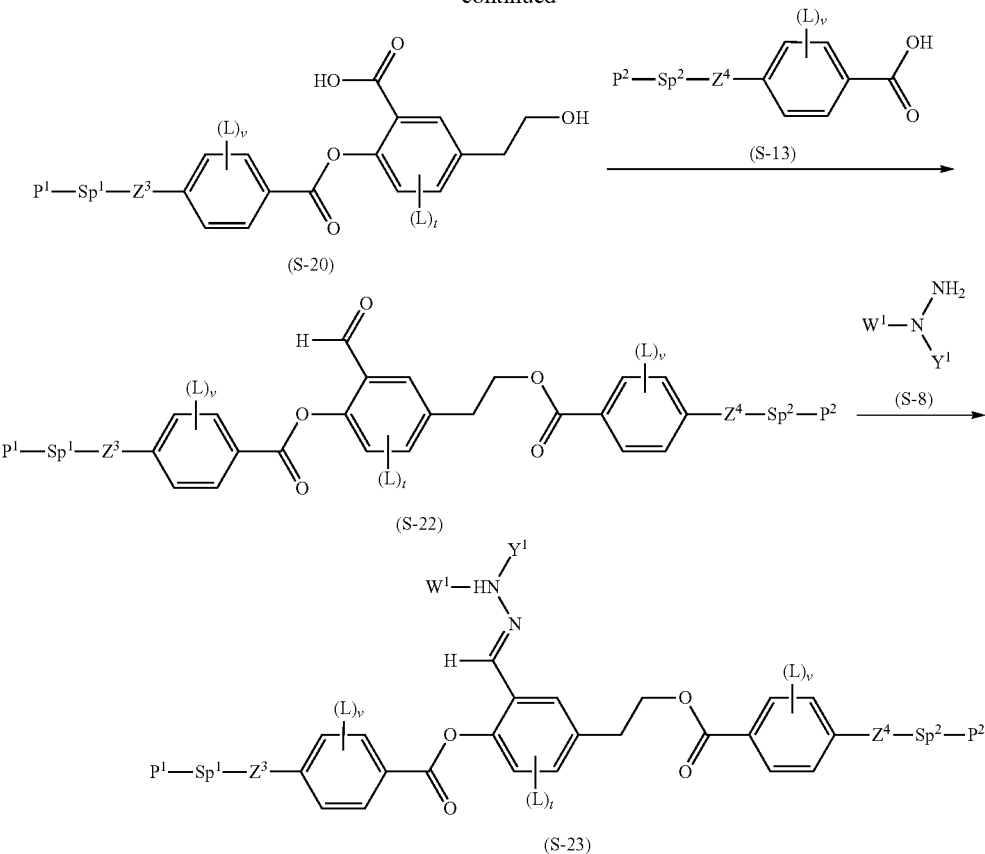

(in the above formulae, $P^1$, $P^2$, $Sp^1$, $Sp^2$, $Z^3$, $Z^4$, $W^1$, and $Y^1$ each independently represent the same things as those defined in General Formula (1); L represents the same thing as the substituent L defined above and, in the case where plural L substituents are present, they may be identical to or different from one another; v represents an integer of 0 to 4; t represents an integer of 0 to 3; and PG represents a protecting group)

A hydroxyl group included in the compound represented by Formula (S-16) is protected with a protecting group (PG). The protecting group (PG) is not limited; any protecting group capable of performing protection consistently until a deprotection step is conducted may be used. Preferable examples of the protecting group (PG) include those described in GREENE'S PROTECTIVE GROUPS IN ORGANIC SYNTHESIS ((Fourth Edition), PETER G. M. WUTS and THEODORA W. GREENE, John Wiley & Sons, Inc., Publication). A specific example of the protecting group is a tetrahydropyranyl group.

As in Production Method 1, formylation of the compound represented by Formula (S-17) gives the compound represented by Formula (S-18).

The compound represented by Formula (S-18) is reacted with the compound represented by Formula (S-13) as in Production Method 2 to produce the compound represented by Formula (S-19).

Subsequently, the protecting group (PG) included in the compound represented by Formula (S-19) is deprotected. The deprotection reaction may be conducted under any conditions that allow the compound represented by Formula (S-20) to be produced but is preferably conducted under the conditions described in the above literature.

The compound represented by Formula (S-20) is reacted with the compound represented by Formula (S-13) as in Production Method 2 to produce the compound represented by Formula (S-22).

The compound represented by Formula (S-22) is reacted with the compound represented by Formula (S-8) as in Production Method 1 to produce the compound represented by Formula (S-23).

Examples of reaction conditions other than those described in the steps of Production Methods 1 to 3 above include the reaction conditions described in the following literature: Jikken Kagaku Kouza ("Course on Experimental Chemistry", edited by The Chemical Society of Japan, printed by Maruzen Co., Ltd.), Organic Syntheses (John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), and Fiesers' Reagents for Organic Synthesis (John Wiley & Sons, Inc.) and the conditions revealed through online search services, such as SciFinder (Chemical Abstracts Service, American Chemical Society) and Reaxys (Elsevier Ltd.).

In each of the above steps, a reaction solvent may be appropriately used. The solvent is not limited; any solvent that enables a desired compound to be produced may be used. Examples of the solvent include tert-butyl alcohol, isobutyl alcohol, isopropyl alcohol, isopentyl alcohol, cyclohexanol, 1-butanol, 2-butanol, 1-octanol, 2-methoxyethanol, ethylene glycol, diethylene glycol, methanol, methylcyclohexanol, ethanol, propanol, chloroform, carbon tetrachloride, dichloromethane, 1,2-dichloroethane, 1,2-dichloroethylene, 1,1,2,2-tetrachloroethane, trichloroethylene, 1-chlorobutane, carbon disulfide, acetone, acetonitrile, benzonitrile, N,N-dimethylformamide, N,N-dimethylacetamide, dimethylsulfoxide, 1,3-dimethyl-2-imidazolidinone, diethyl ether, ethylene glycol monoethyl ether, ethylene glycol monoethyl ether acetate, ethylene glycol monobutyl ether, ethylene glycol monomethyl ether, diethylene glycol diethyl ether, o-dichlorobenzene, xylene, o-xylene, p-xylene, m-xylene, chlorobenzene, isobutyl acetate, isopropyl acetate, isoamyl acetate, ethyl acetate, butyl acetate, propyl acetate, pentyl acetate, methyl acetate, 2-methoxyethyl acetate, hexamethylphosphoric triamide, tris(dimethylamino)phosphine, cyclohexanone, 1,4-dioxane, dichloromethane, styrene, tetrachloroethylene, tetrahydrofuran, pyridine, 1-methyl-2-pyrrolidinone, 1,1,1-trichloroethane, toluene, hexane, pentane, cyclohexane, cyclopentane, heptane, benzene, methyl isobutyl ketone, tert-butyl methyl ether, methyl ethyl ketone, methylcyclohexanone, methyl butyl ketone, diethyl ketone, gasoline, coal tar naphtha, petroleum ether, petroleum naphtha, petroleum benzine, turpentine oil, and mineral spirit. In the case where a reaction is conducted under an organic solvent-water two-phase system, a phase-transfer catalyst may be used. Examples of the phase-transfer catalyst include benzyltrimethylammonium chloride, polyoxyethylene(20) sorbitan monolaurate [Tween 20], and sorbitan monooleate [Span 80].

Purification may be optionally performed in each of the above steps. Examples of a purification method include chromatography, recrystallization, distillation, sublimation, reprecipitation, adsorption, and liquid separation. In the case where a purifying agent is used, examples of the purifying agent include silica gel, alumina, active carbon, active clay, Celite, zeolite, mesoporous silica, carbon nanotube, carbon nanohorn, white charcoal, charcoal, graphene, an ion-exchange resin, Japanese acid clay, silicon dioxide, diatomaceous earth, pearlite, cellulose, an organic polymer, and a porous gel.

<<Composition>>

The compound according to the present invention is preferably included in a nematic liquid crystal composition, a smectic liquid crystal composition, a chiral smectic liquid crystal composition, or a cholesteric liquid crystal composition. A liquid crystal composition including the reactive compound according to the present invention may further include a compound other than the compound according to the present invention.

Specifically, the other polymerizable compound that can be used together with the polymerizable compound according to the present invention in a mixture is preferably a compound represented by General Formula (II-1) below,

[Chem. 66]

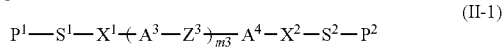

(II-1)

and/or a compound represented by General Formula (II-2) below,

[Chem. 67]

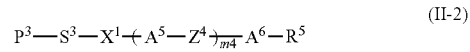

(II-2)

(in General Formulae (II-1) and (II-2), $P^1$, $P^2$, and $P^3$ each independently represent a polymerizable group; $S^1$, $S^2$, and $S^3$ each independently represent a single bond or an alkylene group having 1 to 20 carbon atoms in which one —$CH_2$— group or two or more —$CH_2$— groups that are not adjacent to one another may be each independently replaced with —O—, —COO—, —OCO—, or —OCOO—; $X^1$, $X^2$, and $X^3$ each independently represent —O—, —S—, —$OCH_2$—, —$CH_2O$—, —CO—, —COO—, —OCO—, —CO—S—, —S—CO—, —O—CO—O—, —CO—NH—, —NH— CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO— CH=CH—, —COO—$CH_2CH_2$—, —OCO—$CH_2CH_2$—, —$CH_2CH_2$—COO—, —$CH_2CH_2$—OCO—, —COO— $CH_2$—, —OCO—$CH_2$—, —$CH_2$—COO—, —$CH_2$— OCO—, —CH=CH—, —CF=CF—, —C≡C—, or a single bond; $Z^3$ and $Z^4$ each independently represent —O—, —S—, —$OCH_2$—, —$CH_2O$—, —COO—, —OCO—, —CO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO— CH=CH—, —OCO—CH=CH—, —COO—$CH_2CH_2$—, —OCO—$CH_2CH_2$—, —$CH_2CH_2$—COO—, —$CH_2CH_2$— OCO—, —COO—$CH_2$—, —OCO—$CH_2$—, —$CH_2$— COO—, —$CH_2$—OCO—, —CH=CH—, —CF=CF—, —C≡C—, or a single bond; $A^3$, $A^4$, $A^5$, and $A^6$ each independently represent a 1,4-phenylene group, a 1,4-cyclohexylene group, a pyridine-2,5-diyl group, a pyrimidine-2, 5-diyl group, a naphthalene-2,6-diyl group, a naphthalene-1,4-diyl group, a tetrahydronaphthalene-2,6-diyl group, or a 1,3-dioxane-2,5-diyl group; $A^3$, $A^4$, $A^5$, and $A^6$ may optionally be each independently substituted with an alkyl group, a halogenated alkyl group, an alkoxy group, a halogenated alkoxy group, a halogen atom, a cyano group, or a nitro group; $R^5$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO— S—, —S—CO—, —O—CO—O—, —CO—NH—, —NH—CO—, —CH=CH—COO—, —CH=CH— OCO—, —COO—CH=CH—, —OCO—CH=CH—, —CH=CH—, —CF=CF—, or —C≡C—; m3 and m4 represent 0, 1, 2, or 3; and, when m3 and/or m4 represents 2 or 3, the two or three $A^3$ groups, $A^5$ groups, $Z^3$ groups, and/or $Z^4$ groups may be each identical to or different from one another). It is particularly preferable that $P^1$, $P^2$, and $P^3$ be acrylic groups or methacrylic groups. Specifically, the compound represented by General Formula (II-1) is preferably a compound represented by General Formula (II-1A),

[Chem. 68]

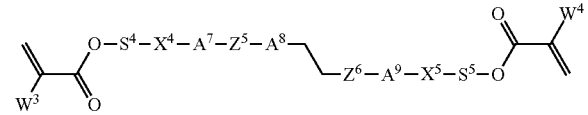

(II-1A)

(in General Formula (II-1A), $W^3$ and $W^4$ each independently represent hydrogen or a methyl group; $S^4$ and $S^5$ each independently represent an alkylene group having 2 to 18 carbon atoms; $X^4$ and $X^5$ each independently represent —O—, —COO—, —OCO—, or a single bond; $Z^5$ and $Z^6$ each independently represent —COO— or —OCO—; and $A^7$, $A^8$, and $A^9$ each independently represent a 1,4-phenylene group that may be optionally substituted with a fluorine atom, a chlorine atom, a linear or branched alkyl group having 1 to 4 carbon atoms, or a linear or branched alkoxy group having 1 to 4 carbon atoms). The compound represented by General Formula (II-1) is particularly preferably selected from compounds represented by Formulae (II-1A-1) to (II-1A-4) below,

[Chem. 69]

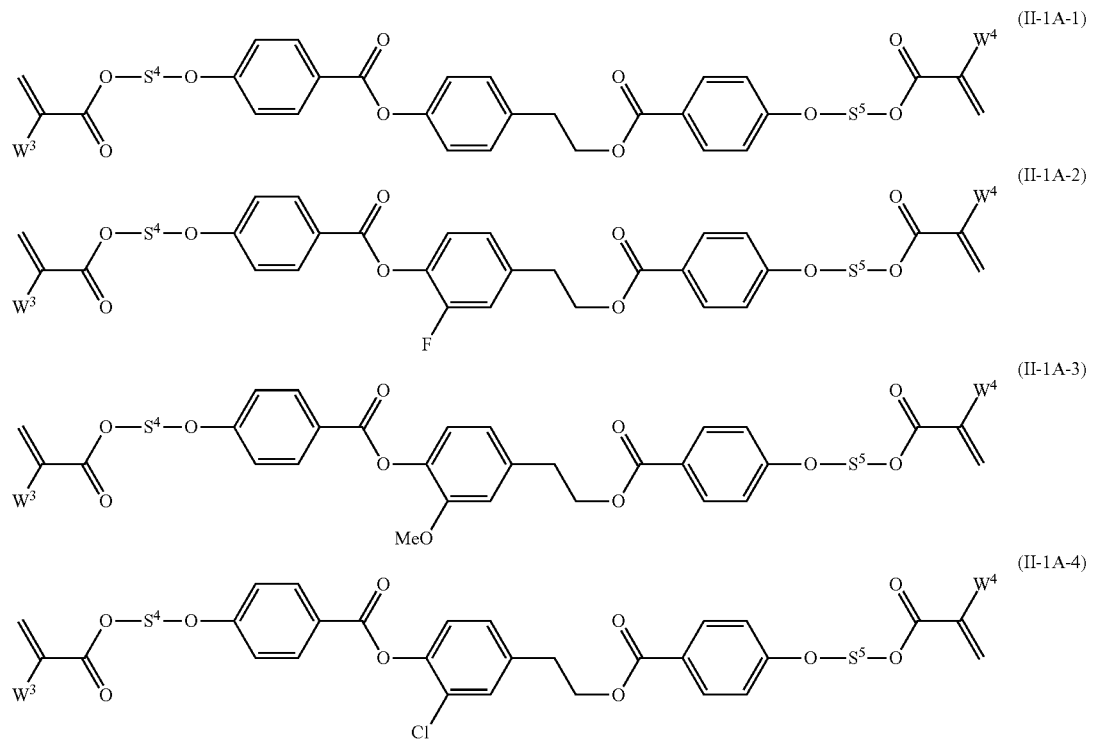

(II-1A-1)
(II-1A-2)
(II-1A-3)
(II-1A-4)

(in Formulae (II-1A-1) to (II-1A-4), $W^3$ and $W^4$ each independently represent hydrogen or a methyl group; $S^4$ represents the same thing as $S^4$ of General Formula (II-1A); and $S^5$ represents the same thing as $S^5$ of General Formula (II-1A)). Compounds represented by Formulae (II-1A-i) to (II-1A-4) in which $S^4$ and $S^5$ each independently represent an alkylene group having 2 to 8 carbon atoms are particularly preferable.

Other preferable examples of a difunctional polymerizable compound include the compounds represented by General Formulae (II-1B-1) to (II-1B-3) below,

[Chem. 70]

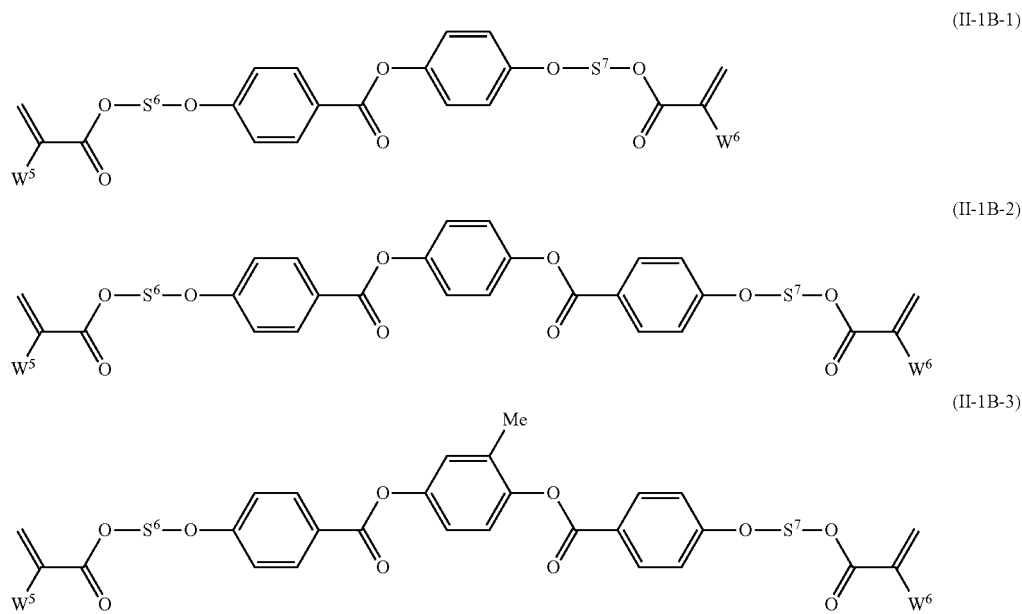

(II-1B-1)
(II-1B-2)
(II-1B-3)

(in General Formulae (II-1B-1) to (II-1B-3), $W^5$ and $W^6$ each independently represent hydrogen or a methyl group; and $S^6$ and $S^7$ each independently represent an alkylene group having 2 to 18 carbon atoms). Compounds represented by Formulae (II-1B-1) to (II-1B-3) in which $S^6$ and $S^7$ each independently represent an alkylene group having 2 to 8 carbon atoms are particularly preferable.

Specific examples of the compound represented by General Formula (II-2) include compounds represented by General Formulae (II-2-1) to (II-2-7) below,

[Chem. 71]

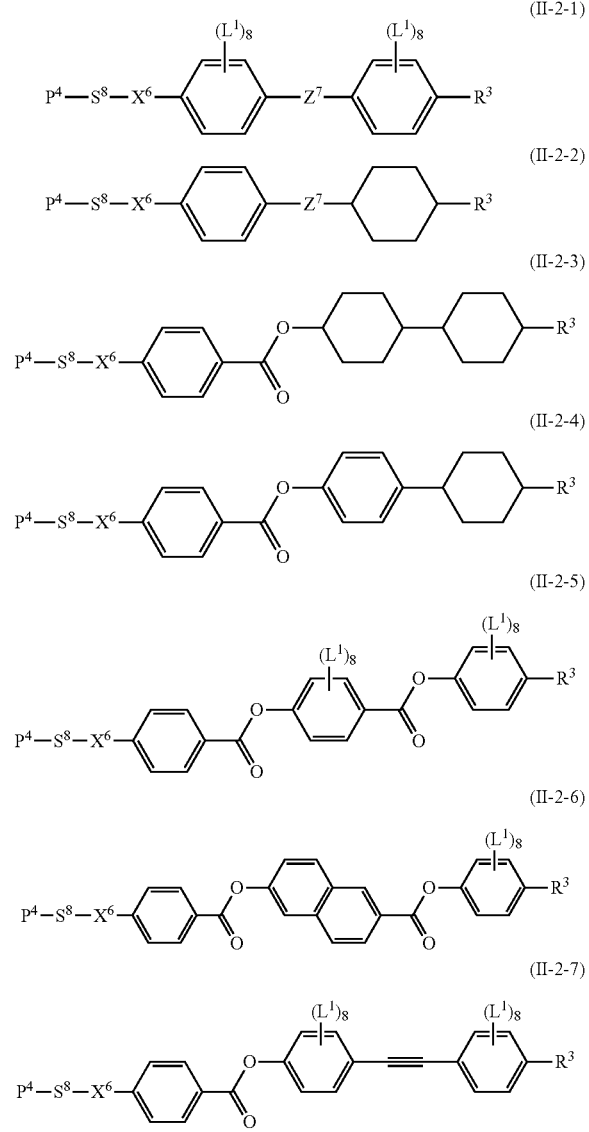

(II-2-1)
(II-2-2)
(II-2-3)
(II-2-4)
(II-2-5)
(II-2-6)
(II-2-7)

(in General Formulae (II-2-1) to (II-2-7), $P^4$ represents the same thing as P of General Formula (I); $S^8$ represents a single bond or an alkylene group having 1 to 20 carbon atoms in which one —$CH_2$— group or two or more —$CH_2$— groups that are not adjacent to one another may each independently replaced with —O—, —COO—, —OCO—, or —O—CO—O—; $X^6$ represents a single bond, —O—, —COO—, or —OCO—; Z represents a single bond, —COO—, or —OCO—; $L^1$ represents a fluorine atom, a chlorine atom, or a linear or branched alkyl group having 1 to 10 carbon atoms in which one —$CH_2$— group or two or more —$CH_2$— groups that are not adjacent to one another may be each independently replaced with —O—, —COO—, or —OCO—; s represents an integer of 0 to 4; $R^3$ represents a hydrogen atom, a fluorine atom, a chlorine atom, a cyano group, a nitro group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—).

The polymerizable composition including the compound according to the present invention may include a polymerizable compound that does not have a liquid crystal property in an amount such that the liquid crystal property of the composition are not impaired significantly. Specifically, any compound known in the related art as a polymer-forming monomer or a polymer-forming oligomer may be used. Specific examples of such a compound include the compounds described in "Hikari Kouka Gijutsu Databook, Zairyou-hen ("Photocuring Technology Databook, Material Section")(monomer, oligomer, photopolymerization initiator)" (supervised by Kunihiro Ichimura and Kiyomi Kato, edited by Technonet).

While the compound according to the present invention can be polymerized without using a photopolymerization initiator, a photopolymerization initiator may be used depending on the purpose. In such a case, the concentration of the photopolymerization initiator in the compound according to the present invention is preferably 0.1% to 15% by mass, is more preferably 0.2% to 10% by mass, and is further preferably 0.4% to 8% by mass. Examples of the photopolymerization initiator include benzoin ethers, benzophenones, acetophenones, benzyl ketals, and acylphosphine oxides. Specific examples of the photopolymerization initiator include 2-methyl-1-(4-methylthiophenyl)-2-morpholinopropan-1-one (IRGACURE 907) and benzoic acid [1-[4-(phenylthio)benzoyl]heptylidene]amino (IRGACURE OXE 01). Examples of thermal polymerization initiators include an azo compound and a peroxide. Specific examples of the thermal polymerization initiators include 2,2'-azobis (4-methoxy-2,4-dimethylvaleronitrile) and 2,2'-azobis (isobutyronitrile). The above polymerization initiators may be used alone or in combination of two or more.

The liquid crystal composition according to the present invention may optionally include a stabilizer in order to enhance preservation stability. Examples of the stabilizer include hydroquinones, hydroquinone monoalkyl ethers, tert-butylcatechols, pyrogallols, thiophenols, nitro compounds, β-naphthylamines, β-naphthols, and nitroso compounds. In the case where the stabilizer is used, the content of the stabilizer added to the composition is preferably 0.005% to 1% by mass, is more preferably 0.02% to 0.8% by mass, and is further preferably 0.03% to 0.5% by mass. The above stabilizers may be used alone or in combination of two or more. Specifically, the stabilizer is preferably selected from the compounds represented by Formulae (III-1) to (III-40) below,

[Chem. 72]
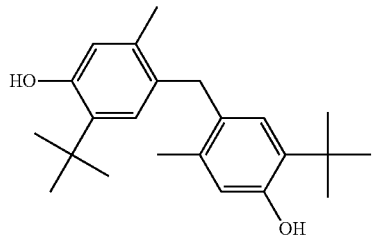 (III-1)
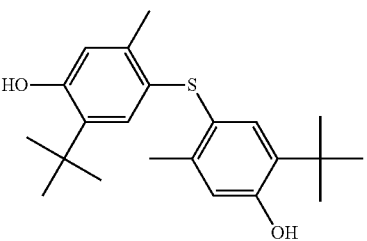 (III-2)
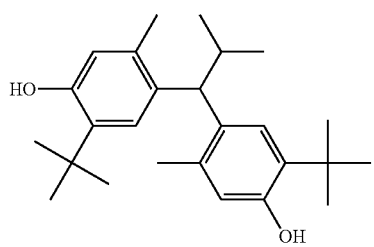 (III-3)
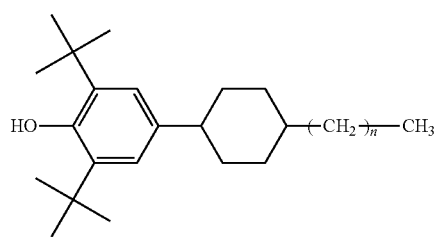 (III-4)
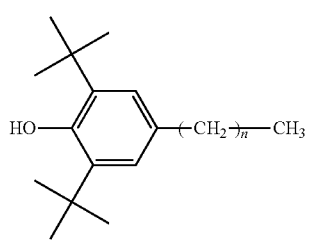 (III-5)
[Chem. 73]
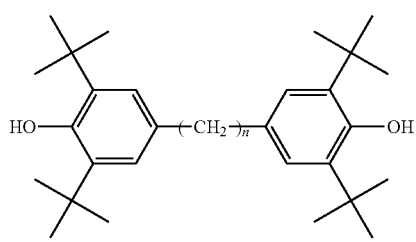 (III-6)
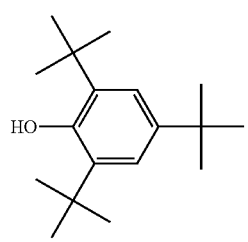 (III-7)
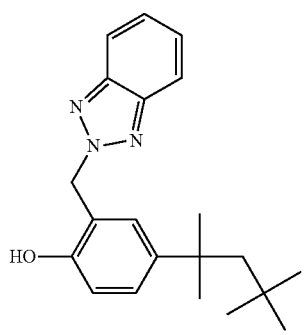 (III-8)
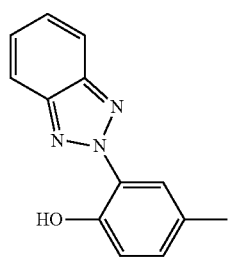 (III-9)

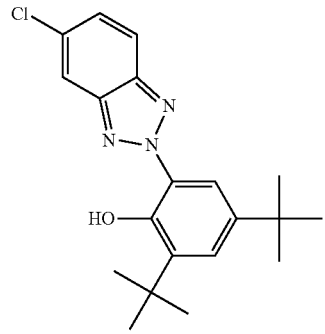
(III-10)
[Chem. 74]
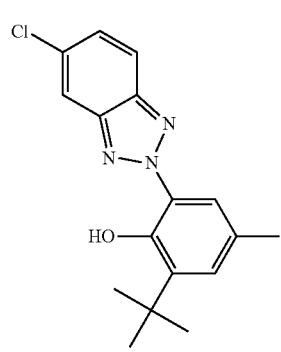
(III-11)
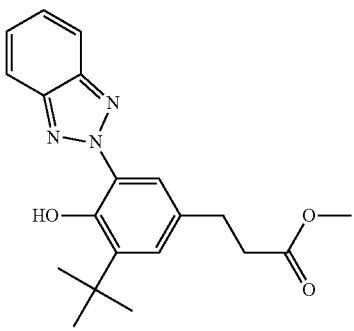
(III-12)
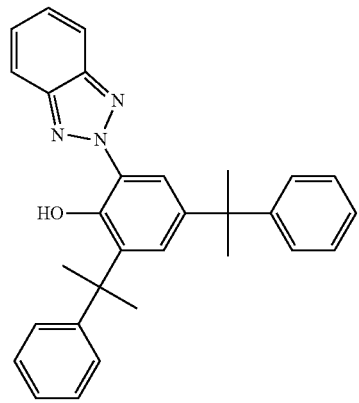
(III-13)
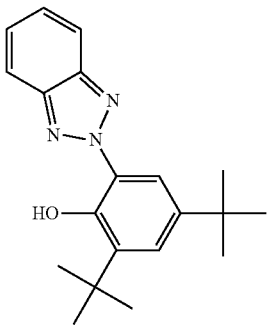
(III-14)
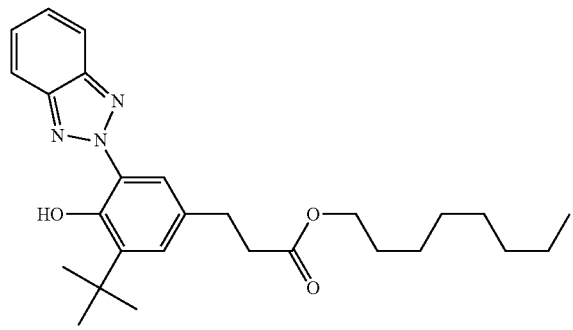
(III-15)

[Chem. 75]
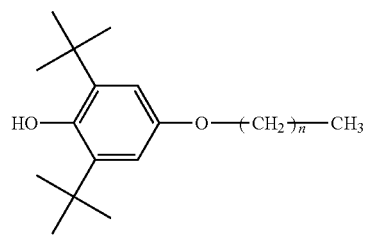 (III-16)
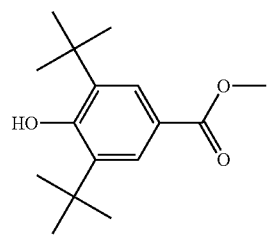 (III-17)
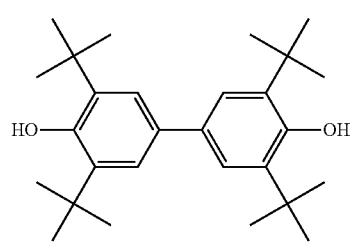 (III-18)
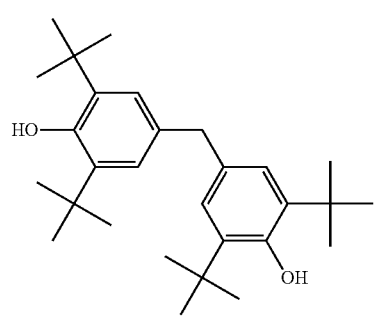 (III-19)
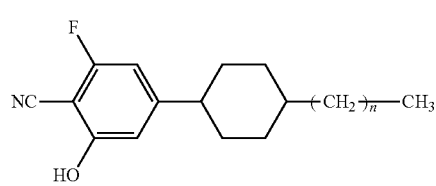 (III-20)
[Chem. 76]
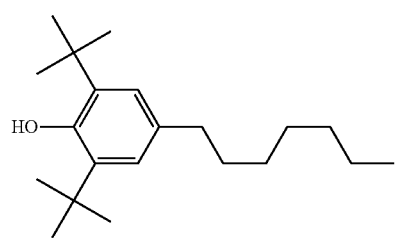 (III-21)
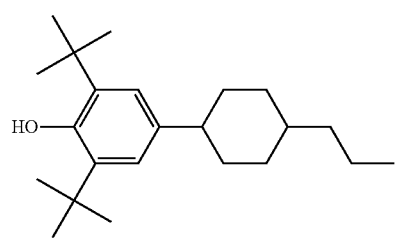 (III-22)
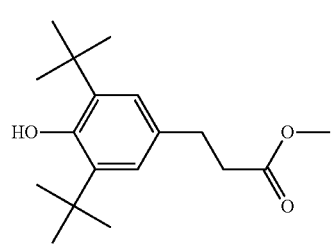 (III-23)
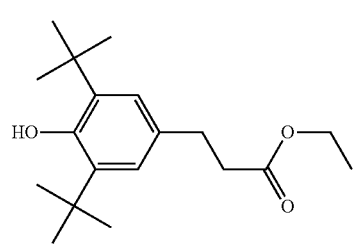 (III-24)

(III-25)
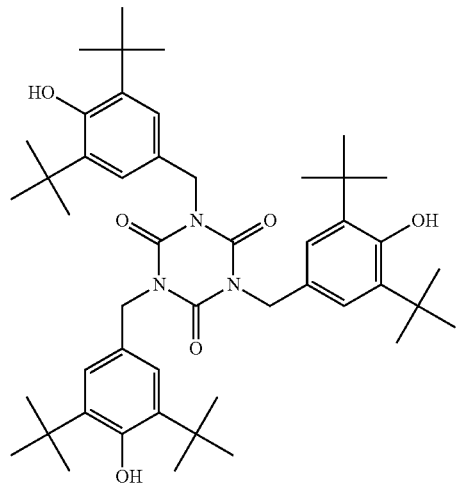
[Chem. 77]
(III-26)
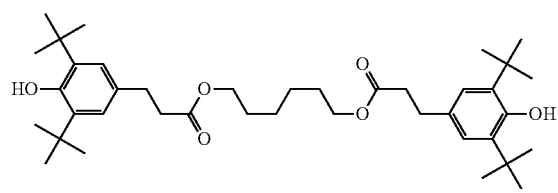
(III-27)
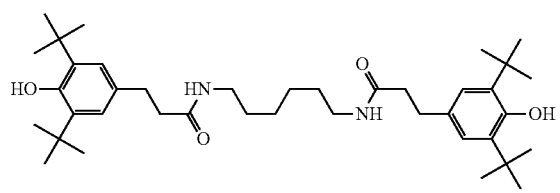
(III-28)
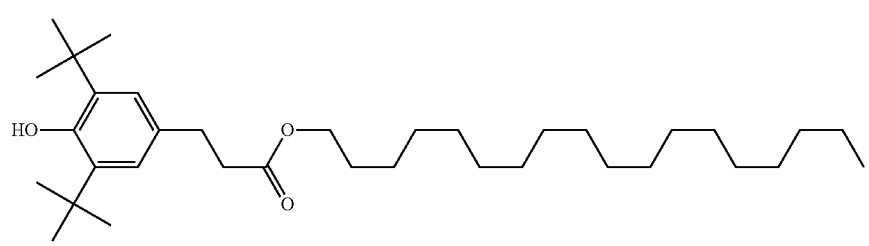
(III-29)
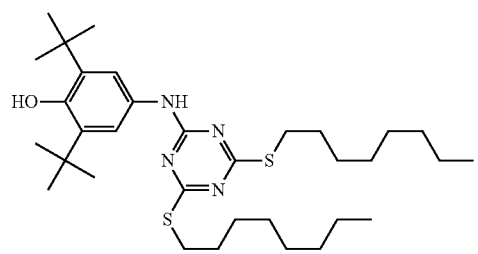
(III-30)
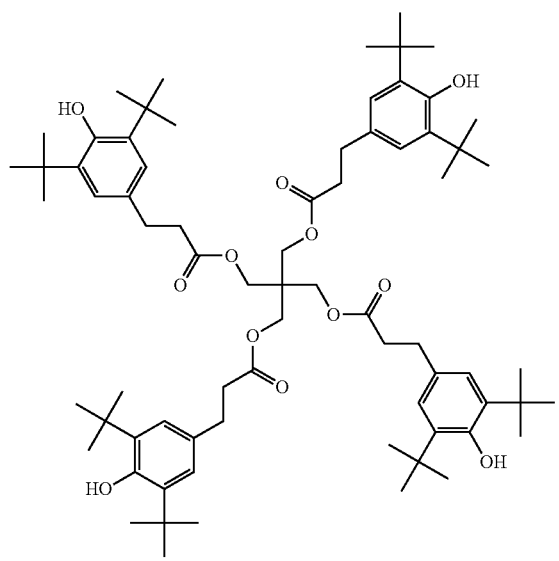

(III-31)
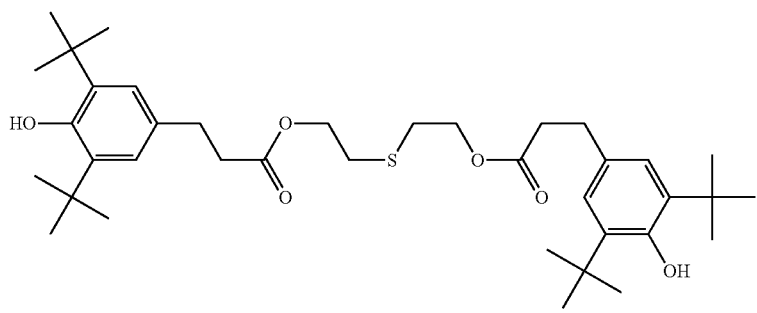
(III-32)
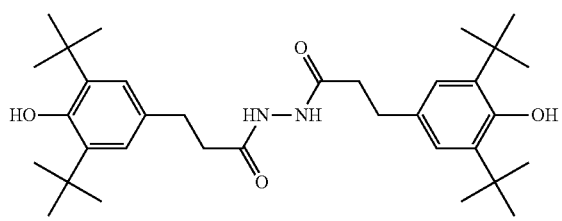
(III-33)
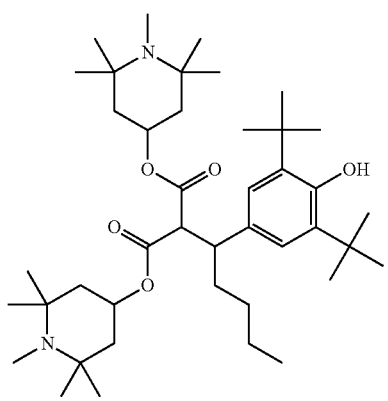
(III-34)
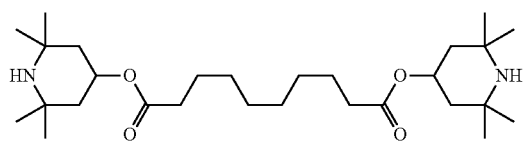
(III-35)
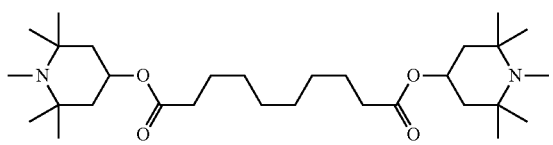
(III-36)
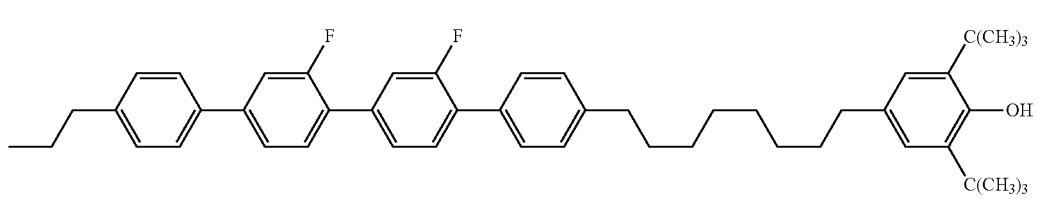
(III-37)
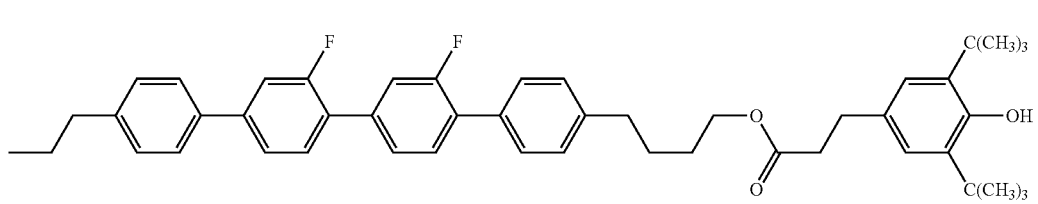
(III-38)
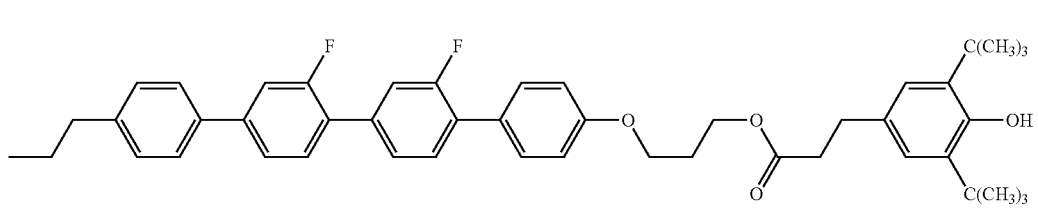

-continued

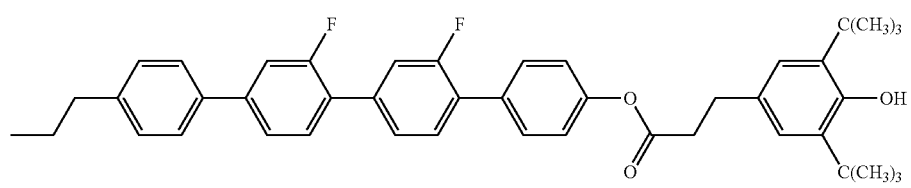
(III-39)

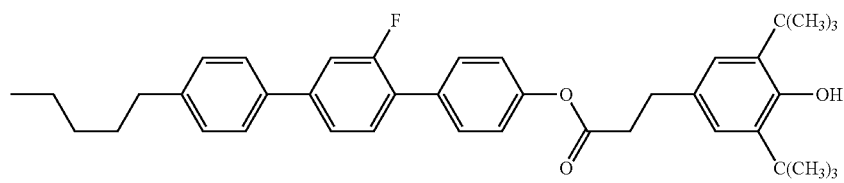
(III-40)

(in Formulae (III-1) to (III-40), n represents an integer of 0 to 20).

In the case where a polymerizable composition including the compound according to the present invention is used for producing films, optical devices, functional pigments, drugs, cosmetics, coating agents, synthetic resins, and the like, the polymerizable composition may include a metal, a metal complex, a dye, a pigment, a colorant, a fluorescent material, a phosphorescent material, a surfactant, a leveling agent, a thixotropic agent, a gelatinizing agent, a polysaccharide, an ultraviolet absorber, an infrared absorber, an anti-oxidizing agent, an ion-exchange resin, a metal oxide such as titanium oxide, and the like depending on the purpose.

A polymer produced by polymerizing a polymerizable composition including the compound according to the present invention may be used in various applications. For example, a polymer produced by polymerizing a polymerizable composition including the compound according to the present invention that has not been aligned may be used for producing a light-scattering plate, a depolarization plate, or a moiré fringe-prevention plate. On the other hand, a polymer produced by polymerizing a polymerizable composition that has been aligned advantageously has an optical anisotropy. Such an optically anisotropic body can be produced by, for example, depositing a polymerizable composition including the compound according to the present invention on a substrate rubbed with a cloth or the like, a substrate provided with an organic thin film formed thereon, or a substrate provided with an alignment film formed thereon by the oblique deposition of $SiO_2$ or interposing the polymerizable composition between substrates and polymerizing the polymerizable composition.

Examples of a method for depositing the polymerizable composition on a substrate include spin coating, die coating, extrusion coating, roll coating, wire bar coating, gravure coating, spray coating, dipping, and printing. When coating is employed, an organic solvent may be added to the polymerizable composition. Examples of the organic solvent include a hydrocarbon solvent, a halogenated hydrocarbon solvent, an ether solvent, an alcohol solvent, a ketone solvent, an ester solvent, and aprotic solvent. Examples of the hydrocarbon solvent include toluene and hexane. Examples of the halogenated hydrocarbon solvent include methylene chloride. Examples of the ether solvent include tetrahydrofuran, acetoxy-2-ethoxyethane, and propylene glycol monomethyl ether acetate. Examples of the alcohol solvent include methanol, ethanol, and isopropanol. Examples of the ketone solvent include acetone, methyl ethyl ketone, cyclohexanone, γ-butyrolactone, and N-methylpyrrolidones. Examples of the ester solvent include ethyl acetate and cellosolve. Examples of the aprotic solvent include dimethylformamide and acetonitrile. The above solvents may be used alone or in combination and selected appropriately with consideration of vapor pressure and the solubility of the polymerizable composition. The organic solvent added to the polymerizable composition can be volatilized by air drying, heat drying, vacuum drying, or vacuum heat drying. It is possible to effectively increase ease of applying the polymerizable material to a substrate by forming an intermediate layer, such as a polyimide thin-film, on the substrate or by adding a leveling agent to the polymerizable material. Forming an intermediate layer, such as a polyimide thin-film, on a substrate effectively enhances the adhesion of a polymer produced by polymerizing the polymerizable material to the substrate.

Examples of an alignment treatment which are other than those described above include an alignment treatment in which the flow orientation of the liquid crystal material is used and an alignment treatment in which an electric field or a magnetic field is used. The above alignment methods may be used alone or in combination. A photo alignment method may also be used as an alignment method instead of rubbing. The shape of the substrate is not limited to planar; the substrate may include a portion having a curved surface. The substrate may be composed of an organic material or an inorganic material. Examples of the organic materials that can be used as a material for the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetylcellulose, cellulose, and polyether ether ketone. Examples of the inorganic materials that can be used as a material for the substrate include silicon, glass, and calcite.

The polymerization of a polymerizable composition including the compound according to the present invention is preferably performed by irradiating the polymerizable composition with an active energy ray, such as ultraviolet radiation or an electron beam, in order to perform polymerization in a short time. In the case where ultraviolet radiation is used, either of a polarized light source and an unpolarized light source may be used. In the case where the polymerization of the liquid crystal composition is performed while the liquid crystal composition is interposed between two substrates, at least one of the substrates which is irradiated with the active energy ray needs to be adequately permeable to the active energy ray. After a specific portion of the liquid crystal composition has been polymerized by using a mask when the liquid crystal composition is irradiated with the light, the conditions such as an electric field, a magnetic field, or a temperature may be changed in order to change the orientation of the other portion of the liquid crystal composition that has not yet been polymerized. In such a case, the other portion of the liquid crystal composition is subsequently polymerized by being irradiated with the active energy ray. The temperature at which the liquid crystal composition is irradiated with the active energy ray is preferably within the temperature range in which the polymerizable composition according to the present invention is present in a liquid crystal state. In particular, in the case where an optically anisotropic body is produced using photopolymerization, polymerization is preferably performed at a temperature closer to room temperature, that is, typically, 25° C., in order not to induce unintended thermal polymerization. The intensity of the active energy ray is preferably 0.1 mW/cm$^2$ to 2 W/cm$^2$. If the intensity of the active energy ray is 0.1 mW/cm$^2$ or less, a large amount of time may be required for the completion of photopolymerization, which degrades productivity. If the intensity of the active energy ray is 2 W/cm$^2$ or more, the polymerizable compound or the polymerizable composition may be degraded.

The optically anisotropic body produced by polymerizing the composition may be subjected to a heat treatment in order to reduce initial changes in the property of the optically anisotropic body and increase the consistency in the property of the optically anisotropic body. The temperature at which the heat treatment is performed is preferably 50° C. to 250° C. The amount of time during which the heat treatment is performed is preferably 30 seconds to 12 hours.

The optically anisotropic body produced by the above-described method may be used alone after being removed from the substrate. Alternatively, the optically anisotropic body may also be used without being removed from the substrate. A multilayer structure constituted by the optically anisotropic bodies may also be used. The optically anisotropic body may be bonded to another substrate.

The present invention is further described in detail with reference to Examples below. The present invention is not limited by Example. Hereinafter, "part" and "%" are on a mass basis unless otherwise specified.

EXAMPLES

Example 1

The polymerizable compound represented by Formula (1-c-1) below was synthesized by the following method.

[Chem. 80]

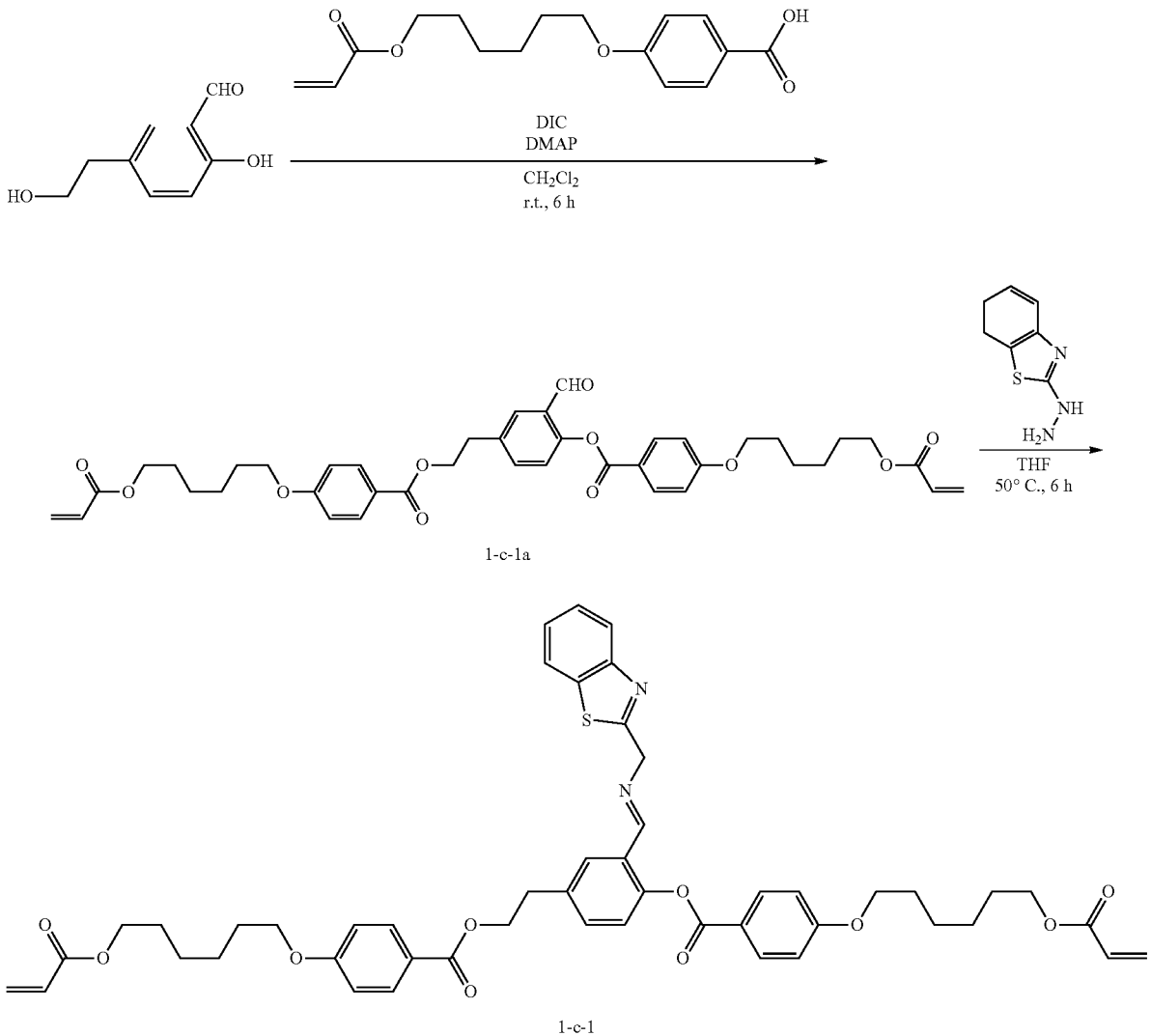

1-c-1a 1-c-1

(Synthesis of Compound 1-c-1a) To a 50-ml three-necked flask, 1.03 g of 5-(2-hydroxy)ethyl-2-hydroxybenzaldehyde, 3.55 g of 4-(6-acryloyloxy)hexyloxybenzoic acid, 0.07 g of N,N-dimethylaminopyridine (DMAP), and 15 ml of dichloromethane were added. The resulting mixture was stirred at 5° C. to 10° C. for 10 minutes. While the mixture was stirred, 1.9 g of N,N-diisopropylcarbodiimide (DIC) was added dropwise to the mixture such that the temperature was maintained to be 5° C. to 10° C. Subsequently, the temperature was increased to 25° C., and stirring was performed for 7 hours. To the resulting reaction mixture, 15 ml of water was added and an organic layer was separated. Then, an aqueous layer was extracted with 15 ml of dichloromethane. To the combined organic layer were added 90 ml of hexane and 2 g of silica gel, and the resulting solid-liquid mixture was stirred. The solid-liquid mixture was charged into a column filled with 5 g of silica gel and 5 g of alumina and passed through the column. After the solvent of the resulting solution had been substantially distilled away, reprecipitation was performed with acetone/methanol. The resulting crystals were filtered and dried to form 1.23 g of the compound (1-c-1a) (yield: 29%).

(Synthesis of Compound 1-c-1) To a 30-ml three-necked flask, 1.4 g of the compound (1-c-1a), 0.35 g of 2-hydrazinobenzothiazole, and 5 ml of tetrahydrofuran were added. The resulting mixture was stirred at 25° C. for 9 hours. Subsequently, 50 ml of water was added to the mixture, and extraction with 30 ml of ethyl acetate was performed twice. The resulting organic phase was dried using sodium sulfate. After sodium sulfate had been removed by filtration, vacuum concentration was performed. The resulting residue was purified by silica-gel column chromatography (hexane/ethyl acetate: 2/1). The resulting crude product was reprecipitated with acetone/methanol. The resulting crystals were filtered and dried to form 0.98 g of the compound (1-c-1).

The upper-limit temperature of the phase sequence of the polymerizable compound (1-c-1) which was determined by differential scanning calorimetry and observing the liquid crystal phase with a polarized light microscope equipped with a temperature-controllable apparatus was "Sm 60 Iso".

$^1$H NMR (CDCl$_3$) δ: 1.40-1.60 (p, 8H), 1.6 (br, 1H), 1.65-1.80 (p, 4H), 1.80-1.97 (p, 4H), 3.15 (t, 2H), 4.01 (t, 2H), 4.17 (t, 2H), 4.31 (t, 2H), 4.40 (t, 2H), 4.57 (t, 2H), 5.81-5.85 (d+d, 2H), 6.08-6.18 (m, 2H), 6.37-6.46 (d+d, 2H), 6.87 (d, 2H), 6.96 (d, 2H), 7.12-7.18 (m, 2H), 7.34 (d, 1H), 7.48 (d, 1H), 7.58 (d, 1H), 7.99-8.02 (s+d, 5H), 8.12 (d, 2H).

LC-MS: m/z 862.60[M+]

The compounds of Examples 2 to 42, which are illustrated below, were synthesized by the same reactions as in Example 1 and, as needed, a method confirming to publicly known methods.

[Chem. 81]

(1-c-2)

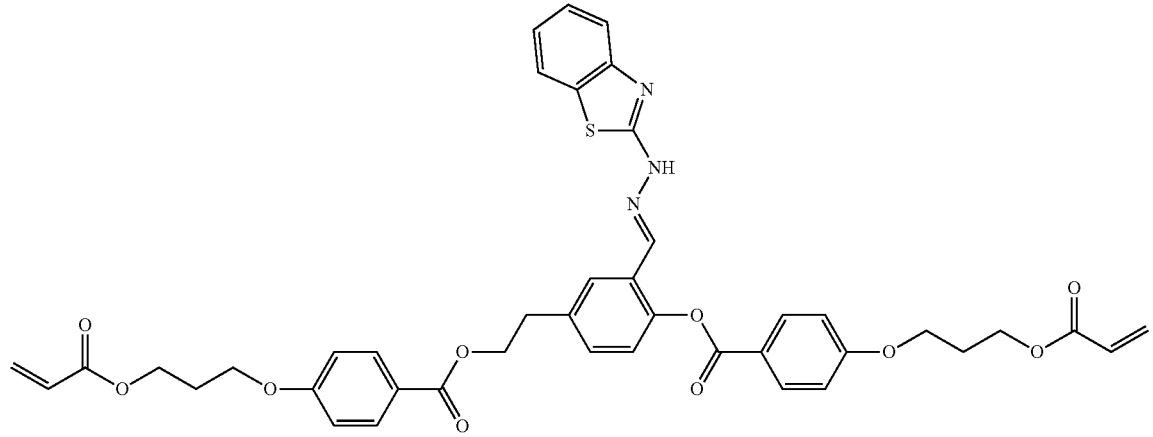

Example 2

(1-c-3)

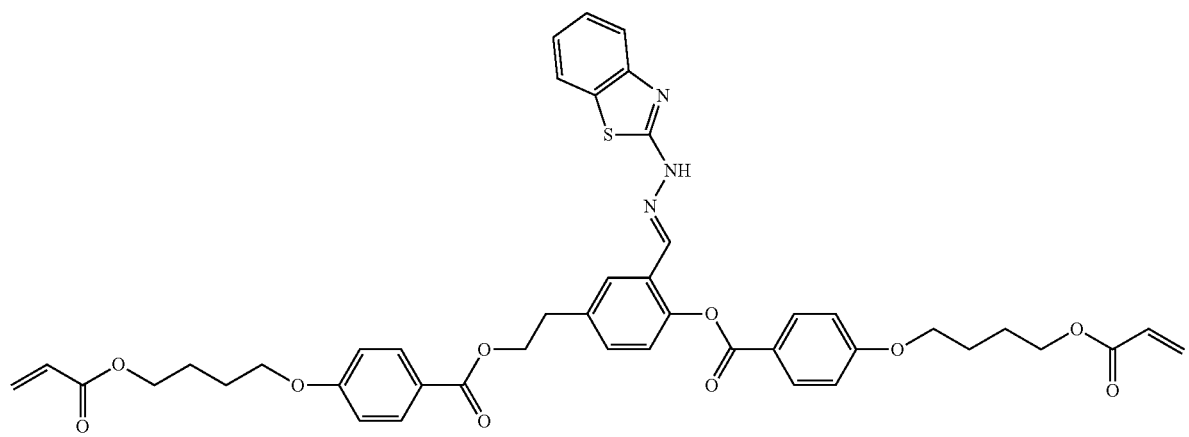

Example 3

-continued
(1-c-4)
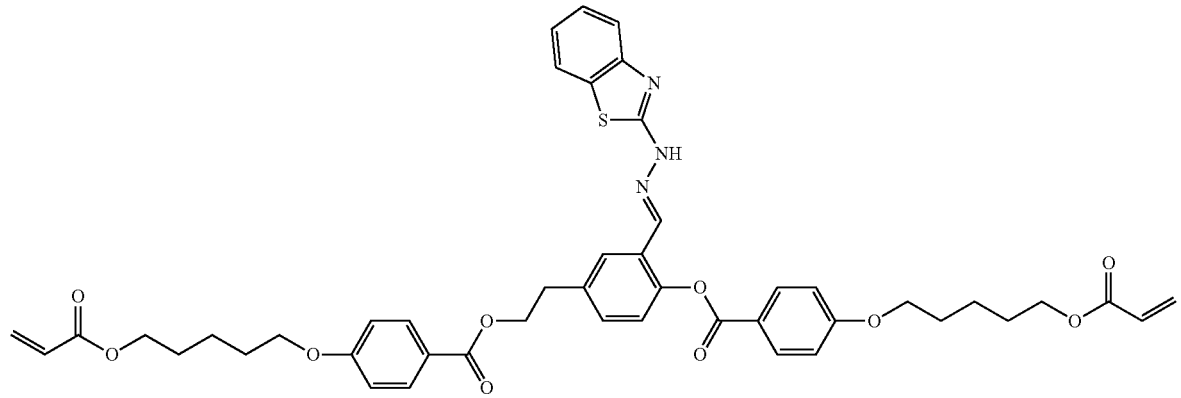
Example 4
Physical Properties of the Compound Represented by Formula (1-c-2)
Dislocation temperature: C 118 I
¹H NMR (CDCl₃) δ: 2.11 (quin, 2H), 2.22 (quin, 2H), 3.15 (t, 2H), 4.01 (t, 2H), 4.14 (t, 2H), 4.31 (t, 2H), 4.40 (t, 2H), 4.57 (t, 2H), 5.83 (m, 2H), 6.13 (m, 2H), 6.41 (m, 2H), 6.88 (m, 4H), 7.09 (m, 1H), 7.16-7.23 (m, 2H), 7.34 (m, 1H), 7.45 (m, 1H), 7.55 (m, 1H), 7.97-8.09 (m, 6H) ppm.
[Chem. 82]
Example 5
(1-c-5)
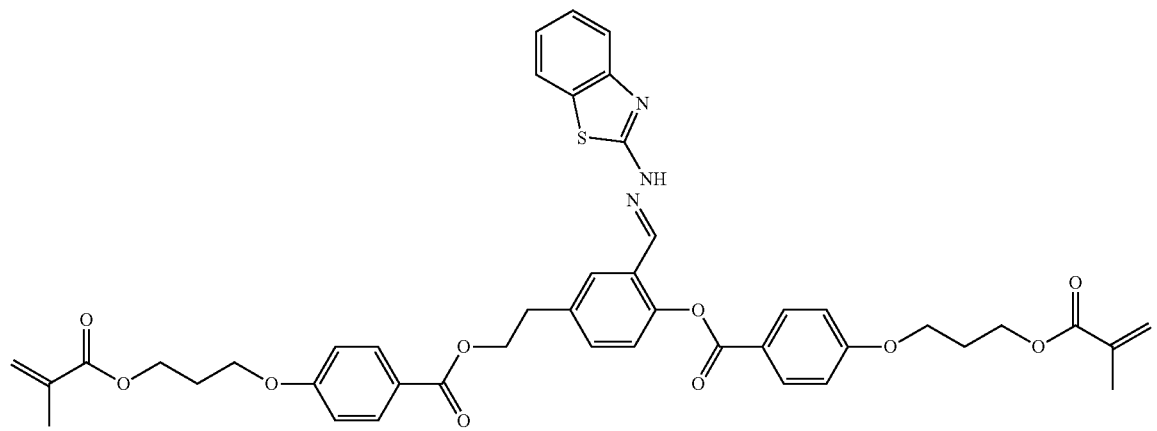
Example 6
(1-c-6)
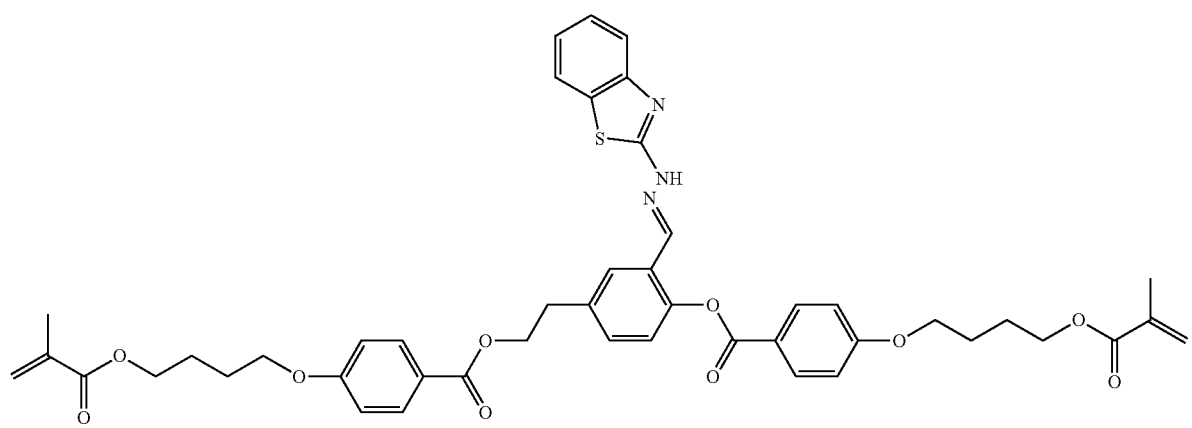

Example 7
(1-c-7)
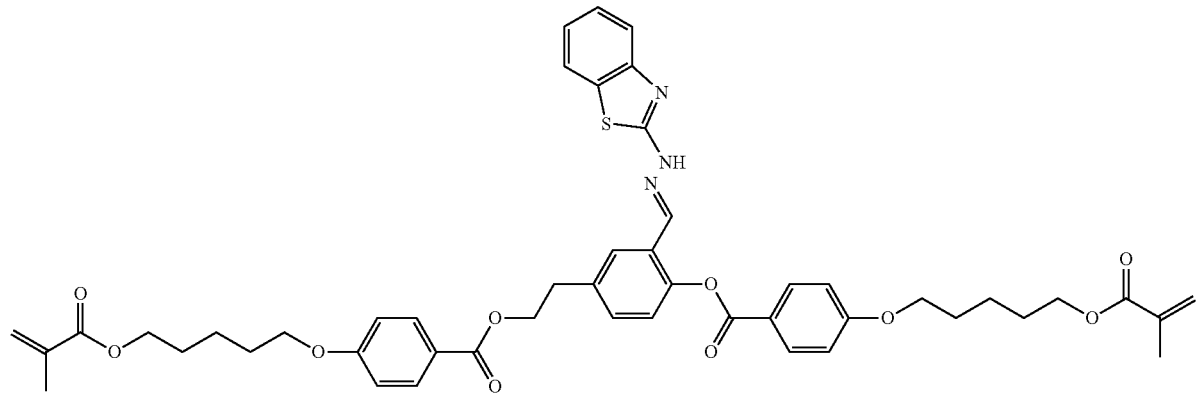
Example 8
(1-c-8)
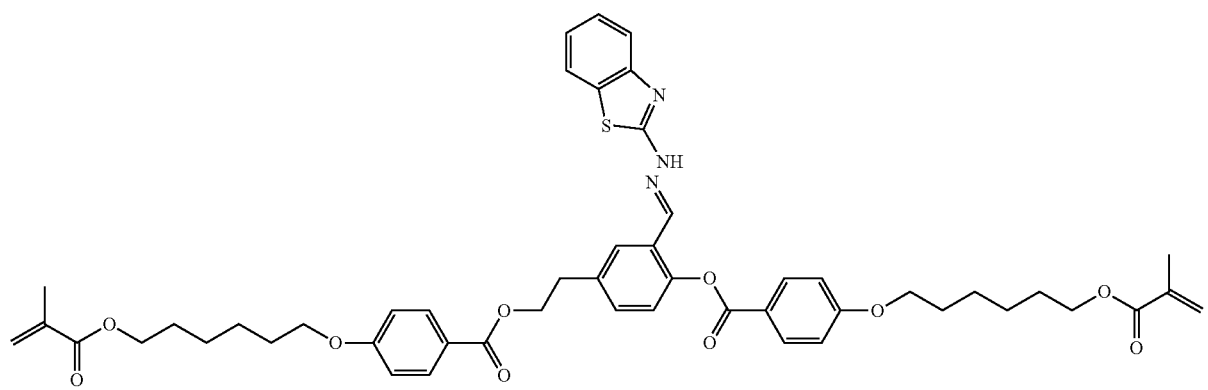
[Chem. 83]
Example 9
(1-c-9)
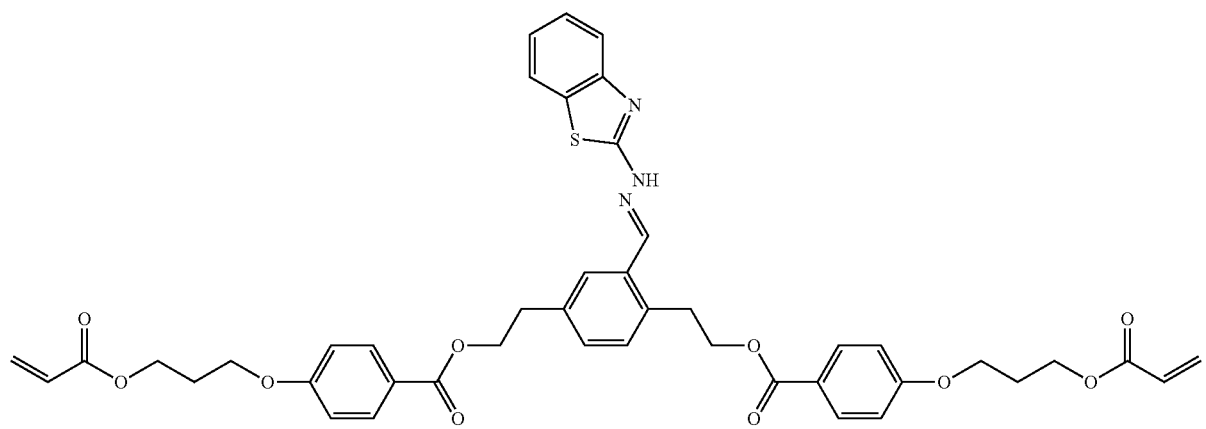

Example 10
(1-c-10)
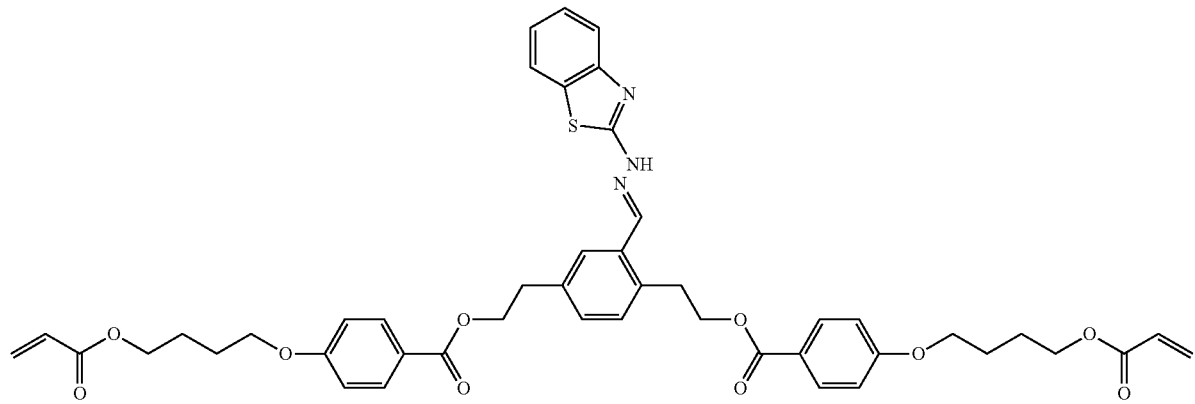
Example 11
(1-c-11)
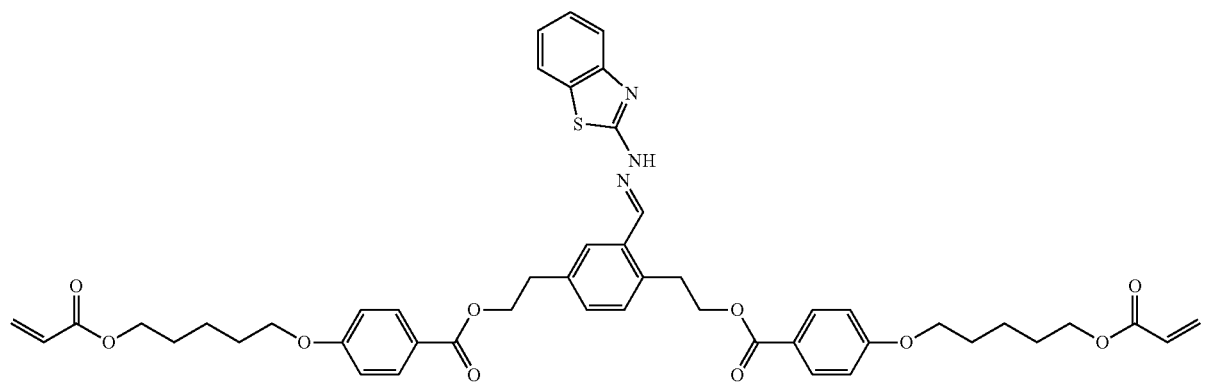
Example 12
(1-c-12)
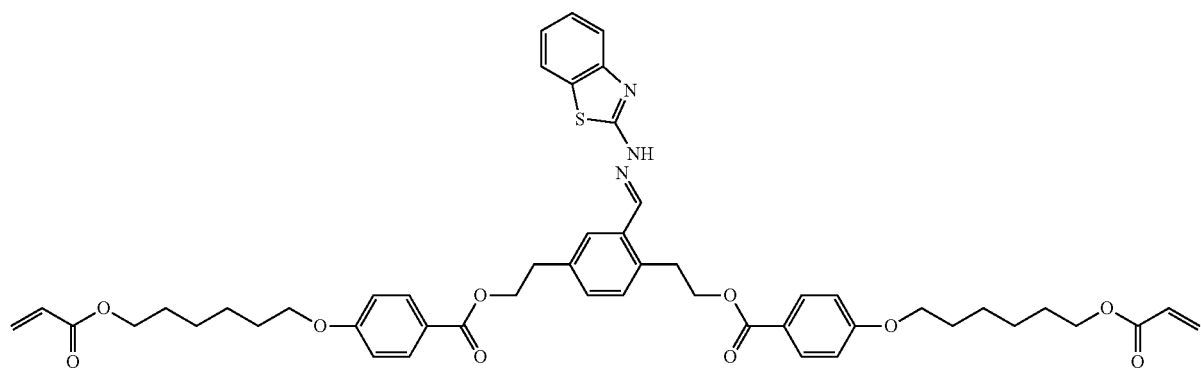

[Chem. 84]
Example 13
(1-c-13)
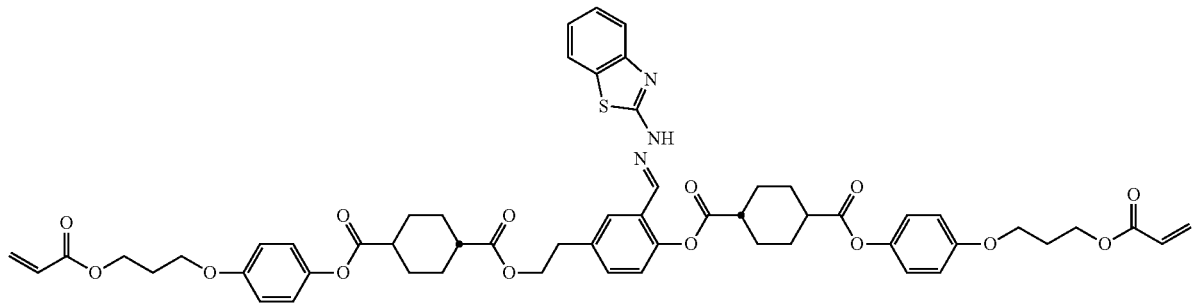
Example 14
(1-c-14)
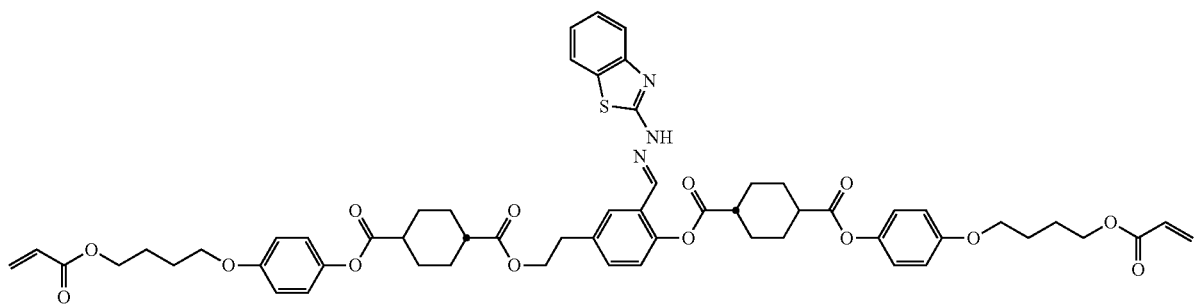
Example 15
(1-c-15)
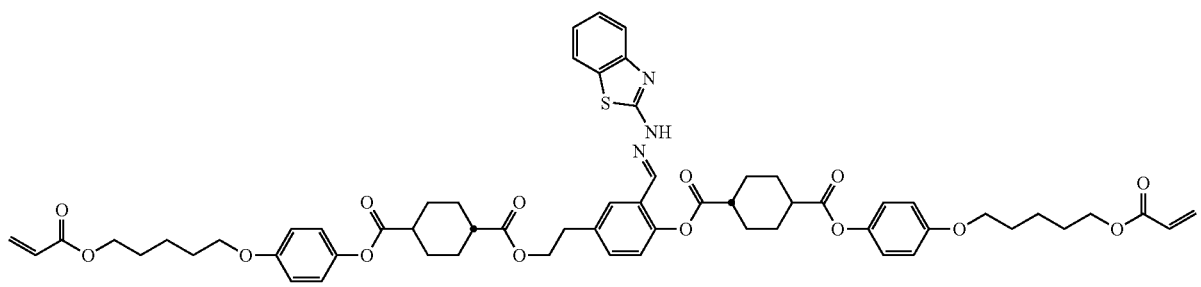
Example 16
(1-c-16)
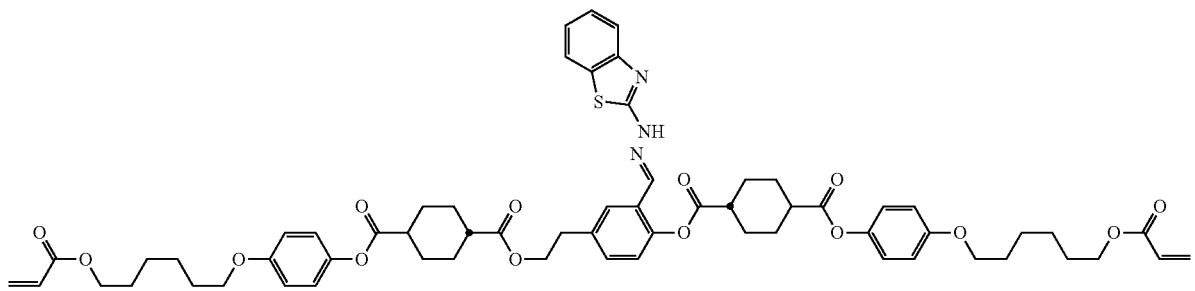
Physical Properties of the Compound Represented by Formula (1-c-16)
Dislocation temperature: C ? N 150 I
1H NMR (CDCl$_3$) δ: 1.40-1.82 (m, 24H), 2.04-2.20 (m, 8H), 2.35-2.49 (m, 4H), 3.02 (t, 2H), 3.92 (t, 2H), 3.95 (t, 2H), 4.17 (t, 2H), 4.18 (t, 2H), 4.36 (t, 2H), 5.82 (dd, 1H), 5.82 (dd, 1H), 6.12 (dd, 1H), 6.13 (dd, 1H), 6.40 (dd, 1H), 6.40 (dd, 1H), 6.82-6.90 (m, 6H), 6.97-7.04 (m, 3H), 7.17 (m, 1H), 7.26 (m, 1H), 7.35 (t, 1H), 7.49 (d, 1H), 7.69 (d, 1H), 7.93 (s, 1H), 8.07 (s, 1H) ppm.

[Chem. 85]
Example 17
(1-f-17)
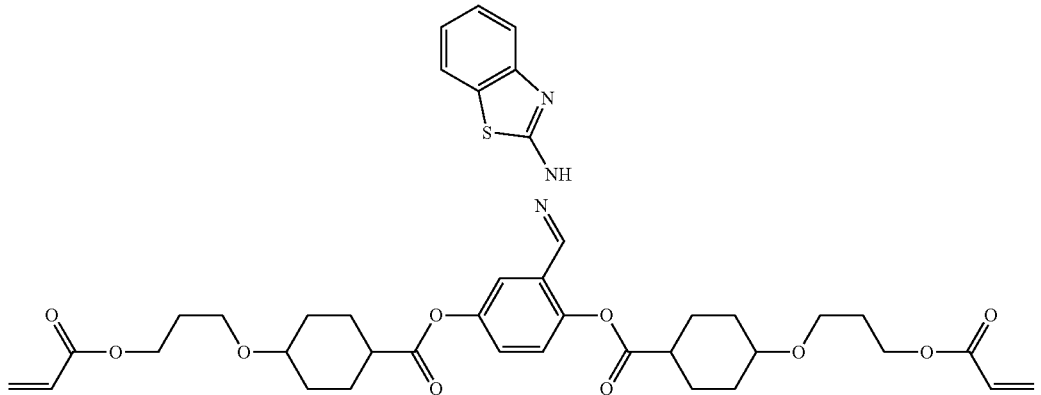
Example 18
(1-f-18)
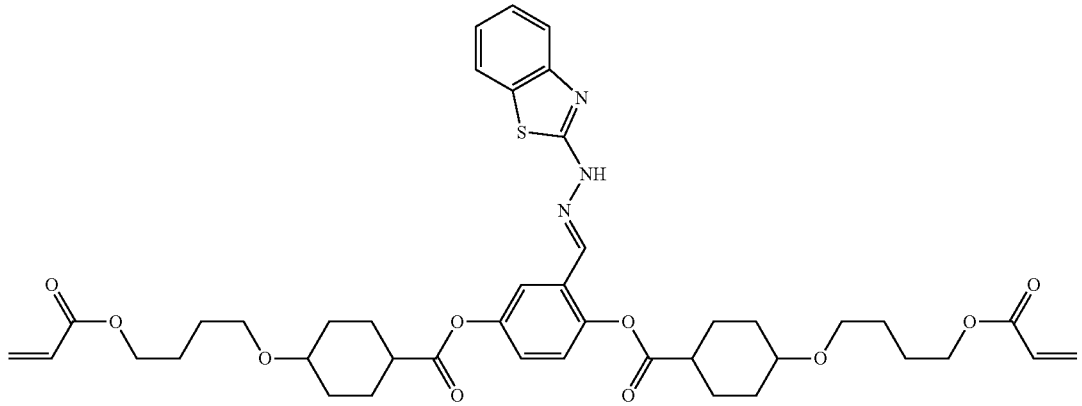
Example 19
(1-f-19)
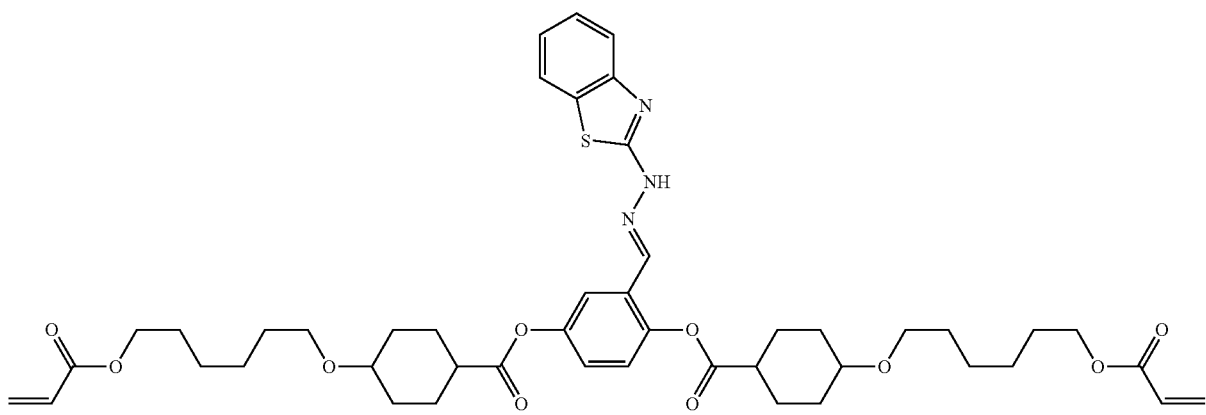

-continued
Example 20
(1-f-20)
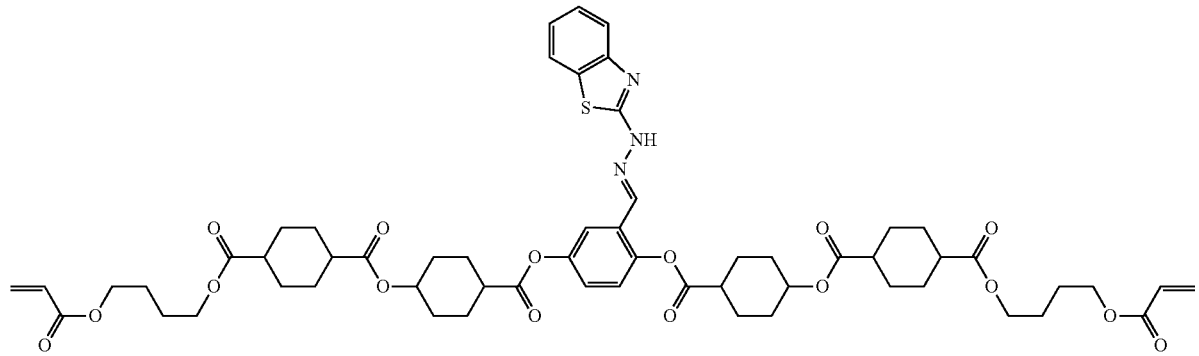
[Chem. 86]
Example 21
(1-f-21)
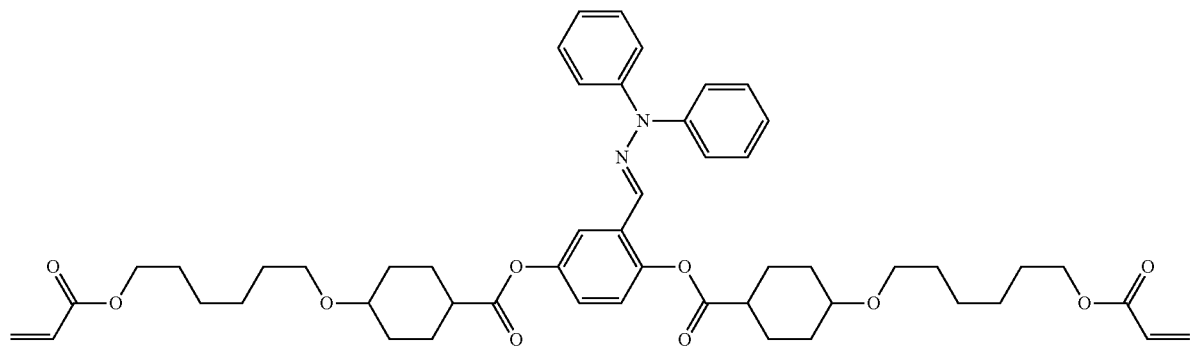
Example 22
(1-f-22)
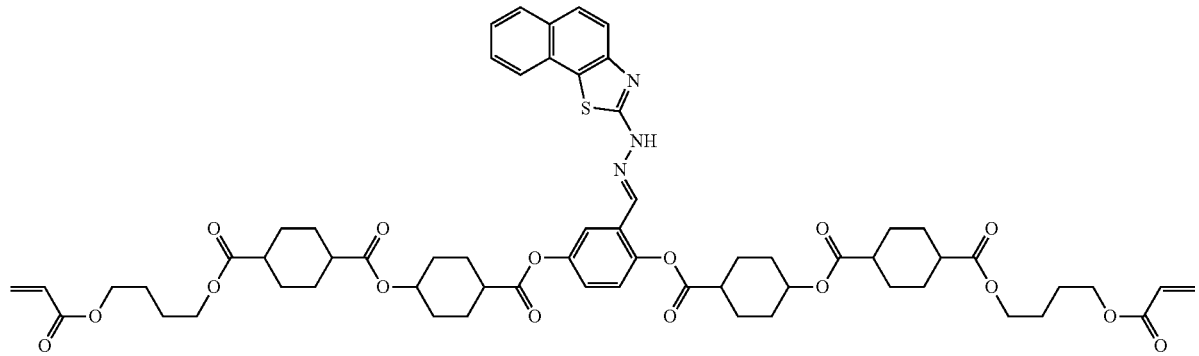

[Chem. 87]
Example 23
(1-c-23)
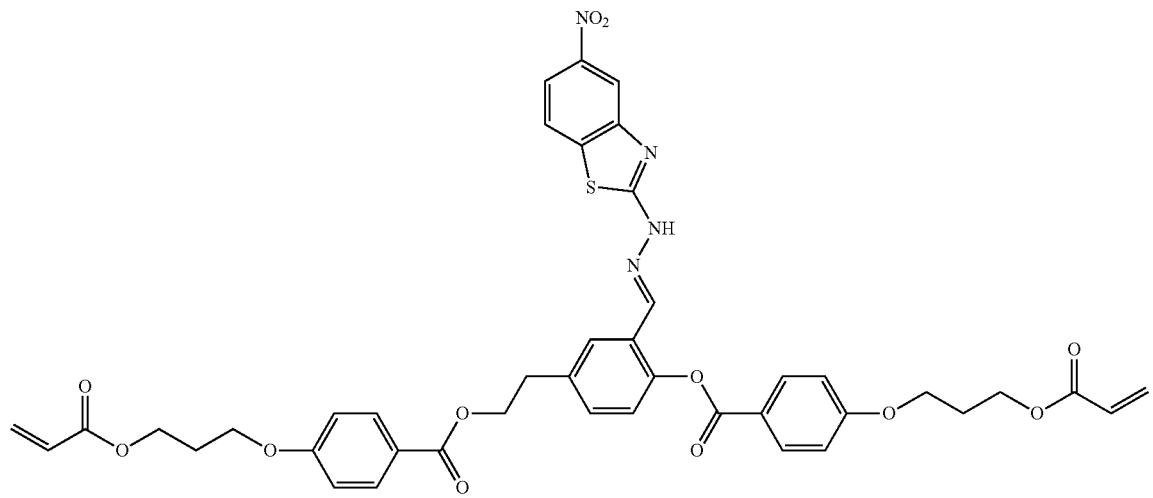
Example 24
(1-c-24)
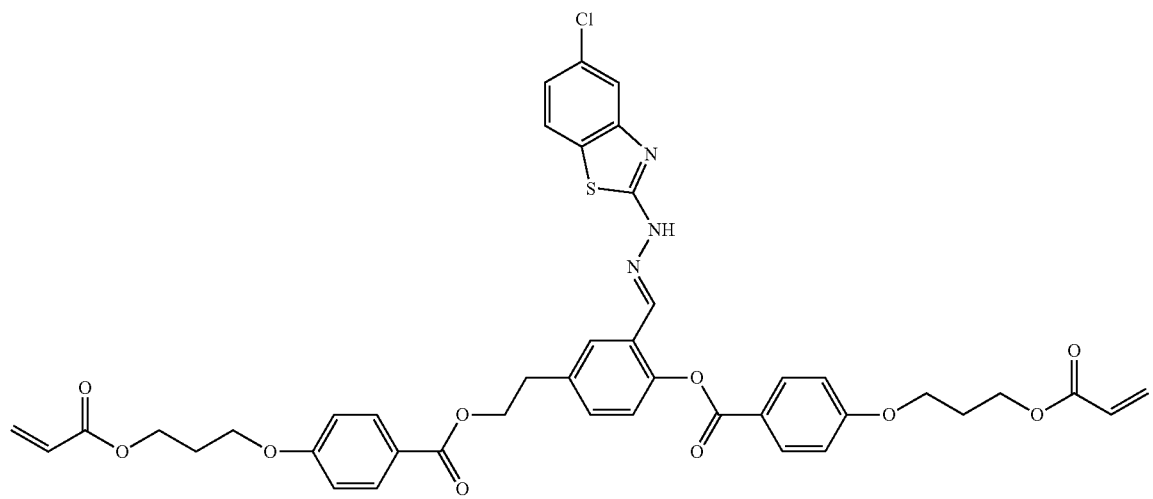

-continued
Example 25
(1-c-25)
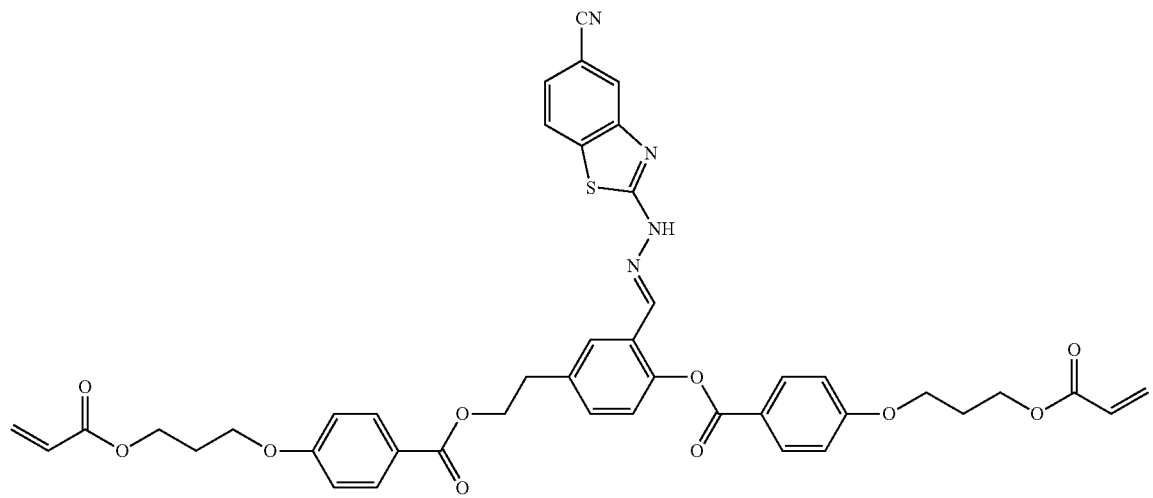
Example 26
(1-c-26)
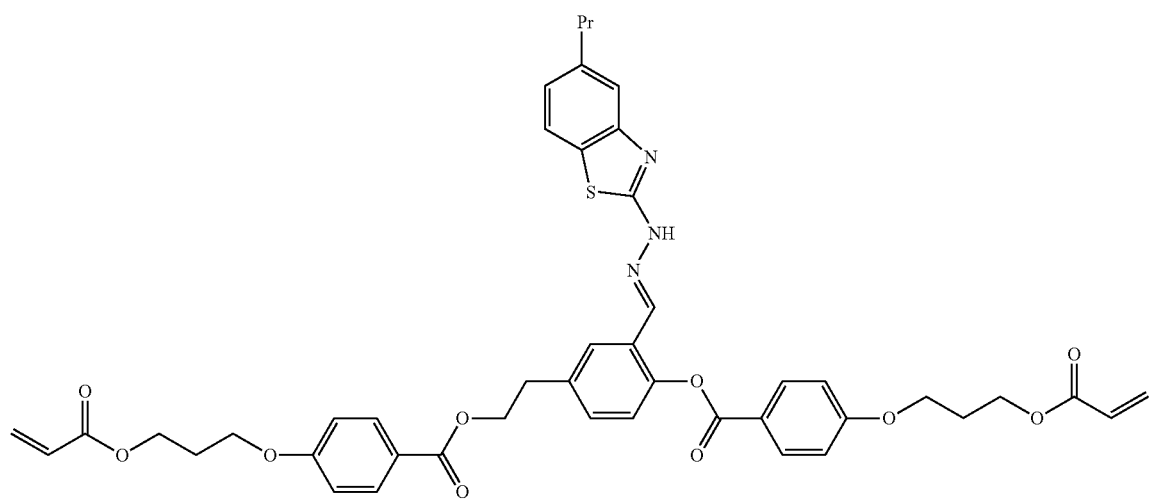
[Chem. 88]
Example 27
(1-c-27)
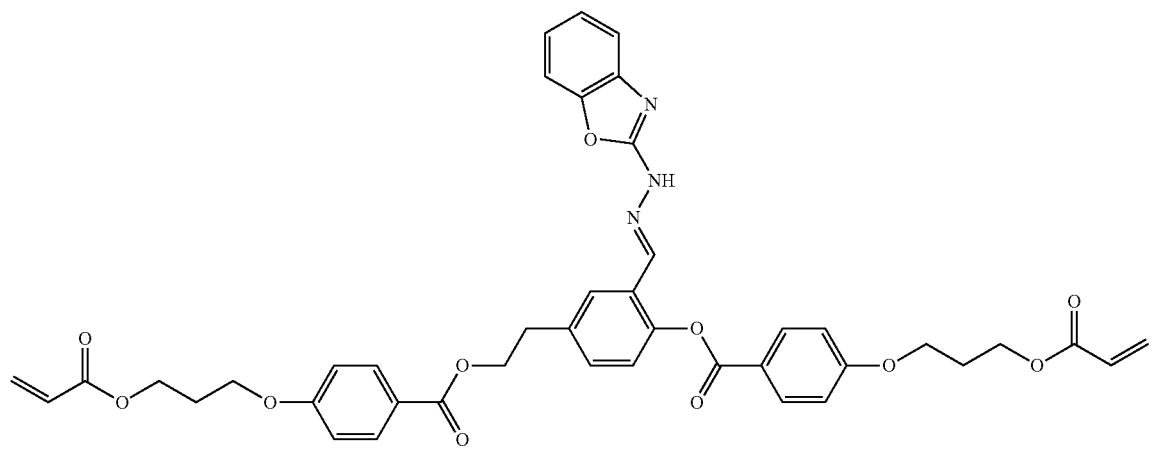

Example 28
(1-c-28)
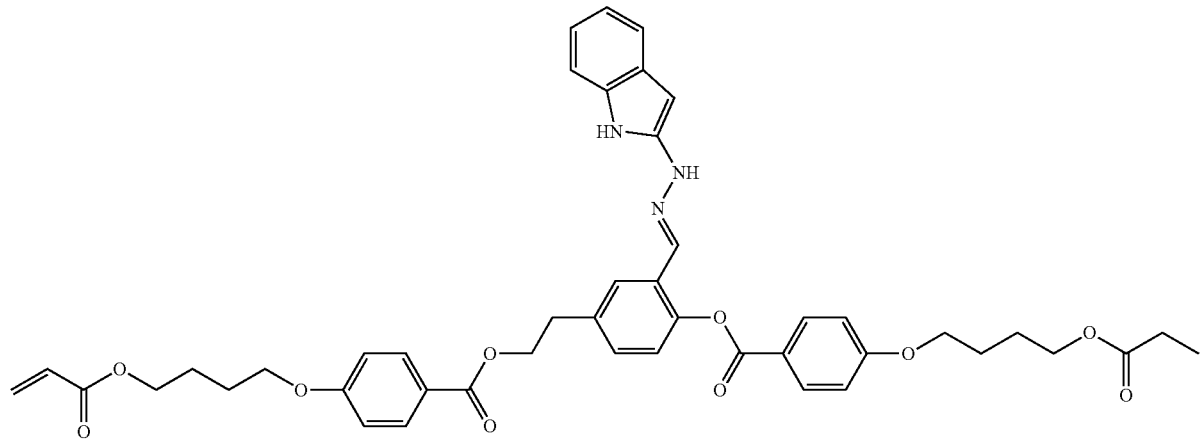
Example 29
(1-c-29)
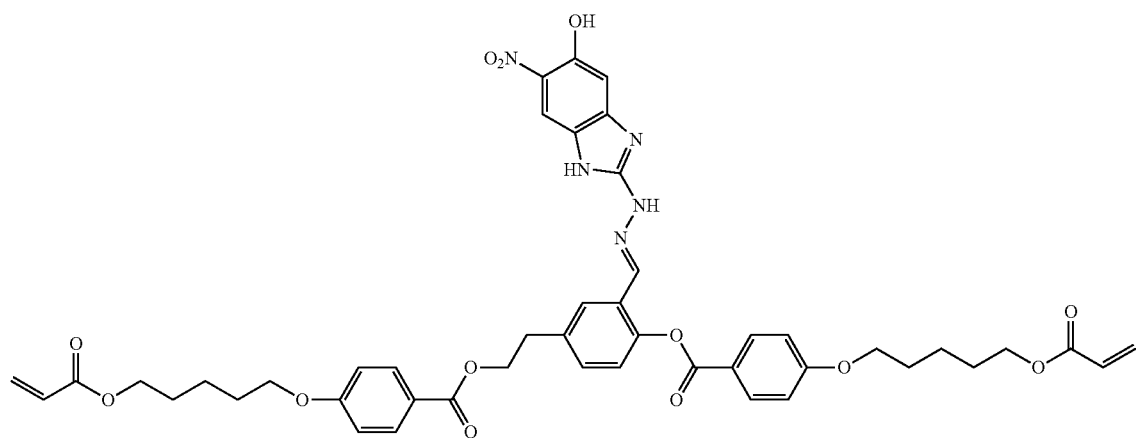
Example 30
(1-c-30)
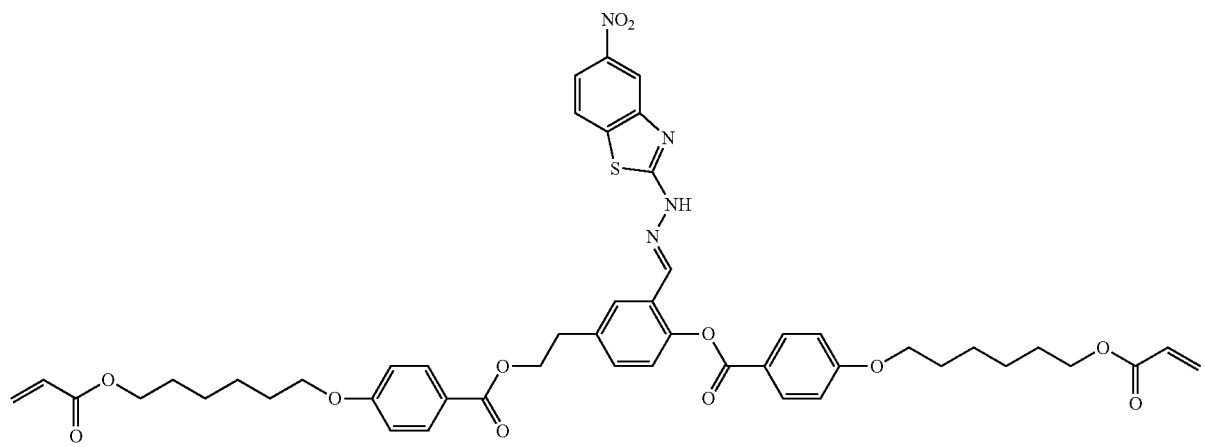

[Chem. 89]
Example 31
(1-c-31)
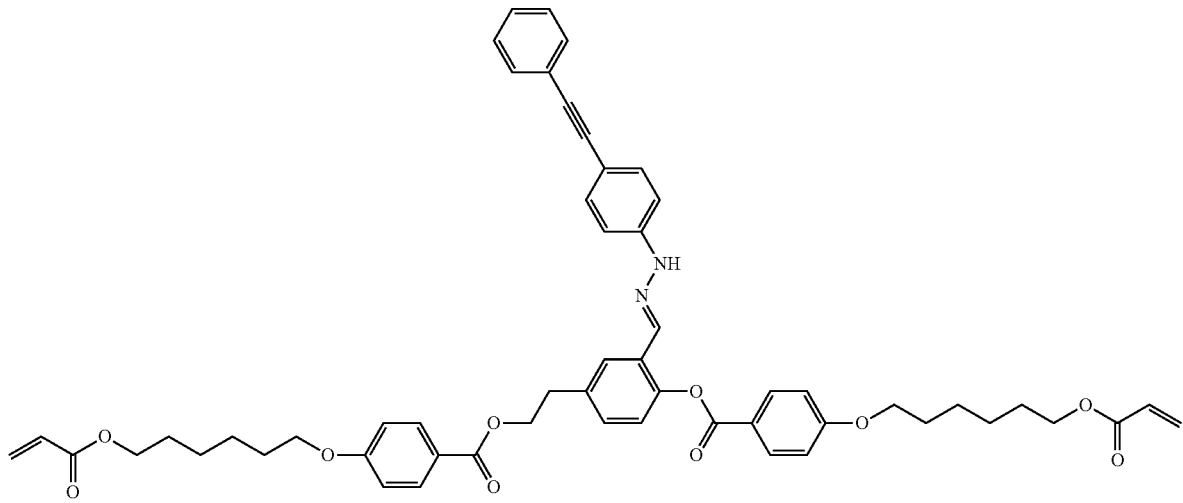
Example 32
(1-c-32)
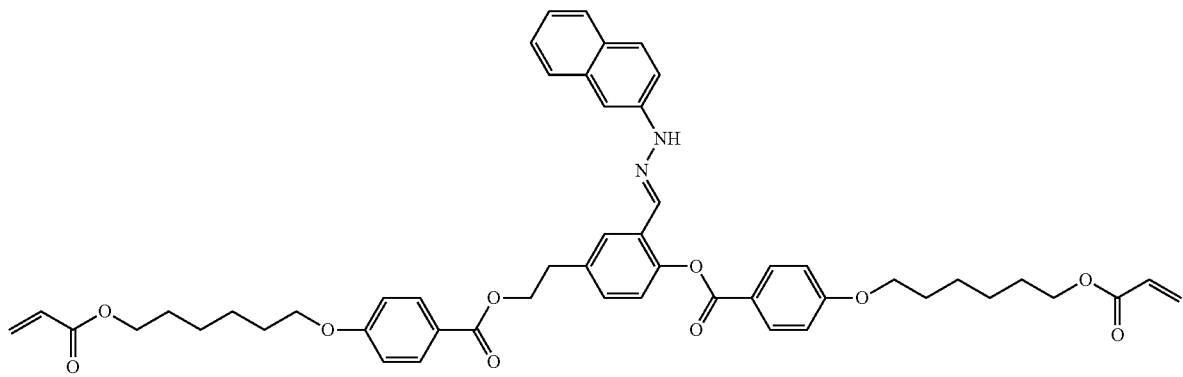
Example 33
(1-c-33)
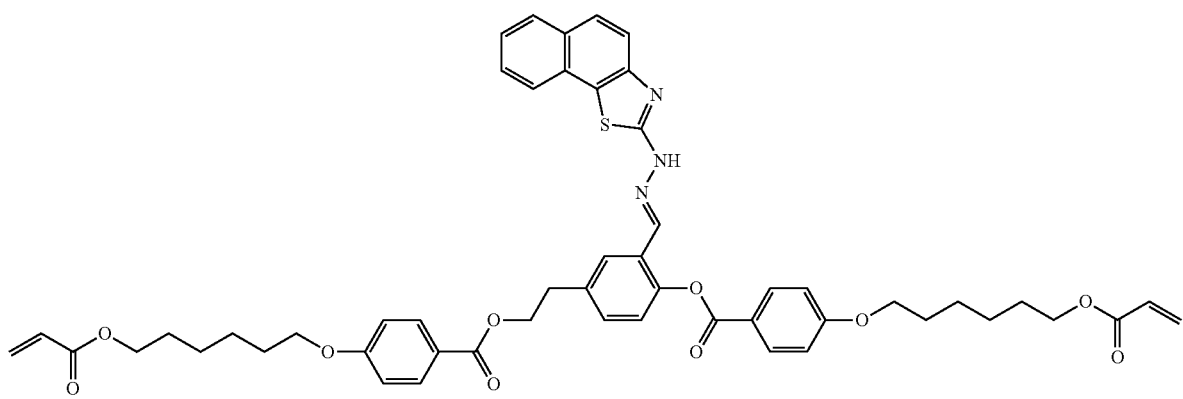

Example 34
(1-c-34)
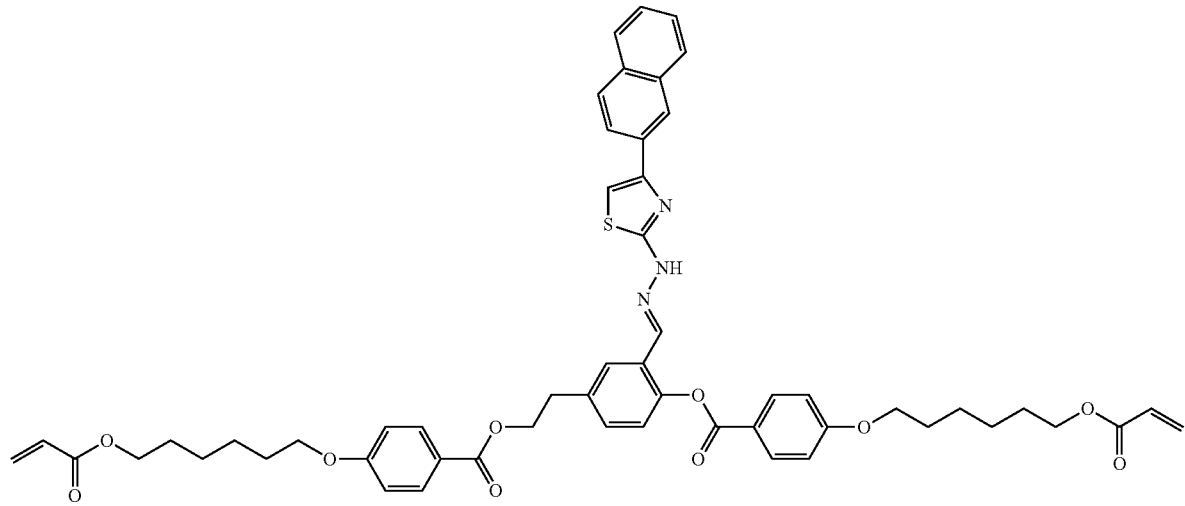
[Chem. 90]
Example 35
(1-g-35)
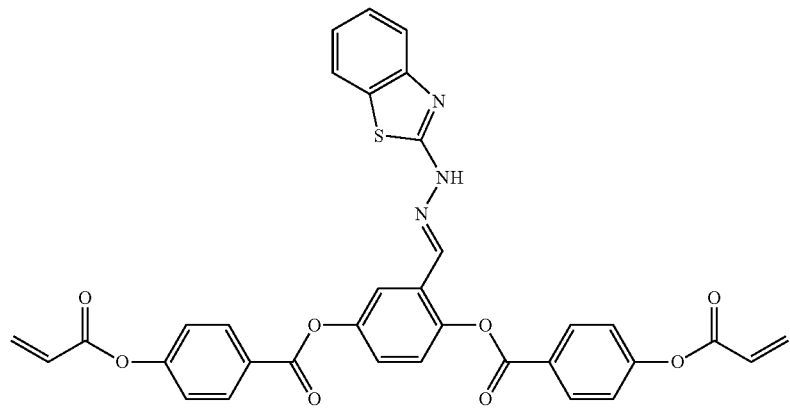
Example 36
(1-cg-36)
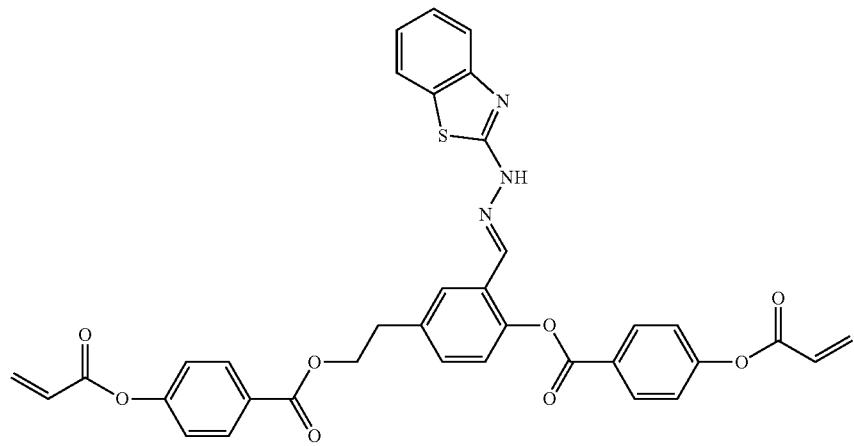

Example 37
(1-cg-37)
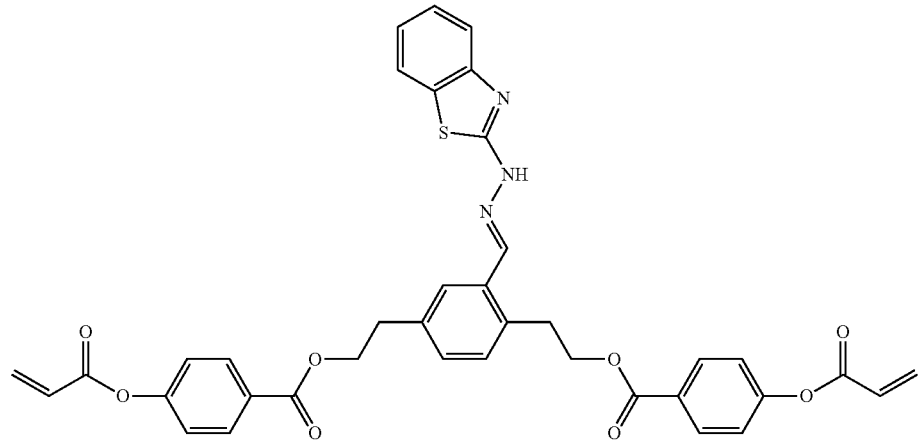
Example 38
(1-c-38)
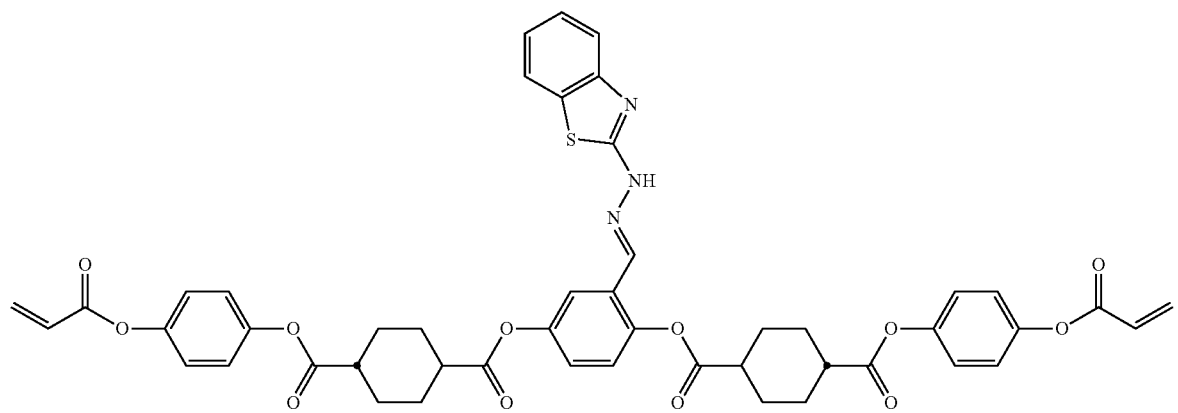
[Chem. 91]
Example 39
(1-c-39)
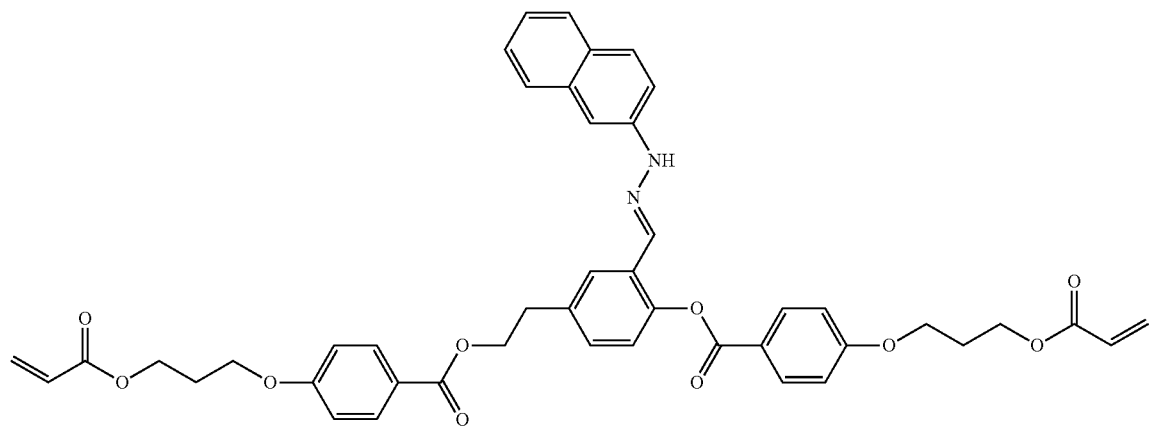

Example 40
(1-c-40)
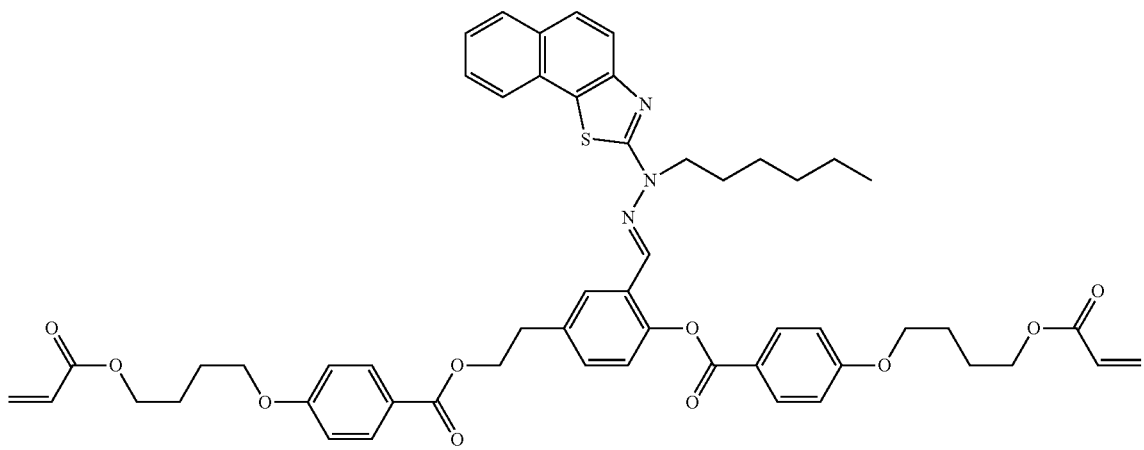
Example 41
(1-c-41)
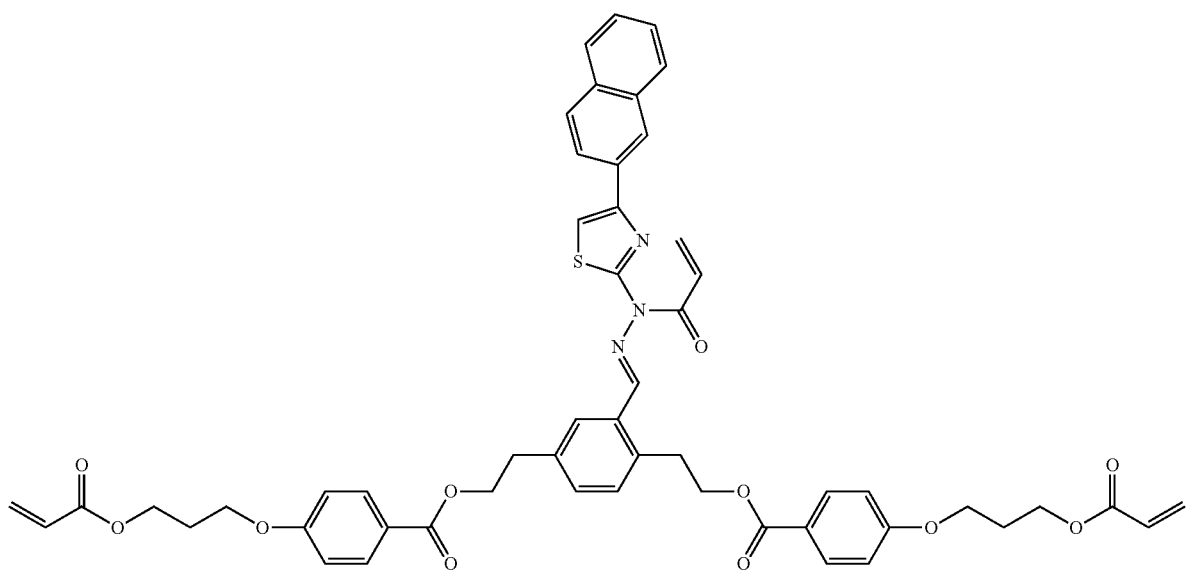
Example 42
(1-c-42)
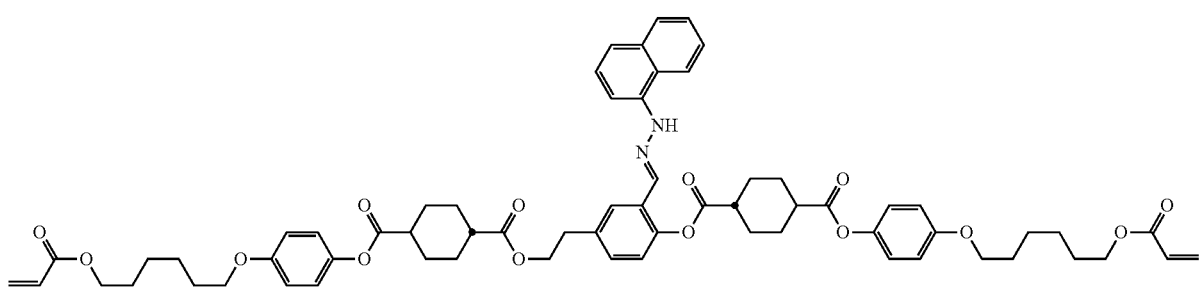
An intermediate compound (9) used for synthesizing the compounds of Examples was synthesized by the following method.

[Chem. 92]

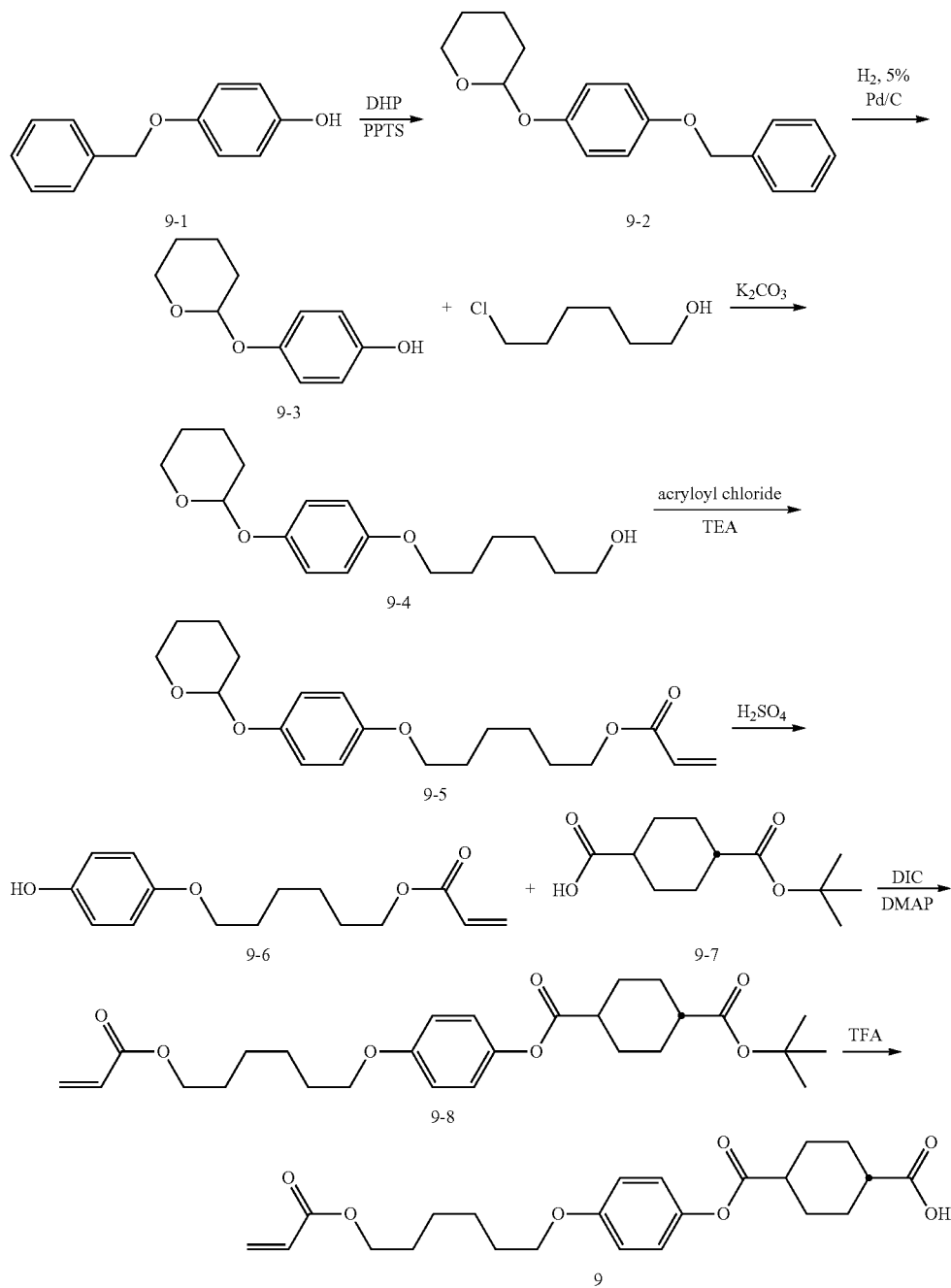

[Synthesis of Compound (9-2)]

To a 500-ml four-necked flask, 40.0 g (200 mmol) of the compound (9-1), 1.0 g (4 mmol) of pyridinium p-toluenesulfonate (PPTS), and 200 ml of dichloromethane were added in a nitrogen atmosphere, and the resulting mixture was stirred. While the mixture was cooled with ice, 25.2 g (300 mmol) of 3,4-dihydro-2H-pyran (DHP) was added dropwise to the mixture. After the mixture had been reacted at room temperature for 8 hours, the reaction liquid was cleaned with a saturated aqueous solution of sodium bicarbonate and a saturated saline solution in this order. The organic layer was dried with sodium sulfate. After sodium sulfate had been removed by filtration, vacuum concentration was performed. Hereby, 56.3 g (yield: 99.0%) of the compound (9-2) was prepared.

[Synthesis of Compound (9-3)]

To a 1-liter autoclave, 56.3 g (198 mmol) of the compound (9-2), 2.8 g of a catalyst (5% Pd/C), and 250 ml of ethanol were added. The resulting mixture was reacted at room temperature for 3 hours while the hydrogen pressure was maintained to be 0.4 MPa. After the catalyst had been removed by filtration, vacuum concentration was performed. Hereby, 38.5 g of the compound (9-3) was prepared (quantitative).

[Synthesis of Compound (9-4)]

In a nitrogen atmosphere, 38.5 g of the compound (9-3), 41.0 g (297 mmol) of potassium carbonate, 27.0 g (198 mmol) of 6-chloro-1-hexanol, and 300 ml of dimethylformamide were added to a 500-ml four-necked flask. The resulting liquid mixture was heated to 100° C. and then reacted for 24 hours. After cooling had been performed, 600 ml of ethyl acetate and 600 ml of water were added to the mixture and liquid separation was performed. The resulting organic layer was cleaned with water and a saturated saline solution in this order. Then, drying with sodium sulfate was performed. After sodium sulfate had been removed by filtration, vacuum concentration was performed. While ice-cooling was performed, hexane was added to the concentrated residue and crystallization was performed. The resulting crystals were filtered and then vacuum-dried. Hereby, 49.5 g of the compound (9-4) was prepared (yield: 84.9%).

[Synthesis of Compound (9-5)]

In a dry-air atmosphere, 44.2 g (150 mmol) of the compound (9-4), 16.7 g (165 mmol) of triethylamine (TEA), and 300 ml of dichloromethane were added to a 500-ml four-necked flask. The resulting mixture was stirred. To the mixture, 14.3 g (158 mmol) of acryloyl chloride was added dropwise at 5° C. or less. Subsequently, reaction was conducted at room temperature for 3 hours. The reaction liquid was cleaned with water, dilute hydrochloric acid, saturated sodium bicarbonate, and a saturated saline solution in this order. The organic layer was dried with sodium sulfate. After sodium sulfate had been removed by filtration, vacuum concentration was performed. Hereby, 52.3 g of the compound (9-5) was prepared (quantitative).

[Synthesis of Compound (9-6)]

To a 500-ml four-necked flask, 52.3 g (150 mmol) of the compound (9-5), 250 ml of tetrahydrofuran (THF), and 50 ml of methanol were added. The resulting liquid mixture was stirred. To the liquid mixture, 1.0 g of concentrated sulfuric acid was added. The liquid mixture was then reacted at room temperature for 3 hours. The reaction liquid was mixed with 500 ml of ethyl acetate. Subsequently, cleaning with a saturated aqueous solution of sodium bicarbonate and a saturated saline solution in this order was performed. The organic layer was concentrated, and the residue was purified by silica-gel column chromatography (dichloromethane). Hereby, 32.4 g of the compound (9-6) was prepared (yield: 81.7%).

The compound (9-7) was synthesized by the following method.

[Chem. 93]

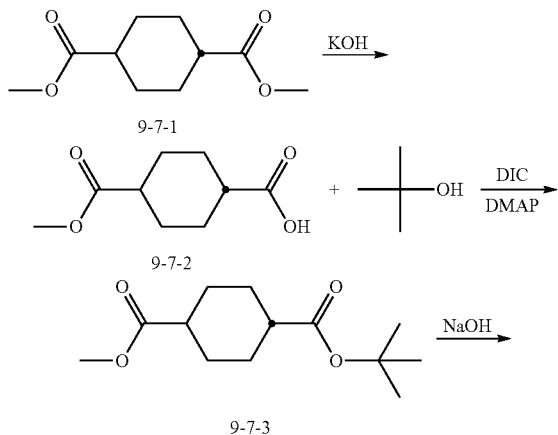

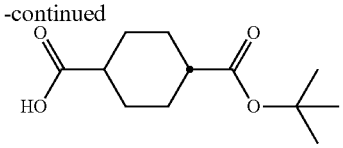

[Synthesis of Compound (9-7-2)]

To a four-necked flask (1 liter), 100.0 g (500 mmol) of trans-1,4-cyclohexanedicarboxylic acid dimethyl ester (9-7-1) and 1000 ml of methanol were added. The resulting mixture was stirred. After 16.8 g (300 mmol) of potassium hydroxide had been added to the mixture, the mixture was reacted for 6 hours while being refluxed. The reaction liquid was cooled and then concentrated. To the residue, 500 ml of water was added. Dilute hydrochloric acid was added to the resulting liquid mixture until the pH of the liquid mixture reached 2. Subsequently, the precipitated crystals were filtered. The crystals were cleaned with water and then vacuum-dried. Hereby, 54.0 g (yield: 58.0%) of the compound (9-7-2) was prepared.

[Synthesis of Compound (9-7-3)]

In a nitrogen atmosphere, 49.5 g (266 mmol) of the compound (9-7-2), 3.3 g (26.7 mmol) of N,N-dimethyl-4-aminopyridine (DMAP), 150 ml of tert-butyl alcohol, and 150 ml of tetrahydrofuran were added to a 300-ml four-necked flask. The resulting mixture was stirred homogeneously. While the mixture was cooled with ice, 50.4 g (399 mmol) of N,N'-diisopropylcarbodiimide (DIC) was added dropwise to the mixture. Subsequently, reaction was conducted at room temperature for 6 hours. To the reaction liquid, 15 ml of water was added, and the reaction liquid was further stirred for another 1 hour. After insoluble components had been removed by filtration, the reaction liquid was vacuum-concentrated. The residue was purified by silica-gel column chromatography (dichloromethane). Hereby, 51.9 g of the compound (9-7-3) was prepared (yield: 80.6%).

[Synthesis of Compound (9-7)]

To a four-necked flask (300 ml), 48.0 g (198 mmol) of the compound (9-7-3), methanol 150 ml, and 150 ml of tetrahydrofuran were added. The resulting mixture was stirred. While the mixture was cooled with ice, 24.0 g (600 mmol) of sodium hydroxide was added to the mixture. The mixture was stirred at 5° C. or less for 3 hours, mixed with 1000 ml of water, and subsequently cleaned with dichloromethane. Dilute hydrochloric acid was added to the aqueous layer until a pH of 2 was achieved. The precipitated crystals were filtered, cleaned with water, and then vacuum-dried. Hereby, 41.4 g of the compound (9-7) was prepared (yield: 91.6%).

[Synthesis of Compound (9-8)]

In a dry-air atmosphere, 29.0 g (128 mmol) of the compound (9-6), 34.4 g (130 mmol) of the compound (9-7), 0.6 g (15 mmol) of N,N-dimethyl-4-aminopyridine (DMAP), and 300 ml of dichloromethane were added to a 500-ml four-necked flask. The resulting mixture was stirred. While the mixture was cooled with ice, 19.3 g (150 mmol) of N,N'-diisopropylcarbodiimide (DIC) was added dropwise to the mixture. The mixture was reacted at room temperature for 6 hours. After 5 ml of water had been added to the reaction liquid, the reaction liquid was further stirred for another 1 hour. After insoluble components had been removed by filtration, the reaction liquid was vacuum-concentrated. The residue was purified by silica-gel column chromatography (dichloromethane). Hereby, 43.1 g of the compound (9-8) was prepared (yield: 71.1%).

[Synthesis of Compound (9)]

In a dry-air atmosphere, 42.0 g (88.5 mmol) of the compound (9-8) and 700 ml of dichloromethane were added to a 2000-ml four-necked flask. The resulting mixture was stirred. While the mixture was cooled with ice, 100.8 g (885 mmol) of trifluoroacetic acid (TFA) was added dropwise to the mixture. The mixture was reacted at room temperature for 8 hours. To the reaction liquid, 1000 ml of hexane was added and dichloromethane was distilled away under a reduced pressure. The precipitated crystals were filtered, cleaned with water and hexane in this order, and vacuum-dried. Hereby, 36.2 g of the compound (9) was prepared (yield: 97.8%).

Example 43

The polymerizable compound represented by Formula (1-c-43) below was synthesized by the following method.

[Chem. 94]

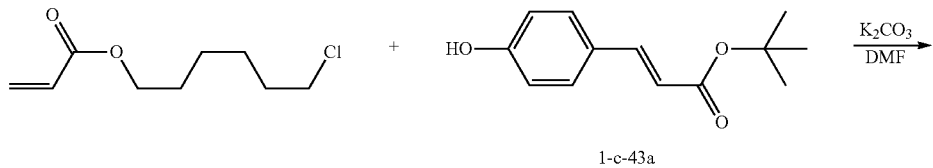

1-c-43a

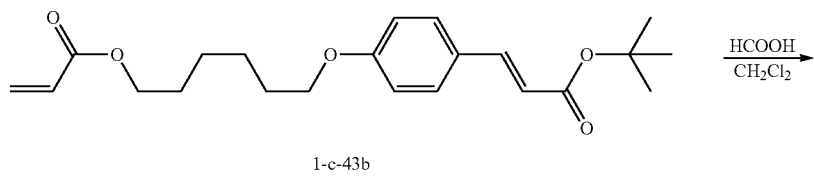

1-c-43b

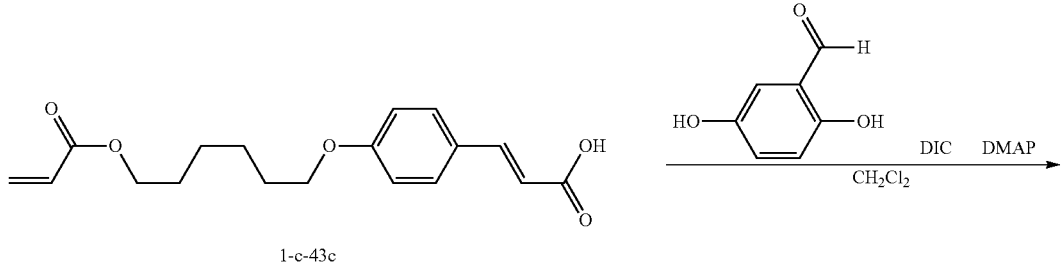

1-c-43c

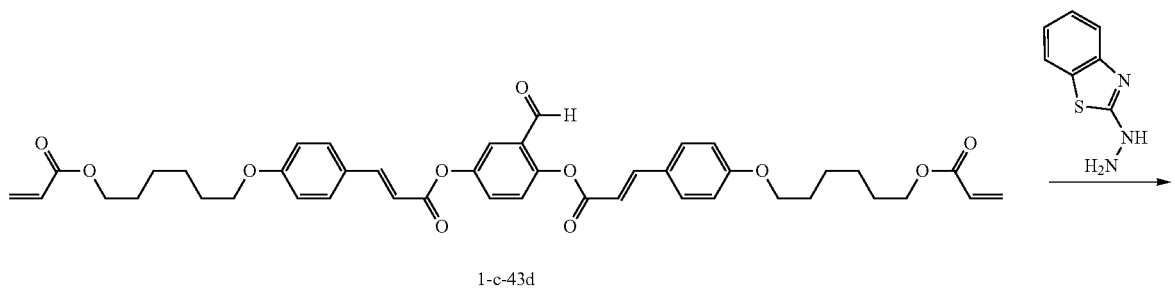

1-c-43d

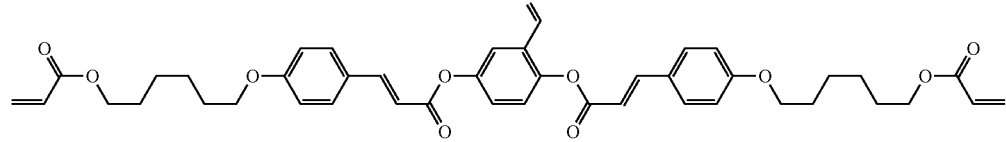

1-c-43

Synthesis Example of Compound (2)

To a 300-ml four-necked flask, 10.08 g (45.4 mmol) of tert-butyl 4-hydroxycinnamate (1-c-43a), 100 ml of N,N-dimethylformamide, and 9.4 g of potassium carbonate were added. The resulting mixture was stirred for 10 minutes. To the mixture, 10.1 g (53 mmol) of acrylic acid-6-chlorohexyl was added, and the mixture was subsequently stirred at 90° C. for 6 hours. The reaction mixture was then cooled to 10° C. After 100 ml of water had been added to the reaction mixture, the reaction mixture was stirred for 1 hour. Subsequently, the mixture was filtered in order to obtain a crude product in a solid form. The solid was dissolved in 25 ml of acetone, and the resulting solution was added dropwise to 45 ml of methanol. Then, the temperature was reduced to 0° C. The resulting solid was filtered and again dissolved in 12 ml of acetone. The resulting solution was added dropwise to 25 ml of hexane. Then, the temperature was reduced to 0° C. The resulting solid was filtered and then dried to form 8.56 g of the compound (1-c-43b) (yield: 50%).

Synthesis Example of Compound (1-c-43c)

To a 200-ml three-neck flask, 8.5 g of the compound (1-c-43b) and 22 ml of dichloromethane were added, and the resulting mixture was stirred. To the mixture, 22 ml of formic acid was added dropwise. Subsequently, the mixture was stirred at 40° C. for 5 hours. The reaction mixture was cooled to 30° C. or less, and 50 ml of dichloromethane was then added to the reaction mixture. After an organic layer had been separated, cleaning with 70 ml of water was performed 4 times. Subsequently, cleaning with 70 ml of a saturated saline solution was performed once. The resulting solution was dried with sodium sulfate. After sodium sulfate had been removed by filtration, the solvent was distilled away. To the resulting solid, 10 ml of hexane and 4 ml of toluene were added, and the resulting mixture was stirred at room temperature for 30 minutes. The mixture was filtered and subsequently dried to form 6.30 g of the compound (1-c-43c) (yield: 87%).

Synthesis Example of Compound (1-c-43d)

To a 100-ml three-neck flask, 1.31 g of 2,5-dihydroxybenzaldehyde, 25 ml of dichloromethane, 6.05 g of the compound (1-c-43c), and 0.07 g of N,N-dimethylaminopyridine were added. The resulting mixture was stirred at 5° C. for 10 minutes. To the mixture, 2.98 g of N,N-diisopropylcarbodiimide was added dropwise while the temperature was maintained to be 10° C. or less. The mixture was subsequently stirred at 30° C. for 6 hours. After 0.08 ml of water had been added to the reaction mixture, a solid was removed by filtration. The resulting solution was passed through columns (silica gel+alumina, dichloromethane). Subsequently, the solvent was distilled away. The resulting solid was dissolved in 10 ml of acetone. The resulting solution was added dropwise to 30 ml of methanol. Then, the temperature was reduced to 0° C. The resulting solid was filtered and then dried to form 4.80 g of the compound (1-c-43d) (yield: 69%).

Synthesis Example of Compound (1-c-43)

To a 100-ml three-necked flask, 4.8 g of the compound, 1.07 g of 2-hydrazinobenzothiazole, and 20 ml of tetrahydrofuran were added, and the resulting mixture was stirred at 50° C. for 15 hours. The reaction mixture was cooled to room temperature in order to precipitate a solid, which was filtered. The solid was purified by silica-gel column chromatography (dichloromethane/ethyl acetate: 10/1). The solution passed through the columns was filtered and then drying was performed. Hereby, 2.40 g of the compound (1-c-43) was prepared.

The upper-limit temperature of the phase sequence of the polymerizable compound (1-c-43) which was determined by differential scanning calorimetry and observing the liquid crystal phase with a polarized light microscope equipped with a temperature-controllable apparatus was "Cry 106 Sm 196 N 203 Iso".

$^1$H NMR (CDCl$_3$) δ: 1.41-1.61 (p, 8H), 1.65-1.80 (p, 4H), 1.7 (br, 1H), 1.80-1.97 (p, 4H), 4.02 (t, 2H), 4.17 (t, 2H), 5.82 (d, 2H), 6.10-6.18 (dd, 2H), 6.39-6.44 (s+d, 3H), 6.93 (dd, 4H), 7.09 (t, 2H), 7.23 (s, 1H), 7.30 (d, 1H), 7.43 (d, 1H), 7.50-7.58 (p, 4H), 7.75-7.89 (p, 3H), 8.10 (s, 1H).

LC-MS: m/z 885.61[M+]

The compounds of Examples 44 to 53, which are illustrated below, were synthesized by the same reactions as in Example 43 and, as needed, a method confirming to publicly known methods.

[Chem. 95]

Example 44

(1-c-44)

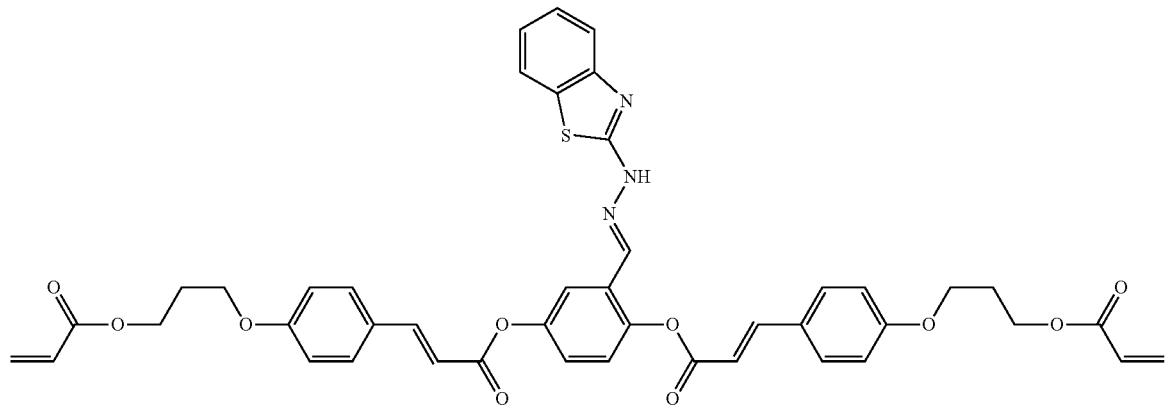

Example 45
(1-c-45)
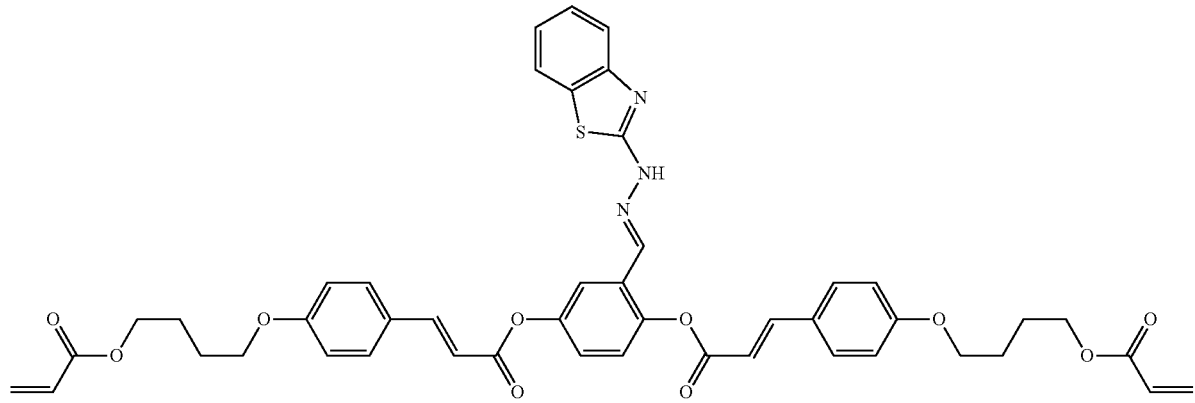
Example 46
(1-c-46)
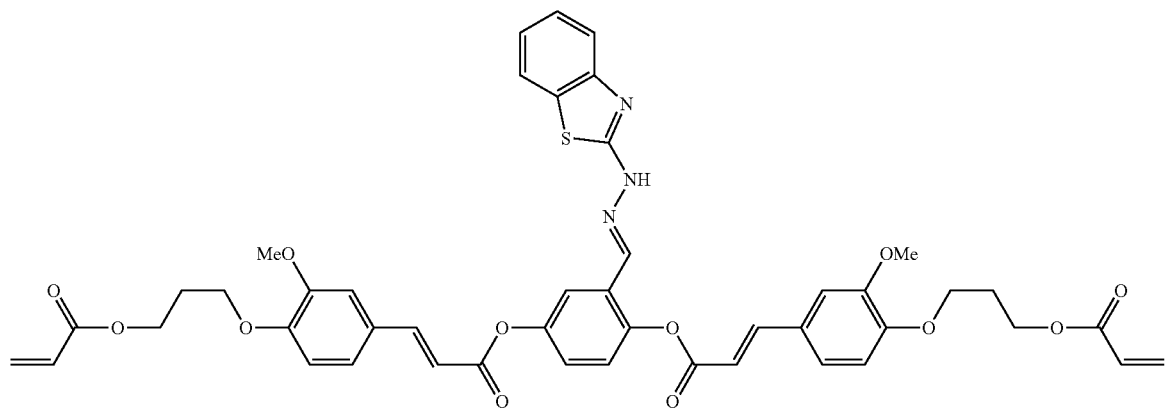
[Chem. 96]
Example 47
(1-c-47)
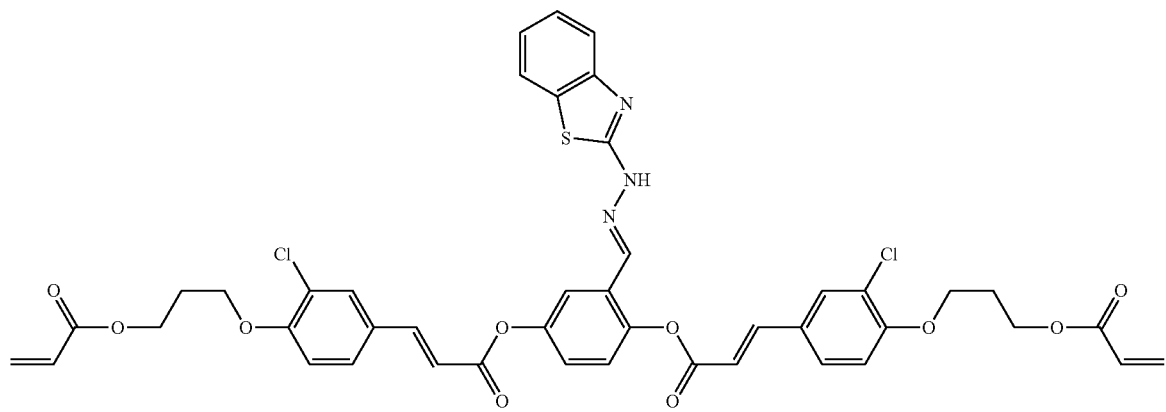

Example 48
(1-c-48)
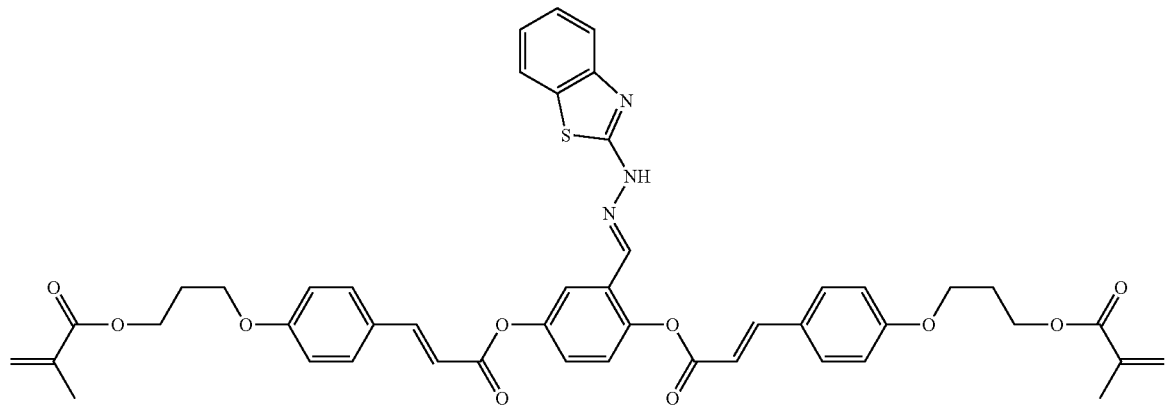
[Chem. 97]
Example 49
(1-c-49)
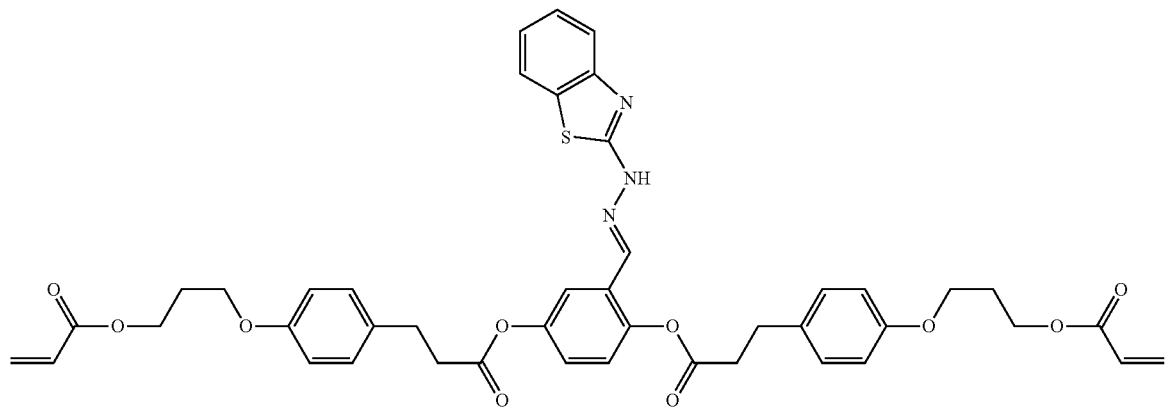
Example 50
(1-c-50)
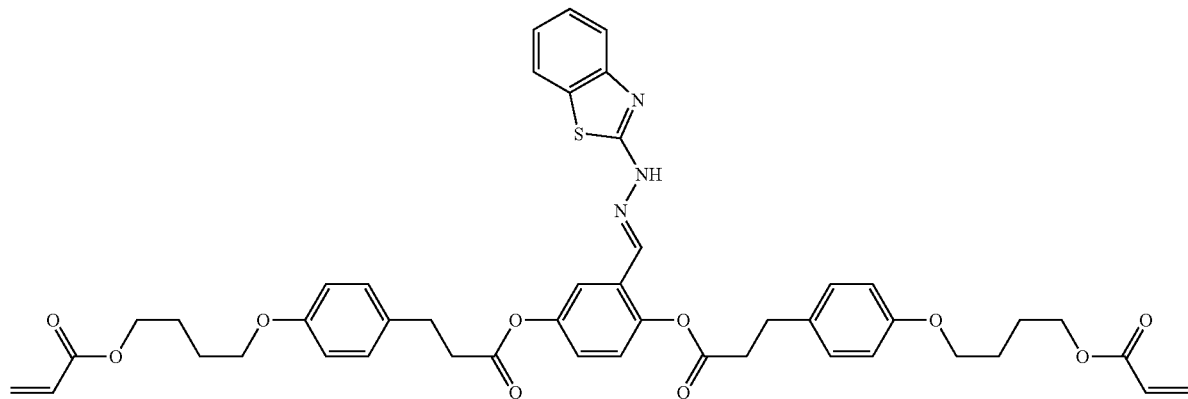

Example 51
(1-c-51)
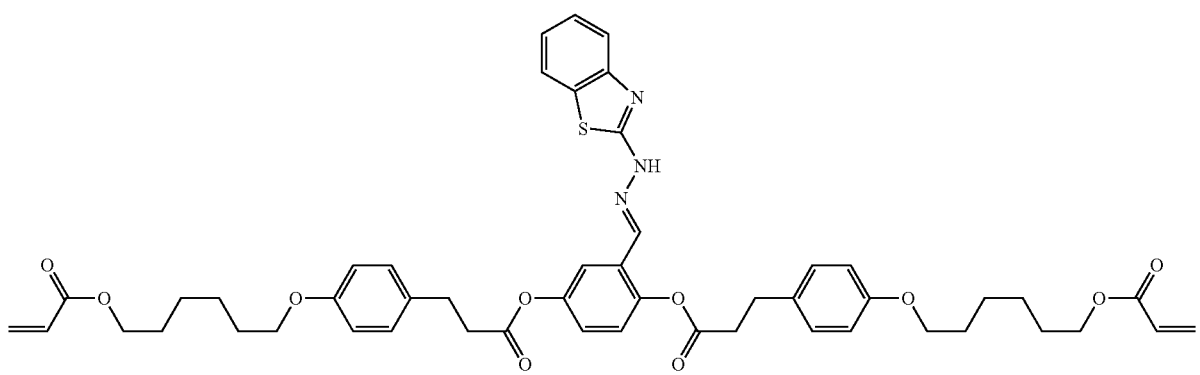
Example 52
(1-c-52)
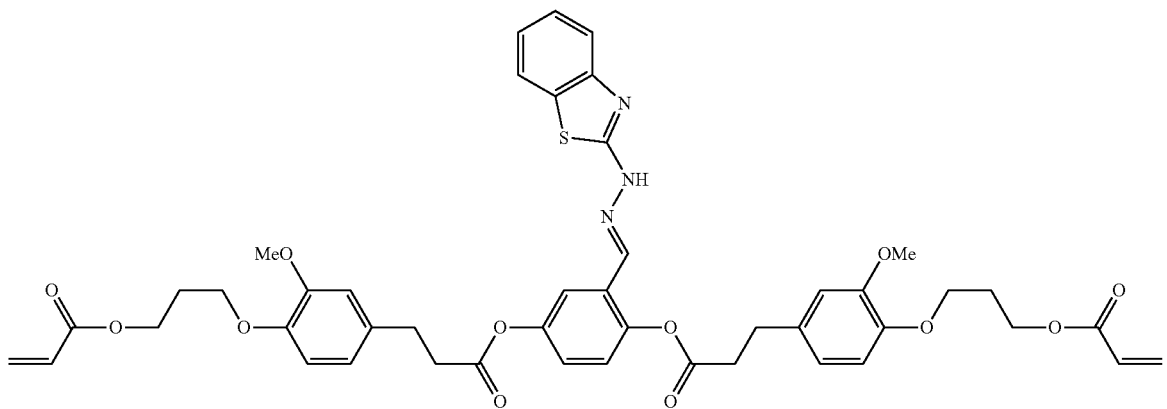
Example 53
(1-c-53)
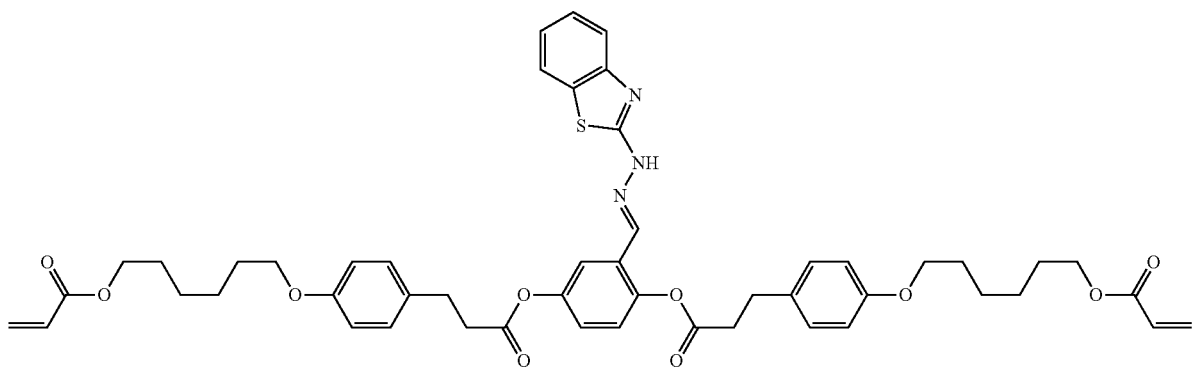
Physical properties of the compound represented by Formula (1-c-51)
Dislocation temperature: C 61-67 (N 40) I
$^1$H NMR (CDCl$_3$) δ: 1.42-1.82 (m, 16H), 2.83-3.09 (m, 8H), 3.97 (m, 4H), 4.17 (m, 4H), 5.84 (d, 2H), 6.15 (dd, 2H), 6.43 (d, 2H), 6.86-6.92 (m, 4H), 7.04 (m, 2H), 7.15-7.23 (m, 5H), 7.36 (t, 1H), 7.42 (s, 1H), 7.57 (d, 1H), 7.68 (m, 2H) ppm.
Example 54
The polymerizable compound represented by Formula (1-j-54) below was synthesized by the following method.

[Chem. 98]

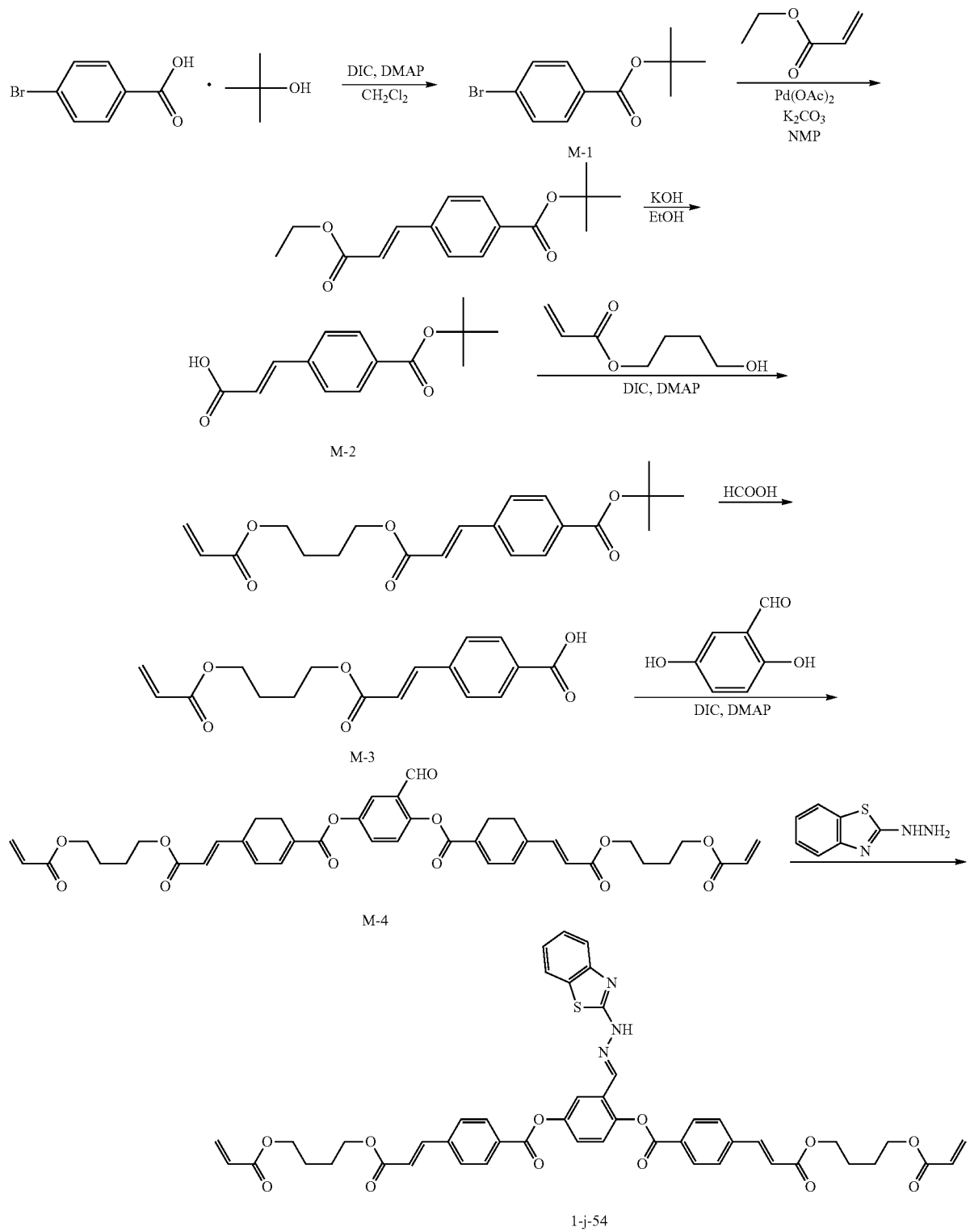

[Synthesis of Compound M-1]

In dichloromethane, 4-bromobenzoic acid (50 g), tert-butyl alcohol (20.3 g), and dimethylaminopyridine (12.2 g) were dissolved. The resulting solution was added dropwise to diisopropylcarbodiimide (DIC, 37.7 g) at 35° C. The resulting mixture was stirred for 5 hours. Subsequently, the reaction liquid was filtered, and the filtrate was concentrated. The resulting solid was purified by column chromatography. Hereby, the compound M-1 (49 g) was prepared.

[Synthesis of Compound M-2]

The compound M-1 (49 g) was dissolved in NMP. Potassium carbonate (34.2 g) and ethyl acrylate (24.8 g) were added to the resulting solution. After nitrogen purge had been performed, palladium acetate (0.43 g) was added to the solution. The solution was then stirred while being heated at 110° C. After stirring had been performed for 4 hours, water (300 ml) was added to the solution. Subsequently, extraction with methyl acetate was performed. The organic layer was cleaned with 1%-hydrochloric acid and a saturated saline solution in this order. Then, dehydration was performed using mirabilite in order to concentrate the organic layer. The resulting compound was dissolved in 100 ml of ethanol. To the resulting solution, potassium hydroxide (15.2 g), 50 mL of ethanol, and 50 mL of water were added. The resulting mixture was stirred at room temperature for 5 hours. Subsequently, 100 mL of water was added to the mixture. Then, neutralization was performed using hydrochloric acid. An aqueous layer was extracted using ethyl acetate and concentration was performed. Hereby, an oily solid (M-2, 14.7 g) was prepared.

[Synthesis of Compound M-3]

The resulting compound was dissolved in dichloromethane. DMAP (2.90 g), 4-hydroxybutyl acrylate (10.3 g), and 400 mL of DMF were added to the resulting solution. DIC (9.0 g) was gradually added dropwise to the resulting mixture at room temperature. The mixture was then stirred for 24 hours. Subsequently, cleaning with water and extraction with dichloromethane were performed. Then, purification was performed by silica-gel column chromatography. Formic acid was added to the resulting oily compound, and the resulting mixture was stirred at room temperature for 9 hours and further stirred at 45° C. for another 4 hours. Then, 100 mL of water was added to the reaction system, neutralization was performed with sodium hydroxide, and subsequently extraction with ethyl acetate was performed. The organic layer was concentrated and dried. Hereby, the compound M-3 (6.5 g) was prepared.

[Synthesis of Compound M-4]

The Compound M-3 (6.5 g) was dissolved in 200 mL of dichloromethane. DMAP (0.6 g) and dihydroxybenzaldehyde (1.2 g) were added to the resulting solution. To the resulting mixture, DIC (2.5 g) was added dropwise at room temperature. The mixture was stirred for 10 hours. The reaction liquid was filtered, and the resulting organic layer was concentrated. Subsequently, purification was performed by silica-gel column chromatography. Hereby, the compound M-4 (5 g) was prepared.

[Synthesis of Compound 1-j-54]

The compound M-4 (5 g) was dissolved in 50 mL of ethanol. A hydrazine derivative of benzothiazole was added to the resulting solution. The resulting mixture was stirred at 45° C. for 5 hours. The temperature was reduced to room temperature in order to precipitate a solid, which was recovered by filtration. Subsequently, purification was performed by recrystallization. Hereby, 3.5 g of the targeted compound 1-j-54 was prepared.

The compounds of Examples 55 to 65, which are illustrated below, were synthesized by the same reactions as in Example 54 and, as needed, a method confirming to publicly known methods.

[Chem. 99]

Example 55

(1-j-55)

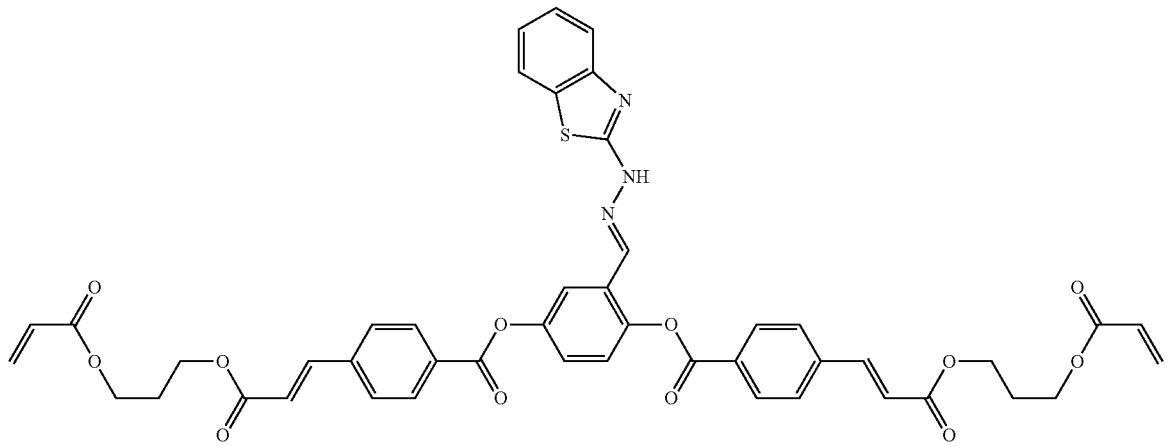

-continued
Example 56
(1-j-56)
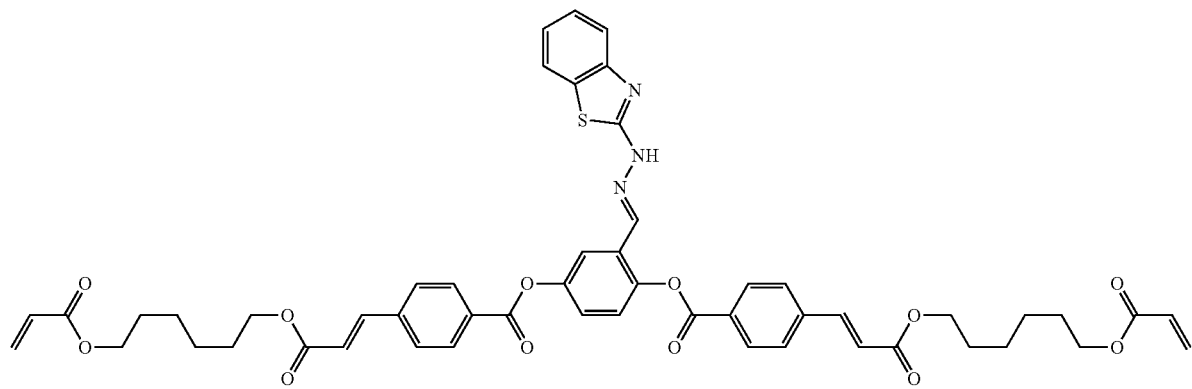
Example 57
(1-j-57)
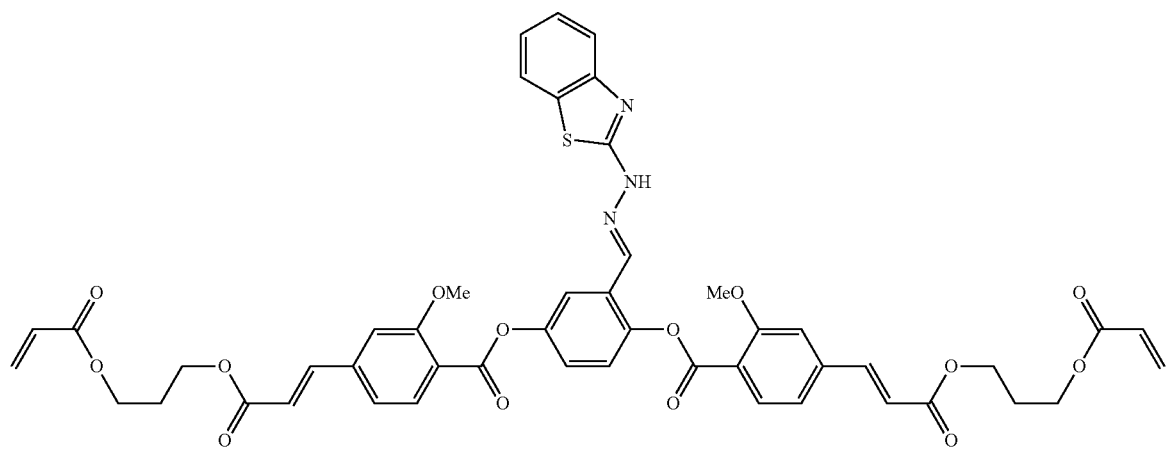
[Chem. 100]
Example 58
(1-cj-58)
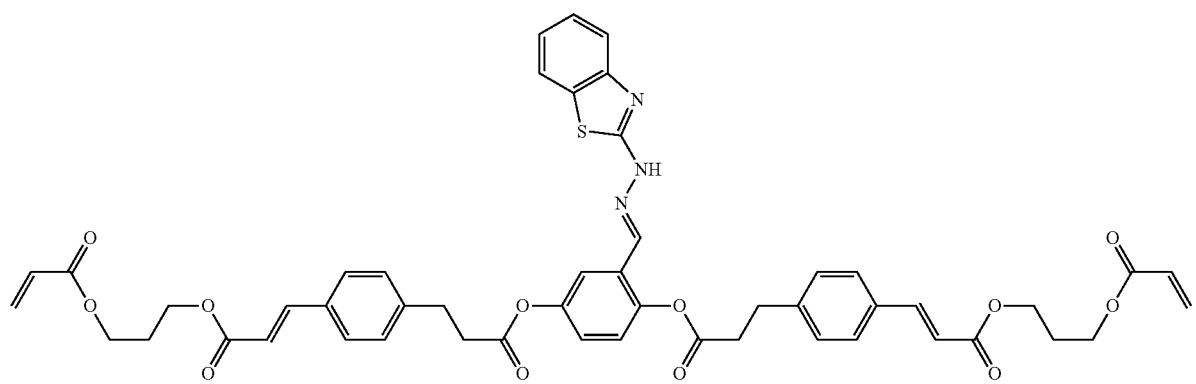

-continued
Example 59
(1-cj-59)
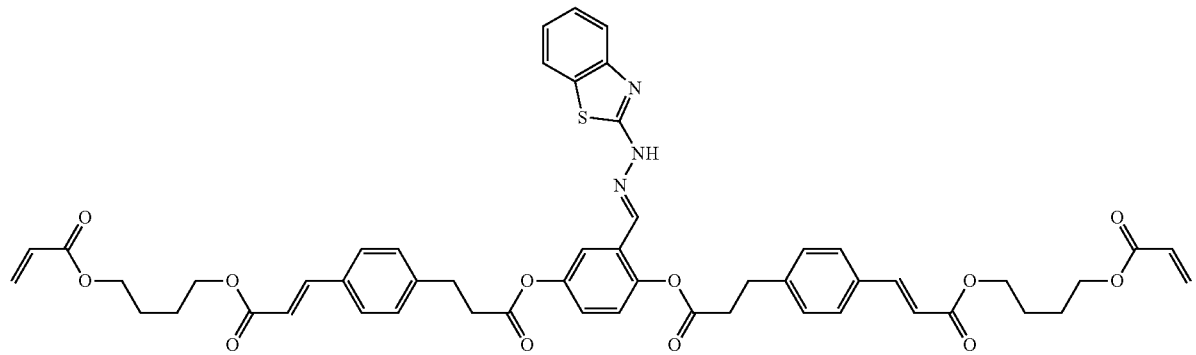
Example 60
(1-cj-60)
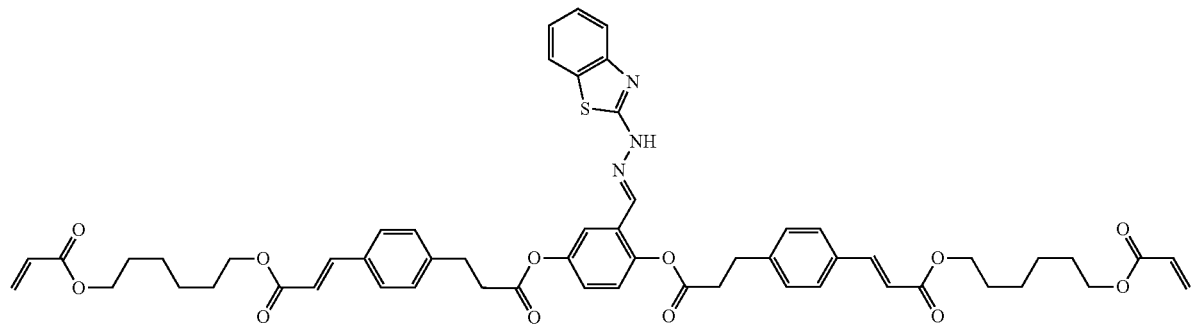
[Chem. 101]
Example 61
(1-j-61)
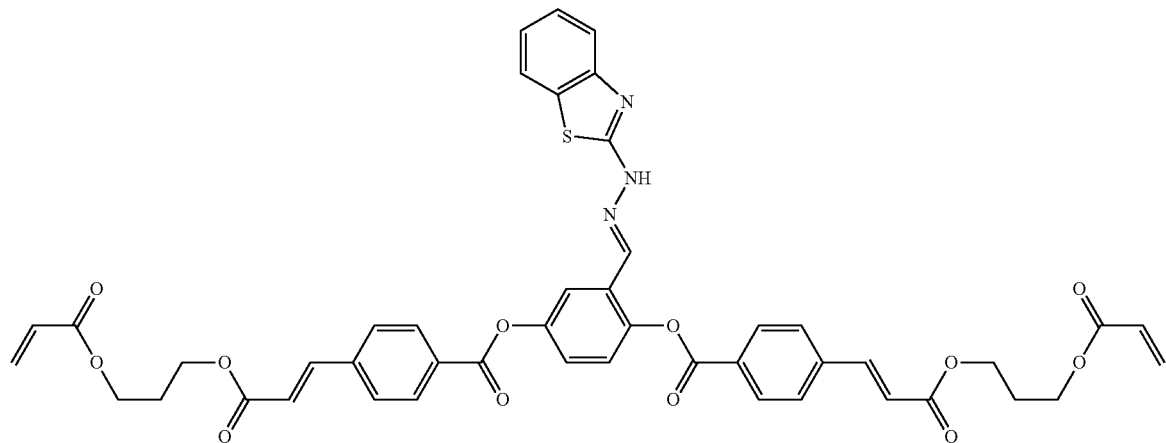

Example 62
(1-j-62)
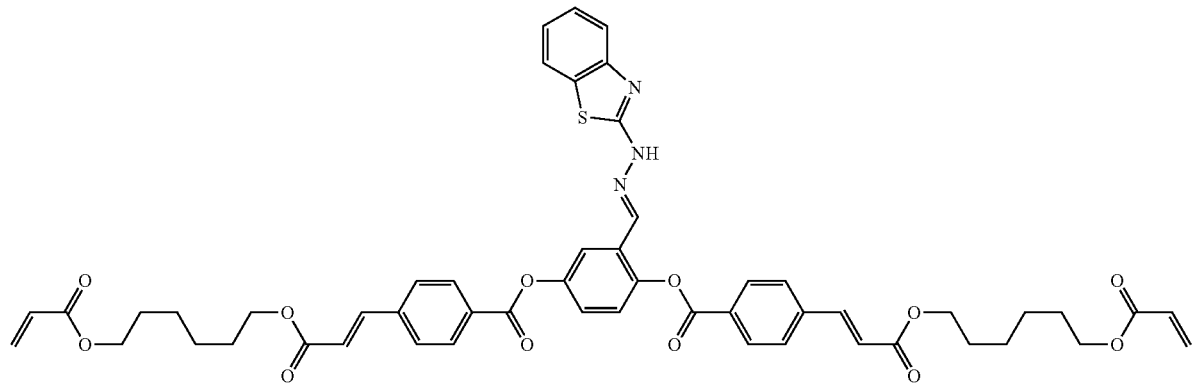
Example 63
(1-cj-63)
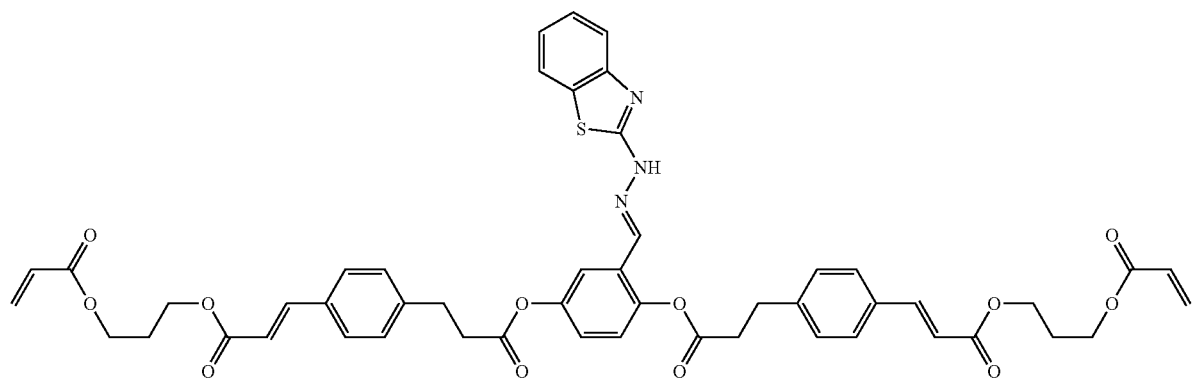
Example 64
(1-j-64)
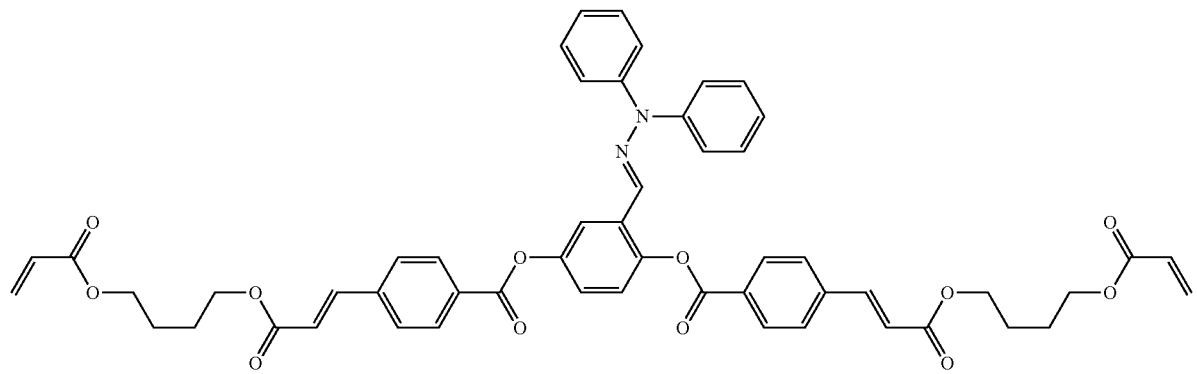

Example 65
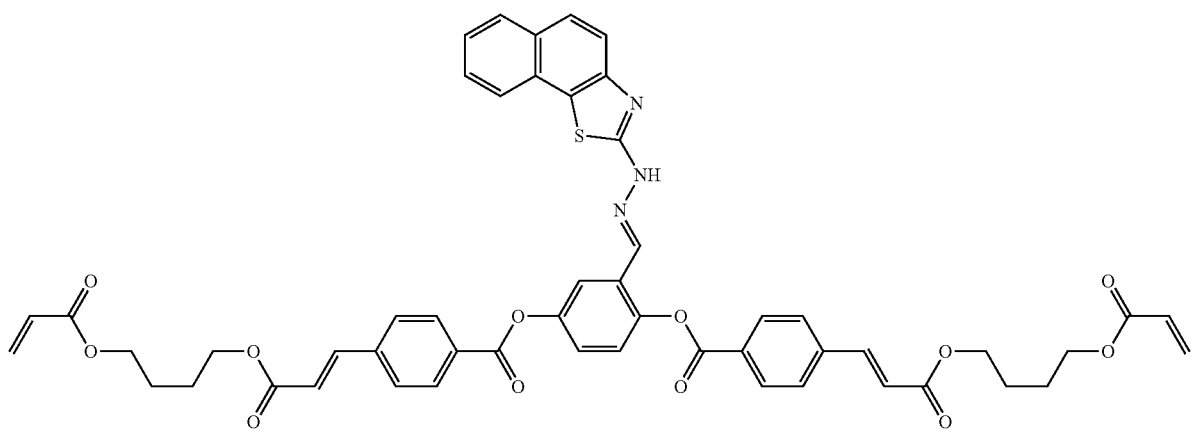
(1-j-65)
Example 66
The polymerizable compound represented by Formula (1-c-66) below was synthesized by the following method.
[Chem. 102]
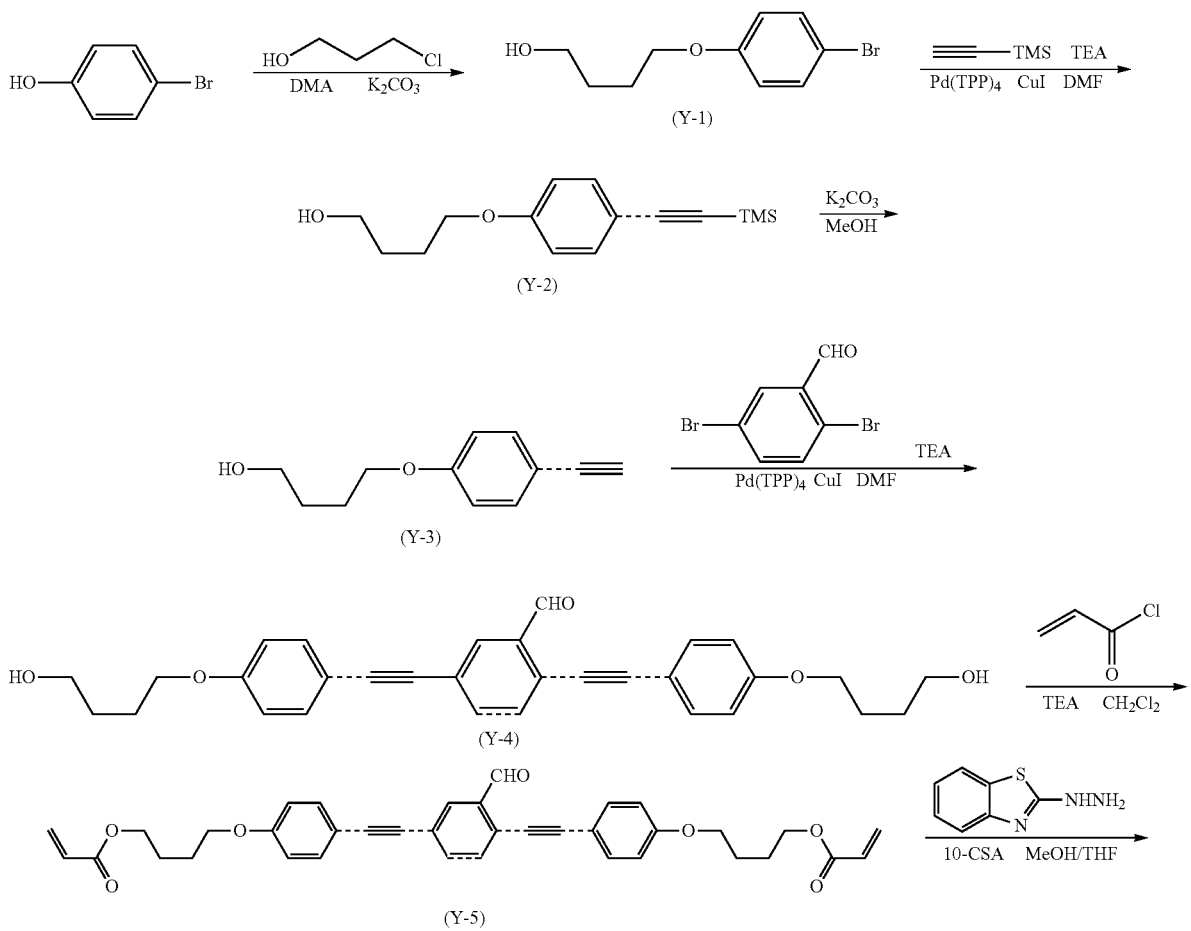

-continued

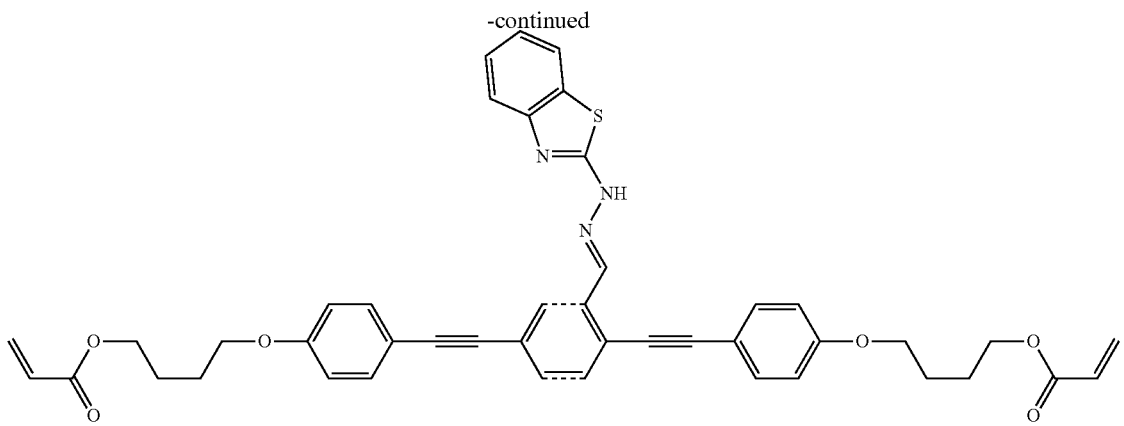

(1-c-66)

Synthesis Example of Compound (Y-1)

To a reaction container equipped with a thermometer and a cooler, 50.0 g (0.289 mol) of 4-bromophenol, 24.6 g (0.260 mol) of 3-chloropropanol, 55.9 g (0.405 mol) of potassium carbonate, and 250 ml of N,N-dimethylacetamide were added. After the resulting mixture had been stirred for 7 hours while being heated at 120° C., the mixture was diluted with ethyl acetate and subsequently cleaned with hydrochloric acid and a saline solution in this order. Then, purification was performed by column chromatography (alumina). Hereby, 45.1 g (0.195 mol) of the compound represented by Formula (Y-1) was prepared.

Synthesis Example of Compound (Y-2)

To a reaction container equipped with a thermometer, 45.1 g (0.195 mol) of the compound represented by Formula (Y-1), 21.6 g (0.214 mol) of trimethylsilylacetylene, 740 mg (3.90 mmol) of copper(I) iodide, 225 ml of N,N-dimethylformamide, and 75 ml of triethylamine were added. After nitrogen purge had been performed, 2.3 g (1.95 mmol) of tetrakis(triphenylphosphine)palladium(0) was added to the resulting mixture. The mixture was stirred for 8 hours while being heated at 90° C. Subsequently, dilution with ethyl acetate and cleaning with hydrochloric acid and a saline solution in this order were performed. Then, purification was performed by column chromatography (alumina). Hereby, 34.6 g (0.139 mol) of the compound represented by Formula (Y-2) was prepared.

Synthesis Example of Compound (Y-3)

To a reaction container, 34.6 g (0.139 mol) of the compound represented by Formula (Y-2), and 300 ml of methanol, and 38.5 g (0.278 mol) of potassium carbonate were added. The resulting mixture was stirred at room temperature for 10 hours. Subsequently, toluene was added to the mixture. Cleaning with a saline solution was then performed. Subsequently, purification was performed by column chromatography (alumina). Hereby, 23.8 g (0.135 mol) of the compound represented by Formula (Y-3) was prepared.

Synthesis Example of Compound (Y-4)

To a reaction container equipped with a thermometer, 20.6 g (0.117 mol) of the compound represented by Formula (Y-3), 14.0 g (0.053 mol) of 2,5-dibromobenzaldehyde, 400 mg (2.12 mmol) of copper(I) iodide, 105 ml of N,N-dimethylformamide, and 35 ml of triethylamine were added. After nitrogen purge had been performed, 1.2 g (1.06 mmol) of tetrakis(triphenylphosphine)palladium(0) was added to the resulting mixture. The mixture was stirred for 8 hours while being heated at 90° C. Subsequently, dilution with ethyl acetate and cleaning with hydrochloric acid and a saline solution in this order were performed. Then, purification was performed by column chromatography (alumina) and recrystallization. Hereby, 8.0 g (0.017 mol) of the compound represented by Formula (Y-4) was prepared.

Synthesis Example of Compound (Y-5)

To a reaction container equipped with a thermometer and a dropping funnel, 8.0 g (0.017 mol) of the compound represented by Formula (Y-4), 4.6 g (0.045 mol) of triethylamine, and 110 ml of dichloromethane were added. While the resulting mixture was cooled with ice, 3.8 g (0.042 mol) of acryloyl chloride was added dropwise to the mixture. After the mixture had been stirred at room temperature for 5 hours, cleaning with hydrochloric acid and a saline solution in this order was performed. Then, purification was performed by column chromatography (silica gel) and recrystallization. Hereby, 9.3 g (0.017 mol) of the compound represented by Formula (Y-5) was prepared.

Synthesis Example of Compound (1-c-66)

To a reaction container, 9.3 g (0.017 mol) of the compound represented by Formula (Y-5), 2.7 g (0.017 mol) of 2-hydrazinobenzothiazole, 77 mg (0.03 mmol) of 10-camphorsulfonic acid, 50 ml of methanol, and 50 ml of THF were added. The resulting mixture was stirred at room temperature for 3 hours. Then, purification was performed by column chromatography (silica gel) and recrystallization. Hereby, 8.4 g (0.012 mol) of the compound represented by Formula (1-c-66) was prepared.

LC-MS: m/z 737.22[M+]

The compounds of Examples 67 and 68, which are illustrated below, were synthesized by the same reactions as in Example 66 and, as needed, a method confirming to publicly known methods.

[Chem. 103]
Example 67
(1-c-67)
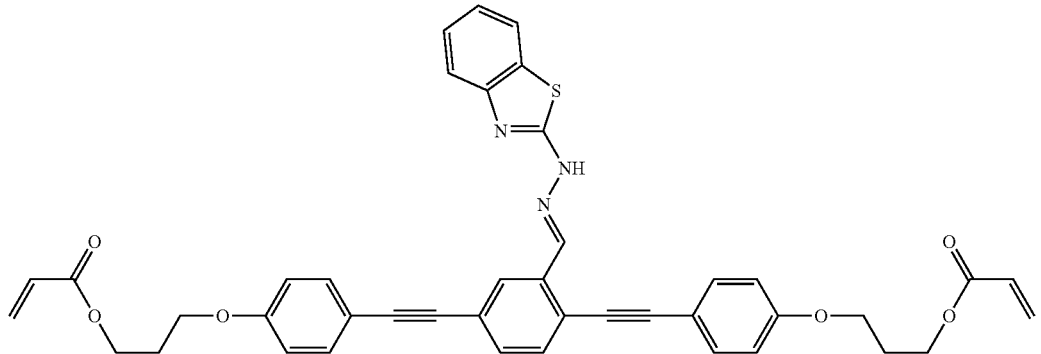
Example 68
(1-c-68)
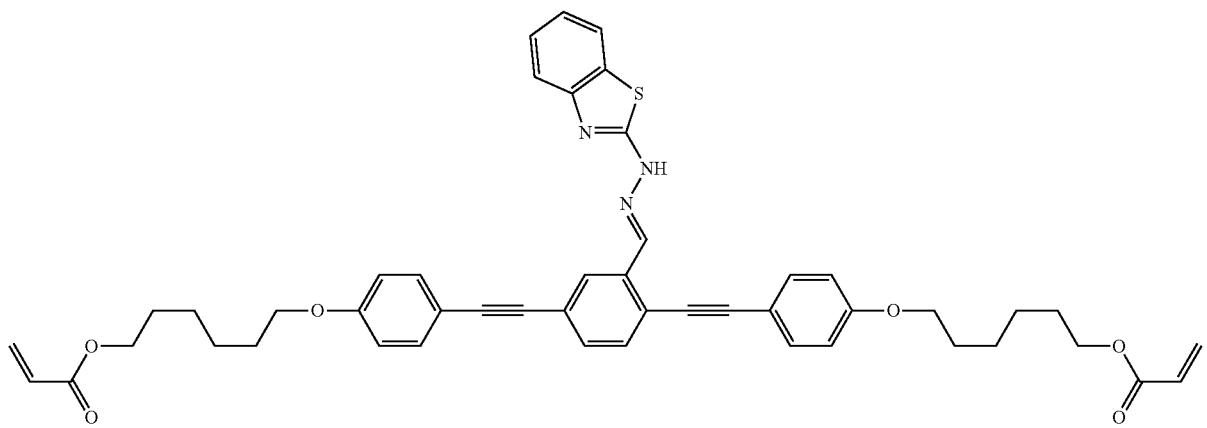
Example 69
The compound represented by Formula (1-e-69) below was synthesized by the following method.
[Chem. 104]
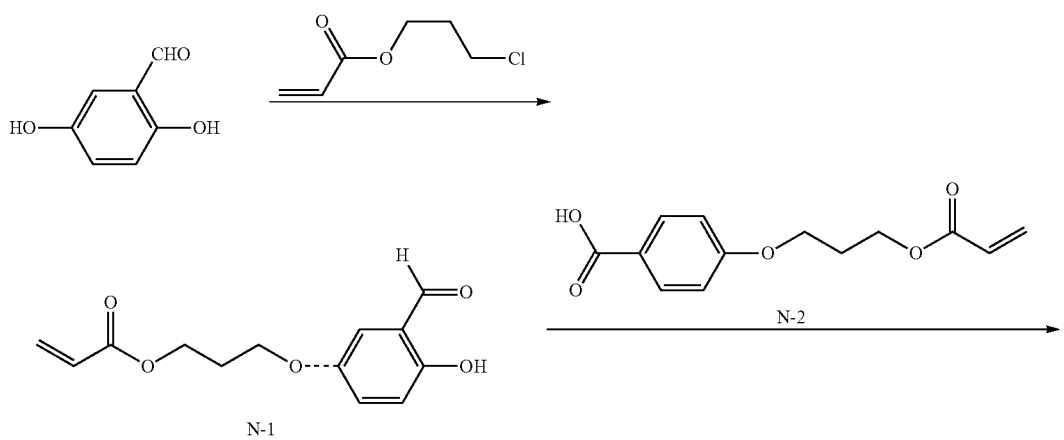

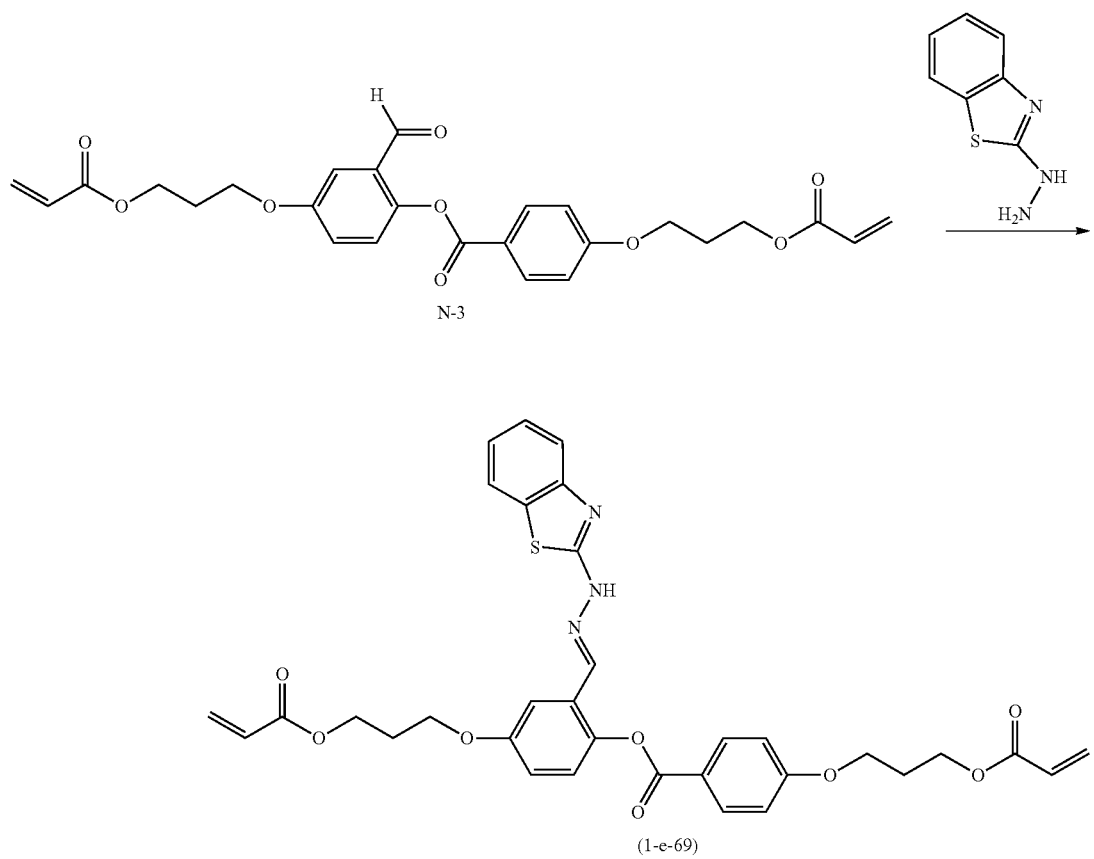

[Synthesis of Compound N-1]

In a nitrogen atmosphere, 2.08 g of 2,5-dihydroxybenzaldehyde, 4.16 g of potassium carbonate, 2.46 g of 3-chloro-1-propanol, and 20 ml of dimethylformamide were added to a 100-ml four-necked flask. The resulting liquid mixture was heated to 100° C. and reacted for 24 hours. After cooling had been performed, 40 ml of ethyl acetate and 40 ml of water were added to the liquid mixture in order to perform liquid separation. The resulting organic layer was cleaned with water and a saturated saline solution in this order. Then, drying with sodium sulfate was performed. After sodium sulfate had been removed by filtration, vacuum concentration was performed. While the concentrated residue was cooled with ice, hexane was added to the concentrated residue in order to induce crystallization. The crystals were filtered and then vacuum-dried. Hereby, 3.09 g of the compound (N-1) was prepared (yield: 82%).

In a nitrogen atmosphere, 3.09 g of the compound (N-1), 3.40 g of the compound (N-2), 0.03 g of N,N-dimethyl-4-aminopyridine (DMAP), and 30 ml of dichloromethane were added to a 100-ml four-necked flask. The resulting liquid mixture was stirred. To the liquid mixture, 2 ml of a dichloromethane solution containing 1.87 g of diisopropylcarbodiimide (DIC) was added dropwise at 5° C. or less. After the addition of the dichloromethane solution had been completed, the resulting liquid mixture was reacted at room temperature for 4 hours. Subsequently, 0.1 ml of water was added to the liquid mixture, which was further stirred for another 1 hour. After insoluble components had been removed by filtration, the filtrate was cleaned with water and then dried with sodium sulfate. After sodium sulfate had been separated by filtration, vacuum concentration was performed. To the residue, 20 ml of methanol was added. While ice cooling was performed, precipitation was performed. The precipitate was filtered, cleaned with methanol and n-hexane in this order, and then vacuum-dried. Hereby, 5.24 g of the compound (N-3) was prepared (yield: 88%).

(Synthesis of Compound 1-e-69) To a 30-ml three-necked flask, 5.24 g of the compound, 1.80 g of 2-hydrazinobenzothiazole, and 15 ml of tetrahydrofuran were added. The resulting mixture was stirred at 25° C. for 9 hours. After 150 ml of water had been added to the mixture, extraction with 100 ml of ethyl acetate was performed twice. The resulting organic phase was dried with sodium sulfate. After sodium sulfate had been removed by filtration, vacuum concentration was performed. The residue was purified by silica-gel column chromatography (hexane/ethyl acetate: 2/1). The resulting crude product was reprecipitated using acetone/methanol. The resulting crystals were filtered and then dried. Hereby, 6.30 g of the compound (1-e-69) was prepared (yield: 92%).

LC-MS: m/z 629.18[M+]

The compounds of Examples 70 to 75, which are illustrated below, were synthesized by the same reactions as in Example 69 and, as needed, a method confirming to publicly known methods.

[Chem. 105]
Example 70
(1-e-70)
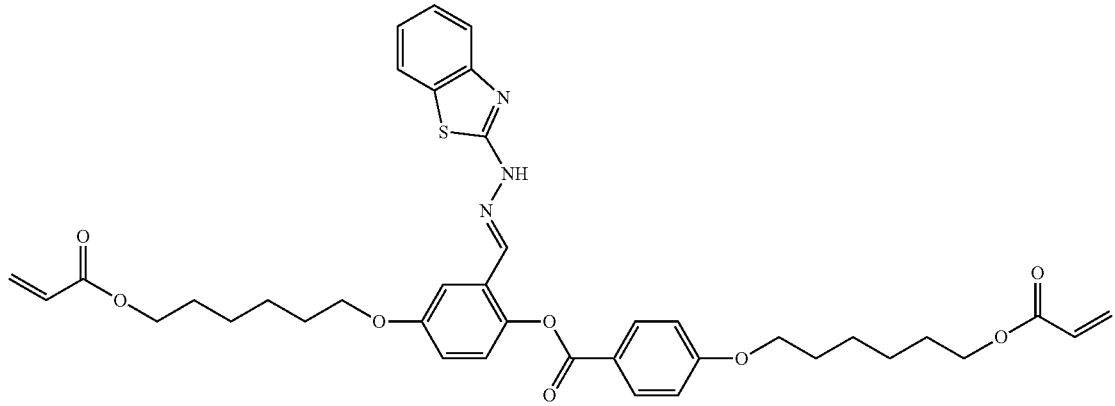
Example 71
(1-eh-71)
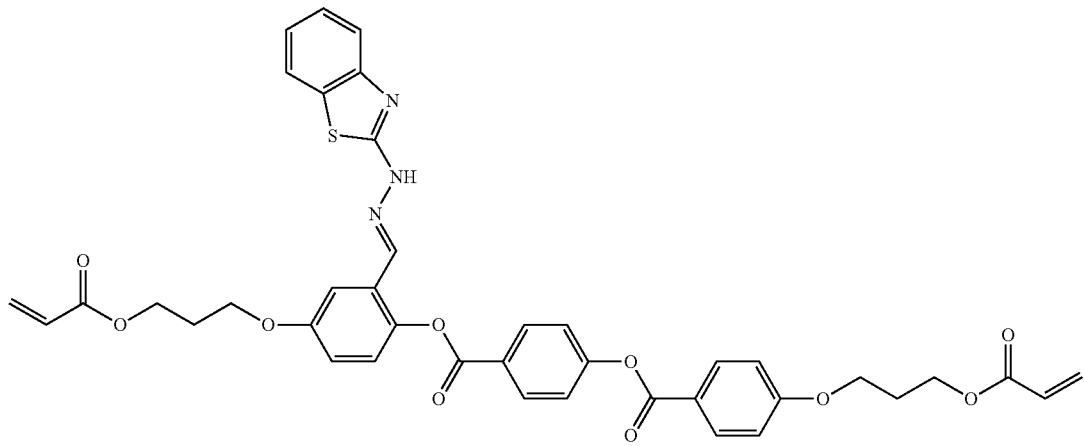
Example 72
(1-eh-72)
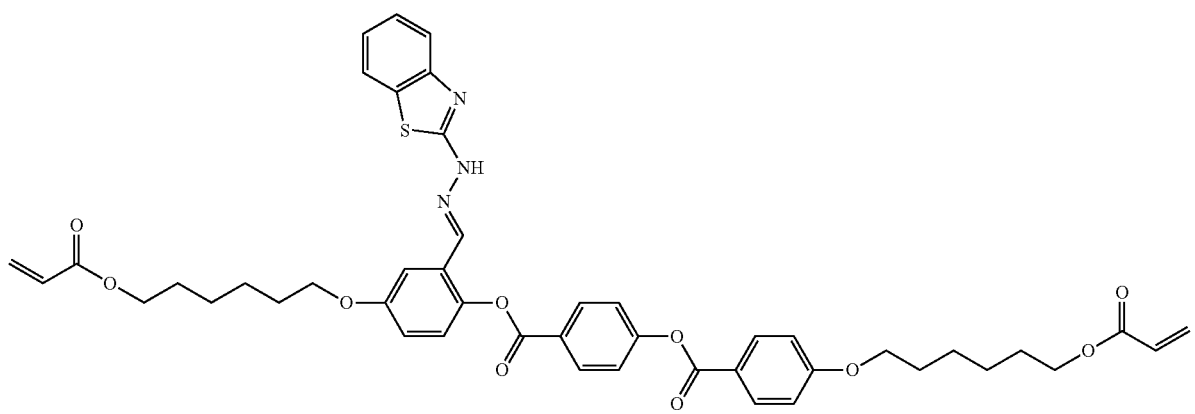

[Chem. 106]
Example 73
(1-e-73)
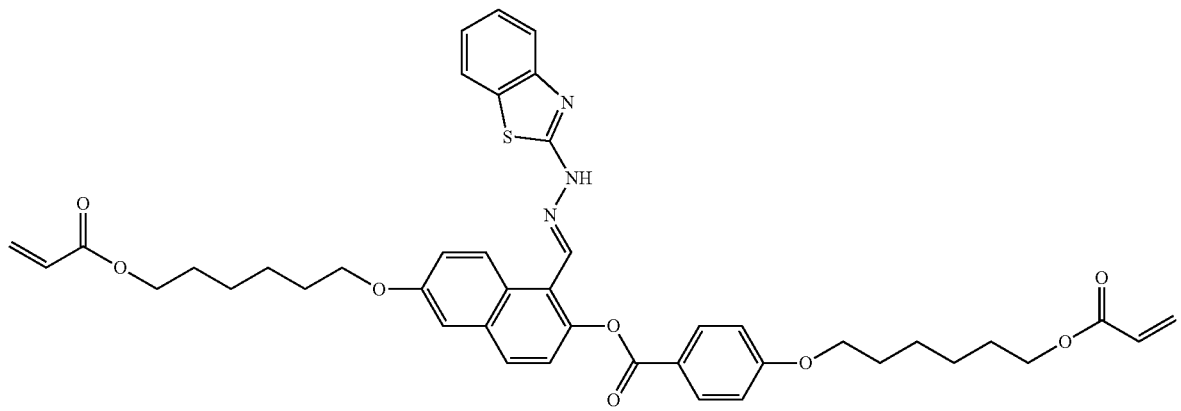
Example 74
(1-eh-74)
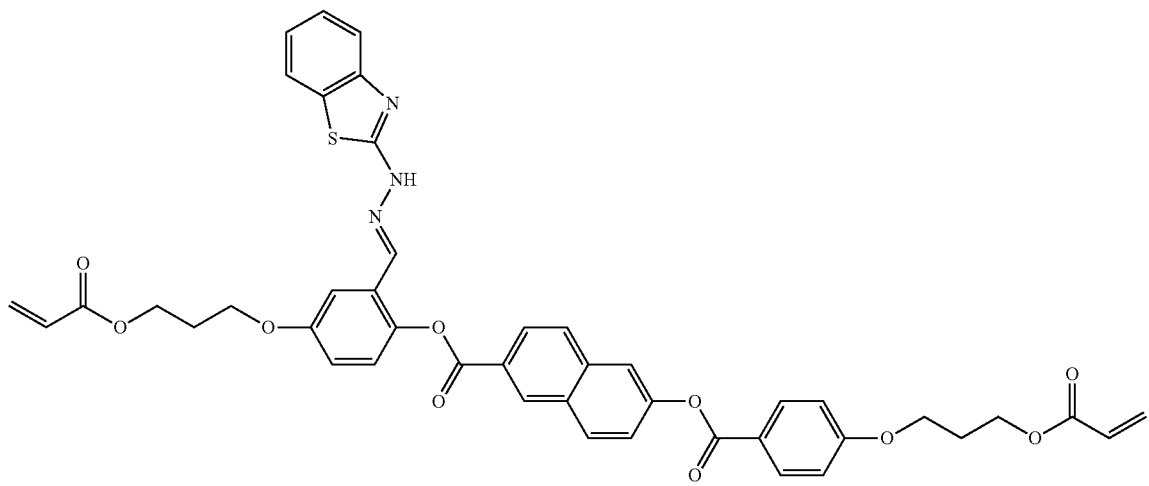
Example 75
(1-eh-75)
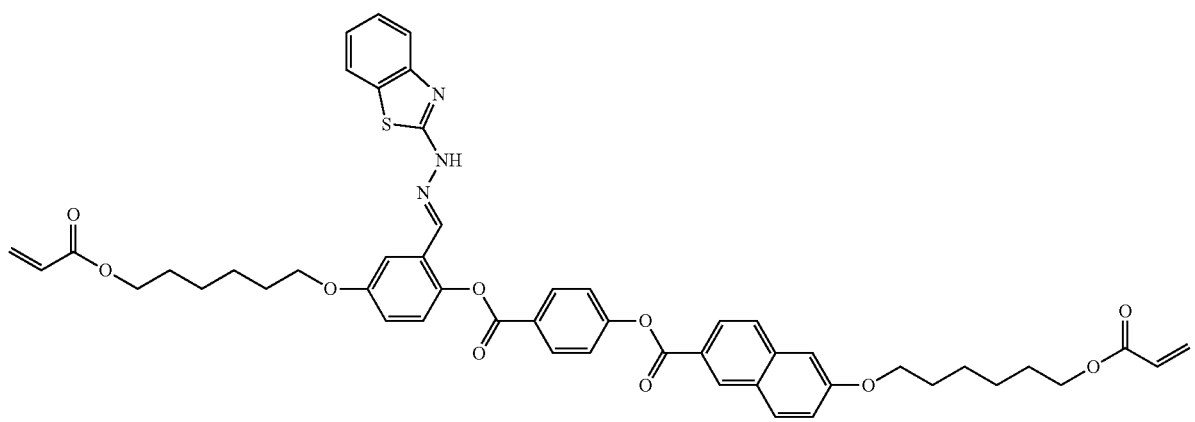
The compounds of Examples 76 to 78, which are illustrated below, were synthesized by the same reactions as in the preparation of the compound (1-c-1) in Example 1 and, as needed, a method confirming to publicly known methods.

[Chem. 107]
Example 76 (1-r-76)
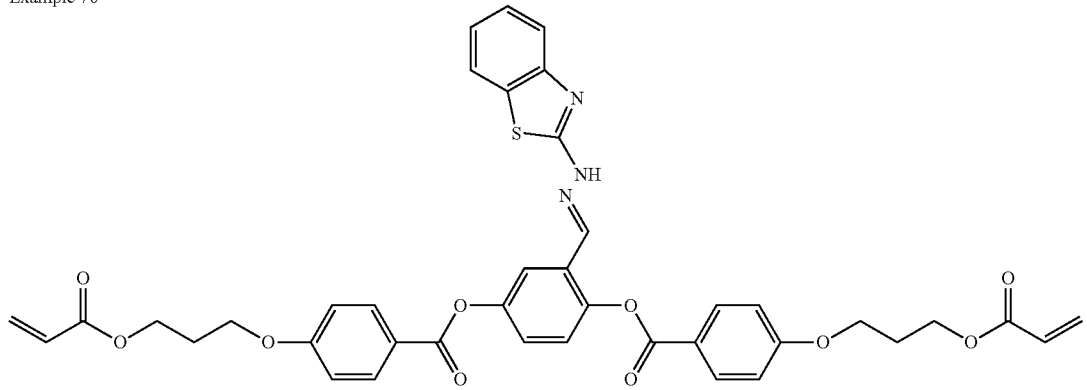
Example 77 (1-r-77)
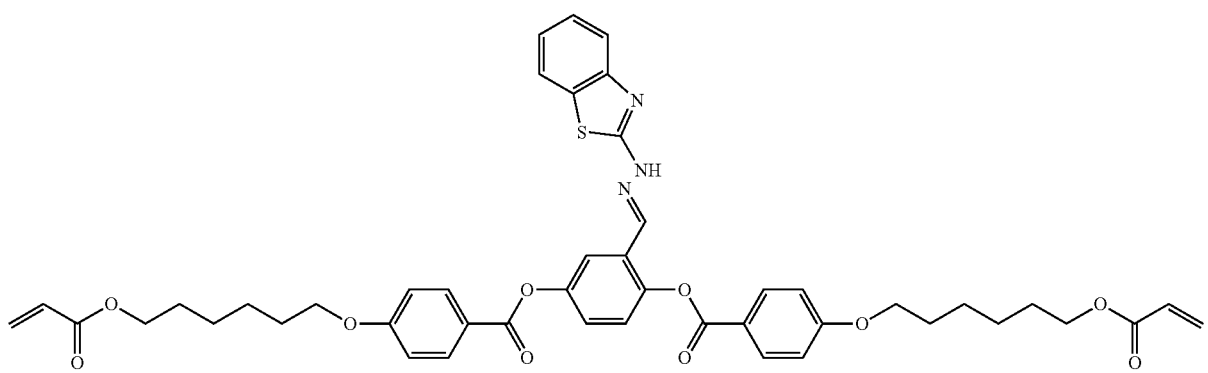
Example 78 (1-r-78)
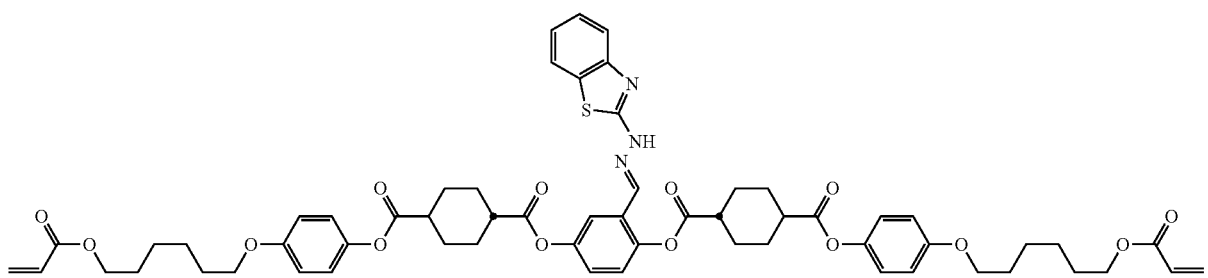
Example 79
The compound represented by Formula (1-ch-79) below was prepared as in Example 1.
[Chem. 108]
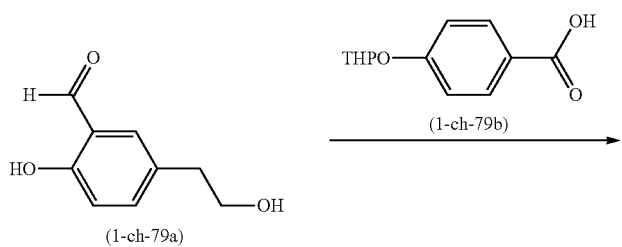

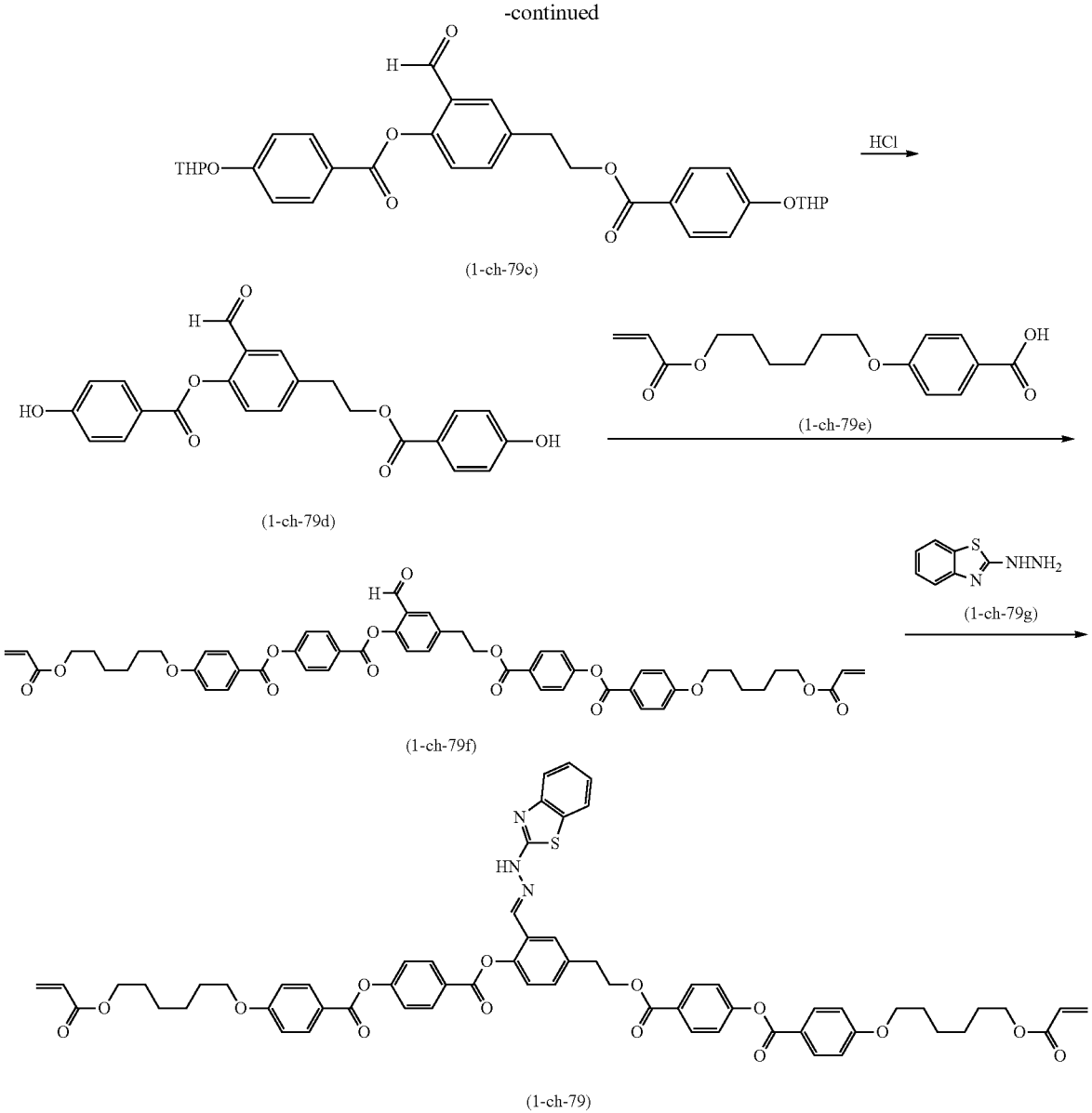
Dislocation temperature: C 145 N 207 I
$^1$H NMR (CDCl$_3$) δ: 1.47-1.87 (m, 16H), 3.17 (t, 2H), 4.05 (t, 2H), 4.06 (t, 2H), 4.18 (t, 2H), 4.19 (t, 2H), 4.62 (t, 2H), 5.82 (dd, 1H), 5.82 (dd, 1H), 6.13 (dd, 1H), 6.13 (dd, 1H), 6.41 (dd, 1H), 6.41 (dd, 1H), 6.96 (m, 4H), 7.09 (m, 1H), 7.19-7.38 (m, 7H), 7.45 (d, 1H), 7.61 (d, 1H), 7.96 (m, 1H), 8.05-8.18 (m, 7H), 8.22 (d, 2H) ppm.
Example 80
The compound represented by Formula (1-c-80) below was prepared by the following method.
[Chem. 109]
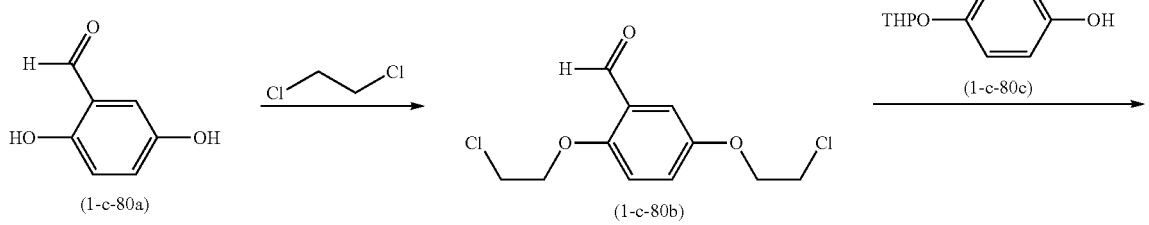

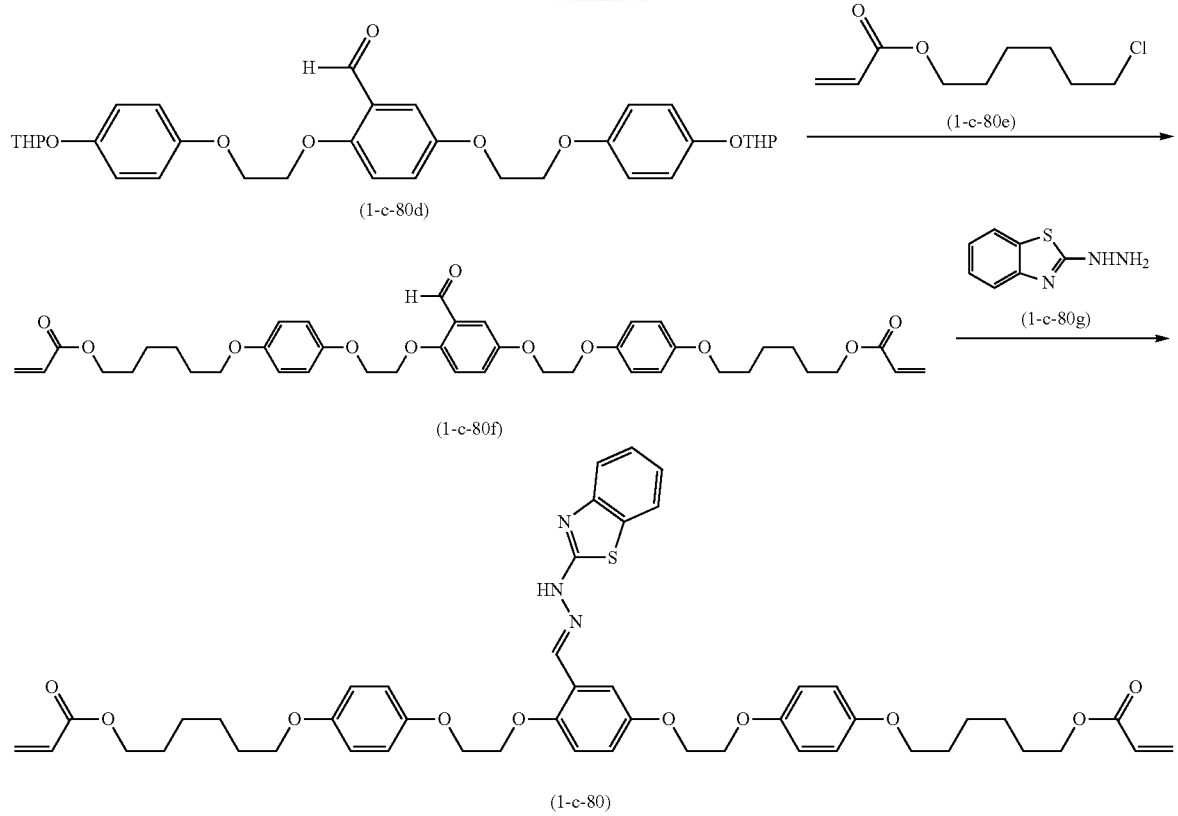
Dislocation temperature: C 141 I
$^1$H NMR (CDCl$_3$) δ: 1.41-1.50 (m, 8H), 1.64-1.81 (m, 8H), 3.88 (t, 2H), 3.91 (t, 2H), 4.16 (m, 6H), 4.26-4.35 (m, 6H), 5.81 (dd, 1H), 5.81 (dd, 1H), 6.12 (dd, 1H), 6.12 (dd, 1H), 6.40 (dd, 1H), 6.40 (dd, 1H), 6.79-6.98 (m, 10H), 7.13 (t, 1H), 7.32 (t, 1H), 7.58 (m, 2H), 7.65 (d, 1H), 8.22 (s, 1H) ppm.
Example 81
The compound represented by Formula (1-cmn-81) below was prepared as in Example 1.
[Chem. 110]
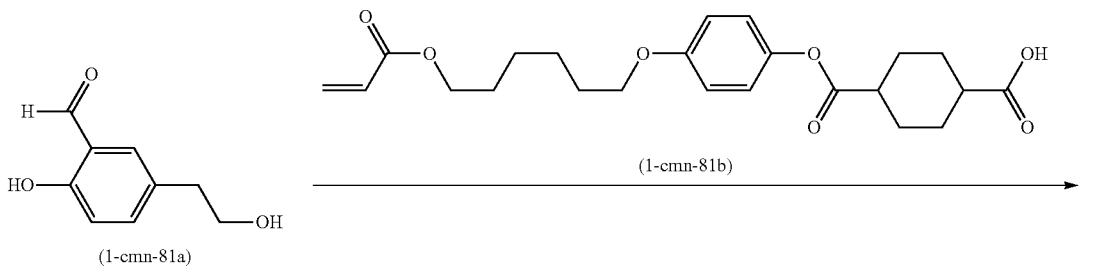
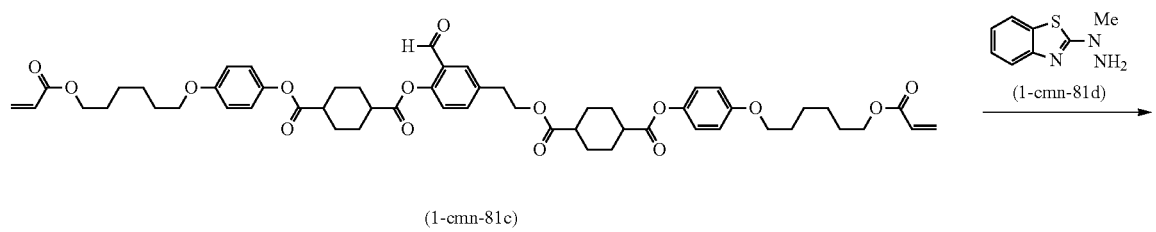

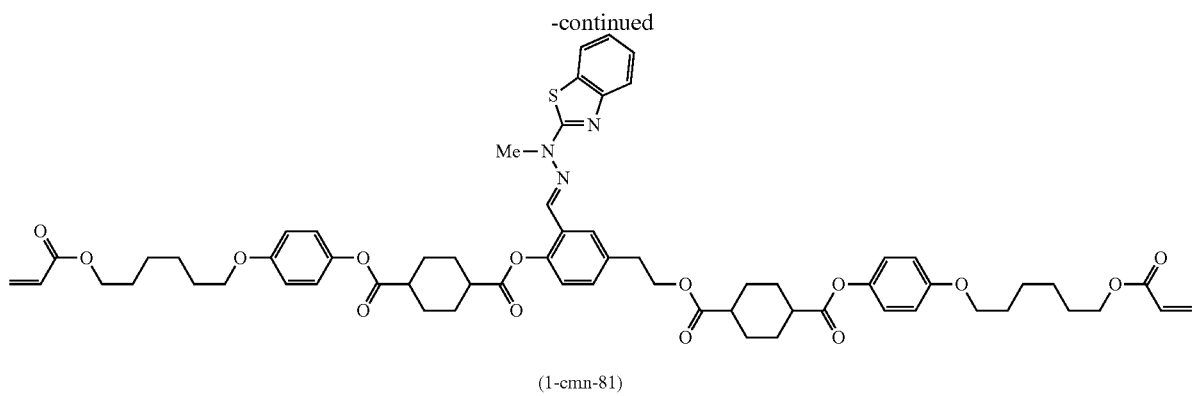

(1-cmn-81)

Dislocation temperature: C 113-123 (N 113) I
$^1$H NMR (CDCl$_3$) δ: 1.40-1.82 (m, 24H), 2.09-2.17 (m, 4H), 2.33 (m, 5H), 2.47 (m, 1H), 2.61 (m, 1H), 2.71 (m, 1H), 3.03 (t, 2H), 3.74 (s, 3H), 3.93 (t, 2H), 3.94 (t, 2H), 4.17 (t, 2H), 4.17 (t, 2H), 4.37 (t, 2H), 5.82 (m, 2H), 6.12 (m, 2H), 6.40 (m, 2H), 6.83-6.90 (m, 6H), 6.98 (d, 2H), 7.04 (d, 1H), 7.16 (t, 1H), 7.25 (m, 1H), 7.34 (t, 1H), 7.66-7.71 (m, 3H), 7.91 (d, 1H) ppm.

Example 82

The compound represented by Formula (1-cmn-82) below was prepared as in Example 1.

[Chem. 111]

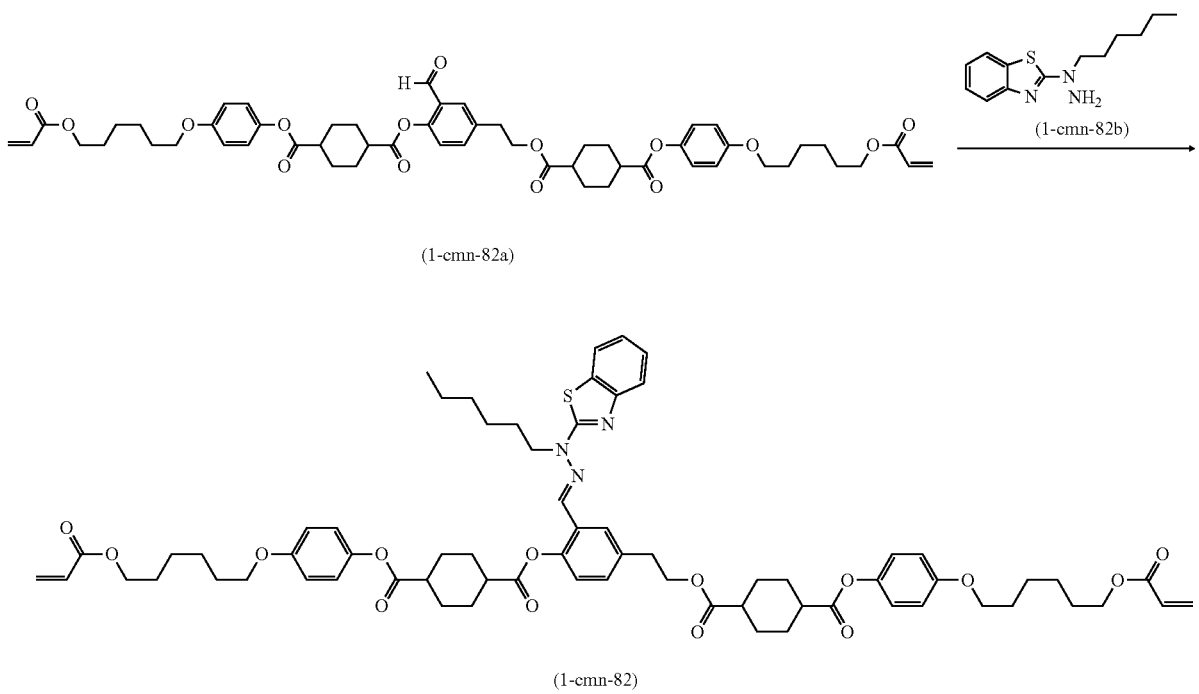

(1-cmn-82)

Dislocation temperature: C 134-139 (N 102) I
$^1$H NMR (CDCl$_3$) δ: 0.89 (t, 3H), 1.32-1.56 (m, 18H), 1.70-1.81 (m, 14H), 2.09-2.17 (m, 4H), 2.33 (m, 5H), 2.46 (m, 1H), 2.59 (m, 1H), 2.69 (m, 1H), 3.03 (t, 2H), 3.93 (t, 2H), 3.94 (t, 2H), 4.17 (t, 2H), 4.17 (t, 2H), 4.30 (t, 2H), 4.37 (t, 2H), 5.81 (dd, 1H), 5.82 (dd, 1H), 6.12 (dd, 1H), 6.13 (dd, 1H), 6.40 (dd, 1H), 6.40 (dd, 1H), 6.83-6.89 (m, 6H), 6.98 (d, 2H), 7.05 (d, 1H), 7.15 (t, 1H), 7.24 (dd, 1H), 7.33 (t, 1H), 7.68 (dd, 2H), 7.71 (s, 1H), 7.93 (d, 1H) ppm.

Example 83

The compound represented by Formula (1-cn-83) was prepared as in Example 1.

[Chem. 112]
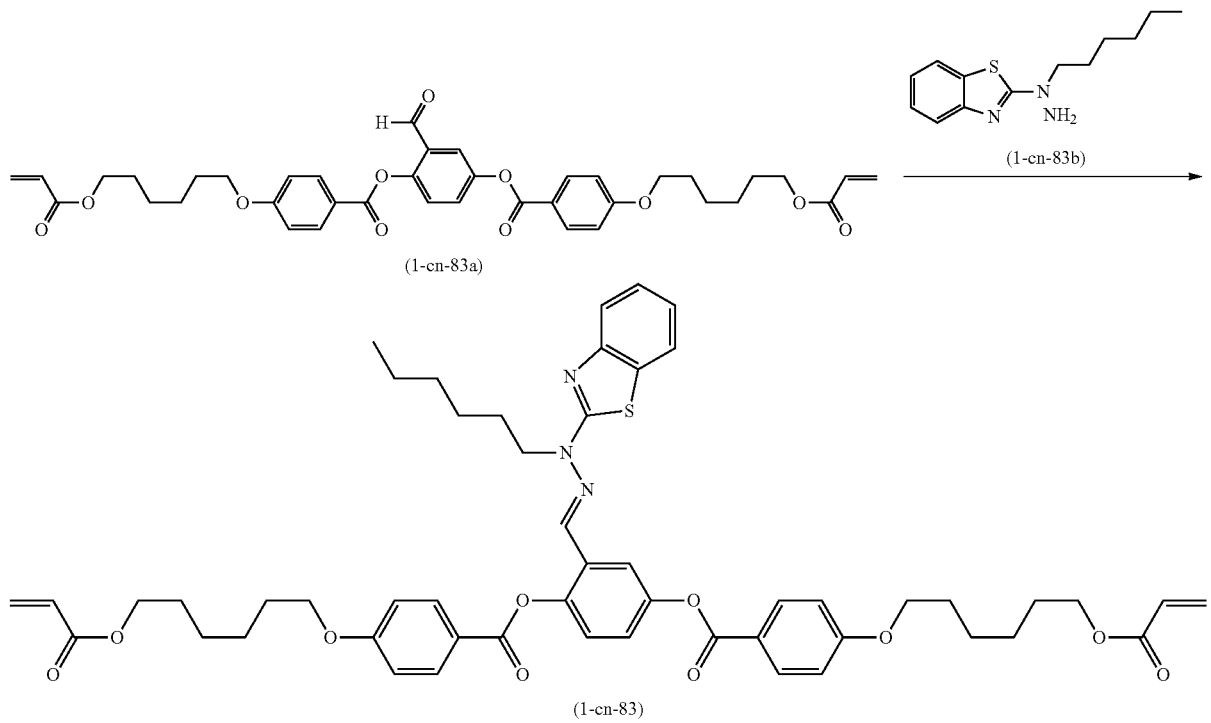
Dislocation temperature: C 60-65 I
$^1$H NMR (CDCl$_3$) δ: 0.78 (t, 3H), 1.11-1.18 (m, 6H), 1.42-1.59 (m, 10H), 1.68-1.77 (m, 6H), 1.86 (quin, 2H), 3.17 (t, 2H), 3.86 (t, 2H), 4.06 (t, 2H), 4.15-4.21 (m, 6H), 4.58 (t, 2H), 5.82 (dd, 1H), 5.82 (dd, 1H), 6.13 (dd, 1H), 6.13 (dd, 1H), 6.40 (dd, 1H), 6.40 (dd, 1H), 6.84 (d, 2H), 7.00 (d, 2H), 7.14 (t, 1H), 7.18 (d, 1H), 7.29-7.35 (m, 2H), 7.63 (m, 2H), 7.76 (s, 1H), 8.00-8.04 (m, 3H), 8.18 (d, 2H) ppm.
Example 84
The compound represented by Formula (1-hk-84) below was prepared by the following method.
[Chem. 113]
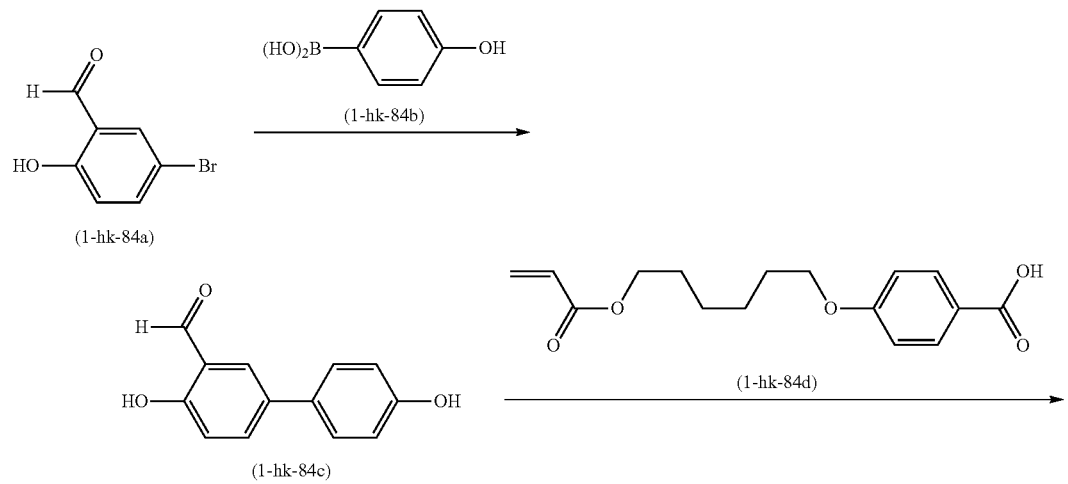

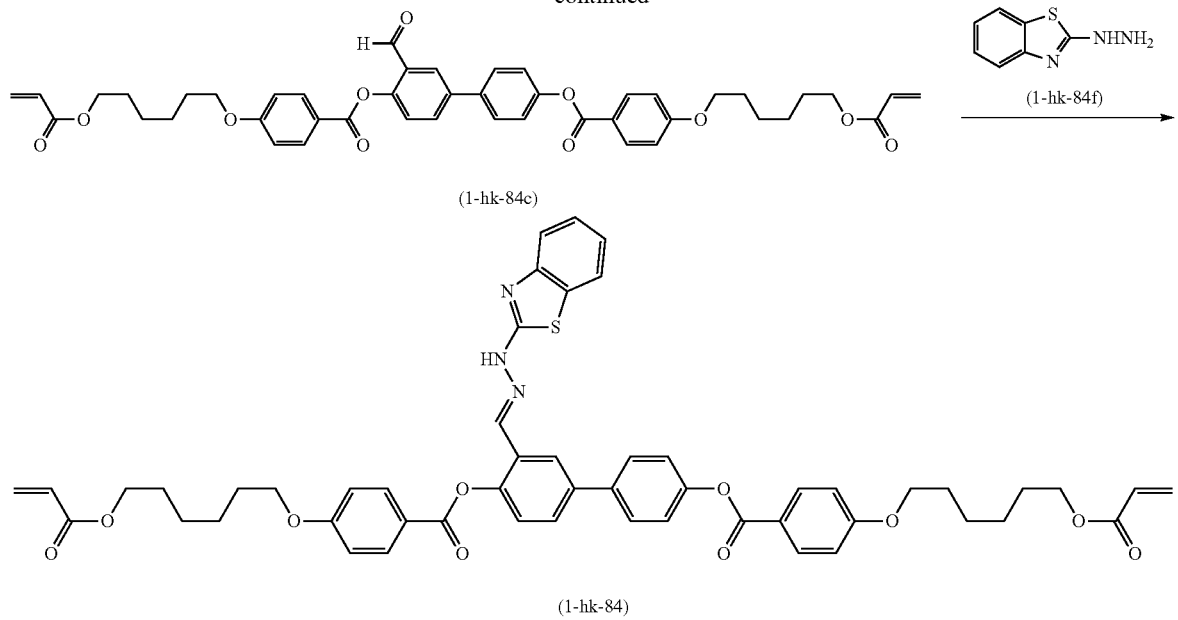

In a nitrogen atmosphere, 5.0 g of the compound represented by Formula (1-hk-84a), 3.4 g of the compound represented by Formula (1-hk-84b), 5.2 of potassium carbonate, 20 mL of ethanol, and 0.6 g of tetrakis(triphenylphosphine)palladium(0) were added to a reaction container, and the resulting mixture was heated to reflux. After a common post-treatment had been performed, purification was performed by column chromatography (silica gel). Hereby, 3.7 g of the compound represented by Formula (1-hk-84c) was prepared. The rest of the production method was the same as in Example 1. Hereby, the compound represented by Formula (1-hk-84) was prepared.

Phase-transition temperature (heating process): C 180 N>220 I $^1$H NMR (CDCl$_3$): 1.42-1.60 (m, 8H), 1.68-1.91 (m, 8H), 3.95 (m, 2H), 4.07 (t, 2H), 4.16-4.22 (m, 4H), 5.83 (dd, 2H), 6.09-6.18 (m, 2H), 6.42 (dd, 2H), 6.82 (br, 2H), 7.00 (d, 2H), 7.09 (br, 1H), 7.21 (br, 1H), 7.33 (m, 3H), 7.45 (br, 1H), 7.62 (m, 2H), 7.70 (d, 2H), 8.02 (br, 2H), 8.19 (d, 3H), 8.25 (br, 1H) ppm.

Example 85

The compound represented by Formula (1-hk-85) below was prepared as in Example 84.

[Chem. 114]

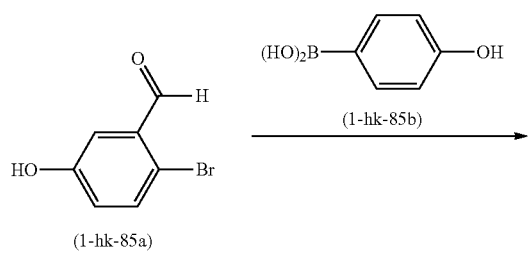

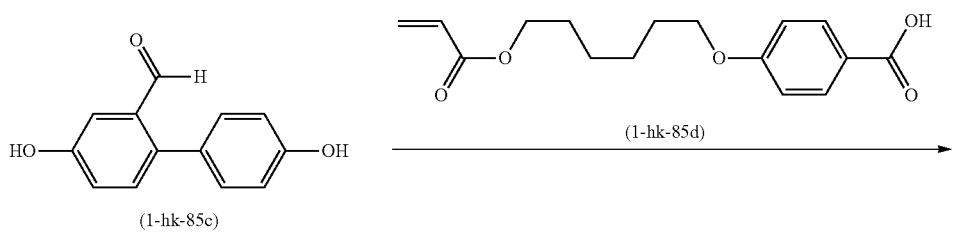

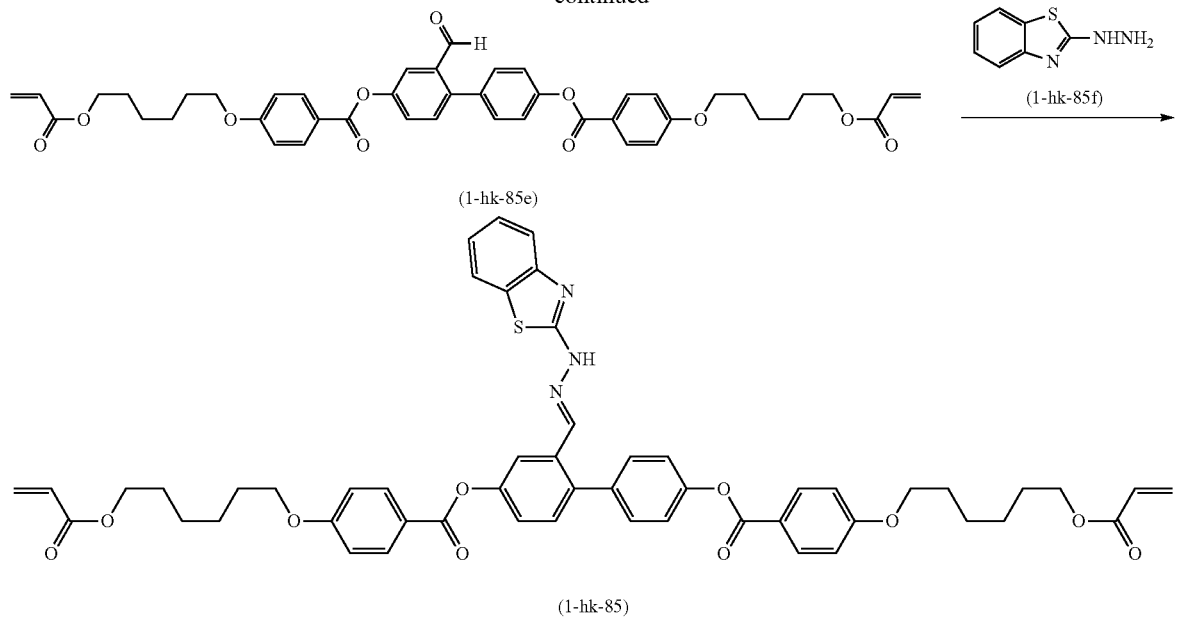
Phase-transition temperature (heating process): C 107 N 217 I
$^1$H NMR (CDCl$_3$): 1.52 (m, 8H), 1.74 (quin, 4H), 1.86 (quin, 4H), 4.07 (td, 4H), 4.20 (td, 4H), 5.84 (d, 2H), 6.14 (dd, 2H), 6.42 (d, 2H), 6.99 (d, 4H), 7.11 (t, 1H), 7.21-7.40 (m, 8H), 7.62 (d, 1H), 7.93 (m, 2H), 8.19 (dd, 4H) ppm.
Example 86
The compound represented by Formula (1-hk-86) below was prepared as in Example 84.
[Chem. 115]
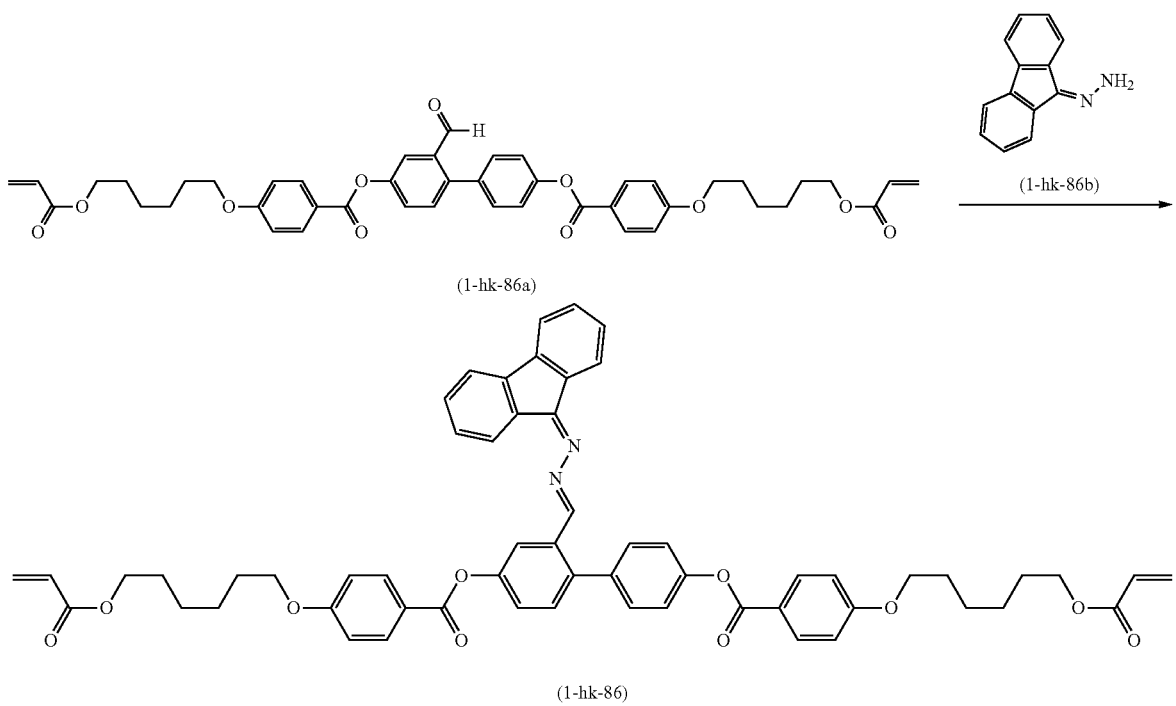

Phase-transition temperature (heating process): C 113 N 171 I $^1$H NMR (CDCl$_3$): 1.48-1.59 (m, 8H), 1.74 (m, 4H), 1.85 (m, 4H), 4.07 (q, 4H), 4.19 (td, 4H), 5.84 (d, 2H), 6.14 (ddd, 2H), 6.42 (dt, 2H), 7.00 (q, 4H), 7.30 (m, 4H), 7.39-7.46 (m, 5H), 7.51 (d, 1H), 7.61 (dd, 2H), 7.85 (d, 1H), 6.17 (d, 2H), 8.22-8.25 (m, 3H), 8.39 (d, 1H), 8.57 (s, 1H) ppm.

Example 87

The compound represented by Formula (1-k-87) below was prepared by the following method.

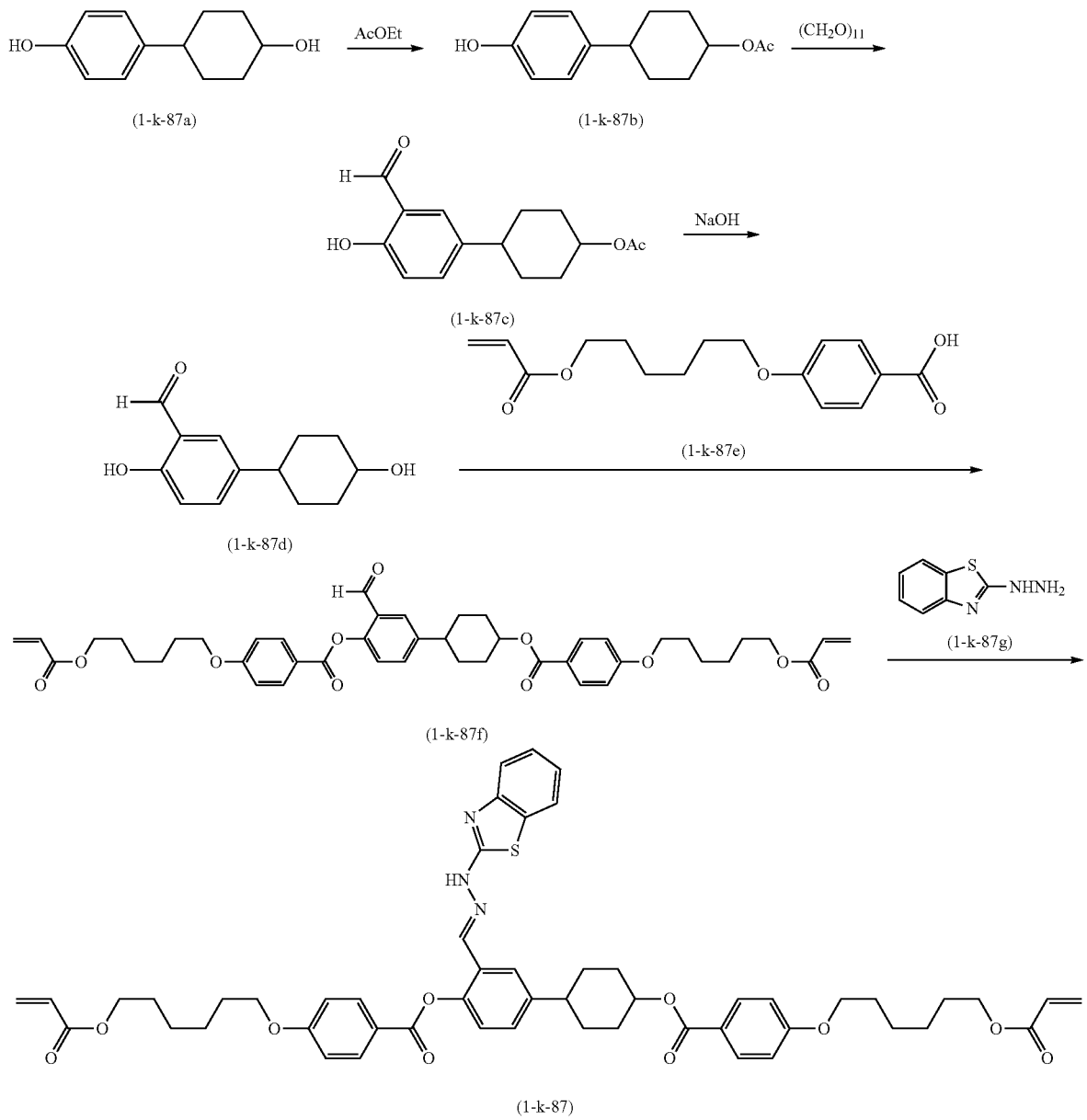

To a reaction container, 5.0 g of the compound represented by Formula (1-k-87a), 0.1 g of p-toluenesulfonic acid monohydrate, and 50 mL of ethyl acetate were added, and the resulting mixture was heated to reflux. After a common post-treatment had been performed, purification was performed by column chromatography (silica gel). Hereby, 5.5 g of the compound represented by Formula (1-k-87b) was prepared.

To a reaction container, 5.5 g of the compound represented by Formula (1-k-87b), 20.0 g of para-formaldehyde, 6.0 g of magnesium chloride, 20 mL of triethylamine, and 60 mL of acetonitrile were added, and the resulting mixture was heated to reflux. After a common post-treatment had been performed, purification was performed by column chromatography (silica gel). Hereby, 4.9 g of the compound represented by Formula (1-k-87c) was prepared.

To a reaction container, 4.9 g of the compound represented by Formula (1-k-87c), 30 mL of methanol, and an aqueous sodium hydroxide solution were added, and the resulting mixture was heated to reflux. After a common post-treatment had been performed, purification was performed by column chromatography (silica gel). Hereby, 3.7 g of the compound represented by Formula (1-k-87d) was prepared. The rest of the production method was the same as in Example 1. Hereby, the compound represented by Formula (1-k-87) was prepared.

Phase-transition temperature (heating process): C 60-80 N 206 I $^1$H NMR (CDCl$_3$): 1.44-1.60 (m, 9H), 1.66-1.90 (m, 13H), 2.07 (m, 2H), 2.29 (m, 2H), 2.68 (m, 1H), 4.03 (td, 4H), 4.19 (td, 4H), 5.07 (m, 1H), 5.84 (dt, 2H), 6.13 (dd, 2H), 6.42 (dd, 2H), 6.86 (d, 2H), 6.93 (d, 2H), 7.06-7.22 (m, 3H), 7.30 (dd, 1H), 7.45 (d, 1H), 7.63 (d, 1H), 7.90 (s, 1H), 8.04 (m, 4H), 8.11 (s, 1H) ppm.

Example 88

The compound represented by Formula (1-cm-88) below was prepared by the following method.

[Chem. 117]

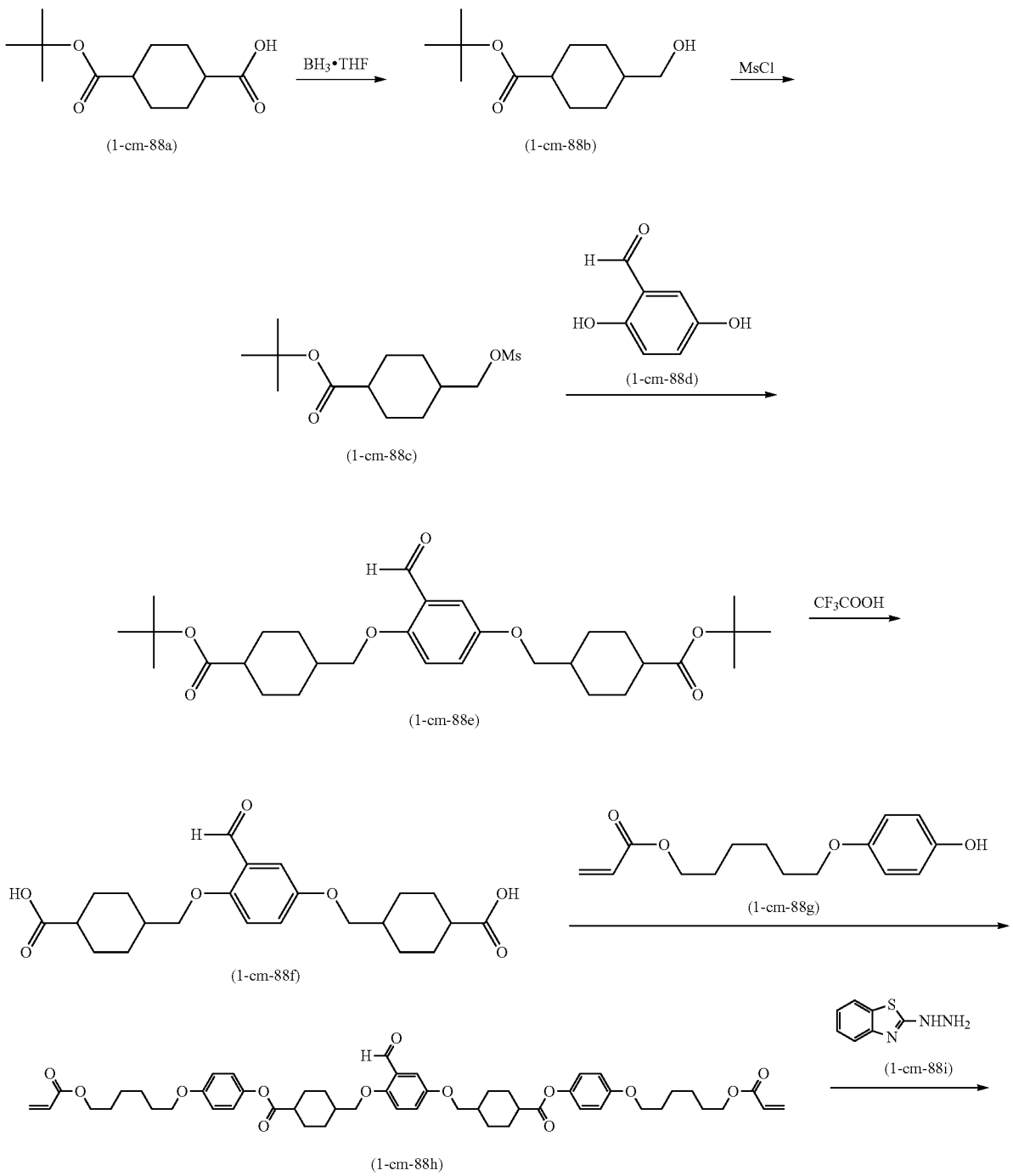

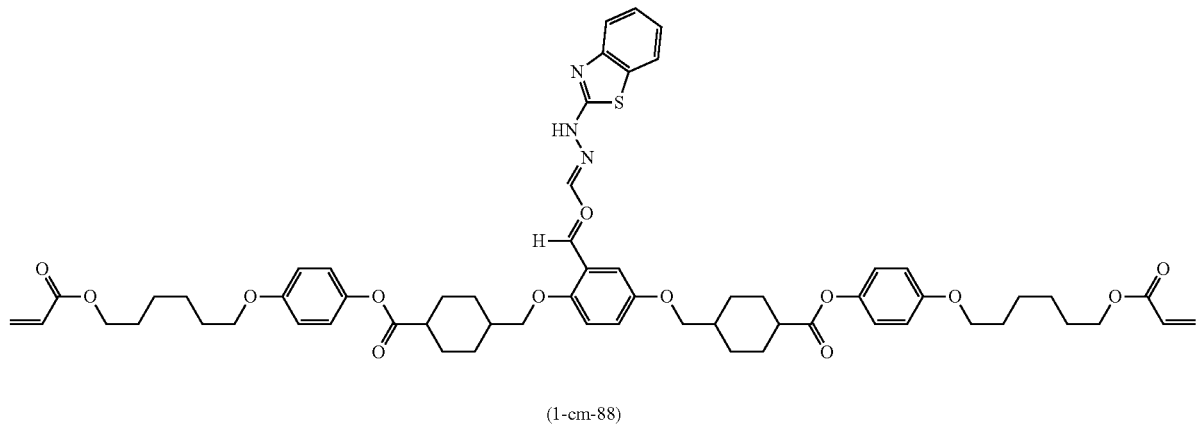

(1-cm-88)

In a nitrogen atmosphere, 17.7 g of the compound represented by Formula (1-cm-88a) and 100 mL of tetrahydrofuran were added to a reaction container. While the resulting mixture was cooled with ice, 103 mL of 0.9-mol/L borane-tetrahydrofuran complex was added dropwise to the mixture. Subsequently, the mixture was stirred for 1 hour. After 5%-hydrochloric acid had been added dropwise to the mixture, extraction with ethyl acetate and cleaning with a saline solution were performed. Then, drying with sodium sulfate was performed, and the solvent was distilled away. Hereby, 14.9 g of the compound represented by Formula (1-cm-88b) was prepared.

In a nitrogen atmosphere, 14.9 g of the compound represented by Formula (1-cm-88b), 7.2 g of pyridine, and 150 mL of dichloromethane were added to a reaction container. While the resulting mixture was cooled with ice, 8.8 g of methanesulfonyl chloride was added dropwise to the mixture. The mixture was then stirred at room temperature for 3 hours. The mixture was mixed with water, and cleaning with 5%-hydrochloric acid and a saline solution in this order was subsequently performed. Then, purification was performed by column chromatography (silica gel, hexane/ethyl acetate) and recrystallization (acetone/hexane). Hereby, 16.3 g of the compound represented by Formula (1-cm-88c) was prepared.

In a nitrogen atmosphere, 2.5 g of the compound represented by Formula (1-cm-88d), 10.6 g of the compound represented by Formula (1-cm-88c), 7.5 g of potassium carbonate, and 70 mL of N,N-dimethylformamide were added to a reaction container. The resulting mixture was stirred at 90° C. for 3 days while being heated. The mixture was then mixed with water, and subsequently extraction with toluene and cleaning with a saline solution were performed. Then, purification was performed by column chromatography (silica gel, toluene) and recrystallization (acetone/methanol). Hereby, 7.7 g of the compound represented by Formula (1-cm-88e) was prepared.

To a reaction container, 7.7 g of the compound represented by Formula (1-cm-88e), 150 mL of dichloromethane, and 100 mL of trifluoroacetic acid were added, and the resulting mixture was stirred. After the solvent had been distilled away, the resulting solid was cleaned with water and then dried. Hereby, 5.5 g of the compound represented by Formula (1-cm-88f) was prepared.

In a nitrogen atmosphere, 5.5 g of the compound represented by Formula (1-cm-88f), 6.9 g of the compound represented by Formula (1-cm-88g), 0.8 g of N,N-dimethylaminopyridine, and 200 mL of dichloromethane were added to a reaction container. While the resulting mixture was cooled with ice, 4.1 g of diisopropylcarbodiimide was added dropwise to the mixture. Subsequently, the mixture was stirred at room temperature for 10 hours. After the resulting precipitate had been removed by filtration, the filtrate was cleaned with 1%-hydrochloric acid, water, and a saline solution in this order. After recrystallization (dichloromethane/methanol) had been performed, purification was performed by column chromatography (silica gel, dichloromethane) and recrystallization (dichloromethane/methanol). Hereby, 8.4 g of the compound represented by Formula (1-cm-88h) was prepared. The rest of the production method was the same as in Example 1. Hereby, the compound represented by Formula (1-cm-88) was prepared.

Dislocation temperature (rate of temperature rise: 5° C./min): C 90-110 N 182-187 I $^1$H NMR (CDCl$_3$) δ: 1.07 (q, 2H), 1.24 (q, 2H), 1.47-1.90 (m, 24H), 2.09 (m, 4H), 2.22 (d, 2H), 2.39 (t, 1H), 2.53 (t, 1H), 3.74 (d, 2H), 3.85 (d, 2H), 3.94 (td, 4H), 4.17 (td, 4H), 5.82 (d, 2H), 6.13 (dd, 2H), 6.40 (d, 2H), 6.80-6.99 (m, 6H), 6.98 (d, 4H), 7.16 (t, 1H), 7.33 (t, 1H), 7.55 (m, 2H), 7.67 (d, 1H), 8.40 (s, 1H) ppm.

Example 89

The compound represented by Formula (1-cm-89) below was prepared as in Example 88.

[Chem. 118]

(1-cmn-89)

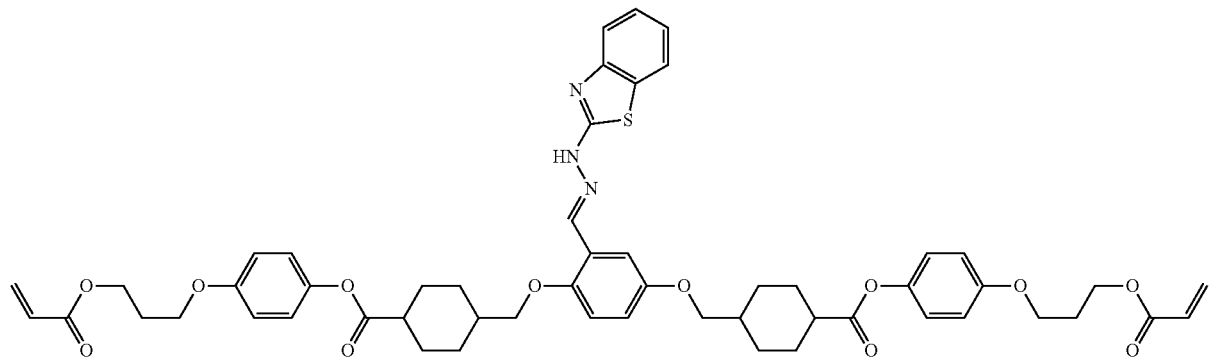

Dislocation temperature (rate of temperature rise: 5° C./min): C 155 N>220 I

1H NMR (CDCl$_3$) δ: 1.12 (q, 2H), 1.26 (q, 2H), 1.50 (q, 2H), 1.67 (qd, 2H), 1.91-2.27 (m, 14H), 2.43 (t, 1H), 2.56 (tt, 2H), 3.77 (d, 2H), 3.88 (d, 2H), 4.09 (t, 4H), 4.40 (t, 4H), 5.88 (d, 2H), 6.17 (ddd, 2H), 6.45 (d, 2H), 6.85 (d, 1H), 6.92 (m, 5H), 7.02 (d, 4H), 7.19 (t, 1H), 7.37 (t, 1H), 7.59 (m, 2H), 7.71 (d, 1H), 8.44 (s, 1H) ppm.

Example 90

The compound represented by Formula (1-cmn-90) below was prepared as in Example 88.

[Chem. 119]

(1-cmn-90)

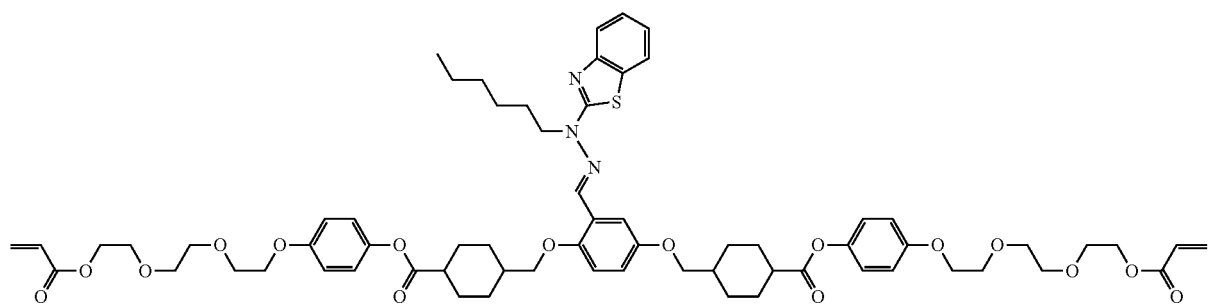

Dislocation temperature (temperature rise: 5° C./min): C 77 S 90 N 109 I $^1$H NMR (CDCl$_3$) δ: 0.89 (t, 3H), 1.20-1.35 (m, 10H), 1.61-1.69 (m, 6H), 1.78 (m, 2H), 1.90 (m, 2H), 2.07 (t, 4H), 2.23 (d, 4H), 2.50 (m, 2H), 3.69-3.76 (m, 12H), 3.83-3.87 (m, 8H), 4.11 (t, 4H), 4.32 (t, 6H), 5.82 (d, 2H), 6.15 (q, 2H), 6.42 (d, 2H), 6.83-6.98 (m, 10H), 7.13 (t, 1H), 7.32 (t, 1H), 7.53 (t, 1H), 7.66 (t, 2H), 8.13 (s, 1H) ppm.

Example 91

The compound represented by Formula (1-cmn-91) below was prepared as in Example 88.

[Chem. 120]

(1-cmn-91)

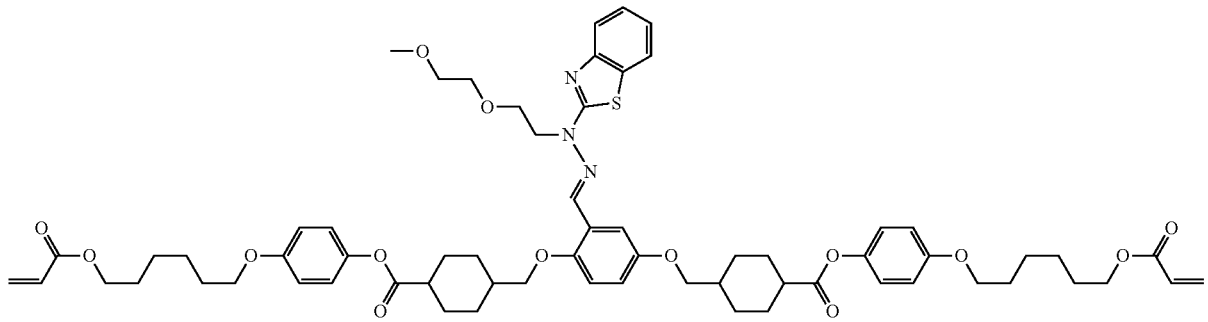

Dislocation temperature (temperature rise: 5° C./min): C 85 N 128 I $^1$H NMR (CDCl$_3$) δ: 1.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.89 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

Example 92

The compound represented by Formula (1-cmn-92) below was prepared as in Example 88.

[Chem. 121]

(1-cmn-92)

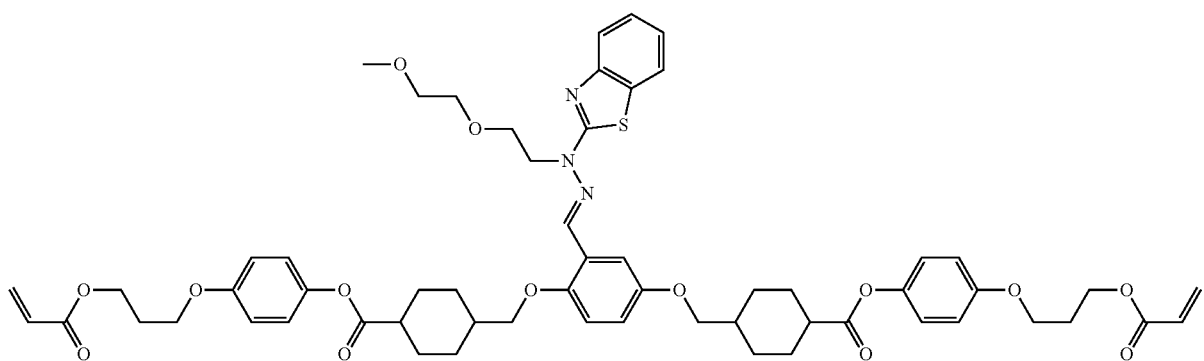

Dislocation temperature (temperature rise: 5° C./min): C 89-95 N 145 I $^1$H NMR (CDCl$_3$) δ: 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36 (t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H) ppm.

Example 93

The compound represented by Formula (1-cmn-93) below was prepared as in Example 88.

[Chem. 122]

(1-cmn-93)

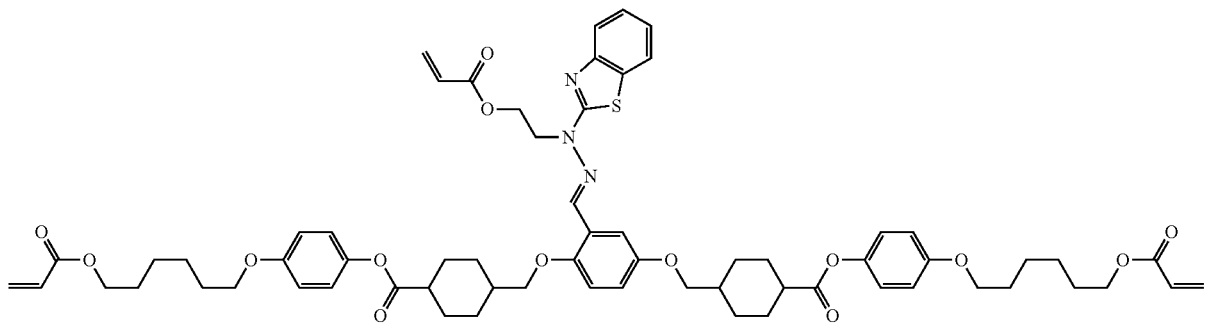

Dislocation temperature (rate of temperature rise: 5° C./min): C 122 N 142 I $^1$H NMR (CDCl$_3$) δ: 1.24 (m, 4H), 1.48 (m, 8H), 1.60-1.83 (m, 12H), 1.93 (m, 2H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.78 (dd, 1H), 5.82 (dd, 2H), 6.08 (dd, 1H), 6.12 (dd, 2H), 6.39 (dd, 1H), 6.40 (dd, 2H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1156[M+1]

Example 94

The compound represented by Formula (1-cmn-94) below was prepared as in Example 88.

[Chem. 123]

(1-cmn-94)

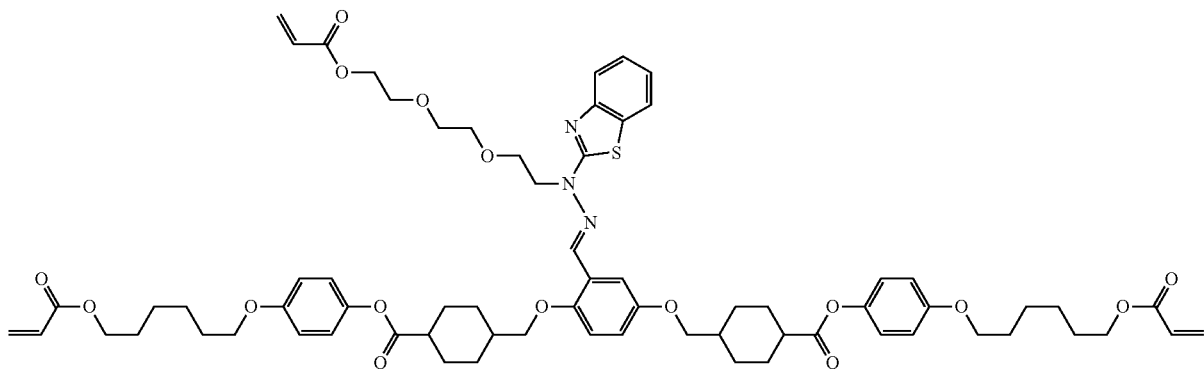

Dislocation temperature (rate of temperature rise: 5° C./min): C 71 N 115 I $^1$H NMR (CDCl$_3$) δ: 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244[M+1]

Example 95

The compound represented by Formula (1-f-95) below was prepared by the same method as described above.

(1-f-95)
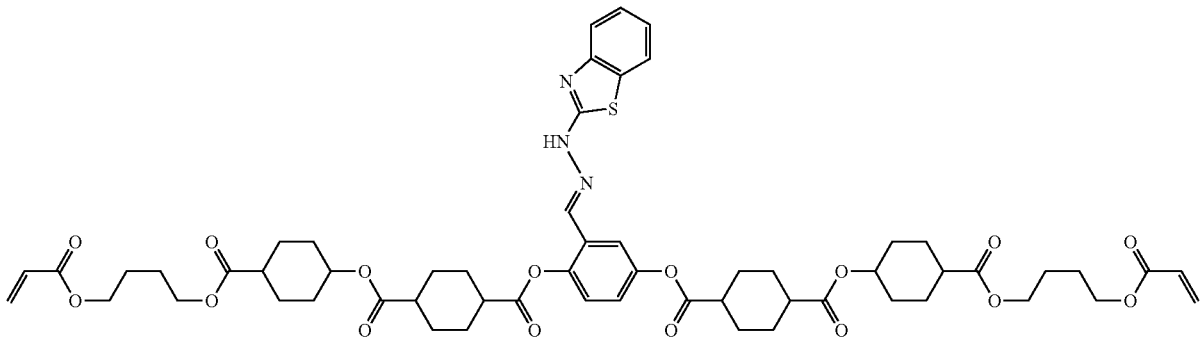
Dislocation temperature: C 99 N>220 I
LCMS: 1098[M+1]
Example 96
The compound represented by Formula (1-f-96) below was prepared by the same method as described above.
(1-f-96)
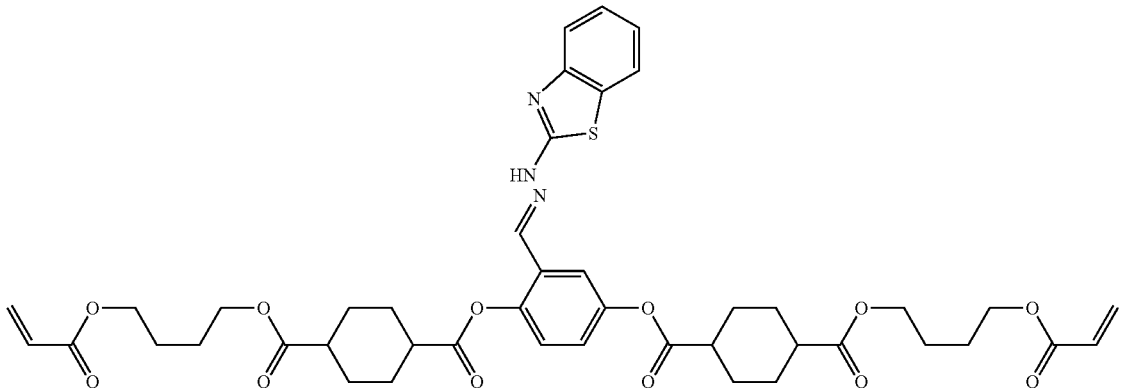
Dislocation temperature: C 125 N
LCMS: 846 [M+1]
The compounds represented by Formulae (1-f-97) to (1-cmn-108) below were prepared by the same method as described above.
(1-f-97)
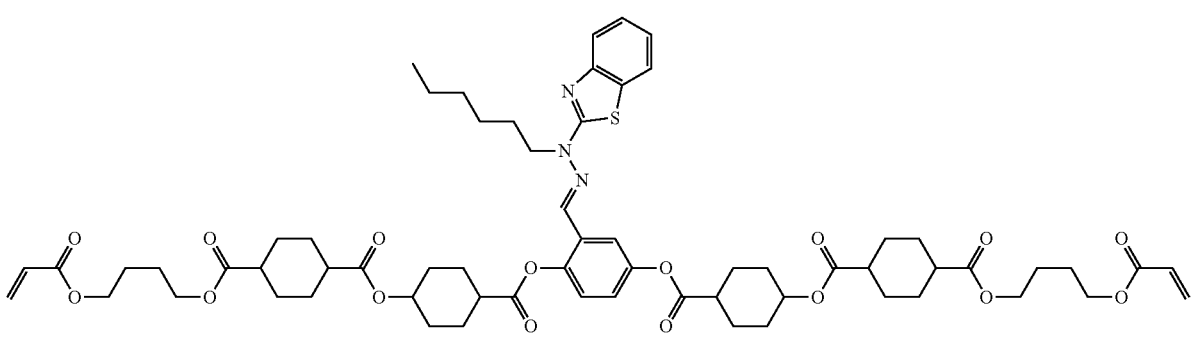

(1-f-98)
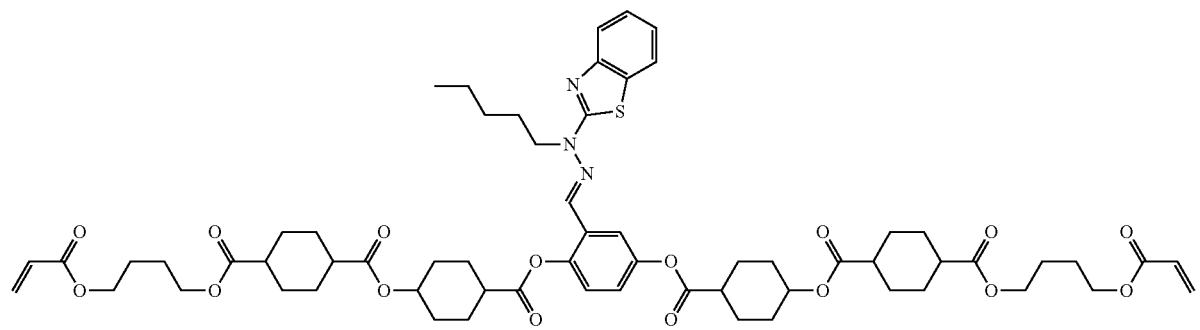
(1-f-99)
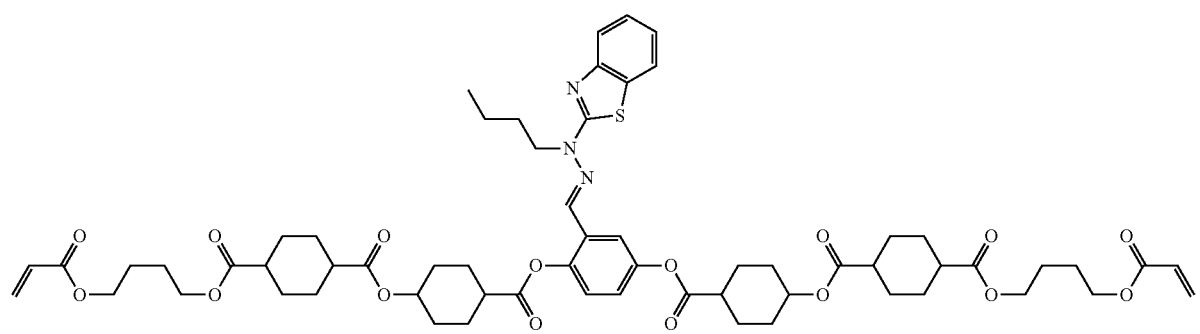
(1-f-100)
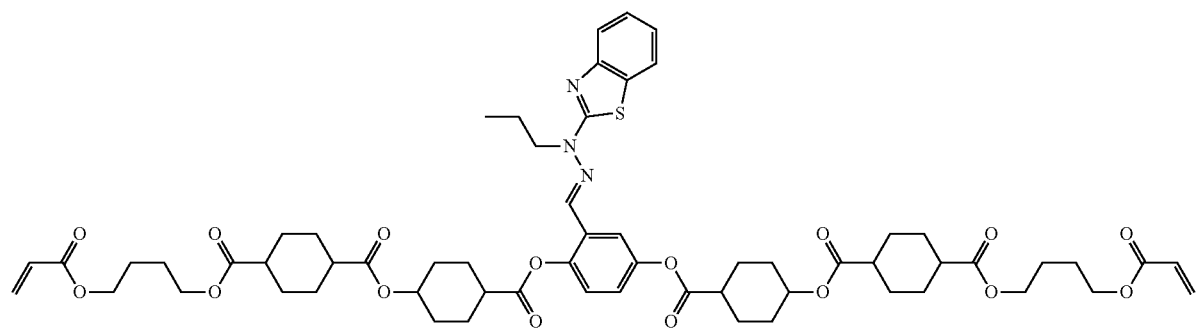
(1-f-101)
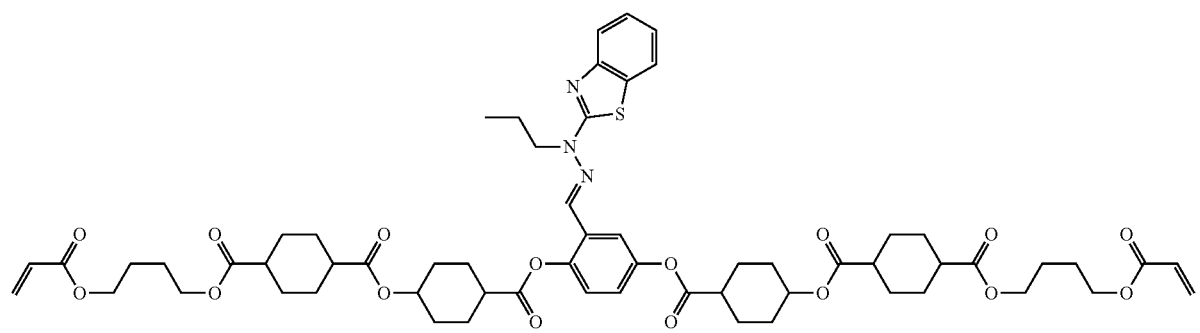

[Chem. 127]
(1-f-102)
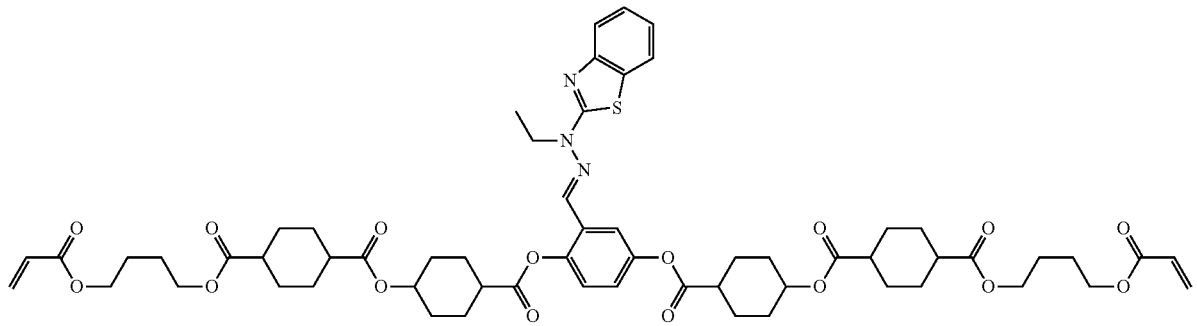
(1-f-103)
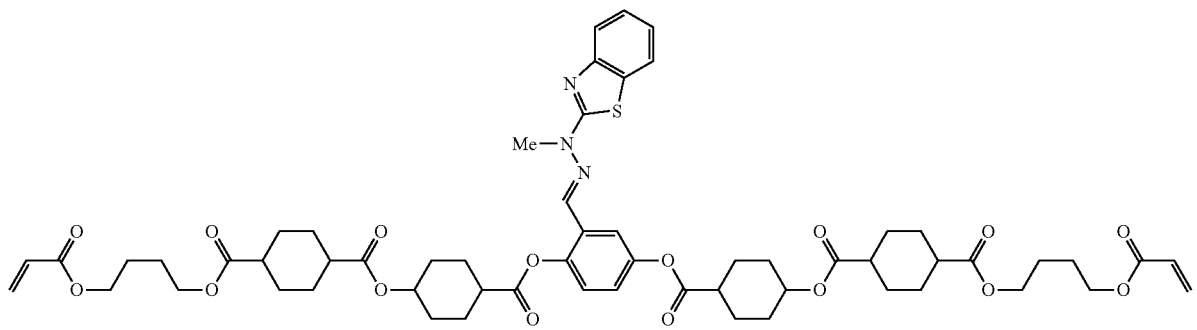
(1-fn-104)
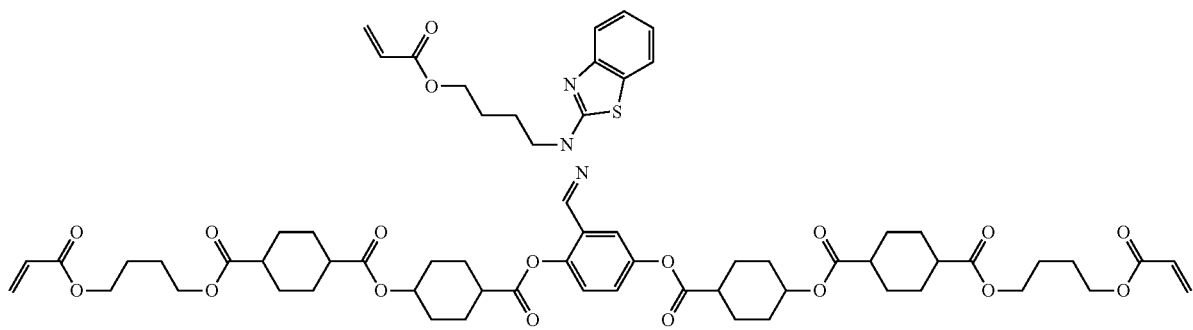
(1-cm-105)
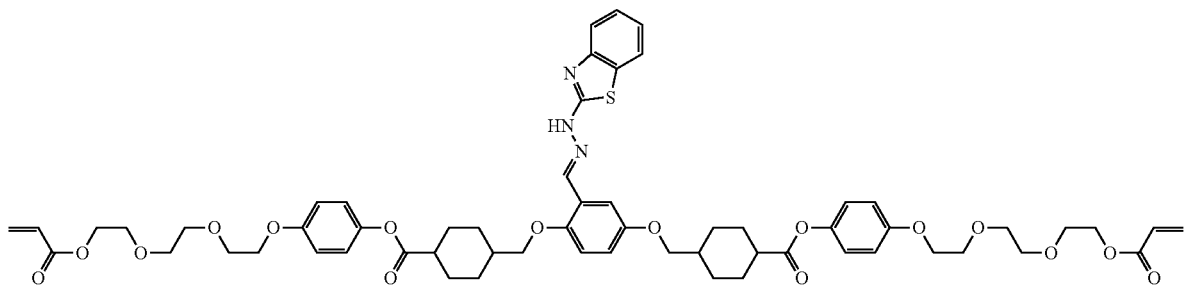

(1-cmn-106)

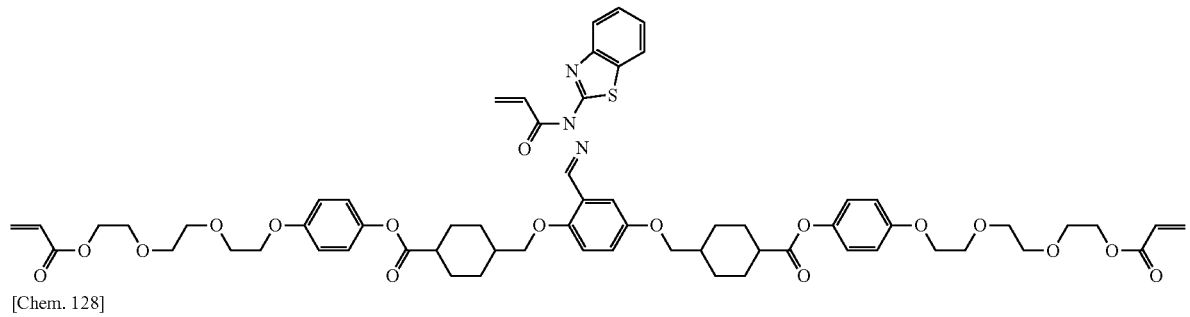

[Chem. 128]

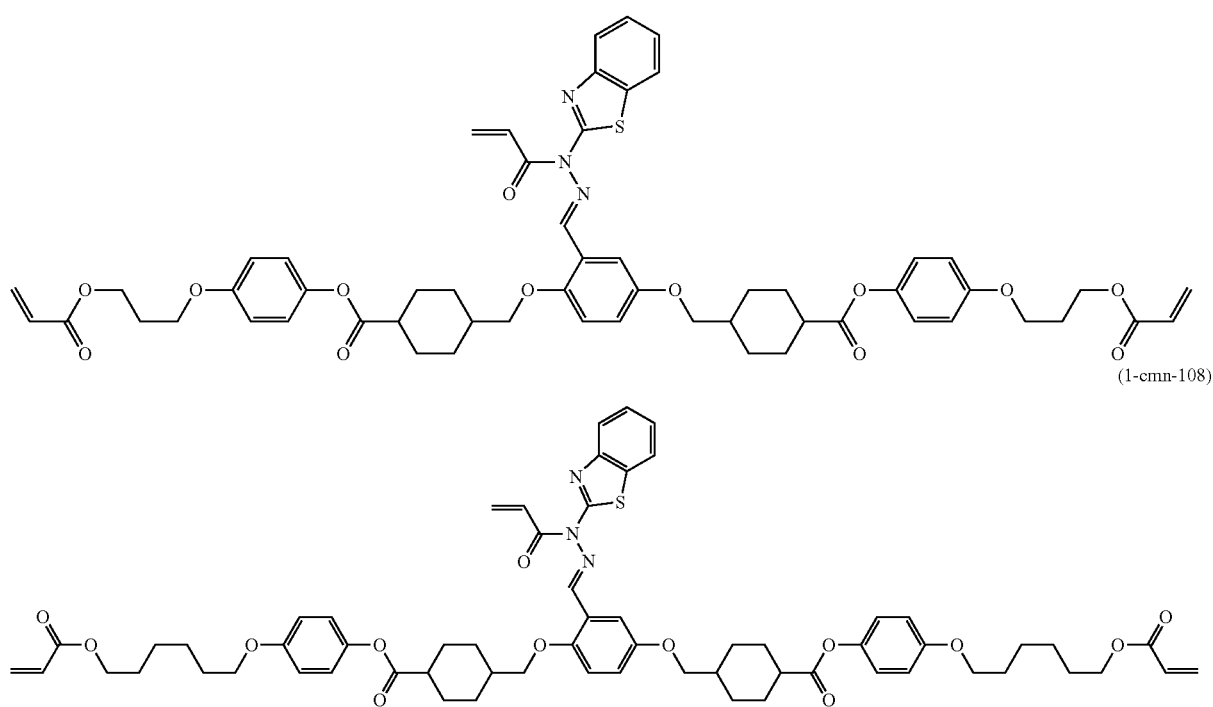

<Preparation of Optical Film>

A coating liquid containing 19.32% by weight polymerizable compound (1-c-1) synthesized in Example 1 above, 0.60% by weight IRGACURE 907 (produced by Ciba Specialty Chemicals Inc.) which served as a polymerization initiator, 0.04% by weight p-methoxyphenol (MEHQ) which served as a polymerization inhibitor, 0.04% by weight BYK-361N (produced by BYK-Chemie Japan KK) which served as a surfactant, and 80.00% by weight chloroform which served as a solvent was prepared.

<Method for Evaluating Solubility>

The coating liquid was evaluated on a scale of A to E on the basis of the state of the polymerizable compound dissolved in the coating liquid.

A: The polymerizable compound dissolved in chloroform at room temperature.

B: The polymerizable compound dissolved in chloroform when the temperature was increased to 50° C. subsequent to the addition of chloroform and did not precipitate when the temperature was reduced to room temperature.

C: The polymerizable compound dissolved in chloroform when the temperature was increased to 50° C. subsequent to the addition of chloroform and slightly precipitated when the temperature was reduced to room temperature.

D: About 80% to 30% of the amount of polymerizable compound dissolved in chloroform when the temperature was increased to 50° C. subsequent to the addition of chloroform.

E: 30% or less of the amount of polymerizable compound dissolved in chloroform even when the temperature was increased to 50° C. subsequent to the addition of chloroform.

<Method for Evaluating Preservation Stability>

The preservation stability of the coating liquid was evaluated on a scale of A to E on the basis of the state of the coating liquid that was stored for 2 months under a condition where the coating liquid was shielded from light at 0° C.

A: No visual change in the appearance of the coating liquid was confirmed. A GPC analysis of the coating liquid confirmed that the change in the composition of the coating liquid was 1% or less.

B: No visual change in the appearance of the coating liquid was confirmed. A GPC analysis of the coating liquid confirmed that the change in the composition of the coating liquid was 2% or less.

C: A visual change in the appearance of the coating liquid was confirmed; a trace amount of insoluble components were confirmed, or a GPC analysis of the coating liquid confirmed that the change in the composition of the coating liquid was 3% or less.

D: A visual change in the appearance of the coating liquid was confirmed; insoluble components were confirmed. The ratio of the weight of the insoluble components to the total solid content was 5% or less.

E: A large amount of insoluble components were visually confirmed. The ratio of the weight of the insoluble components to the total solid content was 5% or more.

The coating liquid was applied to a glass substrate by spin coating, the glass substrate including a rubbed polyimide layer deposited thereon. The glass substrate was then placed on a hot plate, dried at 80° C. for 1 minute, and further dried at 140° C. for another 1 minute. Subsequently, irradiation with ultraviolet radiation at 1000 mJ/cm and 140° C. was performed. Hereby, an optical film (optically anisotropic body) having a thickness of 1.02 µm was prepared.

<Method for Evaluating Optical Property>

The retardation values of the optical film in the wavelength range of 450 to 700 nm were measured with a measuring apparatus (RET-100 produced by Otsuka Electronics Co., Ltd.). Specifically, retardation values at wavelengths of 450, 550, and 650 nm, that is, Re(450), Re(550), and Re(650), were calculated with a program attached to the apparatus. The optical property of the optical film was evaluated on a scale of A to D on the basis of the results.

A: Re(450)/Re(550)≤0.85
B: 0.85<Re(450)/Re(550)≤0.95
C: 0.95<Re(450)/Re(550)≤1.05
D: 1.05<Re(450)/Re(550)

<Method for Evaluating Alignment Property>

The orientation of the optical film was evaluated on a scale of A to E below on the basis of the results of visual inspection of the appearance of the optical film and the results of inspection of the optical film with a polarized light microscope.

A: A uniform orientation of the optical film was visually confirmed. The inspection of the optical film with a polarized light microscope also confirmed no defects.

B: Although a uniform orientation of the optical film was visually confirmed, the inspection of the optical film with a polarized light microscope confirmed that the orientation area was 90% to 100%.

C: Although the degree of the orientation of the optical film which was visually confirmed was lower than those defined in A and B, the inspection of the optical film with a polarized light microscope confirmed that the orientation area was 60% to 90%.

D: Although the orientation of the optical film which was visually confirmed was substantially negligible, the inspection of the optical film with a polarized light microscope confirmed that the orientation area was 40% to 60%.

E: The orientation of the optical film which was visually confirmed was negligible. The inspection of the optical film with a polarized light microscope confirmed that the orientation area was 40% or less.

<Method for Evaluating Optical Stability>

The optical film was irradiated with light at 50 mW/cm$^2$, 25° C., and 100 J using a xenon-lamp irradiation testing machine (SUNTEST XLS, produced by Atlas). The optical stability of the optical film was evaluated on a scale of A to E below.

A: No change in the film was visually confirmed. An inspection of the optical film with a polarized light microscope also confirmed no defects.

B: Although no change in the film was visually confirmed, an inspection of the optical film with a polarized light microscope confirmed slight orientation defects.

C: Slight yellowing of the film was visually confirmed. The degree of orientation defects confirmed by an inspection of the optical film with a polarized light microscope was comparable to that defined in B.

D: Yellowing of the film was visually confirmed. In addition, the optical film was partly detached from the glass substrate.

E: Yellowing of the entire film was visually confirmed. In addition, the optical film was detached from the glass substrate.

A coating liquid and an optical film were prepared using each of the compounds synthesized in Examples 2 to 96 as in the case for the polymerizable compound (1-c-1) of Example 1 and evaluated in terms of solubility, preservation stability, optical property, alignment property, and optical stability. Tables 1 to 8 show the results.

TABLE 1

|  | Polymerizable compound | Solubility | Preservation stability | Optical property | Alignment property | Optical stability |
|---|---|---|---|---|---|---|
| Example 97 | 1-c-1 | A | A | A | A | A |
| Example 98 | 1-c-2 | A | A | A | A | A |
| Example 99 | 1-c-3 | A | A | A | A | A |
| Example 100 | 1-c-4 | A | A | A | A | A |
| Example 101 | 1-c-5 | A | A | A | A | A |
| Example 102 | 1-c-6 | A | A | A | A | A |
| Example 103 | 1-c-7 | A | A | A | A | A |
| Example 104 | 1-c-8 | A | A | A | A | A |
| Example 105 | 1-c-9 | A | A | A | A | A |
| Example 106 | 1-c-10 | A | A | A | A | A |
| Example 107 | 1-c-11 | A | A | A | A | A |
| Example 108 | 1-c-12 | A | A | A | A | A |
| Example 109 | 1-c-13 | A | A | A | A | A |
| Example 110 | 1-c-14 | A | A | A | A | A |
| Example 111 | 1-c-15 | A | A | A | A | A |
| Example 112 | 1-c-16 | A | A | A | A | A |
| Example 113 | 1-f-17 | B | A | A | A | A |
| Example 114 | 1-f-18 | B | A | A | A | A |
| Example 115 | 1-f-19 | B | A | A | A | A |
| Example 116 | 1-f-20 | B | A | A | A | A |
| Example 117 | 1-f-21 | B | A | A | A | A |
| Example 118 | 1-f-22 | B | A | A | A | A |

TABLE 2

| | Polymerizable compound | Solubility | Preservation stability | Optical property | Alignment property | Optical stability |
|---|---|---|---|---|---|---|
| Example 119 | 1-c-23 | A | B | A | A | A |
| Example 120 | 1-c-24 | A | B | A | A | A |
| Example 121 | 1-c-25 | A | B | A | A | A |
| Example 122 | 1-c-26 | A | A | A | A | A |
| Example 123 | 1-c-27 | A | B | A | A | B |
| Example 124 | 1-c-28 | A | B | A | A | A |
| Example 125 | 1-c-29 | A | B | A | A | A |
| Example 126 | 1-c-30 | A | B | A | A | A |
| Example 127 | 1-c-31 | A | B | A | A | B |
| Example 128 | 1-c-32 | A | B | A | A | B |
| Example 129 | 1-c-33 | A | B | A | A | B |
| Example 130 | 1-c-34 | A | B | A | A | B |
| Example 131 | 1-g-35 | B | B | B | A | A |
| Example 132 | 1-cg-36 | A | B | A | A | A |
| Example 133 | 1-cg-37 | A | B | A | A | A |
| Example 134 | 1-g-38 | B | B | A | A | A |
| Example 135 | 1c-39 | A | B | A | A | B |
| Example 136 | 1-c-40 | A | A | A | A | B |
| Example 137 | 1-c-41 | A | A | A | A | B |
| Example 138 | 1-c-42 | A | B | A | A | B |

TABLE 3

| | Polymerizable compound | Solubility | Preservation stability | Optical property | Alignment property | Optical stability |
|---|---|---|---|---|---|---|
| Example 139 | 1-c-43 | A | B | A | A | B |
| Example 140 | 1-c-44 | A | B | A | A | B |
| Example 141 | 1-c-45 | A | B | A | A | B |
| Example 142 | 1-c-46 | A | B | A | A | B |
| Example 143 | 1-c-47 | A | B | A | A | B |
| Example 144 | 1-c-48 | A | B | A | A | B |
| Example 145 | 1-c-49 | A | A | A | A | A |
| Example 146 | 1-c-50 | A | A | A | A | A |
| Example 147 | 1-c-51 | A | A | A | A | A |
| Example 148 | 1-c-52 | A | A | A | A | A |
| Example 149 | 1-c-53 | A | A | A | A | A |

TABLE 4

| | Polymerizable compound | Solubility | Preservation stability | Optical property | Alignment property | Optical stability |
|---|---|---|---|---|---|---|
| Example 150 | 1-j-54 | A | B | A | A | B |
| Example 151 | 1-j-55 | A | B | A | A | B |
| Example 152 | 1-j-56 | A | B | A | A | B |
| Example 153 | 1-j-57 | A | B | A | A | B |
| Example 154 | 1-cj-58 | A | A | A | A | B |
| Example 155 | 1-cj-59 | A | A | A | A | B |
| Example 156 | 1-cj-60 | A | A | A | A | B |
| Example 157 | 1-j-61 | A | B | A | A | B |
| Example 158 | 1-j-62 | A | B | A | A | B |
| Example 159 | 1-cj-63 | A | A | A | A | B |
| Example 160 | 1-j-64 | A | B | A | A | B |
| Example 161 | 1-j-65 | A | B | A | A | B |

TABLE 5

| | Polymerizable compound | Solubility | Preservation stability | Optical property | Alignment property | Optical stability |
|---|---|---|---|---|---|---|
| Example 162 | 1-c-66 | A | B | A | A | B |
| Example 163 | 1-c-67 | A | B | A | A | B |
| Example 164 | 1-c-68 | A | B | A | A | B |
| Example 165 | 1-e-69 | A | A | A | A | A |
| Example 166 | 1-e-70 | A | A | A | A | A |
| Example 167 | 1-eh-71 | A | A | A | A | A |
| Example 168 | 1-eh-72 | A | A | A | A | A |
| Example 169 | 1-e-73 | A | A | A | A | A |
| Example 170 | 1-eh-74 | A | A | A | A | A |

TABLE 5-continued

|  | Polymerizable compound | Solubility | Preservation stability | Optical property | Alignment property | Optical stability |
|---|---|---|---|---|---|---|
| Example 171 | 1-eh-75 | A | A | A | A | A |
| Example 172 | 1-r-76 | C | C | B | B | B |
| Example 173 | 1-r-77 | C | C | B | B | B |
| Example 174 | 1-r-78 | C | C | B | B | B |

TABLE 6

|  | Polymerizable compound | Solubility | Preservation stability | Optical property | Alignment property | Optical stability |
|---|---|---|---|---|---|---|
| Example 175 | 1-ch-79 | A | A | A | A | A |
| Example 176 | 1-c-80 | A | A | A | A | A |
| Example 177 | 1-cmn-81 | A | A | A | A | A |
| Example 178 | 1-cmn-82 | A | A | A | A | A |
| Example 179 | 1-cn-83 | A | A | A | A | A |
| Example 180 | 1-hk-84 | A | A | A | A | A |
| Example 181 | 1-hk-85 | A | A | A | A | A |
| Example 182 | 1-hk-86 | A | A | A | A | A |
| Example 183 | 1-k-87 | A | A | A | A | A |
| Example 184 | 1-cm-88 | A | A | A | A | A |

TABLE 7

|  | Polymerizable compound | Solubility | Preservation stability | Optical property | Alignment property | Optical stability |
|---|---|---|---|---|---|---|
| Example 185 | 1-cm-89 | A | A | A | A | A |
| Example 186 | 1-cmn-90 | A | A | A | A | A |
| Example 187 | 1-cmn-91 | A | A | A | A | A |
| Example 188 | 1-cmn-92 | A | A | A | A | A |
| Example 189 | 1-cmn-93 | A | A | A | A | A |
| Example 190 | 1-cmn-94 | A | A | A | A | A |
| Example 191 | 1-f-95 | B | A | A | A | A |
| Example 192 | 1-f-96 | B | A | A | A | A |
| Example 193 | 1-f-97 | B | A | A | A | A |
| Example 194 | 1-f-98 | B | A | A | A | A |

TABLE 8

|  | Polymerizable compound | Solubility | Preservation stability | Optical property | Alignment property | Optical stability |
|---|---|---|---|---|---|---|
| Example 195 | 1-f-99 | B | A | A | A | A |
| Example 196 | 1-f-100 | B | A | A | A | A |
| Example 197 | 1-f-101 | B | A | A | A | A |
| Example 198 | 1-f-102 | B | A | A | A | A |
| Example 199 | 1-f-103 | B | A | A | A | A |
| Example 200 | 1-fn-104 | B | A | A | A | A |
| Example 201 | 1-cm-105 | A | A | A | A | A |
| Example 202 | 1-cmn-106 | A | A | A | A | A |
| Example 203 | 1-cmn-107 | A | A | A | A | A |
| Example 204 | 1-cmn-108 | A | A | A | A | A |

Comparative Example 1

Compounds of Comparative Examples 1 to 3 below were synthesized with reference to the descriptions in Japanese Unexamined Patent Application Publication No. 2010-031223 and Japanese Unexamined Patent Application Publication No.

[Chem. 129]

Comparative example 1

(r-1)

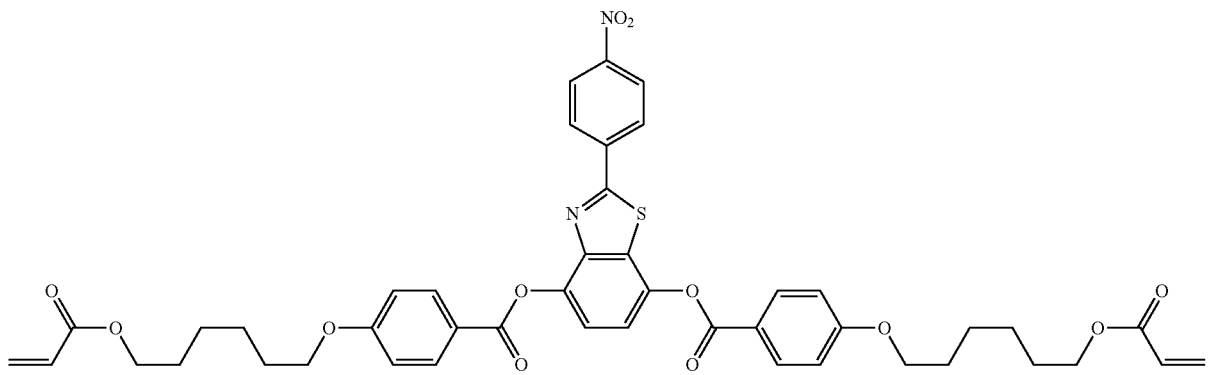

Comparative example 2

(r-2)

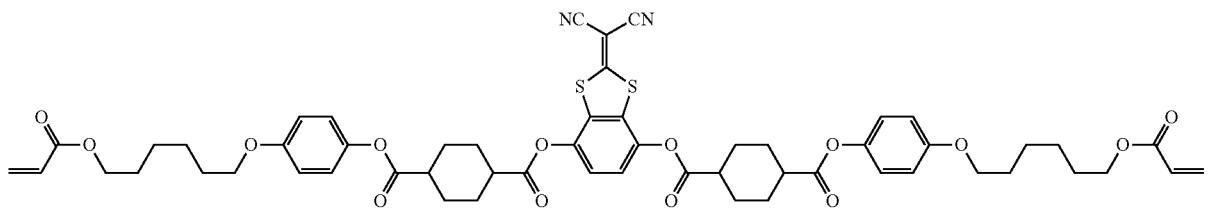

Comparative example 3

(r-3)

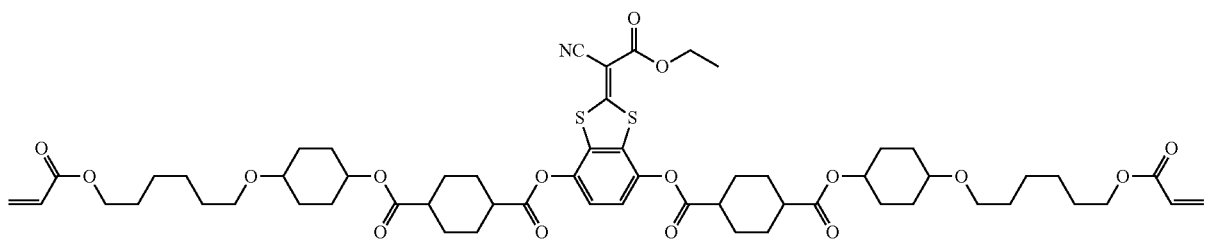

A coating liquid and an optical film were prepared using each of the compounds synthesized in Comparative Examples 1 to 3 and evaluated in terms of solubility, preservation stability, optical property, alignment property, and optical stability. Table 9 shows the results.

TABLE 9

| | Polymerizable compound | Solubility | Preservation stability | Optical property | Alignment property | Optical stability |
|---|---|---|---|---|---|---|
| Comparative example 1 | r-1 | C | D | C | C | C |
| Comparative example 2 | r-2 | D | C | C | C | C |
| Comparative example 3 | r-3 | D | C | C | C | C |

As described above, in Examples 97 to 192, the polymerizable compound according to the present invention had improved solubility, preservation stability, optical property, alignment property, and optical stability compared with the polymerizable compounds of Comparative Examples 1 to 3. This confirms that, as shown in Examples 97 to 192, it is possible to produce an optically anisotropic body having excellent characteristics by using the polymerizable compound according to the present invention.

In Examples 1-j-54 to 1-j-65 (Examples 150 to 161), where specific linking groups were used as a linking group bonded to Sp, the solubility of the compound in solvents was enhanced.

In Examples 1-c-17 to 1-f-22 (Examples 113 to 118), which included a divalent alicyclic hydrocarbon group, the solubility of the compound in solvents was improved. Furthermore, the reversed-dispersion property of a polymer produced using the compound was improved.

In Examples 1-e-69 to 1-eh-75 (Examples 165 to 171), where one of m and n was 0, the solubility of the compound in solvents and the preservation stability of the compound were improved.

In Examples 1-eh-71 and 1-eh-72 and Examples 1-eh-74 and 1-eh-75 (Examples 167, 168, 170, and 171), which included two or more divalent aromatic hydrocarbon groups in a portion of the molecule extending from the U group to an end of the molecule, liquid crystal property and alignment property were improved.

In Examples 1-g-35 to 1-g-38 (Examples 131 to 134), where both of $Sp^1$ and $Sp^2$ were single bonds, a polymer produced by polymerizing a composition including the polymerizable compound had high optical stability.

In Example 1-cmn-81, Example 1-cmn-82, Examples 1-cmn-90 to 1-cmn-94, and Examples 1-cmn-105 to 1-cmn-108 (Examples 177, 178, 186 to 190, and 202 to 204), a polymer having a high optical property, high preservation stability, and high optical stability was prepared.

In Examples 1-hk-84, 1-hk-85, 1-hk-86, and 1-k-87 (Examples 180 to 183), a polymer having a good alignment property and high preservation stability was prepared.

In Examples 1-f-17 to 1-f-22 and Examples 1-f-95 to 1-f-103 (Examples 113 to 118 and Examples 191 to 199), a polymer having a high optical property was prepared.

The components described in the foregoing embodiment, the combinations of the components, and the like are merely examples; the addition, omission, replacement, and any other modification of the components may be made without departing from the scope of the present invention. The present invention is not limited by the embodiment. The present invention is limited only by Claims.

INDUSTRIAL APPLICABILITY

The polymerizable compound according to the present invention may be broadly used in the applications of liquid crystal display elements and organic EL devices. The polymerizable compound according to the present invention may also be broadly used for producing a resin, a resin additive, an oil, a filter, a bonding agent, an adhesive, a fat, an ink, a drug, a cosmetic, a detergent, a building material, a packaging material, a liquid crystal material, an organic EL material, an organic semiconductor material, an electronic material, an automotive component, an aircraft component, a machine component, an agricultural chemical, a food, and products including the above items.

The invention claimed is:

1. A polymerizable compound represented by General Formula (1) below,

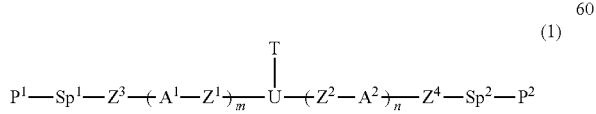

(1)

wherein $P^1$ and $P^2$ represent a polymerizable functional group represented by Formula (P-1) or (P-2),

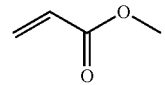

(P-1)

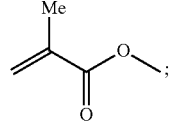

(P-2)

$Sp^1$ and $Sp^2$ represent a divalent spacer group or a single bond;

$A^1$ and $A^2$ each independently represent a divalent alicyclic or aromatic hydrocarbon group having 3 to 20 carbon atoms, the divalent alicyclic or aromatic hydrocarbon group may be optionally substituted with one or more substituents, and a carbon atom included in the alicyclic or aromatic hydrocarbon group may be replaced with a hetero atom;

$Z^1$, $Z^2$, $Z^3$, and $Z^4$ each independently represent a divalent linking group or a single bond in which $Z^1$ directly bonded to U is —CH$_2$O— or —CF$_2$O—, and $Z^2$ directly bonded to U is —CH$_2$O— or —CF$_2$O—;

U represents a trivalent aromatic group selected from the group consisting of Formulae (U-1), (U-2), (U-5) and (U-6), that may be optionally substituted with one or more substituents,

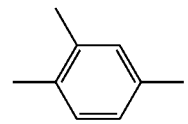

(U-1)

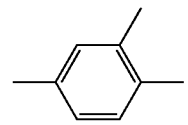

(U-2)

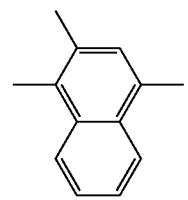

(U-5)

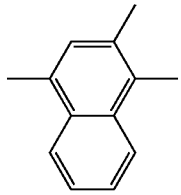

(U-6)

T represents a group selected from Formulae (T-1) and (T-2) below,

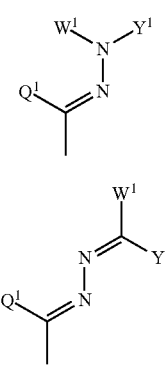

(T-1)

(T-2)

where $Q^1$ represents a hydrogen atom or an alkyl group having 1 to 6 carbon atoms, and the alkyl group may be optionally substituted with one or more substituents;

$W^1$ represents an organic group having 2 to 30 carbon atoms, the organic group includes an aromatic hydrocarbon group, a carbon atom included in the aromatic hydrocarbon group may be replaced with a hetero atom, and the aromatic hydrocarbon group may be optionally substituted with one or more substituents;

$Y^1$ represents $-(Z^5-A^3)q-Z^6-Sp^3-P^3$, $Z^5$ and $Z^6$ represent the same things as $Z^1$ to $Z^4$, $A^3$ represents the same thing as $A^1$ and $A^2$, $Sp^3$ represents the same thing as $Sp^1$ and $Sp^2$, $P^3$ represents the same thing as $P^1$ and $P^2$, and q represents an integer of 0 to 4; and m and n each independently represent an integer of 2 to 4; and, when a plurality of $A^1$ groups, $A^2$ groups, $A^3$ groups, $Z^1$ groups, $Z^2$ groups, and $Z^5$ groups are present, they may be identical to or different from one another.

2. The polymerizable compound according to claim 1, wherein, in General Formula (1), one or both of $Z^3$ and $Z^4$ each independently represent —OCO—CH=CH—*, —OCO—CH$_2$CH$_2$—*, —COO—CH$_2$CH$_2$—*, —O—CH=CH—*, or —O—CH$_2$CH$_2$—* wherein the above groups are bonded to the $A^1$ or $A^2$ group on the side denoted by *.

3. The polymerizable compound according to claim 1, wherein, in General Formula (1), all of the $A^1$ groups and/or all of the $A^2$ groups are divalent alicyclic hydrocarbon groups that may be optionally substituted with one or more substituents.

4. The polymerizable compound according to claim 1, wherein, in General Formula (1), both of m and n are integers of 2 to 4, wherein two or more $A^1$ groups and/or two or more $A^2$ groups are each independently a divalent aromatic hydrocarbon group that may be optionally substituted with one or more substituents, and wherein the $Z^1$ group with which the two or more $A^1$ groups are connected to each other and/or the $Z^2$ group with which the two or more $A^2$ groups are connected to each other is not a single bond.

5. The polymerizable compound according to claim 1, wherein, in General Formula (1), $Sp^1$ and/or $Sp^2$ represents a single bond.

6. The polymerizable compound according to claim 1, wherein, in Formulae (U-1), (U-2), (U-5) and (U-6),
one or more hydrogen atoms bonded to each of the above rings may be replaced with F, Cl, CF$_3$, OCF$_3$, a cyano group, an alkyl group having 1 to 8 carbon atoms, an alkoxy group having 1 to 8 carbon atoms, an alkanoyl group having 1 to 8 carbon atoms, an alkanoyloxy group having 1 to 8 carbon atoms, an alkenyl group having 2 to 8 carbon atoms, an alkenyloxy group having 2 to 8 carbon atoms, an alkenoyl group having 2 to 8 carbon atoms, or an alkenoyloxy group having 2 to 8 carbon atoms.

7. The polymerizable compound according to claim 1, wherein, in General Formula (1), $W^1$ represents a group selected from General Formulae (W-1) to (W-20) below,

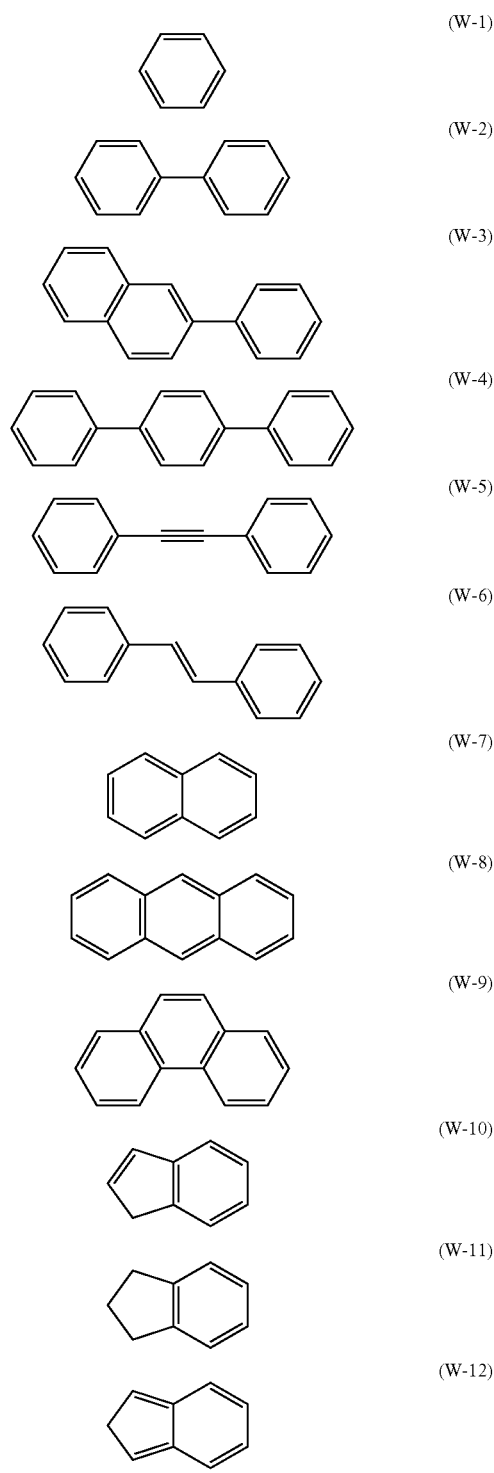

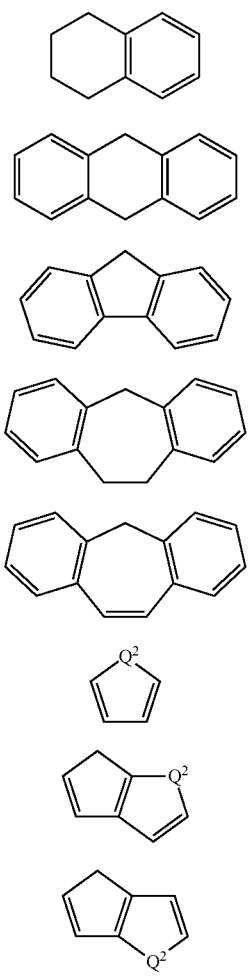

(W-13)
(W-14)
(W-15)
(W-16)
(W-17)
(W-18)
(W-19)
(W-20)

wherein the above groups may have a bond at any position; $Q^2$ represents —O—, —S—, —NR$^4$— wherein R$^4$ represents a hydrogen atom or an alkyl group having 1 to 8 carbon atoms, or —CO—; —CH═ groups included in each of the above groups may be each independently replaced with —N═; —CH$_2$— groups included in each of the above groups may be each independently replaced with —O—, —S—, —NR$^5$— wherein R$^5$ represents a hydrogen atom or an alkyl group having 1 to 8 carbon atoms, —SO—, —SO$_2$—, or —CO— in which the polymerizable compound represented by General Formula (1) does not include two oxygen atoms directly bonded to each other; and the above groups may be optionally substituted with one or more L$^W$ substituents, where L$^W$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 20 carbon atoms, the alkyl group may be linear or branched, a hydrogen atom included in the alkyl group may be replaced with a fluorine atom, and one —CH$_2$— group included in the alkyl group or two or more —CH$_2$— groups that are included in the alkyl group and not adjacent to one another may be each independently replaced with a group selected from —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, and —C≡C—.

8. A composition comprising the polymerizable compound according to claim 1.

9. A method for producing a polymer, the method comprising:
providing the composition according to claim 8; and
polymerizing the composition.

10. A method for producing an optically anisotropic body, the method comprising:
providing the composition according to claim 8;
aligning the polymerizable compound; and
polymerizing the composition.

11. A method for producing the optically anisotropic body according to claim 10, wherein the optically anisotropic body is then provided for producing a liquid crystal display element comprising the optically anisotropic body.

12. A method for producing the optically anisotropic body according to claim 10, wherein the optically anisotropic body is then provided for producing an organic EL device comprising the optically anisotropic body.

13. A liquid crystal material, an organic EL material, an organic semiconductor material, and an electronic material that comprise the polymerizable compound according to claim 1.

* * * * *